United States Patent
Stanton, Jr. et al.

(10) Patent No.: US 6,458,945 B1
(45) Date of Patent: Oct. 1, 2002

(54) METHOD FOR ANALYZING POLYNUCLEOTIDES

(75) Inventors: Vincent P. Stanton, Jr., Belmont, CA (US); Jia Liu Wolfe, Winchester, MA (US); Tomohiko Kawate, Cambridge, MA (US); Gregory L. Verdine, Lexington, MA (US)

(73) Assignee: Variagenics, Inc., Cambridge, MA (US)

( * ) Notice: Subject to any disclaimer, the term of this patent is extended or adjusted under 35 U.S.C. 154(b) by 0 days.

(21) Appl. No.: 09/709,596

(22) Filed: Nov. 9, 2000

Related U.S. Application Data

(62) Division of application No. 09/394,774, filed on Sep. 10, 1999.
(60) Provisional application No. 60/149,533, filed on Aug. 17, 1999, and provisional application No. 60/102,724, filed on Oct. 1, 1998.
(51) Int. Cl.[7] .......................... C12Q 1/68; C12P 19/34; C07H 19/00; C07H 21/00; C07H 12/02
(52) U.S. Cl. .................. 536/25.3; 435/6; 435/91.1; 435/91.2; 536/23.1; 536/25.32
(58) Field of Search ................ 435/6, 91.1, 91.21; 536/23.1, 25.3, 25.32

(56) References Cited

U.S. PATENT DOCUMENTS

| | | | |
|---|---|---|---|
| 4,701,419 A | 10/1987 | Morris | 436/89 |
| 4,879,214 A | 11/1989 | Kornher et al. | 435/91 |
| 5,003,059 A | 3/1991 | Brennan | 536/27 |
| 5,064,754 A | 11/1991 | Mills | 435/6 |
| 5,174,962 A | 12/1992 | Brennan | 422/78 |
| 5,187,085 A | 2/1993 | Lee | 435/91 |
| 5,221,518 A | 6/1993 | Mills | 422/62 |
| 5,332,666 A | 7/1994 | Prober et al. | 435/91.5 |
| 5,424,184 A | 6/1995 | Santamaria et al. | 435/6 |
| 5,547,835 A | 8/1996 | Köster | 435/6 |
| 5,552,278 A | 9/1996 | Brenner | 435/6 |
| 5,580,733 A | 12/1996 | Levis et al. | 435/6 |
| 5,605,798 A | 2/1997 | Köster | 435/6 |
| 5,622,824 A | 4/1997 | Köster | 435/6 |
| 5,691,141 A | 11/1997 | Köster | 435/6 |
| 5,700,642 A | 12/1997 | Monforte et al. | 435/6 |
| 5,830,655 A | 11/1998 | Monforte et al. | 435/6 |
| 5,869,242 A | 2/1999 | Kamb | 435/6 |
| 5,939,292 A | 8/1999 | Gelfand et al. | 435/91.2 |

FOREIGN PATENT DOCUMENTS

| | | |
|---|---|---|
| WO | WO98/00433 | 1/1998 |

OTHER PUBLICATIONS

Zagrebelny et al. Bioorg. Khim 10(9) pp. 1183–1193, 1984.*
Chen et al. Biochemistry 32, pp. 6002–6010, 1993.*
Ghandi et al. Cancer Research 55, pp. 1517–1524, Apr. 1995.*
Patel et al. Tetrahedron Letters 38, pp. 1021–1024, 1997.*
Chen et al. The journal of Biological Chemistry 251, pp. 4833–4838, 1976.*
Andersson, B. et al., "Simultaneous shotgun sequencing of multiple cDNA clones," *DNA Sequence*, 1997, 7:63–70.
Astatke, M., et al, "Deoxynucleoside thriphosphate and pyrophosphate binding sites in the catalytically competent ternary complex for the polymerase reaction catalyzed by DNA polymerase I (Klenow fragment)," *J. Biol. Chem.*, 1995, 270:1945–54.

(List continued on next page.)

*Primary Examiner*—Jezia Riley
(74) *Attorney, Agent, or Firm*—Lyon & Lyon LLP

(57) ABSTRACT

The present invention relates to methods for the analysis of polynucleotides including detection of variance in nucleotide sequence without the need for full sequence determination, full sequence determination of a polynucleotide, genotyping of DNA and labeling a polynucleotide fragment during the process of cleaving it into fragments.

4 Claims, 39 Drawing Sheets

OTHER PUBLICATIONS

Astatke, M., et al., "How *E. coli* DNA polymerase I (Klenow fragment) distinguishes between Deoxy–and Dideoxynucleotides," *J. Mol. Biol.*, 1998, 278:147–165.

Astatke, M., et al., "A single side chain prevents *Escherichia coli* DNA polymerase I (Klenow fragment) from incorporating ribonucleotides," *Proc. Nat. Acad. Sci. USA*, 1998, 95:3402–3407.

Barnes, W.M., "DNA Sequencing by Partial Ribosubstitution," *J. Mol.Bio.*, 1978, 119:83–99.

Barnes, W.M., "PCR amplification of up to 35–kb DNA with high fidelity and high yield from λ bacteriophage templates," *Proc. Natl. Acad. Sci. USA*, 1994, 91:2216–2220.

Beavis, R., et al "Matrix–assisted laser desorption/ionization mass spectrometry of biopolymers," *Anal. Biochem.*, 1991, 63: 1193–1203.

Chen, C.N., et al, "Ordered shotgun sequencing of a 135 kb Xq25 YAC containing ANT2 and four possible genes, including three confirmed by EST matches," *Nucleic Acids Research*, 1996, 24:4034–4041.

Daugherty P.S., et al., "Antibody affinity maturation using bacterial surface display," *Protein Eng* 1998, 11:825–32.

Delarue, M., et al., "An attempt to unify the structure of polymerase," *Protein Eng*, 1990, 3:461–467.

Fichant, G. A. and Quentin, Y., "A frameshift error detection algorithm for DNA sequencing projects," *Nucleic Acid Research*, 23:2900–2908, 1995.

Fu, D. J., et al., "Sequencing exons 5 to 8 of the p53 gene by MALDI–TOF mass spectrometry," *Nature Biotechnology*, 1998, 16:381–384.

Giese, B., et al., "The chemistry of single–stranded 4'–DNA radicals: influence of the radical precursor o anaerobic and aerobic strand cleavage," *Chemistry & Biology*, 1995, 2 No. 6, 367–375.

Giese, B., et al, "The mechanism of anaerobic, Radical–Induced DNA strand scission," *Angew. Chem. Int. Ed. Engl.* 1993, 32:1742–43.

Gish, G., et al., "DNA and RNA Sequence Determination Based on Phosphorothioate Chemistry," *Reports*, 1988 1520–1522.

Gupta and Kool, "A self–cleaving DNA nucleoside," *Chem. Commun.* 1997, pp. 1425–1426.

Harayama, S., "Artificial evolution by DNA shuffling," *Trends Biotechnol.*, 1998, 16:76–82.

Hentosh, P. et al, "Polymerase chain reaction amplification of single–stranded DNA containing a base analog, 2–Chloroadenine,". *Anal. Biochem.*, 1992, 201: 277–281.

Huang, Y., "Determinants of Ribose Specificty in RNA Polymerization: Effects of $Mn^{2+}$ and Deoxynucleoide Monophosphate Incorporation into Transcripts," *Biochemistry*, 1997, 36:13718–13728.

Joyce, C. M., "Choosing the right sugar: How polymerase select a nucleotide substrate," *Proc. Natl. Acad. Sci. USA*, 1997, 94:1619–1622.

Kaczorowski, T., et al., "Assembly of 18–nucleotide primers by ligation of three hexamers: secuqncing of large genomes by primer walking," *Anal. Biochem.*, 1994, 221:127–135.

Khurshid, F., et al, "Error analysis in manual and automated DNA sequencing," *Analytical Biochemistry*, 208:138–143, 1993.

Kirpekar, F., et al, "Matrix–assisted laser desorption–ionization mass spectrometry of enzymatically synthesized RNA up to 150 kDa," *Nucleic Acids Research*, 1994, 22: No. 19 3866–3870.

Kristensen, T., et al, "An estimate of the sequencing error frequency in the DNA sequence databases," *DNA Sequencing*, 2:343–346, 1992.

Landegren, U. et al., Reading Bits of Genetic Information: Methods for Single–nucleotide Polymorphism Analysis, *Genome Research* 1998, 88:769–76.

Liu, D., et al., "Bi–stranded multisite replication of a base pair between difluorotoluene and Adenine: confirmation by 'inverse' sequencing," *Chem. Biol.*, 4:919–929, 1997.

Lodhi, M. A., et al., "High–quality automated DNA sequencing primed with hexamer strings," *Genome Research*, 1996, 6:10–18.

Martin–Gallardo, et al., "Automated DNA sequencing and analysis of 106 kilobases from human chromosome 19q13.3," *Nature Genetics*, 1992 1:34–39.

Marx, A., et al, "Synthesis of 4'–C–Acylated Thymidines," *Helv. Chim. Acta*, 1966, 79:1980–94.

Maxam and Gilbert, "A new method for sequencing DNA" *Proc. Nat. Acad. Sci. USA*, 74, 560–564 1977.

Moran, S., et al., "A thymidine thriphosphate shape analog lacking Watson–Crick pairing ability is replicated with high sequence selectivity," *Proc. Natl. Acad. Sci. USA*, 94:10506–10511, 1997.

Nakamaye, K. et al., "Direct sequencing of polymerase chain reaction amplified DNA fragments through the incorporation of deoxynucleoside α–thiotriphosphates," *Nucleic Acid Research*, 1988, 16:9947–9959.

Nelson, R.W., et al, "Volatilization of High Molecular Weight DNA by Pulsed Laser Ablation of Frozen Aqueous Solutions," *Science* 1989, vol. 246, 1585–1587.

Nickerson, D.A., "DNA sequence diversity in a 9.7–kb region of the human lipoprotein ilipase gene," *Nature Genetics*, 1998, 223–240.

Nordhoff, E. et al., "Comparison of IR– and UV–matrix–assisted laser desorption/ionization mass spectrometry of oligodeoxynucleotides," *Nucleic Acids Research*, 1994, 22: No. 13, 2460–2465.

Nordhoff, E. et al, "Ion stability of nucleic acids in infrared matrix–assisted laser desorption/ionization mass spectrometry," *Nucleic Acids Research*, 1993, 21:No. 15 3347–3357.

Olsen, D.B. et al, "[8] Direct sequencing of polymerase chain reaction products," *Methods of Enzymology*, vol. 218 pp. 79–92, 1993.

Ono, T., et al., "2'Floro modified nucleic acids: polymerase–directed synthesis, properties and stability to analysis by matrix–assisted laser desorption/ionization mass spectrometry," *Nucleic Acids Research*, 1997, 25: 4581–4588.

Pedersen et. al., "A method for directing evolution and functional cloning of enzymes," *Proc. Natl. Acad. Sci. USA*, 1998, 95:10523–8.

Pieles, U, et al, "Matrix–assisted laser desorption ionization time–of–flight mass spectrometry: a powerful tool for the mass and sequence analysis of natural and modified oligonucleotides," *Nucleic Acids Research*, 1993, 21:No. 14 3191–3196.

Polesky et al., "Identification of residues critical for the polymerase activity of the Klenow fragment of DNA polymerase I from *Escherichia coli*\*," *J. Biol. Chem.*, 1990, 265:14579–91.

Pomerantz, S.C., et al., "Determination of oligonucleotide composition from Mass spectrometrically measured molecular weight," *J. Am. Soc. Mass Spectrom.*, 1993, 4: 204–209.

Prober, et al, "A System for Rapid DNA Sequencing with Fluorescent Chain–Terminating Dideoxynucleotides," *Science* 1987, vol. 238, 336–341.

Sanger, et al., "DNA sequencing with chain–terminating inhibitors," *Proc. Nat. Acad. Sci. USA*, 74, 5463–5467 1977.

Schneider, K. and Chait, B.T., "Increased stability of nucleic acids containing 7–deaza–quanosine and 7–deaza–adenosine may enable rapid DNA sequencing by matrix–assisted laser desorption mass spectrometry," *Nucleic Acids Research*, 1995, 23: 1570–1575.

Siebenlist, et al., "Contacts between *Escherichia coli* RNA polymerase and an early promoter of phast T7," *Proc. Natl. Acad. Sci.* USA, 1980, 77:122.

Siuzdak, G. "The emergence of mass spectrometry in biochemical research," *Proc. Natl. Acad. Sci.*, 1994, 91:11290–11297.

Sousa, et al, "A mutant T7 RNA polymerase as a DNA polymerase," *EMBO Journal* vol. 14 No. 18, pp. 4609–4621, 1995.

Stemmer, W. P. C., "Rapid evolution of a protein in vitro by DNA shuffling," *Nature*, 1994, 370:389–391.

Tabor, S., et al., "DNA sequence analysis with a modified bacteriophage T7 DNA polymerase," *Proc. Natl. Acad. Sci.* USA, 1987, 84:4767–4771.

Venter, J. C., et al., "Shotgun sequencing of the human genome," *Science*, 1998, 280:1540–1542.

Verdine, et al, "Immobilized Metal Affinity Chromatography of DNA," *Dept. of Chemistry, Harvard University*, May 29, 1996.

Verdine, et al., "Template–Directed Interference Footprinting of Cytosine Contacts in s Protein–DNA Complex: Potent Interference by 5–Aza–2'–deoxycytidine;" *Biochemistry*, 1992, 31:11265–11273.

Verdine, et al., "Template–Directed Interference Footprinting of Protein–Adenine Contacts," *JACS*, 1996, 118:6116–6120.

Verdine, et al., "Template–Directed Interference Footrpinting of Protein–Guanine Contacts in DNA;" *JACS*, 1991, 113:5104–5106.

Verdine, et al., "Template–Directed Interference Footprinting of Protein–Thymine Contacts," *JACS*, 1993, 115: No. 1 373–374.

Voss, H., et al., "Automated low–redundancy large–scale DNA sequencing by primer walking," *Biotechniques*, 1993, 15:714–721.

Wang, B. H., et al "Matrix–assisted laser desorption/ionization time–of–flight mass spectrometry of chemically modified oligonucleotides," *Analytical Chemical*, 1994, 66: 1918–1924.

Wang, B. H., et al, Sequencing of modified oligonucleotides using in–source fragmentation and delayed pulsed ion extraction matrix–assisted laser desorption ionization time–of–flight mass spectrometry, *Internat'l J. of Mass Spec. and Ion Process*, 1997, 169/170:331–350.

Weber, J. L. "Human whole–genome shotgun sequencing," *Genome Research*, 1997, 7:401–409.

Williams, E. R., "Tandem FTMS of Large Biomolecules," *Anal. Chem.*, 1998, 70:179A–185A.

Wu, K., et al., "Time–of–flight mass spectrometry of underivatized single–stranded DNA oligomers by matrix–assisted laser desorption," *Anal. Chem*, 1994 66, 1637–1645.

* cited by examiner

Fig. 1

*PLUS STRAND PRIMER*

RFCbio    5'-GAAGGCTGTATGAGCTTCTA

RFCBIO-RFC EXTENSION PRODUCT:    GAAGGCTGTATGAGCTTCTAACTCATTGTATTCCTCCTGAGATAATAATGAAGGGCCTTCTC TCAG
RFCBIO-RFCmutEXTENSION PRODUCT:  GAAGGCTGTATGAGCTTCTAACTCATTGTATTCCTCCTGAGATAATAATGAAGGGCCTTCTC CCAG

*MINUS STRAND PRIMERS*

TTCCCGGAAGAGAGTC-5'    RFC
TTCCCGGAAGAGGGTC-5'    RFCmut

Fig. 2

RFC CLEAVAGE PRODUCTS: GAAGGCTGTATGAGCTTCTA ACTCATT TATTCCTCCT A ATAATAAT AA CCTTCTCTCA

| RFC MASS ANALYSIS | LENGTH (nts) | 27 | | 10 | 1 | 8 | 2 | 10 |
|---|---|---|---|---|---|---|---|---|
| | MASS (Da) | 8772.15 | | 3069.92 | | 2557.6 | | 3054.9* |

RFCMUT CLEAVAGE PRODUCTS: GAAGGCTGTATGAGCTTCTA ACTCATT TATTCCTCCT A ATAATAAT AA CCTTCTCCCA

| RFCMUT MASS ANALYSIS | LENGTH (nts) | 27 | | 10 | 1 | 8 | 2 | 10 |
|---|---|---|---|---|---|---|---|---|
| | MASS (Da) | 8772.15 | | 3069.92 | | 2557.6 | | 3039.88* |

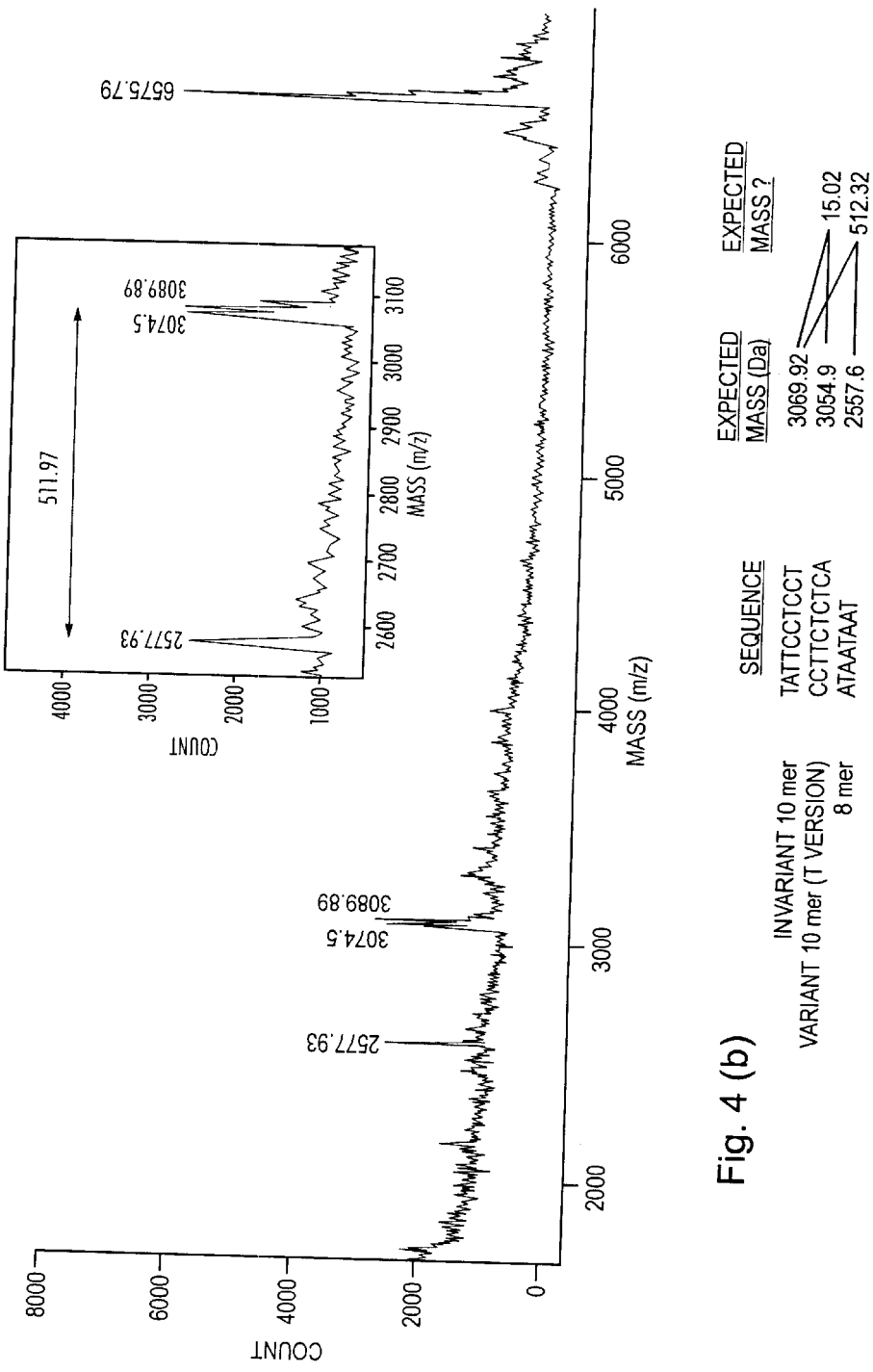

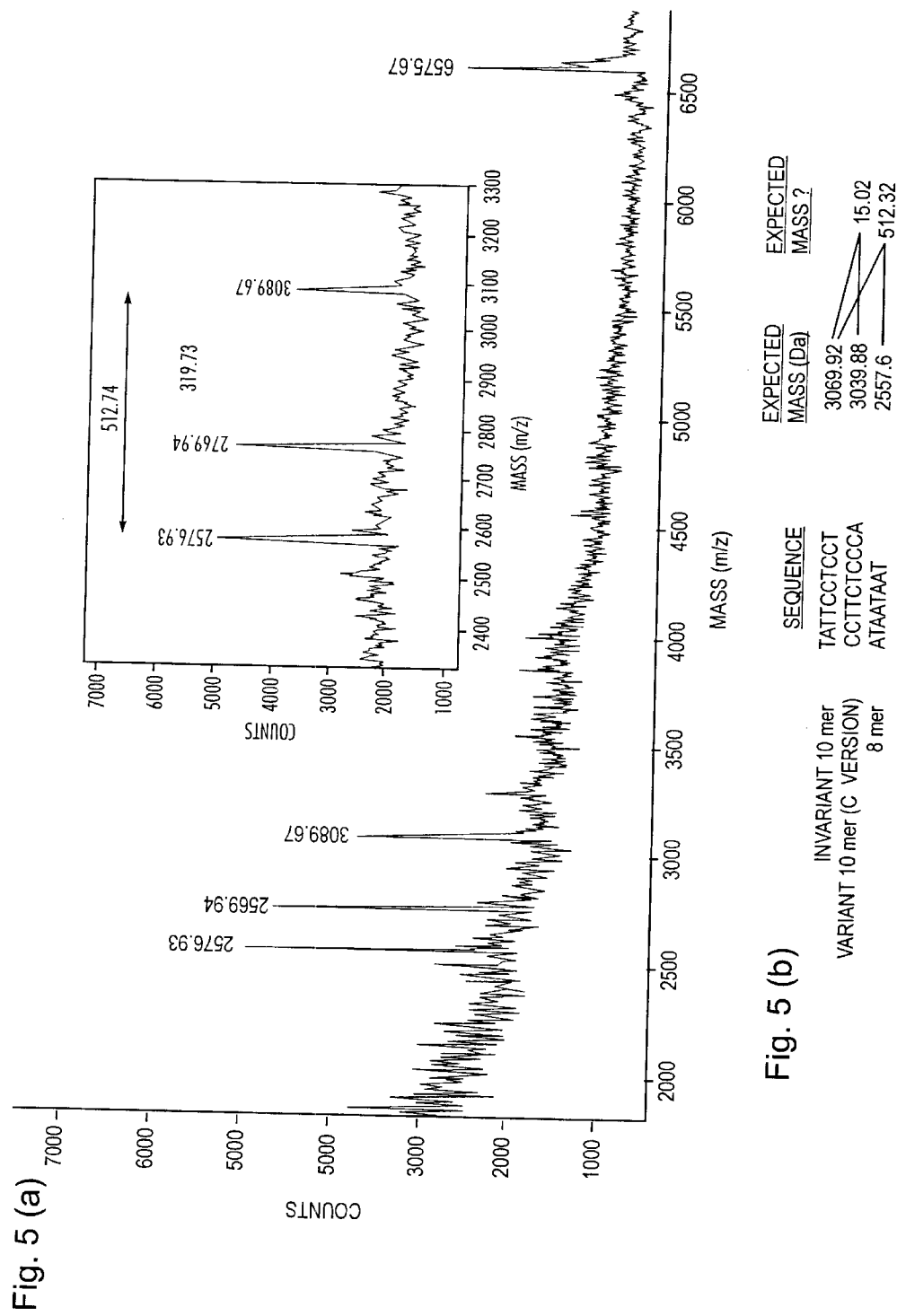

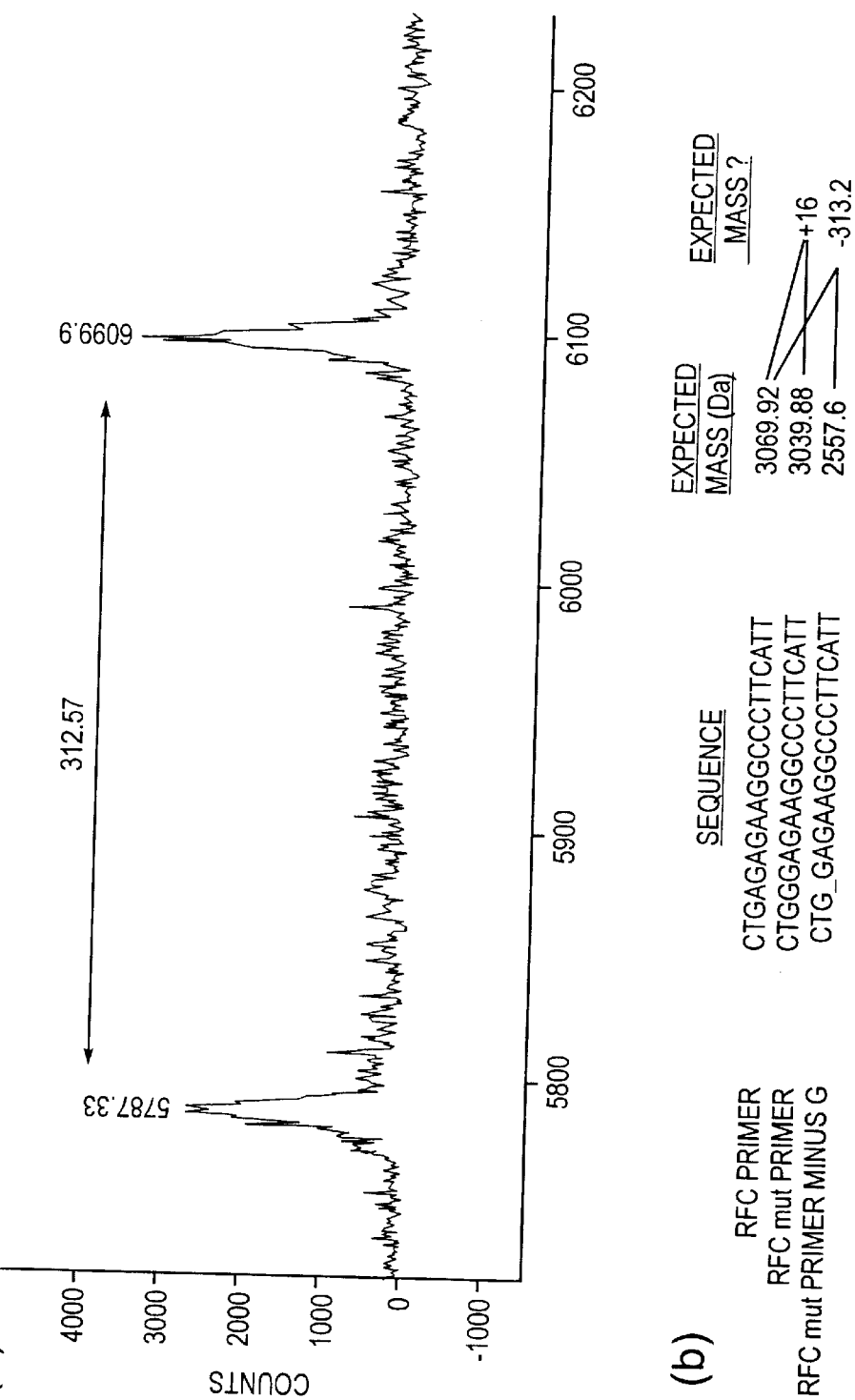

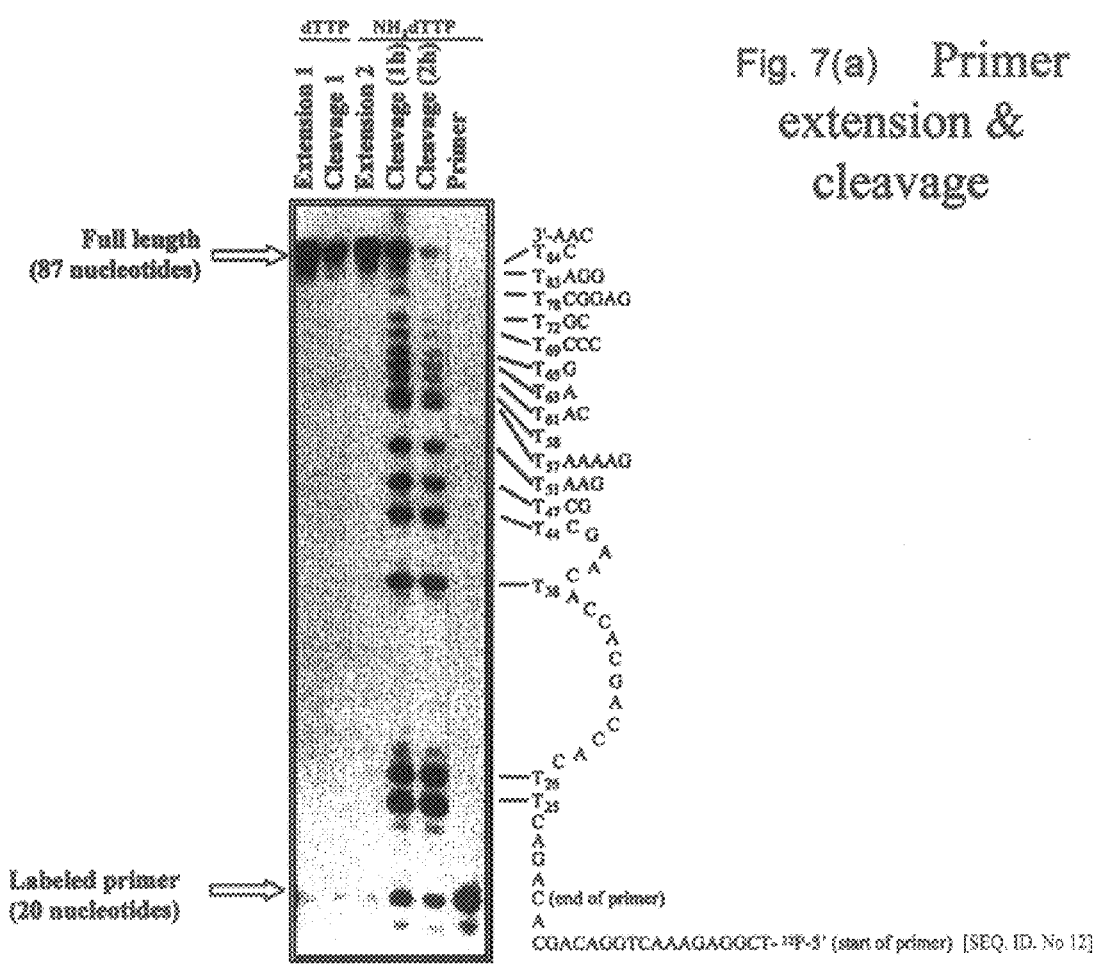

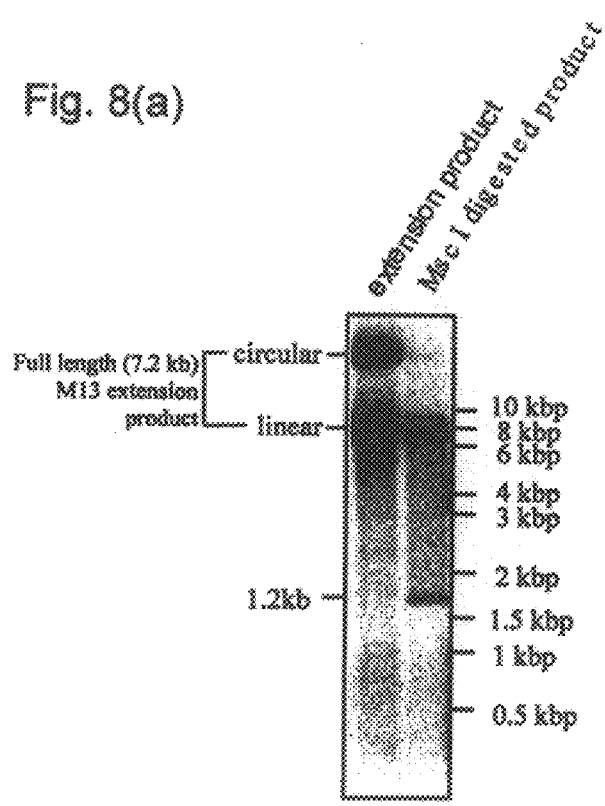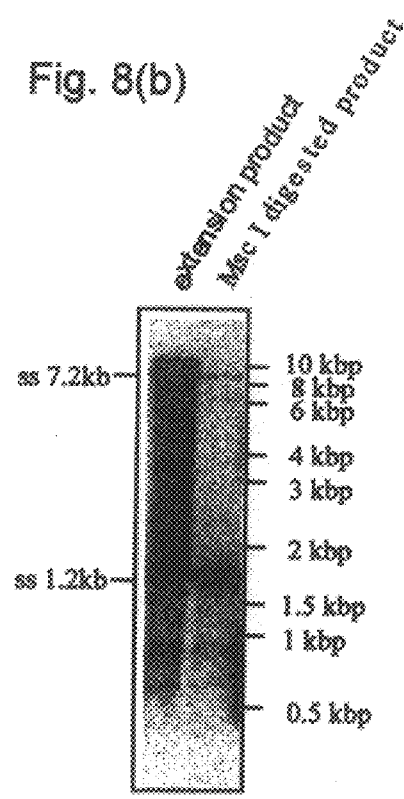

```
         αTTP                                2425
5'-TCGGAGAAACTGGACAGCACAGACTTCACCGG
         αGTP                         22     31 32
         37      43    46    50    5657  60 62
   CACCATCAAGCTGCTGAATGAAAATTCATAT G
             42    45    48    52              64
  64mt
   64    68   71        77      81 83
   TCCCTC GT GAGGCTGGATCTCAA-3'
         71 73 7576     7980
     7nt              16nt
```

12% acrylamide gel

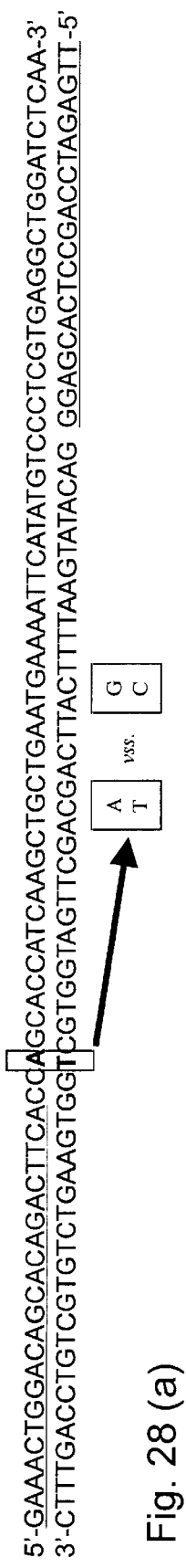
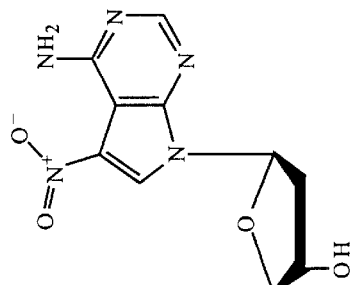
Structure of modified dA*TP
Fig. 28 (a)
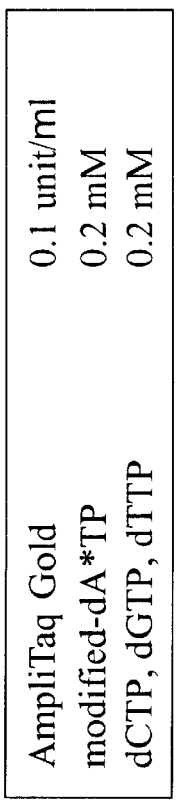
| AmpliTaq Gold | 0.1 unit/ml |
| --- | --- |
| modified-dA*TP | 0.2 mM |
| dCTP, dGTP, dTTP | 0.2 mM |
Fig. 28 (b)

Fig. 29 (a)

5'- GAAACTGGACAGCACAGACTTCA CCAGCA CCATCAAGCTGCTGAATGAAAATTCATATGTCCCTCGTGAGGCTGGATCTCAA -3'
3'- CTTTGACCTGTCGTGTCTGAAGTGGTCGT GGTAGTTCGACGACTTACTTTTAAGTATACAG GGAGCACTCCGACCTAGAGTT -5'

Fig. 29 (b)

| Sequence | Length | MW | Δ MW |
|---|---|---|---|
| 5'- GAAACTGGACAGCACAGACTTCACC<br>or | 25nt | 8057 | ⎫<br>⎬ 948 Da |
| 5'- GAAACTGGACAGCACAGACTTCACCGGC | 28nt | 9005 | ⎭ |
| GGGAGCACTCCGACCTAGAGTT- 5' | 22nt | 7189 | |
| CCTGTCGTGTCTG- 5' | 13nt | 4441 | |
| GTGGTCGTGGT- 5'<br>or | 11nt | 3927 | ⎫<br>⎬ 15 Da |
| GTGGCCGTGGT- 5' | 11nt | 3912 | ⎭ |
| 5'- TGTCCCTCGTG | 11nt | 3807 | |

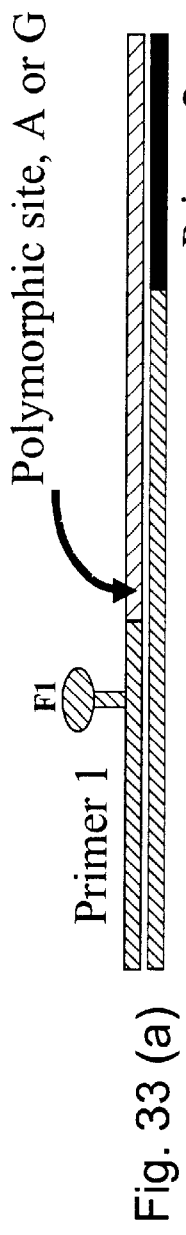
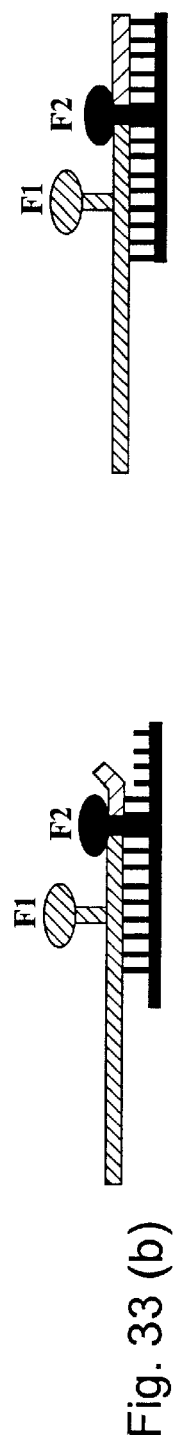
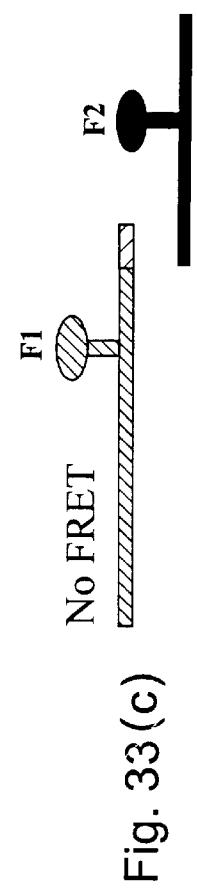
Fig. 33 (a)
Fig. 33 (b)
Fig. 33 (c)
Fig. 33 (d)

METHOD FOR ANALYZING POLYNUCLEOTIDES

RELATED APPLICATIONS

The present application is a divisional of Application Ser. No. 09/394,7744 and is related to and claims priority from provisional application serial No. 60/102,724, filed Oct. 1, 1998, and provisional application serial No. 60/149,533 filed Aug. 17,1999, both of which are incorporated by reference as if fully set forth herein.

FIELD OF THE INVENTION

The present invention relates generally to organic chemistry, analytical chemistry, biochemistry, molecular biology, genetics, diagnostics and medicine. In particular, it relates to a method for analyzing polynucleotides; i.e., for determining the complete nucleotide sequence of a polynucleotide, for detecting variance in the nucleotide sequence between related polynucleotides and for genotyping DNA.

BACKGROUND OF THE INVENTION

The following is offered as background information only and is not intended nor admitted to be prior art to the present invention.

DNA is the carrier of the genetic information of all living cells. An organism's genetic and physical characteristics, its genotype and phenotype, respectively, are controlled by precise nucleic acid sequences in the organism's DNA. The sum total of all of the sequence information present in an organism's DNA is termed the organism's "genome." The nucleic acid sequence of a DNA molecule consists of a linear polymer of four "nucleotides." The four nucleotides are tripartite molecules, each consisting of (1) one of the four heterocyclic bases, adenine (abbreviated "A"), cytosine ("C"), guanine ("G") and thymine ("T"); (2) the pentose sugar derivative 2-deoxyribose which is bonded by its 1-carbon atom to a ring nitrogen atom of the heterocyclic bases; and (3) a monophosphate monoester formed between a phosphoric acid molecule and the 5'-hydroxy group of the sugar moiety. The nucleotides polymerize by the formation of diesters between the 5'-phosphate of one nucleotide and the 3'-hydroxy group of another nucleotide to give a single strand of DNA. In nature, two of these single strands interact by hydrogen bonding between complementary nucleotides, A being complementary with T and C being complementary with G, to form "base-pairs" which results in the formation of the well-known DNA "double helix" of Watson and Crick. RNA is similar to DNA except that the base thymine is replaced with uracil ("U") and the pentose sugar is ribose itself rather than deoxyribose. In addition, RNA exists in nature predominantly as a single strand; i.e., two strands do not normally combine to form a double helix.

When referring to sequences of nucleotides in a polynucleotide, it is customary to use the abbreviation for the base; i.e., A, C, G, and T (or U) to represent the entire nucleotide containing that base. For example, a polynucleotide sequence denoted as "ACG" means that an adenine nucleotide is bonded through a phosphate ester linkage to a cytosine nucleotide which is bonded through another phosphate ester linkage to a guanine nucleotide. If the polynucleotide being described is DNA, then it is understood that "A" refers to an adenine nucleotide which contains a deoxyribose sugar. If there is any possibility of ambiguity, the "A" of a DNA molecule can be designated "deoxyA" or simply "dA." The same is true for C and G. Since T occurs only in DNA and not RNA, there can be no amibiguity so there is no need to refer to deoxyT or dT.

As a rough approximation, it can be said that the number of genes an organism has is proportional to the organism's phenotypic complexity; i.e., the number of genome products necessary to replicate the organism and allow it to function. The human genome, presently considered one of the most complex, consists of approximately 60,000–100,000 genes and about three billion three hundred million base pairs. Each of these genes codes for an RNA, most of which in turn encodes a particular protein which performs a specific biochemical or structural function. A variance, also known as a polymorphism or mutation, in the genetic code of any one of these genes may result in the production of a gene product, usually a protein or an RNA, with altered biochemical activity or with no activity at all. This can result from as little change as an addition, deletion or substitution (transition or transversion) of a single nucleotide in the DNA comprising a particular gene which is sometimes referred to as a "single nucleotide polymorphism" or "SNP. The consequence of such a mutation in the genetic code ranges from harmless to debilitating to fatal. There are presently over 6700 human disorders believed to have a genetic component. For example, hemophilia, Alzheimer's disease, Huntington's disease, Duchernne muscular dystrophy and cystic fibrosis are known to be related to variances in the nucleotide sequence of the DNA comprising certain genes. In addition, evidence is being amassed suggesting that changes in certain DNA sequences may predispose an individual to a variety of abnormal conditions such as obesity, diabetes, cardiovascular disease, central nervous system disorders, auto-immune disorders and cancer. Variations in DNA sequence of specific genes have also been implicated in the differences observed among patients in their responses to, for example, drugs, radiation therapy, nutritional status and other medical interventions. Thus, the ability to detect DNA sequence variances in an organism's genome is an important aspect of the inquiry into relationships between such variances and medical disorders and responses to medical interventions. Once an association has been established, the ability to detect the variance(s) in the genome of a patient can be an extremely useful diagnostic tool. It may even be possible, using early variance detection, to diagnose and potentially treat, or even prevent, a disorder before the disorder has physically manifested itself. Furthermore, variance detection can be a valuable research tool in that it may lead to the discovery of genetic bases for disorders the cause of which were hitherto unknown or thought to be other than genetic. Variance detection may also be useful for guiding the selection of an optimal therapy where there is a difference in response among patients to one or more proposed therapies.

While the benefits of being able to detect variances in the genetic code are clear, the practical aspects of doing so are daunting: it is estimated that sequence variations in human DNA occur with a frequency of about 1 in 100 nucleotides when 50 to 100 individuals are compared. Nickerson, D. A., *Nature Genetics,* 1998, 223-240. This translates to as many as thirty million variances in the human genome. Not all, in fact very few, of these variances have any measurable effect on the physical well-being of humans. Detecting these 30 million variances and then determining which of them are relevant to human health is clearly a formidable task.

In addition to variance detection, knowledge of the complete nucleotide sequence of an organism's genome would contribute immeasurably to the understanding of the organism's overall biology, i.e., it would lead to the identification of every gene product, its organization and arrangement in the organism's genome, the sequences required for controlling gene expression (i.e., production of each gene product) and replication. In fact, the quest for such knowledge and understanding is the raison d'etre for the Human Genome Project, an international effort aimed at sequencing the entire human genome. Once the sequence of a single genome is available, whatever the organism, it then becomes useful to obtain the partial or complete sequence of other organisms of that species, particularly those organisms within the species that exhibit different characteristics, in order to identify DNA sequence differences that correlate with the different characteristics. Such different characteristics may include, for microbial organisms, pathogenicity on the negative side or the ability to produce a particular polymer or to remediate pollution on the positive side. A difference in growth rate, nutrient content or pest resistance are potential differences which might be observed among plants. Even among human beings, a difference in disease susceptibility or response to a particular therapy might relate to a genetic, i.e., DNA sequence, variation. As a result of the enormous potential utility to be realized from DNA sequence information, in particular, identification of DNA sequence variances between individuals of the same species, the demand for rapid, inexpensive, automated DNA sequencing and variance detection procedures can be expected to increase dramatically in the future.

Once the DNA sequence of a DNA segment; e.g., a gene, a cDNA or, on a larger scale, a chromosome or an entire genome, has been determined, the existence of sequence variances in that DNA segment among members of the same species can be explored. Complete DNA sequencing is the definitive procedure for accomplishing this task. Thus, it is possible to determine the complete sequence of a copy of a DNA segment obtained from a different member of the species and simply compare that complete sequence to the one previously obtained. However, current DNA sequencing technology is costly, time consuming and, in order to achieve high levels of accuracy, must be highly redundant. Most major sequencing projects require a 5- to 10-fold coverage of each nucleotide to reach an acceptable error rate of 1 in 2,000 to 1 in 10,000 bases. In addition, DNA sequencing is an inefficient way to detect variances. For example, a variance between any two copies of a gene, for example when two chromosomes are being compared, may occur as infrequently as once in 1,000 or more bases. Thus, only a small portion of the sequence is of interest, that in which the variance exists. However, if full sequencing is employed, a tremendous number of nucleotides have to be sequenced to arrive at the desired information involving the aforesaid small portion. For example, consider a comparison of ten versions of a 3,000 nucleotide DNA sequence for the purpose of detecting, say, four variances among them. Even if only a 2-fold redundancy is employed (each strand of the double-stranded 3,000 nucleotide DNA segment from each individual is sequenced once), 60,000 nucleotides would have to be sequenced (10×3,000×2). In addition, it is more than likely that problem areas will be encountered in the sequencing requiring additional runs with new primers; thus, the project could engender the sequencing of as many as 100,000 nucleotides to determine four variances. A variety of procedures have been developed over the past 15 years to identify sequence differences and to provide some information about the location of the variant sites (Table 1). Using such a procedure, it would only be necessary to sequence four relatively short portions of the 3000 nt (nucleotide) sequence. Furthermore, only a few samples would have to be sequenced in each region because each variance produces a characteristic change (Table 1) so, if, for example, 22 of 50 samples exhibit a such a characteristic change with a variation detection procedure, then sequencing as few as four samples of the 22 would provide information on the other 18. The length of the segments that require sequencing could, depending on the variance detection procedure employed, be as short as 50–100 nt. Thus, the scale of the sequencing project could be reduced to: 4 (sites)×50 (nt per site)×2 (strands from each individual)×2 (individuals per site) or only about 800 nucleotides. This amounts to about 1% of the sequencing required in the absence of a preceding variance detection step.

As presently practiced, the technique for determining the full nucleotide sequence of a polynucleotide and that for detecting previously unknown variances or mutations in related polynucleotides ends up being the same; that is, even when the issue is the presence or absence of a single nucleotide variance between related polynucleotides, the complete sequences of at least a segment of the related polynucleotides is determined and then compared. The only difference is that a variance detection procedure such as those described in Table 1 may be employed as a first step to reduce the amount of complete sequencing necessary in the detection of unknown variances.

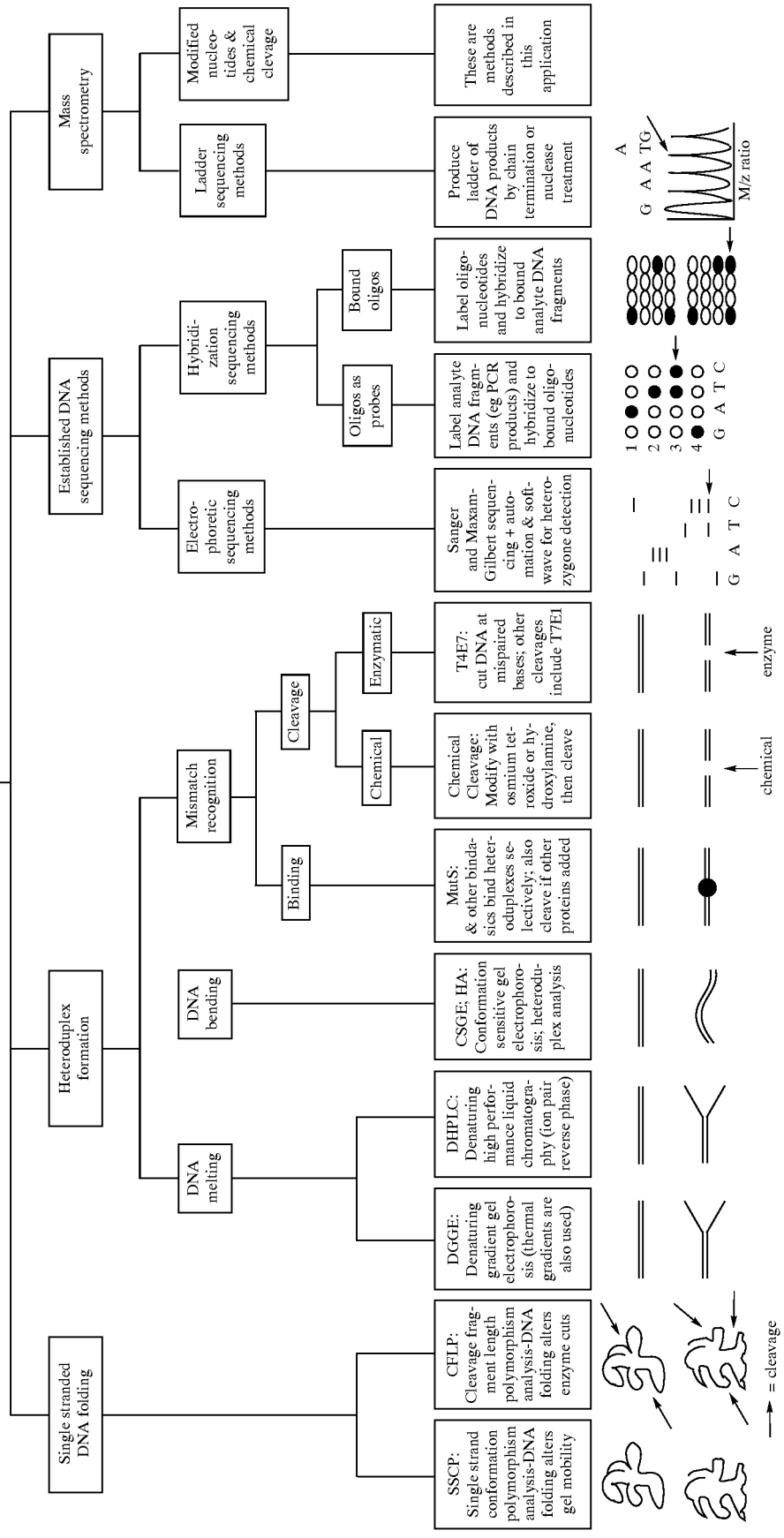

The two classical methods for carrying out complete nucleotide sequencing are the Maxam and Gilbert chemical procedure (*Proc. Nat. Acad. Sci. USA,* 74, 560–564 (1977)) and the Sanger, et al., chain-terminating procedure (*Proc. Nat. Acad. Sci. USA,* 74, 5463–5467 (1977)). The Maxam-Gilbert method of complete nucleotide sequencing involves end-labeling a DNA molecule with, for example, $^{32}$p, followed by one of two discrete reaction sequences involving two reactions each; i.e., four reactions overall. One of these reaction sequences involves the selective methylation of the purine nucleotides guanine (G) and adenine (A) in the polynucleotide being investigated which, in most instances, is an isolated naturally-occurring polynucleotide such as DNA. The N7 position of guanine methylates approximately five times as rapidly as the N3 position of adenine. When heated in the presence of aqueous base, the methylated bases are lost and a break in the polynucleotide chain occurs. The reaction is more effective with methylated guanine than with methylated adenine so, when the reaction product is subjected to electrophoresis on polyacrylamide gel plates, G cleavage ladders are predominant. Under acidic conditions, on the other hand, both methylated bases are removed effectively. Treatment by piperidine cleaves DNA at these abasic sites, generating sequencing ladders that correspond to A+G.

Thus, four chemical reactions followed by electrophoretic analysis of the resulting end-labeled ladder of cleavage products will reveal the exact nucleotide sequence of a DNA molecule. It is key to the Maxam-Gilbert sequencing method that only partial cleavage, on the order of 1–2% at each susceptible position, occurs. This is because electrophoresis separates fragments by size. To be meaningful, the fragments produced should represent, on the average, a single modification and cleavage per molecule. Then, when the fragments of all four reactions are aligned according to size, the exact sequence of the target DNA can be determined.

The Sanger method for determining complete nucleotide sequences consists of preparing four series of base-specifically chain-terminated terminated labeled DNA fragments by enzymatic polymerization. As in the Maxam-Gilbert procedure, four separate reactions can be performed. In the Sanger method each of the four reaction mixtures contains the same oligonucleotide template (either a single- or a double-stranded DNA), the four nucleotides, A, G, C and T (one of which may be labeled), a polymerase and a primer, the polymerase and primer being present to effect the polymerization of the nucleotides into a complement of the template oligonucleotide. To one of the four reaction mixtures is added an empirically determined amount of the dideoxy derivative of one of the nucleotides. A small amount of the dideoxy derivative of one of the remaining three nucleotides is added to a second reaction mixture, and so on, resulting in four reaction mixtures each containing a different dideoxy nucleotide. The dideoxy derivatives, by virtue of their missing 3'-hydroxyl groups, terminates the enzymatic polymerization reaction upon incorporation into the nascent oligonucleotide chain. Thus, in one reaction mixture, containing, say, dideoxyadenosine triphosphate (ddATP), a series of oligonucleotide fragments are produced all ending in ddA which when resolved by electrophoresis produce a series of bands corresponding to the size of the fragment created up to the point that the chain-terminating ddA became incorporated into the polymerization reaction. Corresponding ladders of fragments can be obtained from each of the other reaction mixtures in which the oligonucleotide fragments end in C, G and T. The four sets of fragments create a "sequence ladder," each rung of which represents the next nucleotide in the sequence of bases comprising the subject DNA. Thus, the exact nucleotide sequence of the DNA can simply be read off the electrophoresis gel plate after autoradiography or computer analysis of chromatograms in the case of an automated DNA sequencing instrument. As mentioned above, dye-labelled chain terminating dideoxynucleotides and modified polymerases that efficiently incorporate modified nucleotides are an improved method for chain-terminating sequencing.

Both the Maxam-Gilbert and Sanger procedures have their shortcomings. They are both time-consuming, labor-intensive (particularly with regard to the Maxam-Gilbert procedure which has not been automated like the Sanger procedure), expensive (e.g., the most optimized versions of the Sanger procedure require very expensive reagents) and require a fair degree of technical expertise to assure proper operation and reliable results. Furthermore, the Maxam-Gilbert procedure suffers from a lack of specificity of the modification chemistry, which can result in artifactual fragments resulting in false ladder readings from the gel plate. The Sanger method, on the other hand, is susceptible to template secondary structure formation, which can cause interference in the polymerization reaction. This causes terminations of the polymerization at sights of secondary struction (called "stops") which can result in erroneous fragments appearing in the sequence ladder rendering parts of the sequence unreadable, although this problem is ameliorated by the use of dye labelled dideoxy terminator. Furthermore, both sequencing methods are is susceptible to "compressions," another result of DNA secondary structure which can affect fragment mobility during electrophoresis thereby rendering the sequence ladder unreadable or subject to erroneous interpretation in the vicinity of the secondary structure. In addition, both methods are plagued by uneven intensity of the ladder and by non-specific background interference. These concerns are magnified when the issue is variance detection. In order to discern a single nucleotide variance, the procedure employed must be extremely accurate, a "mistake" in reading one nucleotide can result in a false positive; i.e., an indication of a variance where none exists. Neither the Maxam-Gilbert nor the Sanger procedures are capable of such accuracy in a single run. In fact, the frequency of errors in a "one pass" sequencing experiment is equal to or greater than 1%, which is on the order of ten times the frequency of actual DNA variances when any two versions of a sequence are compared. The situation can be ameliorated somewhat by performing multiple runs (usually in the context of a "shotgun" sequencing procedure) for each polynucleotide being compared, but this simply increases cost in terms of equipment, reagents, manpower and time. The high cost of sequencing becomes even less acceptable when one considers that it is often not necessary when looking for nucleotide sequence variances among related polynucleotides to determine the complete sequence of the subject polynucleotides or even the exact nature of the variance (although, as will be seen, in some instances even this is discernable using the method of this invention); detection of the variance alone may be sufficient.

While not avoiding all of the problems associated with the Maxam-Gilbert and Sanger procedures, several techniques have been devised to at least make one or the other of the procedures more efficient. One such approach has been to develop ways to circumvent slab gel electrophoresis, one of the most time-consuming steps in the procedures. For instance, in U.S. Pat. Nos. 5,003,059 and 5,174,962, the Sanger method is employed; however, the dideoxy derivative of each of the nucleotides used to terminate the polymerization reaction is uniquely tagged with an isotope of sulfur, $^{32}S$, $^{33}S$, $^{34}S$ or $^{36}S$. Once the polymerization reactions are complete, the chain terminated sequences are separated by capillary zone electrophoresis, which, compared to slab gel electrophoresis, increases resolution, reduces run time and allows analysis of very small samples. The separated chain terminated sequences are then combusted to convert the incorporated isotopic sulfur to isotopic sulfur dioxides ($^{32}SO_2$, $^{33}SO_2$, $^{34}SO_2$ and $^{36}SO_2$). The isotopic sulfur dioxides are then subjected to mass spectrometry. Since each isotope of sulfur is uniquely related to one of the four sets of base-specifically chain terminated fragments, the nucleotide sequence of the subject DNA can be determined from the mass spectrogram.

Another method, disclosed in U.S. Pat. No. 5,580,733, also incorporates the Sanger technique but eliminates gel electrophoresis altogether. The method involves taking each of the four populations of base-specific chain-terminated oligonucleotides from the Sanger reactions and forming a mixture with a visible laser light absorbing matrix such as 3-hydroxypicolinic acid. The mixtures are then illuminated with visible laser light and vaporized, which occurs without further fragmentation of the chain-terminated nucleic acid fragments. The vaporized molecules, which are charged, are then accelerated in an electric filed and the mass to charge (m/z) ratio of the ionized molecules determined by time-of-flight mass spectrometry (TOF-MS). The molecular weights are then aligned to determine the exact sequence of the subject DNA. By measuring the mass difference between successive fragments in each of the mixtures, the lengths of fragments terminating in A, G, C or T can then be inferred. A significant limitation of current MS instruments is that polynucleotide fragments greater than 100 nucleotides in length (with many instruments, 50 nucleotides) cannot be efficiently detected in routine use, especially if the fragments are part of a complex mixture. This severe limitation on the size of fragments that can be analyzed has limited the development of polynucleotide analysis by MS. Thus, there is a need for a procedure that adapts large polynucleotides, such as DNA, to the capabilities of current MS instruments. The present invention provides such a procedure.

A further approach to nucleotide sequencing is disclosed in U.S. Pat. No. 5,547,835. Again, the starting point is the Sanger sequencing strategy. The four base specific chain-terminated series of fragments are "conditioned" by, for example, purification, cation exchange and/or mass modification. The molecular weights of the conditioned fragments are then determined by mass spectrometry and the sequence of the starting nucleic acid is determined by aligning the base-specifically terminated fragments according to molecular weight.

Each of the above methods involves complete Sanger sequencing of a polynucleotide prior to analysis by mass spectrometry. To detect genetic mutations; i.e., variances, the complete sequence can be compared to a known nucleotide sequence. Where the sequence is not known, comparison with the nucleotide sequence of the same DNA isolated from another of the same organisms which does not exhibit the abnormalities seen in the subject organism will likewise reveal mutations. This approach, of course, requires running the Sanger procedure twice; i.e., eight separate reactions. In addition, if a potential variance is detected, the entire procedure would in most instances be run again, sequencing the opposite strand using a different primer to make sure that a false positive had not been obtained. When the specific nucleotide variance or mutation related to a particular disorder is known, there are a wide variety of known methods for detecting a variance without complete sequencing. For instance, U. S. Pat. No. 5,605,798 describes such a method. The method involves obtaining a nucleic acid molecule containing the target sequence of interest from a biological sample, optionally amplifying the target sequence, and then hybridizing the target sequence to a detector oligonucleotide which is specifically designed to be complementary to the target sequence. Either the detector oligonucleotide or the target sequence is "conditioned" by mass modification prior to hybridization. Unhybridized detector oligonucleotide is removed and the remaining reaction product is volatilized and ionized. Detection of the detector oligonucleotide by mass spectrometry indicates the presence of the target nucleic acid sequence in the biological sample and thus confirms the diagnosis of the variance-related disorder.

Variance detection procedures can be divided into two general categories although there is a considerable degree of overlap. One category, the variance discovery procedures, is useful for examining DNA segments for the existence, location and characteristics of new variances. To accomplish this, variance discovery procedures may be combined with DNA sequencing.

The second group of procedures, variance typing (sometimes referred to as genotyping) procedures, are useful for repetitive determination of one or more nucleotides at a particular site in a DNA segment when the location of a variance or variances has previously been identified and characterized. In this type of analysis, it is often possible to design a very sensitive test of the status of a particular nucleotide or nucleotides. This technique, of course, is not well suited to the discovery of new variances.

As noted above, Table 1 is a list of a number of existing techniques for nucleotide examination. The majority of these are used primarily in new variance determination. There are a variety of other methods, not shown, for gene typing. Like the Maxam-Gilbert and Sanger sequencing procedures, these techniques are generally time-consuming, tedious and require a relatively high skill level to achieve the maximum degree of accuracy possible from each procedure. Even then, some of the techniques listed are, even at their best, inherently less accurate than would be desirable.

The methods of Table 1, though primarily devised for variance discovery, can also be used when a variant nucleotide has already been identified and the goal is to determine its status in one or more unknown DNA samples (variance typing or genotyping). Some of the methods that have been developed specifically for genotyping include (1) primer extension methods in which dideoxynucleotide termination of the primer extension reaction occurs at the variant site generating extension products of different length or with different terminal nucleotides, which can then be determined by electrophoresis, mass spectrometry or fluorescence in a plate reader; (2) hybridization methods in which oligonucleotides corresponding to the two possible sequences at a variant site are attached to a solid surface and hybridized with probes from the unknown sample; (3) restriction fragment length polymorphism analysis, wherein a restriction endonuclease recognition site includes the polymorphic nucleotide in such a manner that the site is cleavable with one variant nucleotide but not another; (4) methods such as "TaqMan" involving differential hybridization and consequent differential 5' endonuclease digestion of labelled oligonucleotide probes in which there is fluorescent resonance energy transfer (FRET) between two fluors on the probe that is abrogated by nuclease digestion of the probe; (5) other FRET based methods involving labelled oligonucleotide probes called molecular beacons which exploit allele specific hybridization; (6) ligation dependent methods that require enzymatic ligation of two oligonucleotides across a polymorphic site that is perfectly matched to only one of them; and, (7) allele specific oligonucleotide priming in a polymerase chain reaction (PCR). U. Landegren, et al., 1998, Reading Bits of Genetic Information: Methods for Single-nucleotide Polymorphism Analysis, *Genome Research* 8(8):769–76.

When complete sequencing of large templates such as the entire genome of a virus, a bacterium or a eukaryote (e.g., higher organisms including man) or the repeated sequencing of a large DNA region or regions from different strains or individuals of a given species for purposes of comparison is desired, it becomes necessary to implement strategies for making libraries of templates for DNA sequencing. This is because conventional chain terminating sequencing (i.e., the Sanger procedure) is limited by the resolving power of the analytical procedure used to create the nucleotide ladder of the subject polynucleotide. For gels, this resolving power is approximately 500–800 nt at a time. For mass spectrometry, the limitation is the length of a polynucleotide which can be efficiently vaporized prior to detection in the instrument. Although larger fragments have been analyzed by highly specialized procedures and instrumentation, presently this limit is approximately 50–60 nt. However, in large scale sequencing projects such as the Human Genome Project, "markers" (DNA segments of known chromosomal location whose presence can be relatively easily ascertained by the polymerase chain reaction (PCR) technique and which, therefore, can be used as a point of reference for mapping new areas of the genome) are currently about 100 kilobases (Kb) apart. The markers at 100 Kb intervals must be connected by efficient sequencing strategies. If the analytical method used is gel electrophoresis, then to sequence a 100 kb stretch of DNA would require hundreds of sequencing reactions. A fundamental question which must be addressed is how to divide up the 100 kB segment (or whatever size is being dealt with) to optimize the process; i.e., to minimize the number of sequencing reactions and sequence assembly work necessary to generate a complete sequence with the desired level of accuracy. A key issue in this regard is how to initially fragment the DNA in such a manner that the fragments, once sequenced, can be correctly reassembled to recreate the full length target DNA. Presently, two general approaches provide both sequence-ready fragments and the information necessary to recombine the sequences into the full-length target DNA: "shotgun sequencing" (see, e.g., Venter, J. C., et al., *Science,* 1998, 280:1540–1542; Weber, J. L. and Myers, E. W., *Genome Research,* 1997, 7:401–409; Andersson, B. et al., *DNA Sequence,* 1997, 7:63–70) and "directed DNA sequencing" (see, e.g., Voss, H., et al., *Biotechniques,* 1993,15:714–721; Kaczorowski, T., et al., *Anal. Biochem.,* 1994,221:127–135; Lodhi, M. A., et al., Genome Research, 1996, 6:10–18).

Shotgun sequencing involves the creation of a large library of random fragments or "clones" in a sequence-ready vector such as a plasmid or phagemid. To arrive at a library in which all portions of the original sequence are relatively equally represented, DNA which is to be shotgun sequenced is often fragmented by physical procedures such as sonication which has been shown to produce nearly random fragmentation. Clones are then selected at random from the shotgun library for sequencing. The complete sequence of the DNA is then assembled by identifying overlapping sequences in the short (approx. 500 nt) shotgun sequences. In order to assure that the entire target region of the DNA is represented among the randomly selected clones and to reduce the frequency of errors (incorrectly assigned overlaps), a high degree of sequencing redundancy is necessary; for example, 7 to 10-fold. Even with such high redundancy, additional sequencing is often required to fill gaps in the coverage. Even then, the presence of repeat sequences such as Alu (a 300 base-pair sequence which occurs in 500,000–1,000,000 copies per haploid genome) and LINES ("Long INterspersed DNA sequence Elements" which can be 7,000 bases long and may be present in as many as 100,000 copies per haploid genome), either of which may occur in different locations of multiple clones, can render DNA sequence re-assembly problematic. For instance, different members of these sequence families can be over 90% identical which can sometimes make it very difficult to determine sequence relationships on opposite sides of such repeats. FIGS. 14A–C illustrates the difficulties of the shotgun sequencing approach in a hypothetical 10 kb sequence modeled after the sequence reported in Martin-Gallardo, et al., *Nature Genetics,* (1992) 1:34–39.

Directed DNA sequencing, the second general approach, also entails making a library of clones, often with large inserts (e.g., cosmid, P1, PAC or BAC libraries). In this procedure, the location of the clones in the region to be sequenced is then mapped to obtain a set of clones that constitutes a minimum-overlap tiling path spanning the region to be sequenced. Clones from this minimal set are then sequenced by procedures such as "primer walking" (see, e.g., Voss, supra). In this procedure, the end of one sequence is used to select a new sequencing primer with which to begin the next sequencing reaction, the end of the second sequence is used to select the next primer and so on. The assembly of a complete DNA is easier by direct sequencing and less sequencing redundancy is required since both the order of clones and the completeness of coverage is known from the clone map. On the other hand, assembling the map itself requires significant effort. Furthermore, the speed with which new sequencing primers can be synthesized and the cost of doing so is often a limiting factor with regard to primer walking. While a variety of methods for simplifying new primer construction have aided in this process (see, e.g. Kaczorowski, et al. and Lodhi, et al. , supra), directed DNA sequencing remains a valuable but often expensive and slow procedure.

Most large-scale sequencing projects employ aspects of both shotgun sequencing and directed sequencing. For example, a detailed map might be made of a large insert library (e.g., BACs) to identify a minimal set of clones which gives complete coverage of the target region but then sequencing of each of the large inserts is carried out by a shotgun approach; e.g., fragmenting the large insert and re-cloning the fragments in a more optimal sequencing vector (see, e.g., Chen, C. N., *Nucleic Acids Research,* 1996, 24:4034–4041). The shotgun and directed procedures are also used in a complementary manner in which specific regions not covered by an initial shotgun experiment are subsequently determined by directed sequencing.

Thus, there are significant limitations to both the shotgun and directed sequencing approaches to complete sequencing of large molecules such as that required in genomic DNA sequencing projects. However, both procedures would benefit if the usable read length of contiguous DNA was expanded from the current 500–800 nt which can be effectively sequenced by the Sanger method. For example, directed sequencing could be significantly improved by reducing the need for high-resolution maps which could be achieved by longer read lengths which in turn would permit greater distances between landmarks.

A major limitation of current sequencing procedures is the high error rate (Kristensen, T., et al, *DNA Sequencing,* 2:243–346, 1992; Kurshid, F. and Beck, S., *Analytical Biochemistry,* 208:138–143, 1993; Fichant, G. A. and Quentin, Y., *Nucleic Acid Research,* 23:2900–2908, 1995). It is well-known that many of the errors associated with the Maxam-Gilbert and Sanger procedures are systematic; i.e., the errors are not random; rather, they occur repeatedly. To avoid this, two mechanistically different sequencing methods may be used so that the systematic errors in one may be detected and thus corrected by the second and visa versa. Since a significant fraction of the cost of current sequencing methods is associated with the need for high redundancy to reduce sequencing errors, the use of two procedures can reduce the overall cost of obtaining highly accurate DNA sequence.

The production and/or chemical cleavage of polynucleotides composed of ribonucleotides and deoxyribonucleotides has been previously described. In particular, mutant polymerases that incorporate both ribonucleotides and deoxyribonucleotides into a polynucleotide have been described; production of mixed ribo- and deoxyribo-containing polynucleotides by polymerization has been described; and generation of sequence ladders from such mixed polynucleotides, exploiting the well known lability of the ribo sugar to chemical base, has been described.

The use of such procedures, however, have been limited to: (i) polynucleotides where one ribonucleotide and three deoxyribonucleotides are incorporated; (ii) cleavage at ribonucleotides is effected using chemical base, (iii) only partial cleavage of the ribonucleotide containing polynucleotides is pursued, and (iv) the utility of the procedure is confined to production of sequence ladders, which are resolved electrophoretically.

In addition, the chemical synthesis of polynucleotide primers containing a single ribonucleotide, which at a subsequent step is substantially completely cleaved by chemical base, has been reported. The size of a primer extension product is then determined by mass spectrometry or other methods.

SUMMARY OF THE INVENTION

It is clear from the foregoing that there exists a need for a simple, low cost, rapid, yet sensitive and accurate, method for analyzing polynucleotides such as, without limitation, DNA, to determine both complete nucleotide sequences and the presence of variance(s). Further, there is a need for methods to enable assembly of very long DNA sequences across repeat dense regions. The methods of the present invention fulfill each of these needs. In general, the present invention supplies new methods for genotyping, DNA sequencing and variance detection based on specific cleavage of DNA and other polynucleotides modified by enzymatic incorporation of chemically modified nucleotides.

Thus, in one aspect, this invention relates to a method for cleaving a polynucleotide, comprising:
  a. replacing a natural nucleotide at substantially each point of occurrence in a polynucleotide with a modified nucleotide to form a modified polynucleotide wherein said modified nucleotide is not a ribonucleotide;
  b. contacting said modified polynucleotide with a reagent or reagents which cleave(s) the modified polynucleotide at substantially each said point of occurrence.

In another aspect, this invention relates to the above-described method for use in detection of variance in nucleotide sequence in related polynucleotides by the additional steps of:

c. determining the masses of said fragments obtained from step b; and,
  d. comparing the masses of said fragments with the masses of fragments expected from cleavage of a related polynucleotide of known sequence, or
  e. repeating steps a–c with one or more related polynucleotides of unknown sequence and comparing the masses of said fragments of said polynucleotide with the masses of fragments obtained from the related polynucleotides.

A further aspect of this invention is the use of the first method above whereby the nucleotide sequence of a polynucleotide is determined, by the additional steps of:
  c. determining the masses of said fragments obtained from step 1b;
  d. repeating steps 1a, 1b and 1c, each time replacing a different natural nucleotide in said polynucleotide with a modified nucleotide until each natural nucleotide in said polynucleotide has been replaced with a modified polynucleotide, each modified polynucleotide has been cleaved and the masses of the cleavage fragments have been determined; and,
  e. constructing said nucleotide sequence of said polynucleotide from said masses of said first fragments.

Another aspect of this invention is the use of the first mentioned method above whereby a nucleotide known to contain a polymorpism or mutation is genotyped, by:
  using as the natural nucleotide to be replaced, a nucleotide known to be involved in said polymorphism or mutation;
  replacing the natural nucleotide by amplifying the portion of the polynucleotide using a modified nucleotide to form a modified polynucleotide;
  cleaving the modified polynucleotide into fragments at each point of occurrence of the modified nucleotide;
  analyzing the fragments to determine genotype.

In the method immediately above, analysis of the fragments by electrophoresis, mass spectrometry or FRET detection, is an aspect of this invention.

Another aspect of this invention is a method for cleaving a polynucleotide, comprising:
  a. replacing a first natural nucleotide at substantially each point of occurrence in a polynucleotide with a modified nucleotide to form a once modified polynucleotide;
  b. replacing a second natural nucleotide at substantially each point of occurrence in the once modified nucleotide with a second modified nucleotide to form a twice modified nucleotide; and,
  c. contacting said twice modified polynucleotide with a reagent or reagents which cleave the twice modified polynucleotide at each point in said twice modified polynucleotide where said first modified nucleotide is followed immediately by, and linked by a phosphodiester or modified phosphodiester linkage to, said second modified nucleotide.

An aspect of this invention is, in the method immediately above, variance in nucleotide sequence of related polynucleotides is detected by the additional steps of:
  d. determining the masses of said fragments obtained from step c;
  e. comparing the masses of said fragments with the masses of fragments expected from cleavage of a related polynucleotide of known sequence, or
  f. repeating steps a–d with one or more related polynucleotides of unknown sequence and comparing the masses of said fragments with masses of fragments obtained from cleavage of the related polynucleotides.

An aspect of this invention is a method for detecting variance in nucleotide sequence in related polynucleotides, comprising:

a. replacing three of four natural nucleotides at substantially each point of occurrence in a polynucleotide with three stabilizing modified nucleotides to form a modified polynucleotide having one remaining natural nucleotide;

b. cleaving said modified polynucleotide into fragments at substantially each point of occurrence of said one remaining natural nucleotide;

c. determining the masses of said fragments; and, d. comparing the masses of said fragments with the masses of fragments expected from cleavage of a related polynucleotide of known sequence, or e. repeating steps a–c with one or more related polynucleotides of unknown sequence and comparing the masses of said fragments with masses obtained from cleavage of the related polynucleotides.

Another aspect of this invention is, in the method immediately above, replacing the remaining natural nucleotide with a destabilizing modified nucleotide.

A further aspect of this invention is a method for detecting variance in nucleotide sequence in related polynucleotides, comprising:

a. replacing two or more natural nucleotides at substantially each point of occurrence in a polynucleotide with two or more modified nucleotides wherein each said modified nucleotide has a different cleaving characteristic from each other of said modified nucleotides, to form a modified polynucleotide;

b. cleaving said modified polynucleotide into first fragments at substantially each point of occurrence of a first of said two or more modified nucleotides;

c. cleaving said first fragments into second fragments at each point of occurrence of a second of said two or more modified nucleotides in said first fragments;

d. determining the masses of said first fragments and said second fragments; and, e. comparing the masses of said first fragments and said second fragments with the masses of first fragments and second fragments expected from the cleavage of a related polynucleotide of known sequence, or f. repeating steps a–d with one or more related polynucleotides of unknown sequence and comparing the masses of said first and second fragments with masses obtained from the cleavage of the related polynucleotides.

It is an aspect of this invention that, in the above method, the steps are repeated using a modified nucleotide obtained by replacing different pairs of natural nucleotides with modified nucleotides; that is, given four natural nucleotides, 1, 2, 3, and 4, replacing 1 and 3 in one experiment, 2 and 4 in another, 1 and 4 in yet another, 2 and 3 in another or 3 and 4 in a final experiment with modified nucleotides.

It is an aspect of this invention that the modified polynucleotides obtained by the methods just above can be cleaved in a mass spectrometer, in particular, a tandem mass spectrometer.

A further aspect of this invention is a method for determining nucleotide sequence in a polynucleotide, comprising:

a. replacing a natural nucleotide at a percentage of points of occurrence in a polynucleotide with a modified nucleotide to form a modified polynucleotide wherein said modified polynucleotide is not a ribonucleotide;

b. cleaving said modified polynucleotide into fragments at substantially each point of occurrence of said modified nucleotide;

c. repeating steps a and b, each time replacing a different natural nucleotide in said polynucleotide with a modified nucleotide; and, d. determining the masses of said fragments obtained from each cleavage; and, e. constructing said sequence of said polynucleotide from said masses, or f. analyzing a sequence ladder obtained from the fragments in step c.

An aspect of this invention is a method for determining nucleotide sequence in a polynucleotide, comprising:

a. replacing a natural nucleotide at a first percentage of points of occurrence in a polynucleotide with a modified nucleotide to form a modified polynucleotide wherein said modified nucleotide is not a ribonucleotide;

b. cleaving said modified polynucleotide into fragments at a second percentage of said points of occurrence of said modified nucleotide such that the combination of said first percentage and said second percentage results in partial cleavage of said modified polynucleotide;

c. repeating steps a and b, each time replacing a different natural nucleotide in said polynucleotide with a modified nucleotide;

d. determining the masses of said fragments obtained from each cleavage reaction; and, e. constructing said sequence of said polynucleotide from said masses or, f. analyzing a sequence ladder obtained from said fragments from steps a and b.

An aspect of this invention is a method for determining nucleotide sequence in a polynucleotide, comprising:

a. replacing two or more natural nucleotides at substantially each point of occurrence in a polynucleotide with two or more modified nucleotides to form a modified polynucleotide;

b. separating said modified polynucleotide into two or more aliquots, the number of said aliquots being the same as the number of natural nucleotides replaced in step a; and, c. cleaving said modified polynucleotide in each said aliquot into fragments at substantially each point of occurrence of a different one of said modified nucleotides such that each of said aliquots contains fragments from cleavage at a different modified nucleotide than each other said aliquot;

d. determining masses of said fragments; and, e. constructing said nucleotide sequence from said masses; or, f. cleaving said modified polynucleotide in each said aliquot into fragments at a percentage of points of occurrence of a different modified nucleotide such that each of said aliquots contains fragments from cleavage at a different modified nucleotide than each other said aliquot; and, g. analyzing a sequence ladder obtained from said fragments in step f.

Furthermore, an aspect of this invention is a method for determining nucleotide sequence in a polynucleotide, comprising:

a. replacing a first natural nucleotide at a percentage of points of incorporation in a polynucleotide with a first modified nucleotide to form a first partially modified polynucleotide wherein said first modified nucleotide is not an ribonucleotide;

b. cleaving said first partially modified nucleotide into fragments using said cleaving procedure of known cleavage efficiency to form a first set of nucleotide specific cleavage products;

c. repeating steps a and b replacing a second, a third and a fourth natural nucleotide with a second, third and fourth modified nucleotide to form a second, third and fourth partially modified polynucleotide which, upon cleavage, afford a second, third and fourth set of nucleotide specific cleavage products;

d. performing gel electrophoresis on said first, second, third and fourth set of nucleotide specific cleavage products to form a sequence ladder; and, e. reading said sequence of said polynucleotide from said sequence ladder.

As aspect of this invention is a method for cleaving a polynucleotide during polymerization, comprising: mixing together four different nucleotides, one or two of which are modified nucleotides; and, two or more polymerases, at least one of which produces or enhances cleavage at points where said modified nucleotide is being incorporated or, if two modified nucleotides are used, at points wherein said adjacent pair of modified nucleotides are being incorporated and are a proper spatial relationship; provided that, when only one modified nucleotide is used, it does not contain ribose as its only modifying characteristic.

In the method just above, when two modified nucleotides are used, it is an aspect of this invention that one of them is a ribonucleotide and one of them is a 5'-amino-2',5'-dideoxynucleotide.

Furthermore, in the method just above using the specific modified nucleotides, it is an aspect of this invention to use two polymerases, one being Klenow (exo-) polymerase and one being mutant E710A Klenow (exo-) polymerase.

In any of the above methods, it is an aspect of this invention that all natural nucleotides not being replaced with modified nucleotides can be replaced with mass-modified nucleotides.

It is also an aspect of all methods of this invention that the polynucleotide being modified is selected from the group consisting of DNA and RNA.

Another aspect of all of the above methods is detection of said masses of said fragments by mass spectrometry. Presently preferred types of mass spectrometry are electrospray ionization mass spectrometry and matrix assisted desorption/ionization mass spectrometry (MALDI).

In the above methods requiring the generation of a sequence ladder, such generation can be accomplished using gel electrophoresis.

Furthermore, in the above method relating to determining a polynucleotide sequence by partially replacing a natural nucleotide with a modified nucleotide, cleaving said first, second, third and fourth partially modified polynucleotide obtained in step "a" with one or more restriction enzymes, labeling the ends of the restriction fragments obtained, and purifying the restriction fragments, prior to performing step "b" is another aspect of this invention.

An aspect of this invention is a method for cleaving a polynucleotide such that substantially all fragments obtained from the cleavage carry a label, comprising:

a. replacing a natural nucleotide partially or at substantially each point of occurrence in a polynucleotide with a modified nucleotide to form a modified polynucleotide;

b. contacting, in the presence of a phosphine covalently bonded to a label, said modified polynucleotide with a reagent or reagents which cleave(s) the modified polynucleotide partially or at substantially each said point of occurrence.

In a presently preferred embodiment of this invention, the phosphine in the above method is tris(carboxyethyl) phosphine (TCEP).

Also in the method just above, the label is a fluorescent tag or a radioactive tag in another aspect of this invention.

It is an aspect of this invention that the above methods can be used for diagnosing a genetically-related disease. The methods can also be used as a means for obtaining a prognosis of a genetically related disease or disorder. They can also be used to determine if a particular patient is eligible for medical treatment by procedures applicable to genetically related diseases or disorders.

An aspect of this invention is a method for detecting a variance in nucleotide sequence in a polynucleotide, for sequencing a polynucleotide or for genotyping a polynucleotide known to contain a polymorphism or mutation comprising:

a. replacing one or more natural nucleotides in said polynucleotide with one or more modified nucleotides, one or more of which comprises a modified base;

b. contacting said modified polynucleotide with a reagent or reagents which cleave the modified polynucleotide into fragments at site(s) of incorporation of said modified nucleotide;

c. analyzing said fragments to detect said variance, to construct said sequence or to genotype said polynucleotide.

The modified base in the above method can be adenine in another aspect of this invention. It can also be 7-deaza-7-nitroadenine.

A polynucleotide modified as above can be cleaved into fragments by contact with chemical base in another aspect of this invention.

In the above method, cleaving said modified polynucleotide into fragments comprises contacting said modified polynucleotide with a phosphine in yet another aspect of this invention.

Using TCEP as the phosphine in the above method is another aspect of this invention.

The modified base in the above method can also be modified cytosine such as, without limitation, azacytosine or cytosine substituted at the 5-position with an electron withdrawing group wherein the electron withdrawing group is, also without limitation, nitro or halo.

Once again, polynucleotides modified as noted just above can be cleaved with chemical base.

Inclusion of TCEP in the cleaving reaction immediately above is another aspect of this invention.

The modified base in the above method can also be modified guanine such as, without limitation, 7-methylguanine and cleavage can be carried out with chemical base.

The modified guanine is $N^2$-allylguanine in a further aspect of this invention. Cleaving this modified guanine by contacting said modified polynucleotide with an electrophile, such as, without limitation, iodine, is another aspect of this invention.

In another aspect of this invention, the modified base in the above method can also be modified thymine and modified uracil. A presently preferred embodiment of this invention is the use of 5-hydroxyuracil in place of either thymine or uracil. When 5-hydroxyuracil is used, cleavage is accomplished by:

a. contacting said polynucleotide with a chemical oxidant; and, then b. contacting said polynucleotide with chemical base.

Another aspect of this invention is a method for detecting a variance in nucleotide sequence in a polynucleotide, sequencing a polynucleotide or genotyping a polynucleotide comprising replacing one or more natural nucleotides in said polynucleotide with one or more modified nucleotides, one or more of which comprises a modified sugar with the proviso that, when only one nucleotide is being replaced, said modified sugar is not ribose.

The modified sugar is a 2-ketosugar in a further aspect of this invention. The keto sugar can be cleaved with chemical base.

The modified sugar can also be arabinose which is also susceptible to chemical base.

The modified sugar can also be a sugar substituted with a 4-hydroxymethyl group which, likewise, renders a polynucleotide susceptible to cleavage with chemical base.

On the other hand, the modified sugar can be hydroxycyclopentane, in particular 1-hydroxy- or 2-hydroxycyclopentane. The hydroxycyclopentanes can also be cleaved with chemical base.

The modified sugar can be azidosugar, for example, without limitation, 2'-azido, 4'-azido or 4'-azidomethyl sugar. Cleaving an azido sugar can be accomplished in the presence of TCEP.

The sugar can also be substituted with a group capable of photolyzing to form a free radical such as, without limitation, a phenylselenyl or a t-butylcarboxy group. Such groups render the polynucleotide susceptible to cleavage with ultraviolet light.

The sugar can also be a cyanosugar. In a presently preferred embodiment, the cyanosugar is 2'-cyanosugar or 2"-cyanosugar. The cyanosugar-modified polynucleotides can be cleaved with chemical base.

A sugar substituted with an electron withdrawing group, such as, without limitation, fluorine, azido, methoxy or nitro in the 2',2" or 4' position of the modified sugar is another aspect of this invention. These modified sugars render the modified polynucleotide susceptible to cleavage with chemical base.

On the other hand, a sugar can be modified by inclusion of an electron-withdrawing element in the sugar ring. Nitrogen is an example of such a group. The nitrogen can replace the ring oxygen of the sugar or a ring carbon and the resultant modified sugar is cleavable with chemical base.

In yet another aspect of this invention, the modified sugar can be a sugar containing a mercapto group. The 2' position of the sugar is a presently preferred embodiment, such a sugar being cleavable by chemical base.

In particular, the modified sugar can be a 5'-methylenyl-sugar, a 5'-keto-sugar or a 5',5'-difluoro-sugar, all of which are cleavable with chemical base.

Another aspect of this invention is a method for detecting a variance in nucleotide sequence in a polynucleotide, sequencing a polynucleotide or genotyping a polynucleotide known to contain a polymorphism or mutation comprising replacing one or more natural nucleotides in said polynucleotide with one or more modified nucleotides, one or more of which comprises a modified phosphate ester.

The modified phosphate ester can be a phosphorothioate.

In one embodiment, the sulfur of the phosphorothioate is not covalently bonded to the sugar ring. In this case, cleaving said modified polynucleotide into fragments comprises:

a. contacting said sulfur of said phosphorothiolate with an alkylating agent; and, b. then contacting said modified polynucleotide with chemical base.

In a presently preferred embodiment of this invention, the alkylating agent is methyl iodide.

In another aspect of this invention the phosphorothioate containing modified polynucleotide can be cleaved into fragments by contacting said sulfur of said phosphorothioate with β-mercaptoethanol in a chemical base such as, without limitation, sodium methoxide in methanol.

On the other hand, the sulfur atom of said phosphorothiolate can be covalently bonded to a sugar ring in another embodiment of this invention. Cleavage of a polynucleotide so modified can be carried out with chemical base.

The modified phosphate ester can also be a phosphoramidate. Cleavage of a phosphoramidate-containing polynucleotide can be performed using acid.

It is an aspect of this invention that the modified phosphate ester comprises a group selected from the group consisting of alkyl phosphonate and alkyl phosphorotriester wherein the alkyl group is preferably methyl. Such a modified polynucleotide can also be cleaved with acid.

Another aspect of this invention is a method for detecting a variance in nucleotide sequence in a polynucleotide, sequencing a polynucleotide or genotyping a polynucleotide known to contain a polymorphism or mutation, comprising replacing a first and a second natural nucleotide in said polynucleotide with a first and a second modified nucleotides such that said polynucleotide can be specifically cleaved at sites where the first modified nucleotide is followed immediately in the modified polynucleotide sequence by said second modified nucleotide.

In the above method, the first modified nucleotide is covalently bonded at its 5' position to a sulfur atom of a phosphorothioate group and said second modified nucleotide, which is modified with a 2'-hydroxy group, is contiguous to, and 5' of, said first modified nucleotide. This dinucleotide pair is cleavable with chemical base.

Also in the above method the first modified nucleotide can be covalently bonded at its 3' position to a sulfur atom of a phosphorothioate group where said second modified nucleotide, which is modified with a 2'-hydroxy group, is contiguous to and 3' of said first modified nucleotide. This modified nucleotide pair can also be cleaved with chemical base.

It is also an aspect of this invention that, in the above method, said first modified nucleotide is covalently bonded at its 5' position to a first oxygen atom of a phosphorothioate group, said second modified nucleotide is substituted at its 2' position with a leaving group and said second modified nucleotide is covalently bonded at its 3' position to a second oxygen of said phosphorothioate group. Any leaving group can be used, fluorine, chlorine, bromine and iodine are examples. The polynucleotide so modified can be cleaved with chemical base. Sodium methoxide is an example, without limitation, of a useful chemical base.

In another embodiment of this invention, said first modified nucleotide is covalently bonded at its 5' position to a first oxygen atom of a phosphorothioate group, said second modified nucleotide is substituted at its 4' position with a leaving group and said second modified nucleotide is covalently bonded at its 3' position to a second oxygen of said phosphorothioate group. Here, again, any good leaving group can be used of which fluorine, chlorine, bromine and iodine are non-limiting examples. These groups likewise render the modified polynucleotide susceptible to cleavage by chemical base such as, without limitation, sodium methoxide.

In a further embodiment of this invention, said first modified nucleotide is covalently bonded at its 5' position to a first oxygen atom of a phosphorothioate group, said second modified nucleotide is substituted at its 2' position with one or two fluorine atoms and said second modified nucleotide is covalently bonded at its 3' position to a second oxygen of said phosphorothioate group. Such a modified polynucleotide can be cleaved by
  a. contacting said modified polynucleotide with ethylene sulfide or β-mercaptoethanol; and then,
  b. contacting said modified polynucleotide with a chemical base such as, without limitation, sodium methoxide.

Another embodiment of this invention has said first modified nucleotide covalently bonded at its 5' position to a first oxygen atom of a phosphorothioate group, said second modified nucleotide substituted at its 2' position with a hydroxy group and said second modified nucleotide covalently bonded at its 3' position to a second oxygen of said phosphorothioate group. Here, cleavage can be accomplished by:
  a. contacting said modified polynucleotide with a metal oxidant; and then,
  b. contacting said modified polynucleotide with a chemical base.

Non-limiting examples of metal oxidants are $Cu^{II}$ and $Fe^{III}$ and equally non-limiting examples of useful bases are dilute hydroxide, piperidine and dilute ammonium hydroxide.

It is also an embodiment of this invention that said first modified nucleotide is covalently bonded at its 5' position to a nitrogen atom of a phosphoramidate group and said second modified nucleotide, which is modified with a 2'-hydroxy group, is contiguous to and 5' of said first modified nucleotide. This type of modification renders the modified polynucleotide susceptible to acid cleavage.

A still further embodiment of this invention is one in which said first modified nucleotide is covalently bonded at its 3' position to a nitrogen atom of a phosphoramidate group and said second modified nucleotide, which is modified with a 2'-hydroxy group, is contiguous to and 3' of said first modified nucleotide. Again, such a substitution pattern is cleavable with acid.

It also may be that said first modified nucleotide is covalently bonded at its 5' position to an oxygen atom of an alkylphosphonate or an alkylphosphorotriester group and said second modified nucleotide, which is modified with a 2'-hydroxy group, is contiguous to said first modified nucleotide. This alternative dinucleotide grouping is also cleavable with acid.

Another cleavable dinucleotide grouping is one in which said first modified nucleotide has an electron-withdrawing group at its 4' position and said second modified nucleotide, which is modified with a 2'-hydroxy group, is contiguous to and 5' of said first modified nucleotide. Again, cleavage can be accomplished by contact with acid.

Another aspect of this invention is a method for detecting a variance in nucleotide sequence in a polynucleotide, for sequencing a polynucleotide or for genotyping a polynucleotide known to contain a polymorphism or mutation comprising:

a. replacing one or more natural nucleotides in said polynucleotide with one or more modified nucleotides wherein each modified nucleotide is modified with one or more modifications selected from the group consisting of a modified base, a modified sugar and a modified phosphate ester, provided that, if only one modified nucleotide is used, said modified nucleotide is not a ribonucleotide;

b. contacting said modified polynucleotide with a reagent or reagents which cleave the modified polynucleotide into fragments at site(s) of incorporation of said modified nucleotide;

c. analyzing said fragments to detect said variance, to construct said sequence or to genotype said polynucleotide.

An aspect of this invention is compound having the chemical structure:

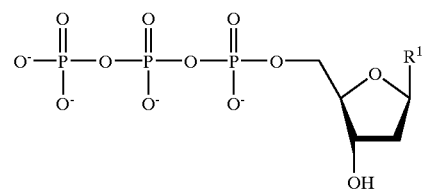

wherein $R^1$ is selected from the group consisting of:

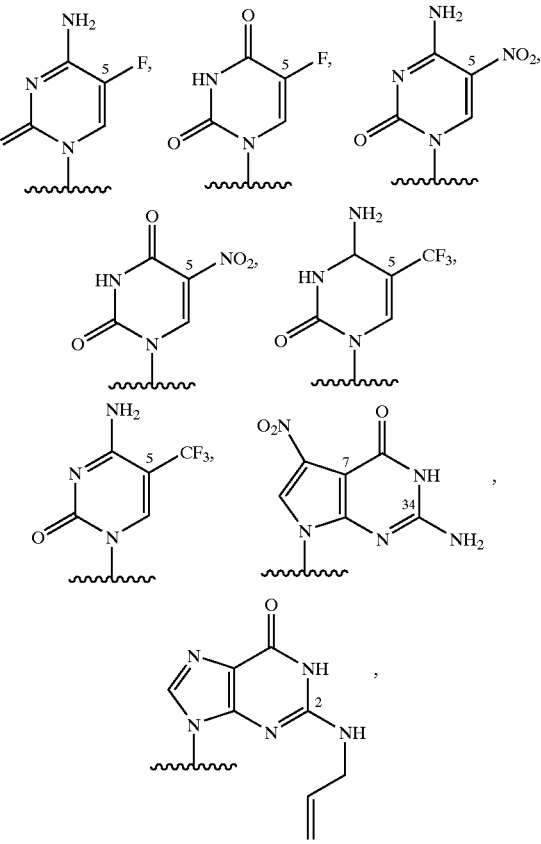

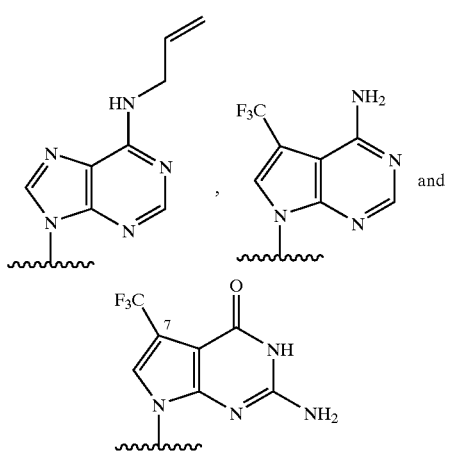

A compound having the chemical structure:

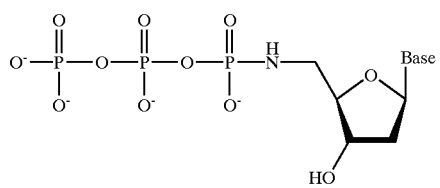

wherein said "Base" is selected from the group consisting of cytosine, guanine, inosine and uracil is another aspect of this invention.

Another aspect of this invention is a compound having the chemical structure:

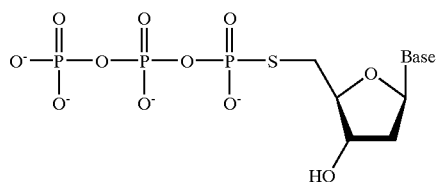

wherein base is selected from the group consisting of cytosine, guanine, inosine and uracil.

A still further aspect of this invention is a compound having the chemical structure:

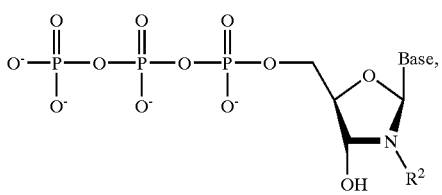

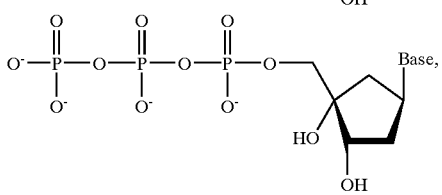

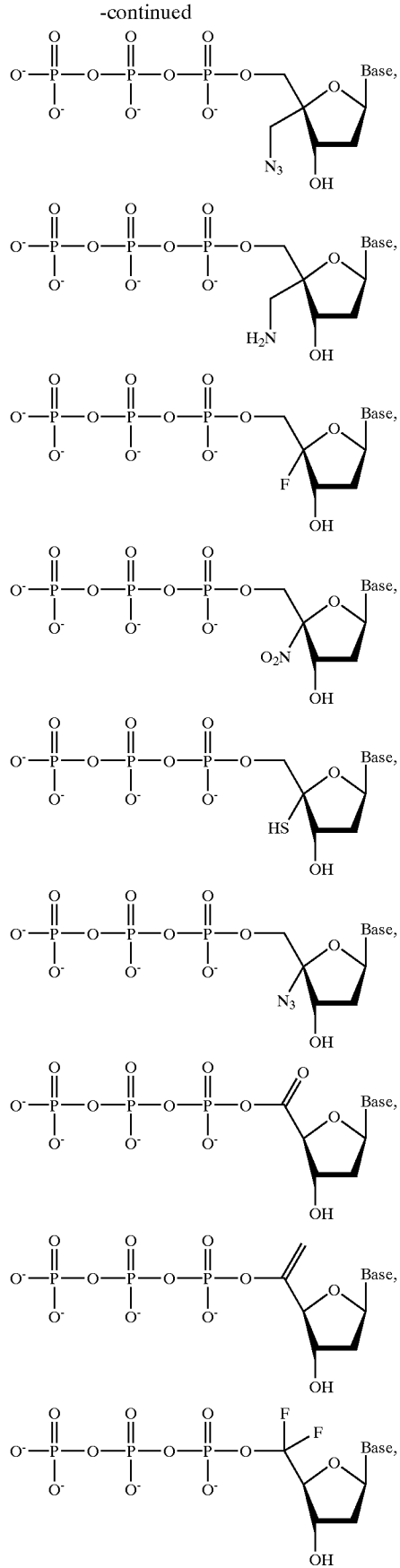

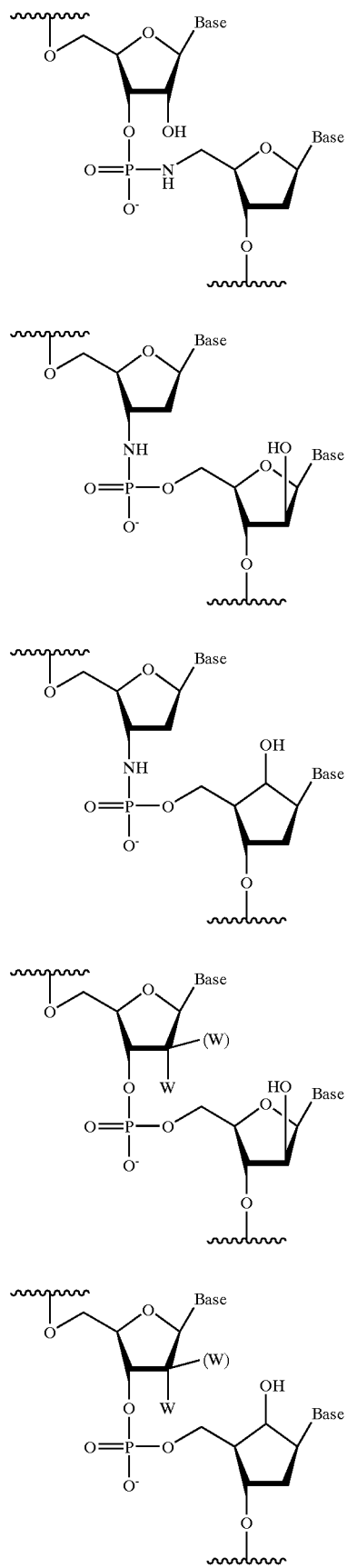
wherein said "Base" is selected from the group consisting of adenine, cytosine, guanine, inosine, thymine and uracil.
A polynucleotide comprising a dinucleotide sequence selected from the group consisting of:

-continued
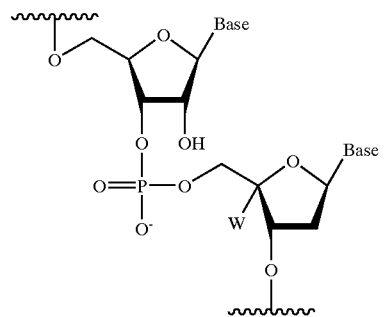
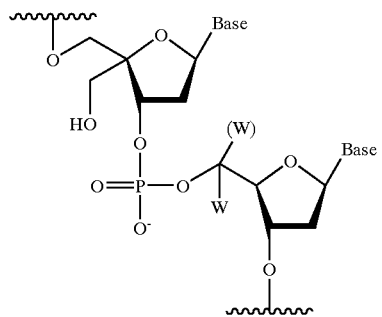
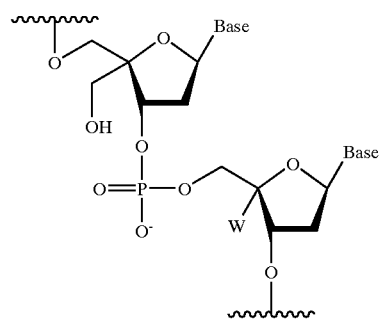
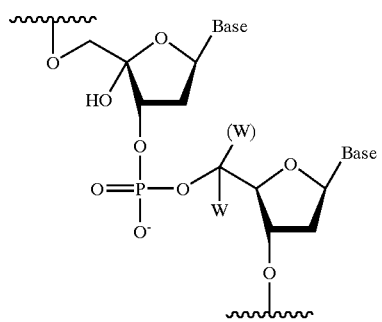
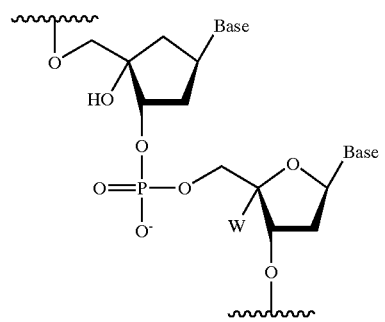
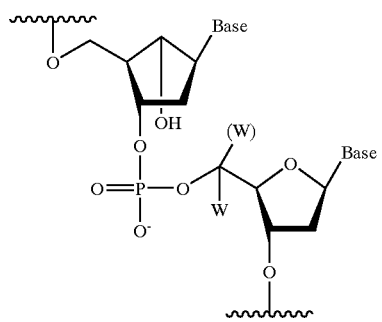
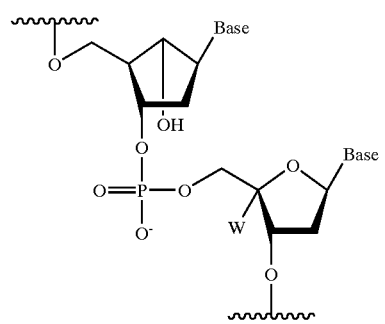
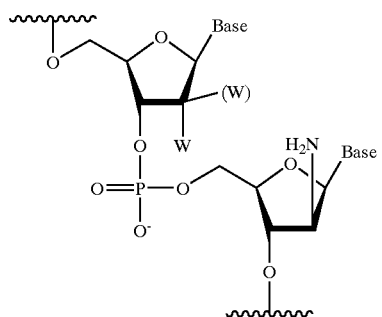
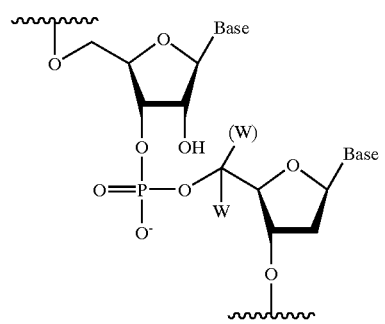
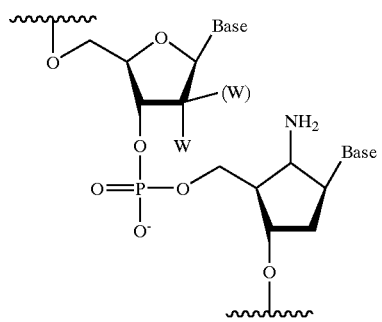

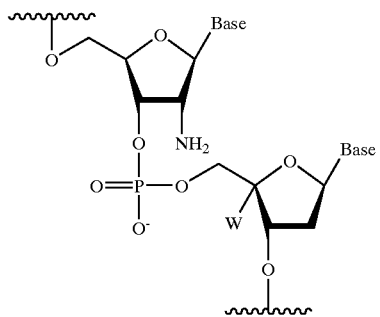
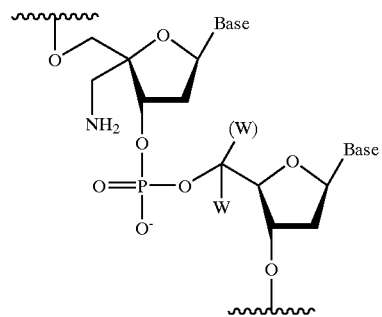
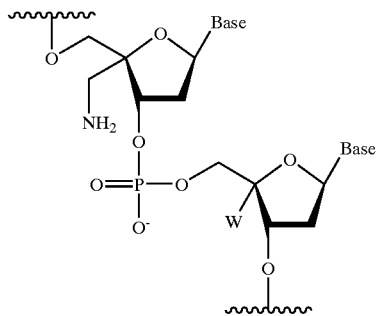
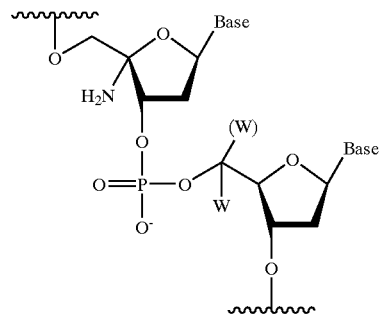
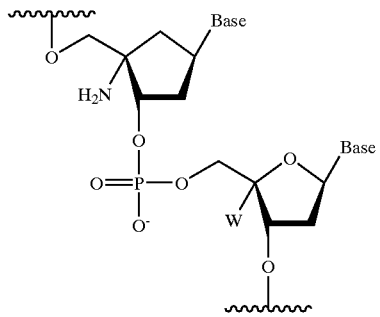
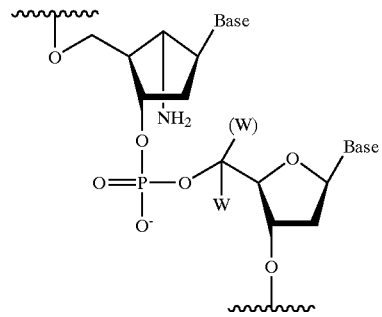
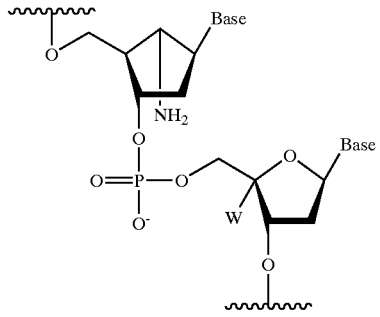
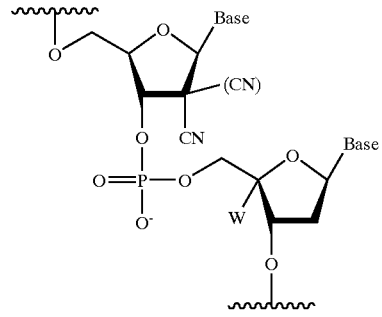
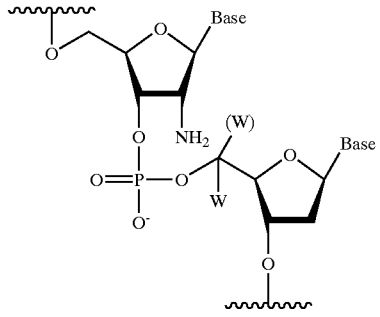
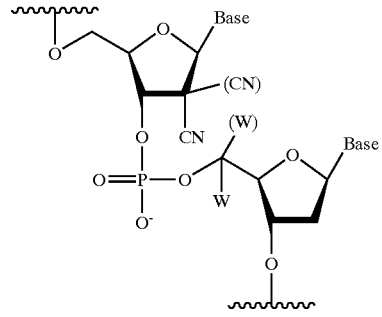

31
-continued
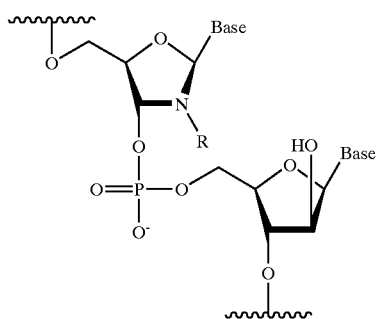
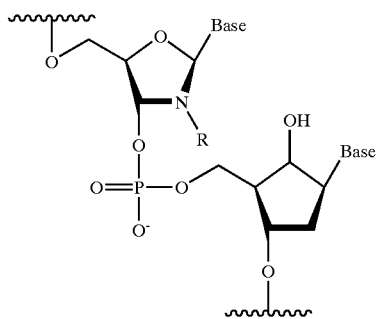
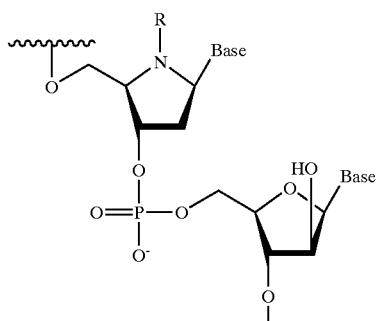
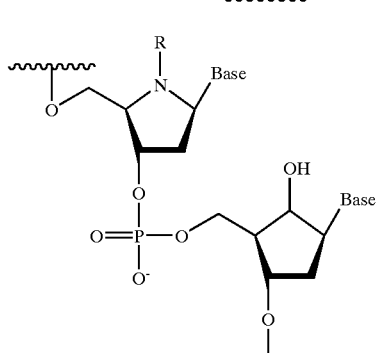
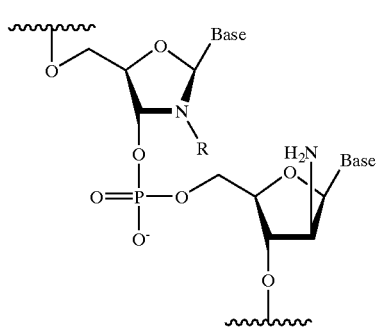
32
-continued
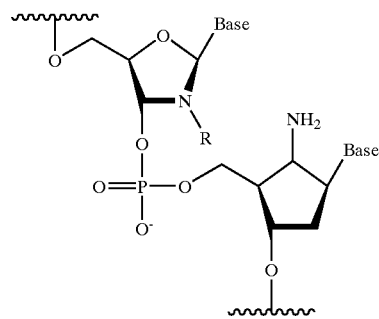
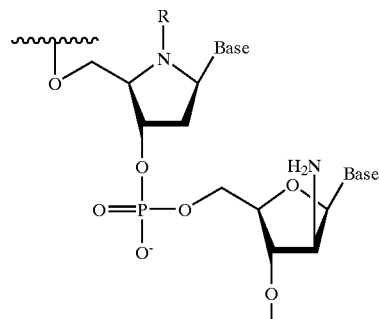
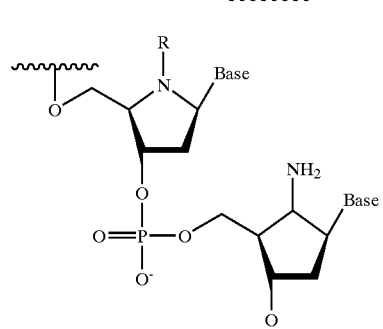
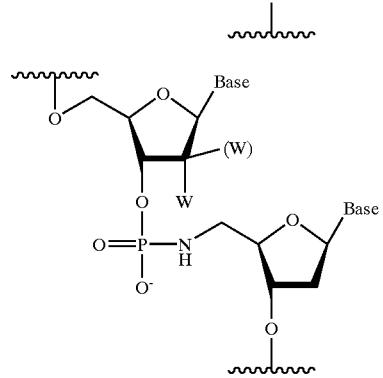
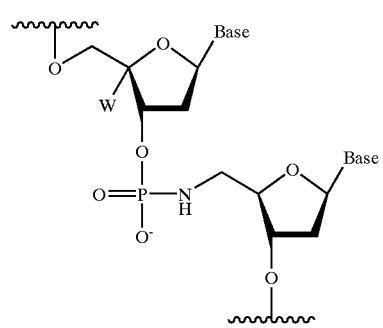

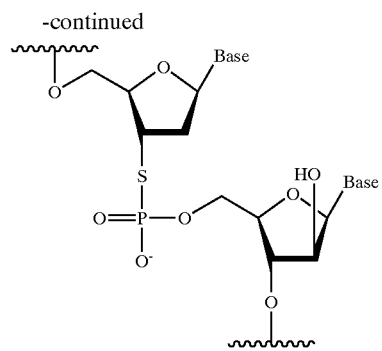
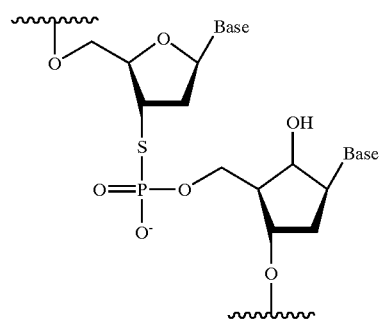
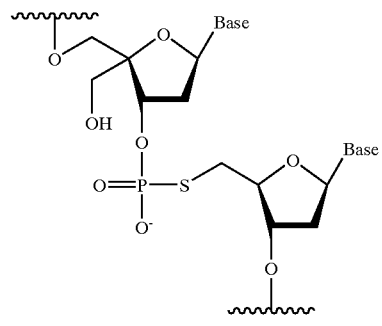
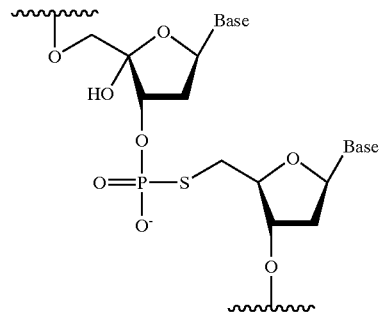
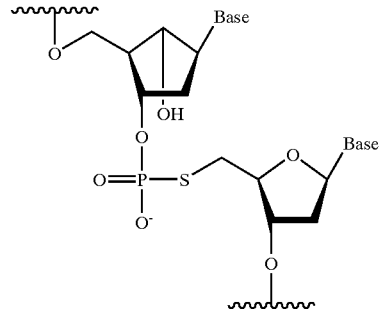
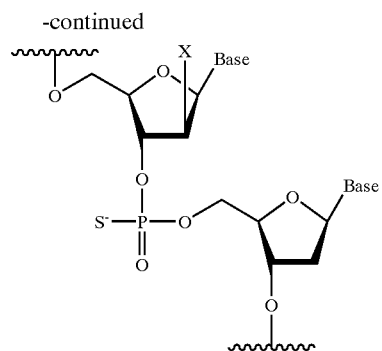
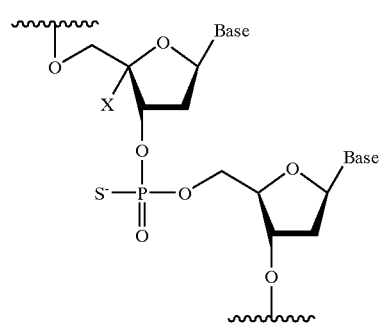
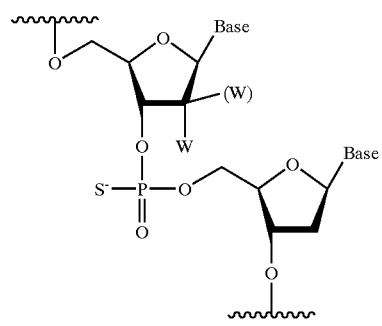
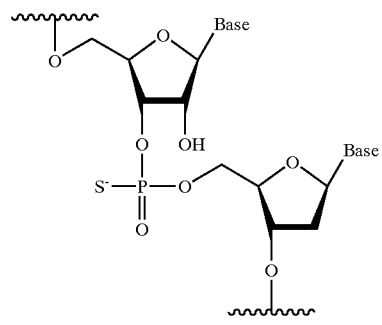
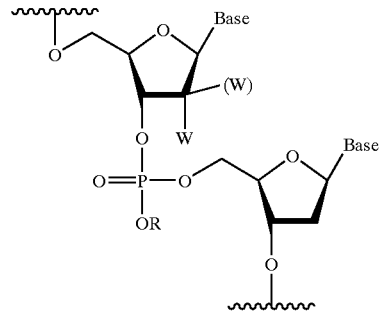

35
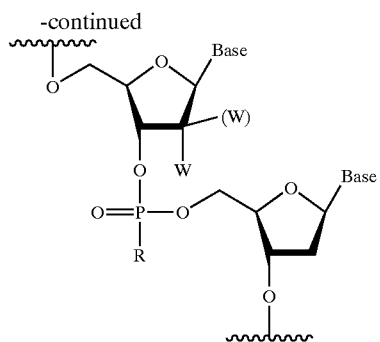
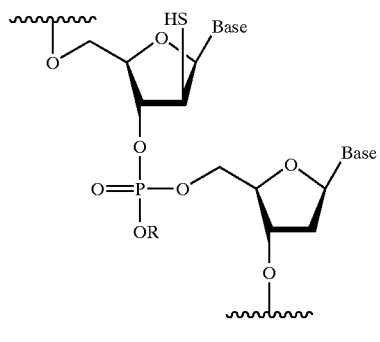
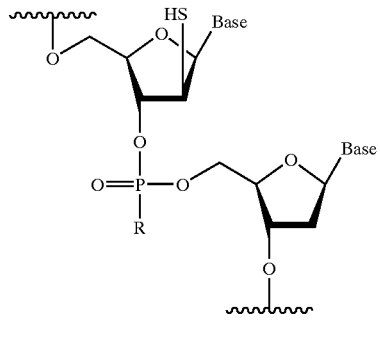
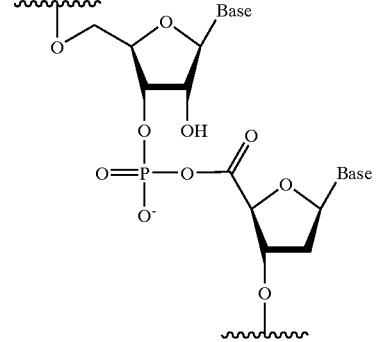
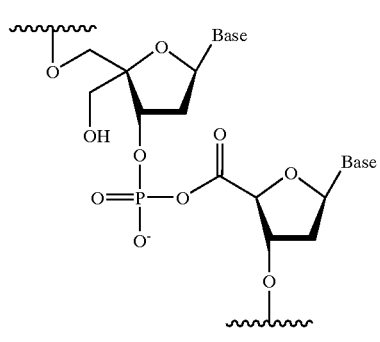
36
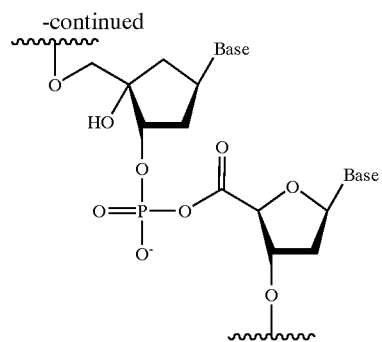
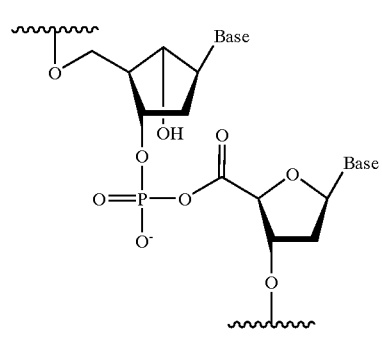
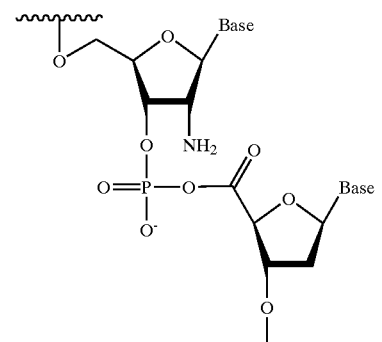
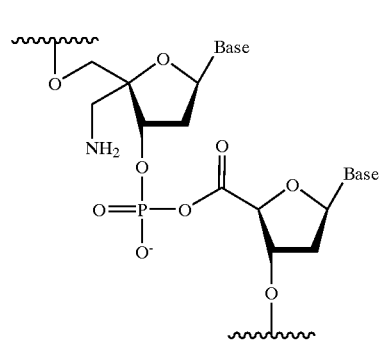
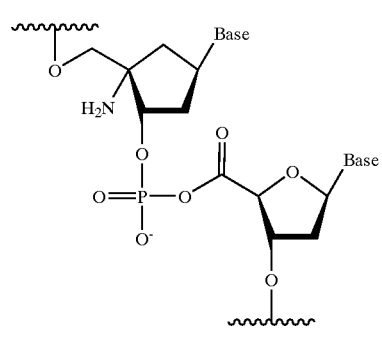

-continued

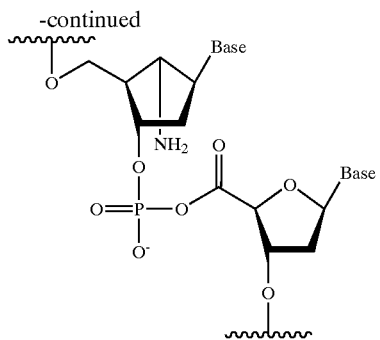

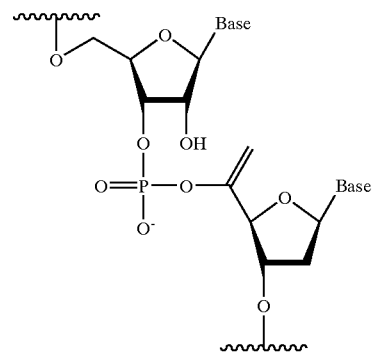

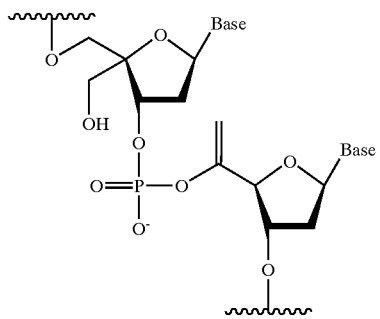

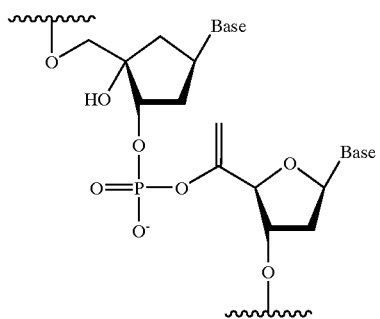

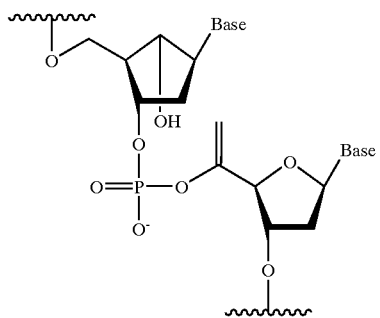

-continued

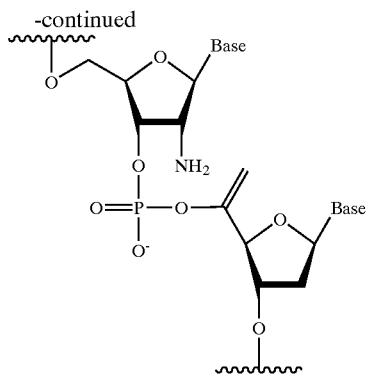

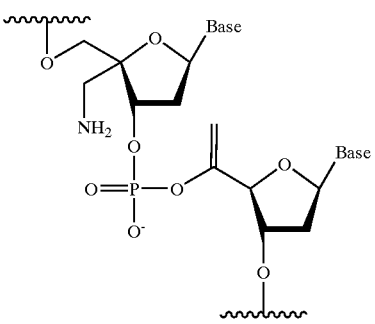

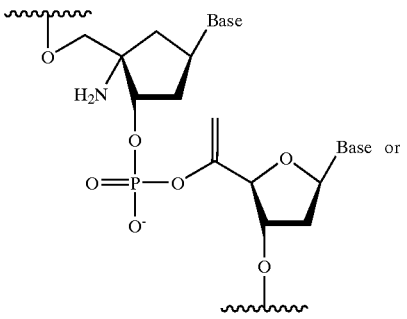

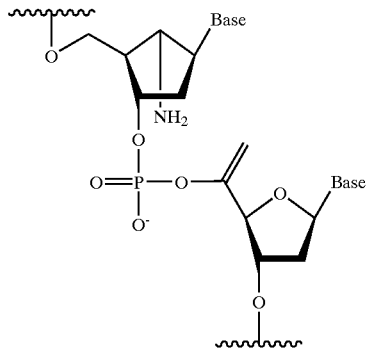

wherein each "Base" is independently selected from the group consisting of adenine, cytosine, guaninine and thymine; W is an electron withdrawing group; X is a leaving group and R is an alkyl, preferrably a lower alkyl, group is also an aspect of this invention. The electron withdrawing group is selected from the group consisting of F, Cl, Br, I, $NO_2$, $C\equiv N$, —C(O)OH and OH in another aspect of this invention and, in a still further aspect, the leaving group is selected from the group consisting of Cl, Br, I and OTs.

An aspect of this invention is a method for synthesizing a polynucleotide comprising mixing a compound having the chemical structure:

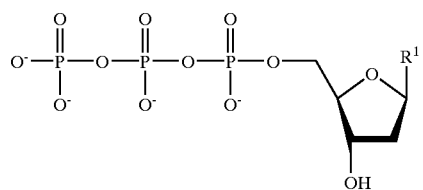

wherein R¹ is selected from the group consisting of:

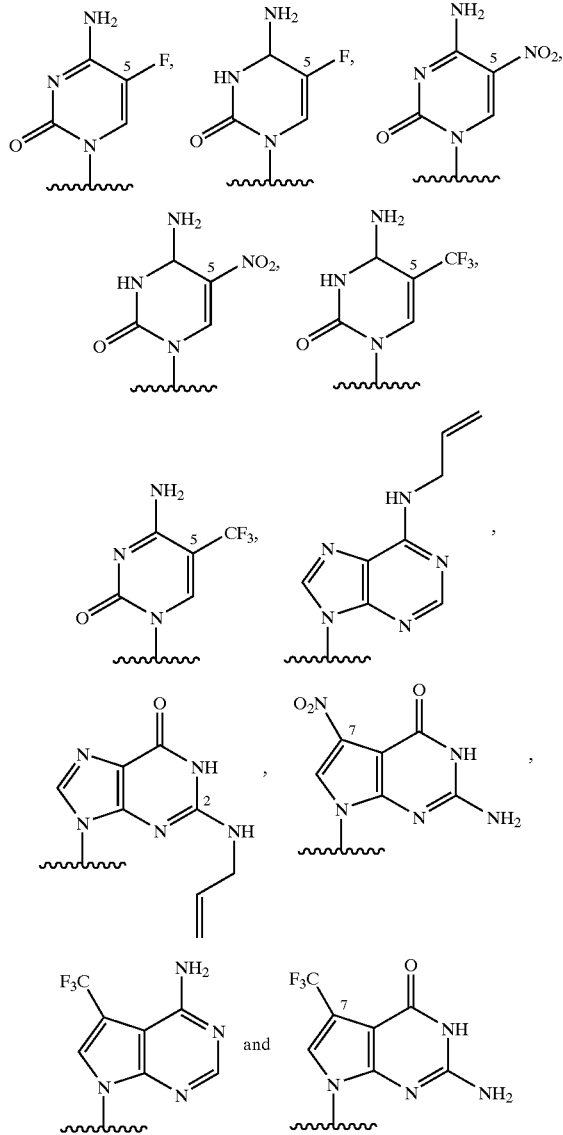

with adenosine triphosphate, guanosine triphosphate, and thymidine or uridine triphosphate in the presence of one or more polymerases.

A method for synthesizing a polynucleotide comprising mixing a compound having the chemical structure:

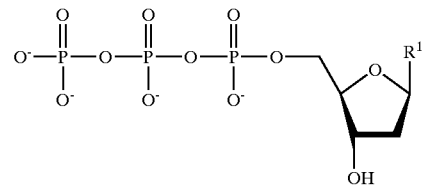

wherein R¹ is selected from the group consisting of:

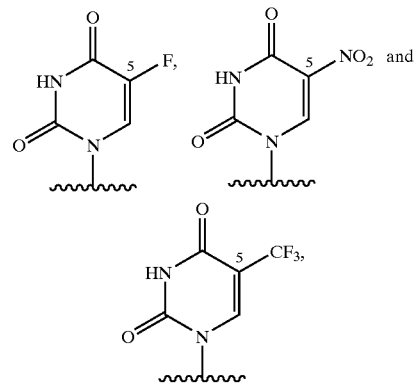

with adenosine triphosphate, cytidine triphosphate and guanosine triphosphate in the presence of one or more polymerases is also an aspect of this invention.

A method for synthesizing a polynucleotide, comprising mixing a compound having the chemical structure:

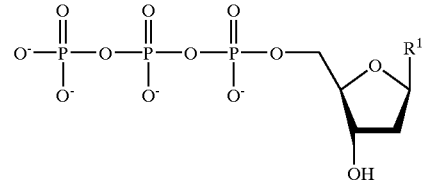

wherein R¹ is selected from the group consisting of:

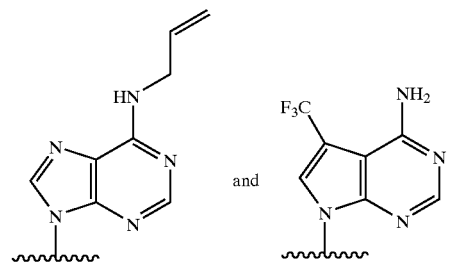

with cytidine triphosphate, guanosine triphosphate, and thymidine triphosphate in the presence of one or more polymerases is a further aspect of this invention.

An aspect of this invention is a method for synthesizing a polynucleotide, comprising mixing a compound having the chemical structure:

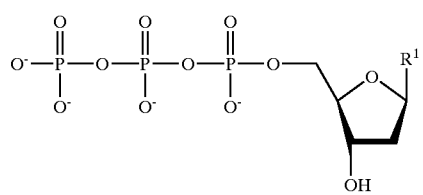

wherein R¹ is selected from the group consisting of:

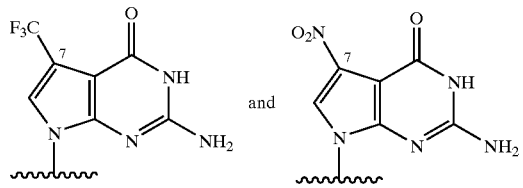

with adenosine triphosphate, cytidine triphosphate and thymidine triphosphate in the presence of one or more polymerases.

Another aspect of this invention is a method for synthesizing a polynucleotide, comprising mixing a compound selected from the group consisting of:

a compound having the chemical structure:

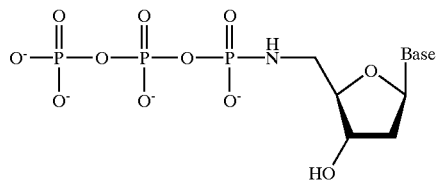

wherein said "Base" is selected from the group consisting of cytosine, guanine, inosine and uracil;

a compound having the chemical structure:

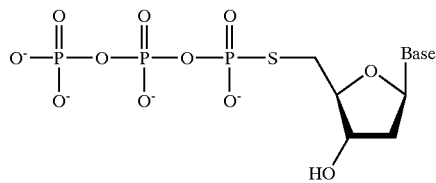

wherein said "Base" is selected from the group consisting of adenine, cytosine, guanine, inosine and uracil; and a compound having the chemical structure:

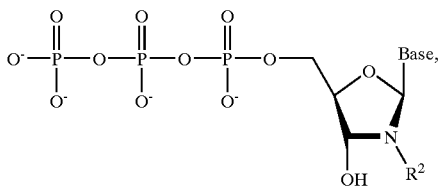

-continued

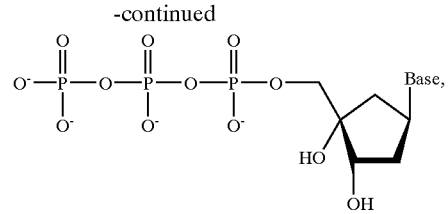
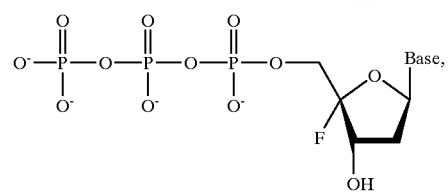
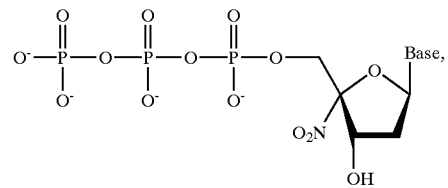
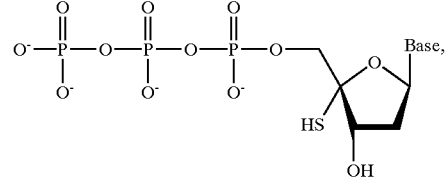
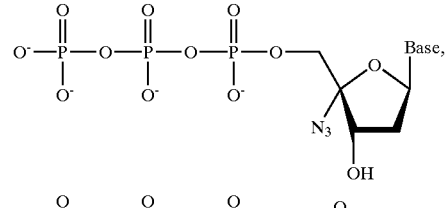
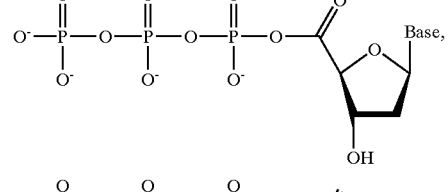
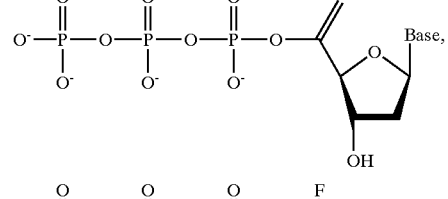
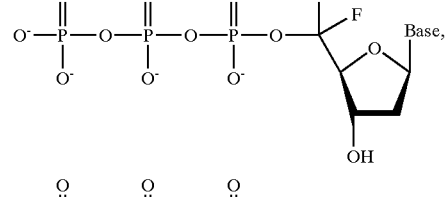
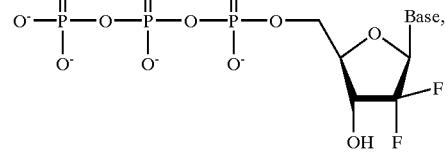

-continued

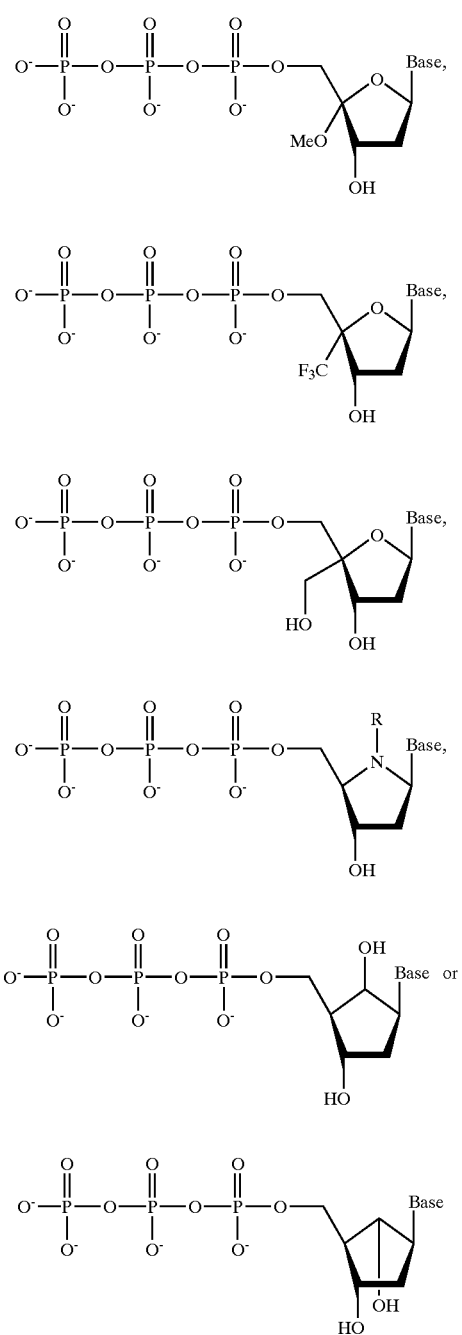

wherein the "Base" is selected from the group consisting of adenine, cytosine, guanine or inosine, and thymine or uracil, with whichever three of the four nucleosides triphosphates, adenosine triphosphate, cytidine triphosphate, guanosine triphosphate and thymidine triphosphate, do not contain said base (or its substitute), in the presence of one or more polymerases.

Another aspect of this invention is a method for synthesizing a polynucleotide, comprising mixing one of the following pairs of compounds:

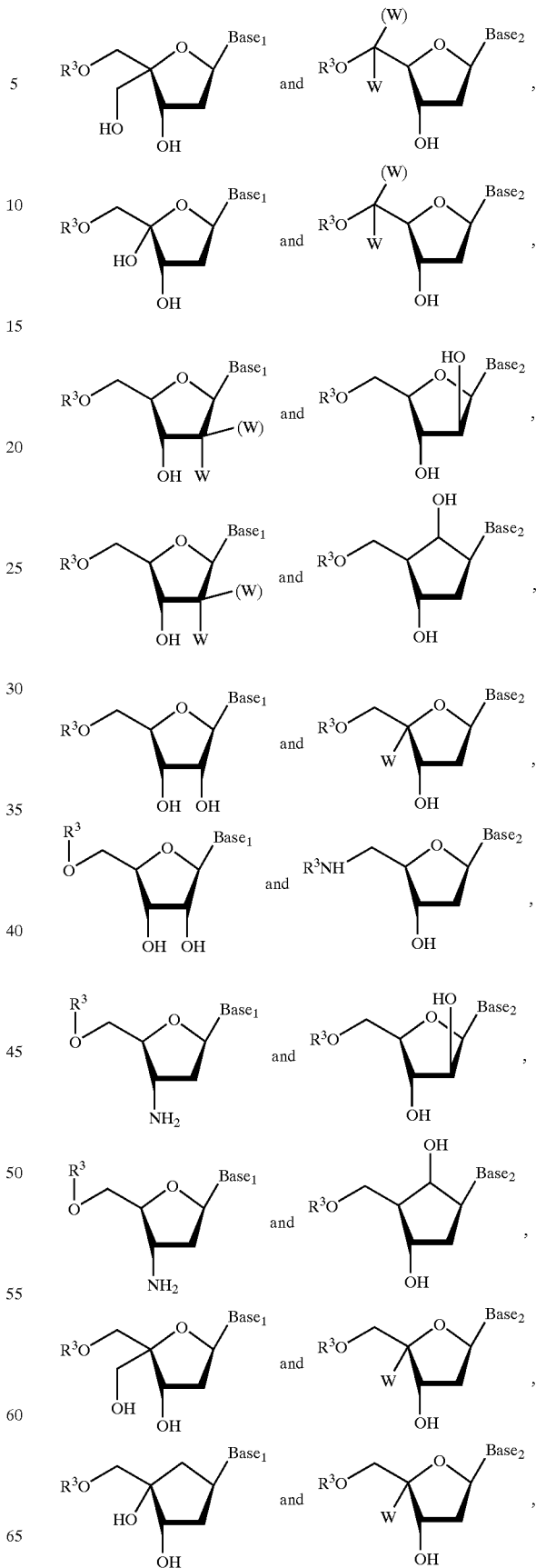

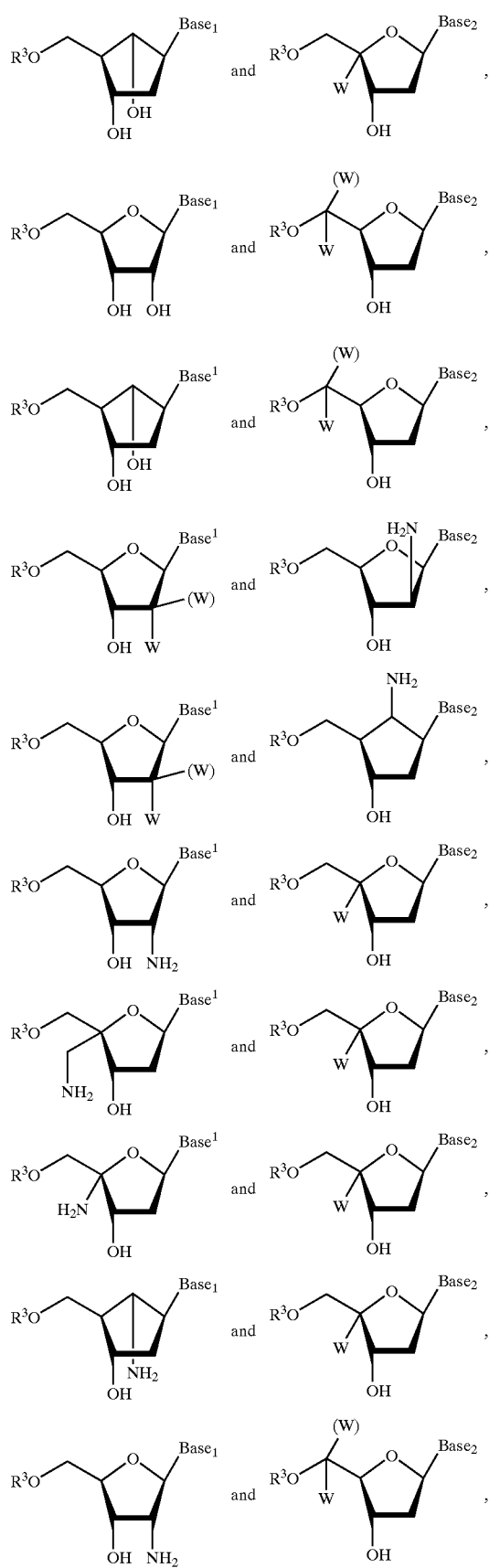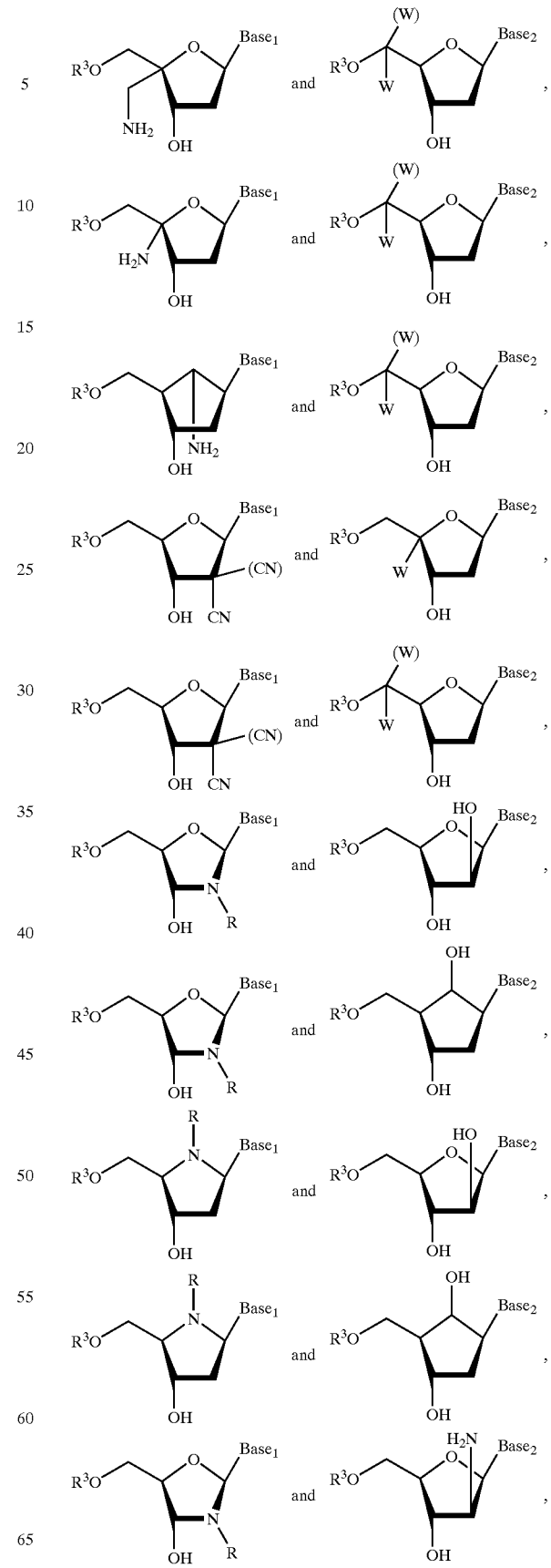

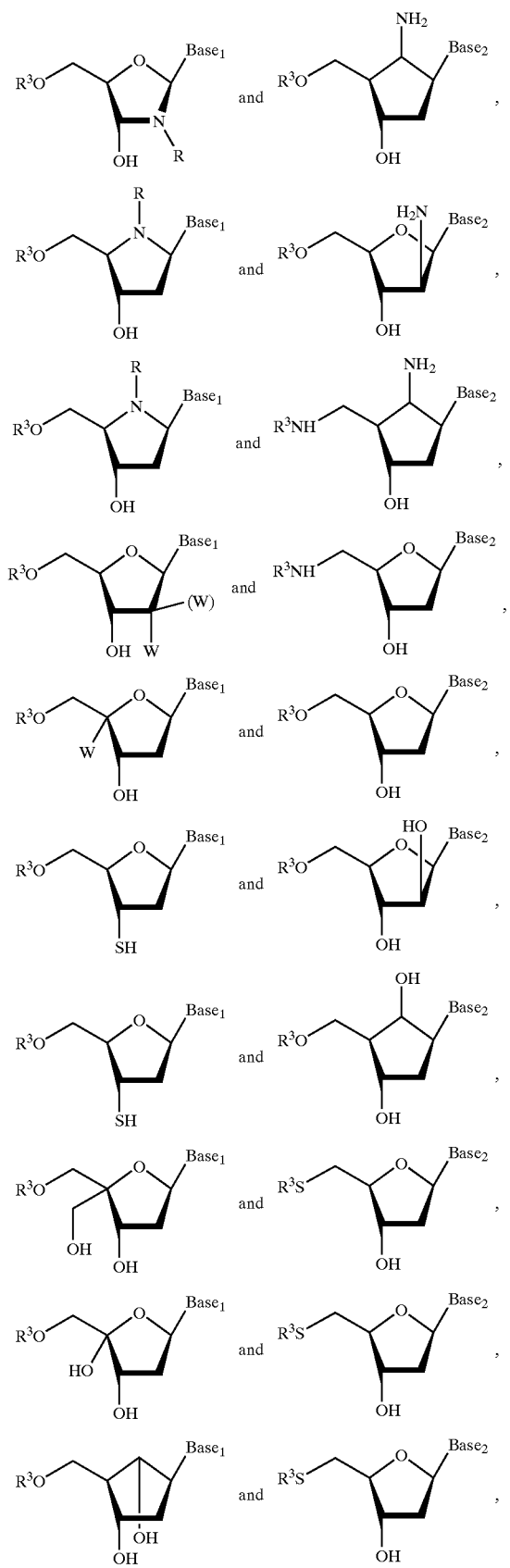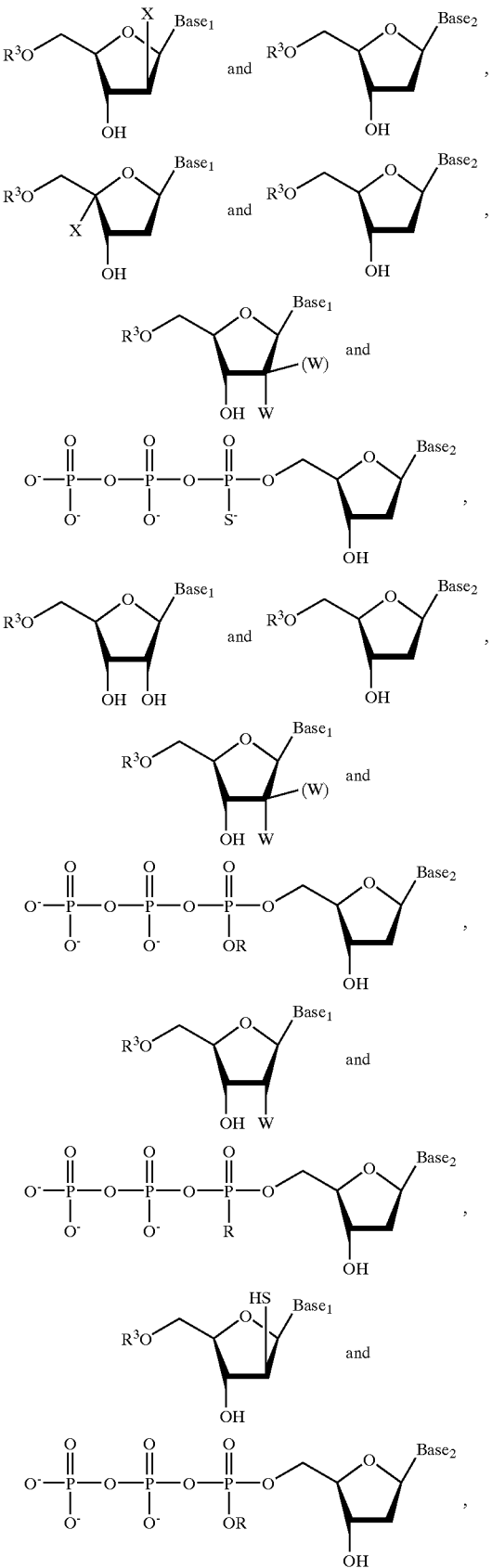

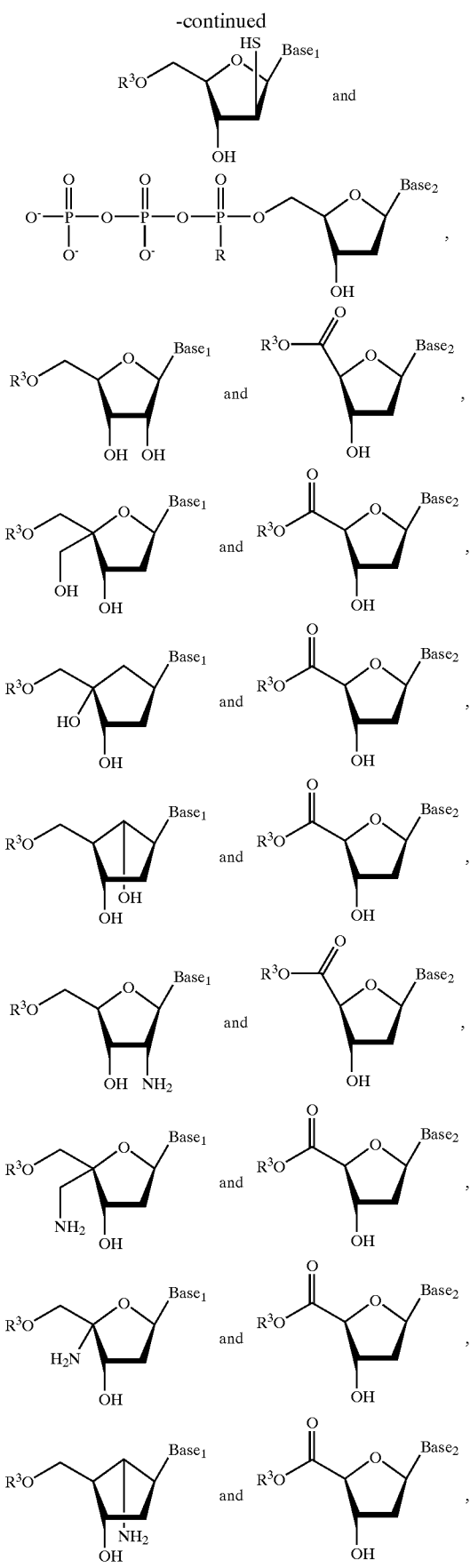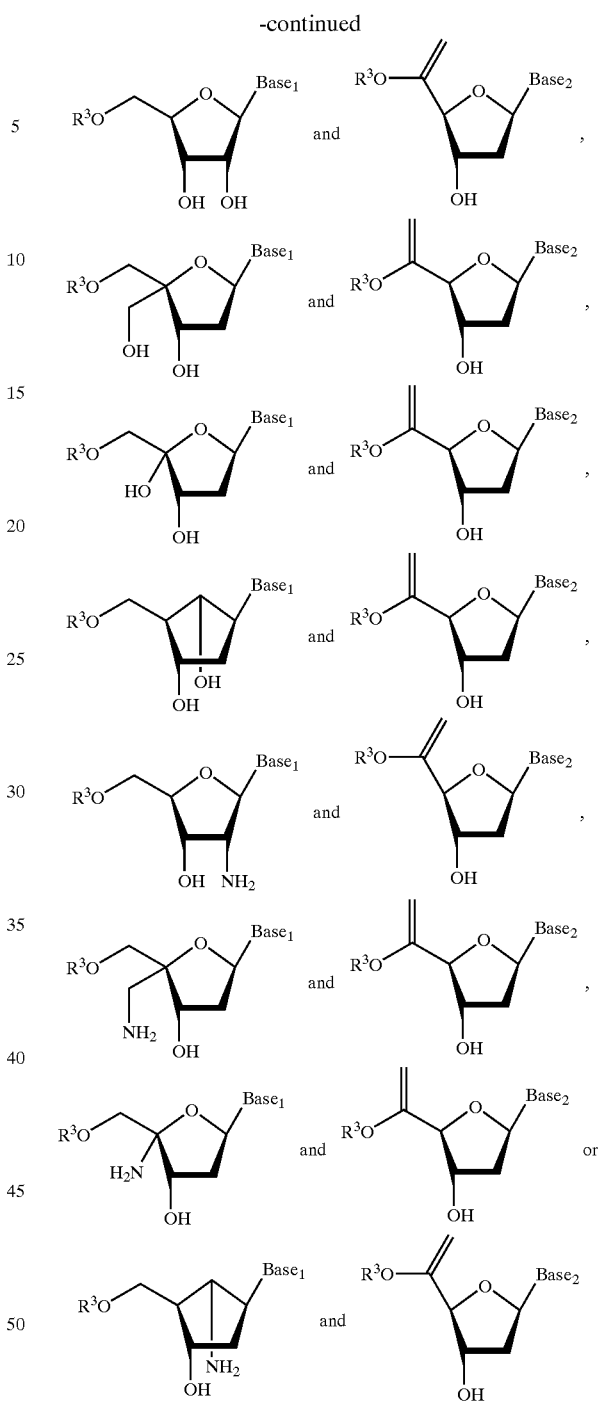

wherein:
Base, is selected from the group consisting of adenine, cytosine, guanine or inosine, and thymine or uracil;
Base₂ is selected from the group consisting of the remaining three bases which are not Base;
$R^3$ is O—P(=O)(O⁻)—O—P(=O)(O⁻)—O—P(=O)(O⁻)—O—; and,
W is an electron withdrawing group;
X is leaving group;
a second W or X shown in parentheses on the same carbon atom means that
a single W or X group can be in either position on the sugar or both W or both
X groups can be present at the same time; and, R is a lower alkyl group;

with whichever two of the four nucleoside triphosphates, adenosine triphosphate, cytidine triphosphate, guanosine triphosphate and thymidine triphosphate, do not contain base-1 or base-2 (or their substitutes), in the presence of one or more polymerases.

An aspect of this invention is a mutant polymerase which is capable of catalyzing the incorporation of a modified nucleotide into a polynucleotide wherein said modified nucleotide is not a ribonucleotide, said polymerase being obtained by a process comprising DNA shuffling in another aspect of this invention.

The DNA shuffling including process can comprise the following steps:

a. selecting one or more known polymerase(s);
b. performing DNA shuffling;
c. transforming shuffled DNA into a host cell;
d. growing host cell colonies;
e. forming a lysate from said host cell colony;
f. adding a DNA template containing a detectable reporter sequence, the modified nucleotide or nucleotides whose incorporation into a polynucleotide is desired and the natural nucleotides not being replaced by said modified nucleotide(s); and,
g. examining the lysate for the presence of the detectable reporter.

The DNA-shuffling including process can also comprise:

a. selecting a known polymerase or two or more known polymerases having different sequences or different biochemical properties or both;
b. performing DNA shuffling;
c. transforming said shuffled DNA into a host to form a library of transformants in host cell colonies;
d. preparing first separate pools of said transformants by plating said host cell colonies;
e. forming a lysate from each said first separate pool host cell colonies;
f. removing all natural nucleotides from each said lysate;
g. combining each said lysate with:
   i. a single-stranded DNA template comprising a sequence corresponding to an RNA polymerase promoter followed by a reporter sequence;
   ii. a single-stranded DNA primer complementary to one end of said template;
   iii. the modified nucleotide or nucleotides whose incorporation into said polynucleotide is desired;
   iv. each natural nucleotide not being replaced by said modified nucleotide or nucleotides;
h. adding RNA polymerase to each said combined lysate;
i. examining each said combined lysate for the presence of said reporter sequence;
j. creating second separate pools of transformants in host cell colonies from each said first separate pool of host cell colonies in which the presence of said reporter is detected;
k. forming a lysate from each said second separate pool of host cell colonies;
l. repeating steps g, h, I, j, k and l to form separate pools of transformants in host cell colonies until only one host cell colony remains which contains said polymerase; and,
m. recloning said polymerase from said one host cell colony into a protein expression vector.

A polymerase which is capable of catalyzing the incorporation of a modified nucleotide into a polynucleotide, wherein said modified nucleotide is not a ribonucleotide obtained by a process comprising cell senescence selection is another aspect of this invention.

The cell senscence selection process can comprise the following steps:

a. mutagenizing a known polymerase to form a library of mutant polymerases;
b. cloning said library into a vector;
c. transforming said vector into host cells selected so as to be susceptible to being killed by a selected chemical only when said cell is actively growing;
d. adding a modified nucleotide;
e. growing said host cells;
f. treating said host cells with said selected chemical;
g. separating living cells from dead cells; and,
h. isolating said polymerase or polymerases from said living cells.

Steps d to h of the above method can be repeated one or more times to refine the selection of the polymerase in another aspect of this invention.

The cell senescence procedure for obtaining a polymerase can also comprise the steps of:

a. mutagenizing a known polymerase to form a library of mutant polymerases;
b. cloning said library of mutant polymerases into a plasmid vector;
c. transforming with said plasmid vector bacterial cells that, when growing, are susceptible to an antibiotic;
d. selecting transfectants using said antibiotic;
e. introducing a modified nucleotide, as the corresponding nucleoside triphosphate, into the bacterial cells;
f. growing the cells;
g. adding an antibiotic which will kill bacterial cells that are actively growing;
h. isolating said bacterial cells;
i. growing said bacterial cells in fresh medium containing no antibiotic;
j. selecting live cells from growing colonies;
k. isolating said plasmid vector from said live cells;
l. isolating said polymerase; and,
m. assaying said polymerase.

Repeating steps c to k of the above process one or more additional times before proceeding to step I is another aspect of this invention.

A polymerase may also be obtained by a process comprising phage display.

The phage display process may comprise the steps of:

a. selecting a DNA polymerase;
b. expressing said polymerase in a bacteriophage vector as a fusion to a bacteriophage coat protein;
c. attaching an oligonucleotide to the surface of the phage;
d. forming a primer template complex either by addition of a second oligonucleotide complementary to the oligonucleotide of c or by formation of a self priming complex using intramolecular complementarity of the oligonucleotide of c;
e. performing a primer extension in the presence of the modified nucleotide or nucleotides whose incorporation into a polynucleotide is desired, and the natural nucleotides not being replaced by said modified nucleotide(s) where successful primer extension results in the presence of a detectable reporter sequence;

f. sorting the phage with the detectable reporter from those without the detectable reporter;

The detectable reporter sequence is formed by incorporation of one or more dye-labeled natural or modified nucleotides in the primer extension reaction in another aspect of this invention.

The indicated sorting procedure may comprise use of a fluorescence activated cell sorter in yet another aspect of this invention.

An aspect of this invention is that the detectable reporter in the above method is a restriction endonuclease cleavage site and the sorting procedure entails restriction endonuclease digestion.

That the polymerase obtained in the above methods be a thermostable polymerase is another aspect of this invention.

The polymerase obtained by any of the above methods wherein the modified nucleotide being incorporated is selected from the group consisting of:

a compound having the chemical structure:

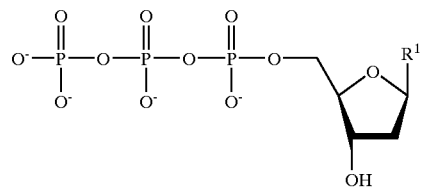

wherein R¹ is selected from the group consisting of:

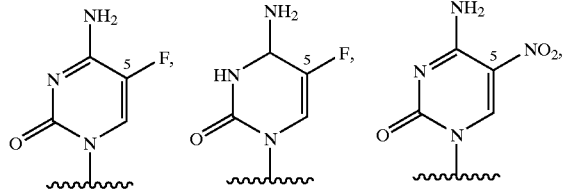

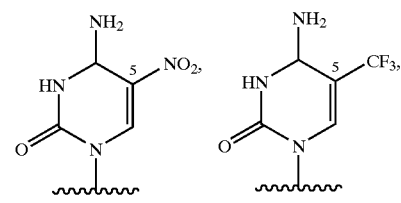

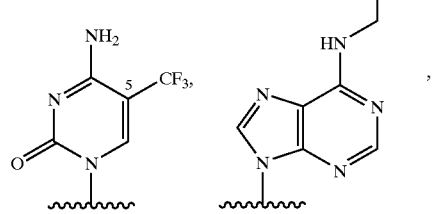

-continued

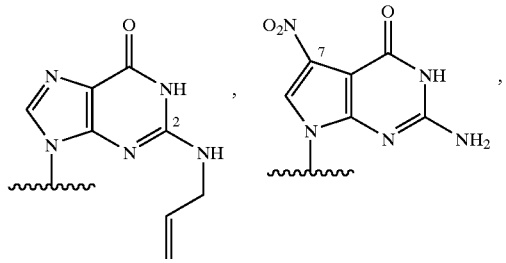

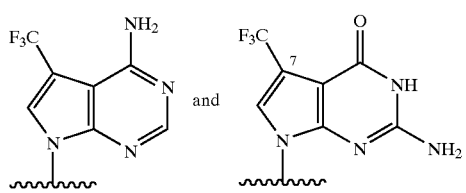

a compound having the chemical structure:

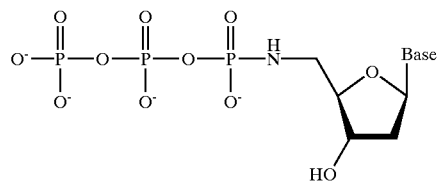

wherein said "Base" is selected from the group consisting of cytosine, guanine, inosine and uracil, a compound having the chemical structure:

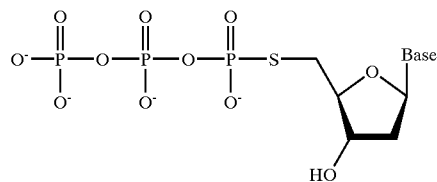

wherein said "Base" is selected from the group consisting of adenine, cytosine, guanine, inosine and uracil;

a compound having the chemical structure:

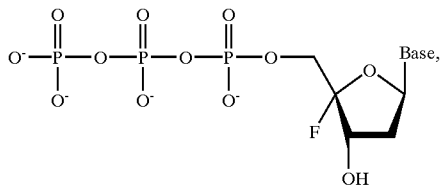

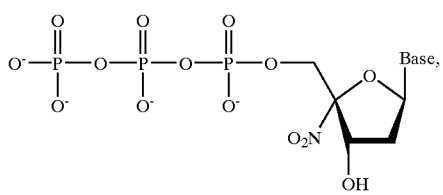

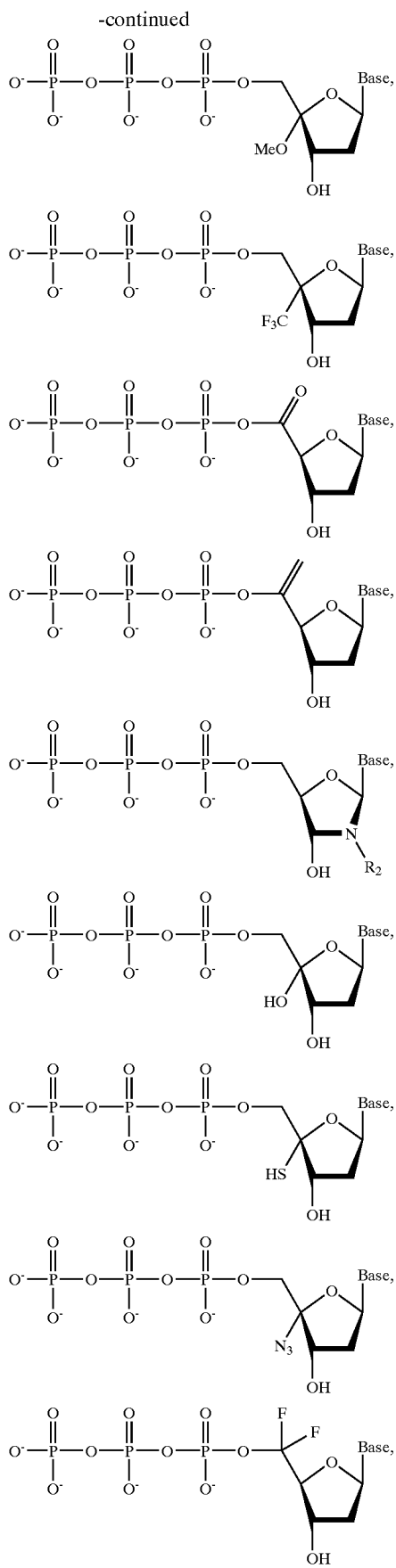
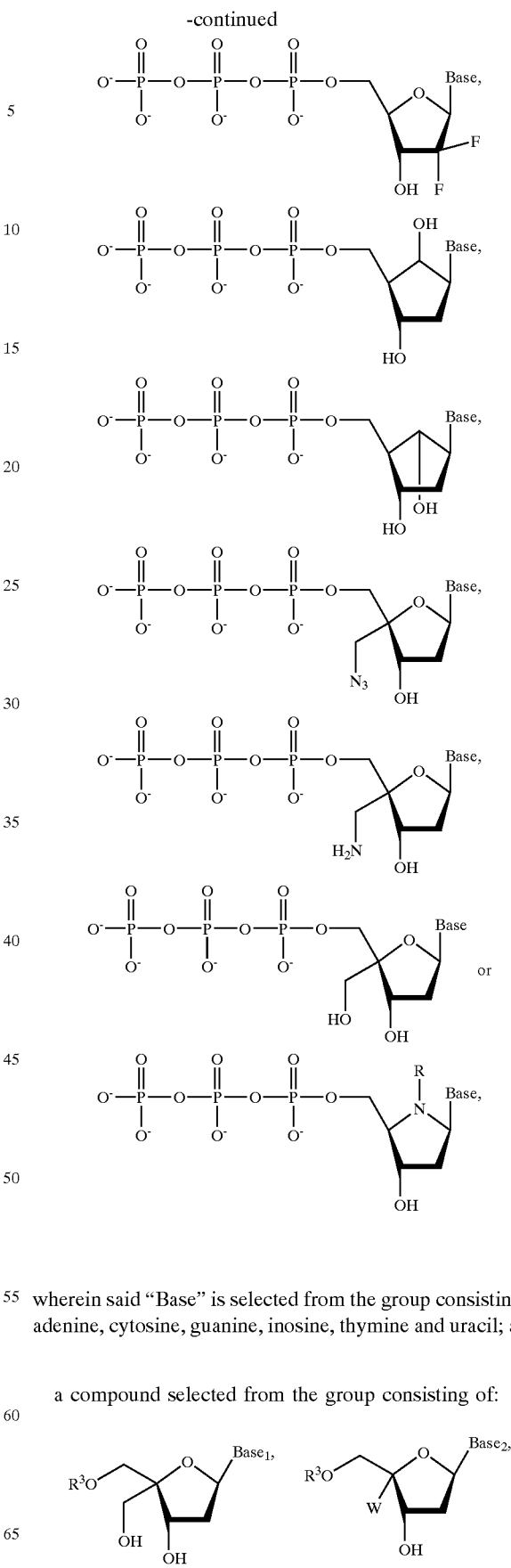
wherein said "Base" is selected from the group consisting of adenine, cytosine, guanine, inosine, thymine and uracil; and,
a compound selected from the group consisting of:
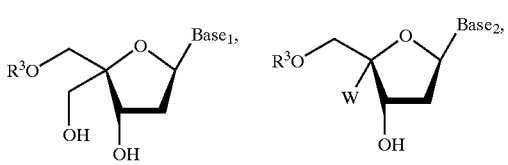

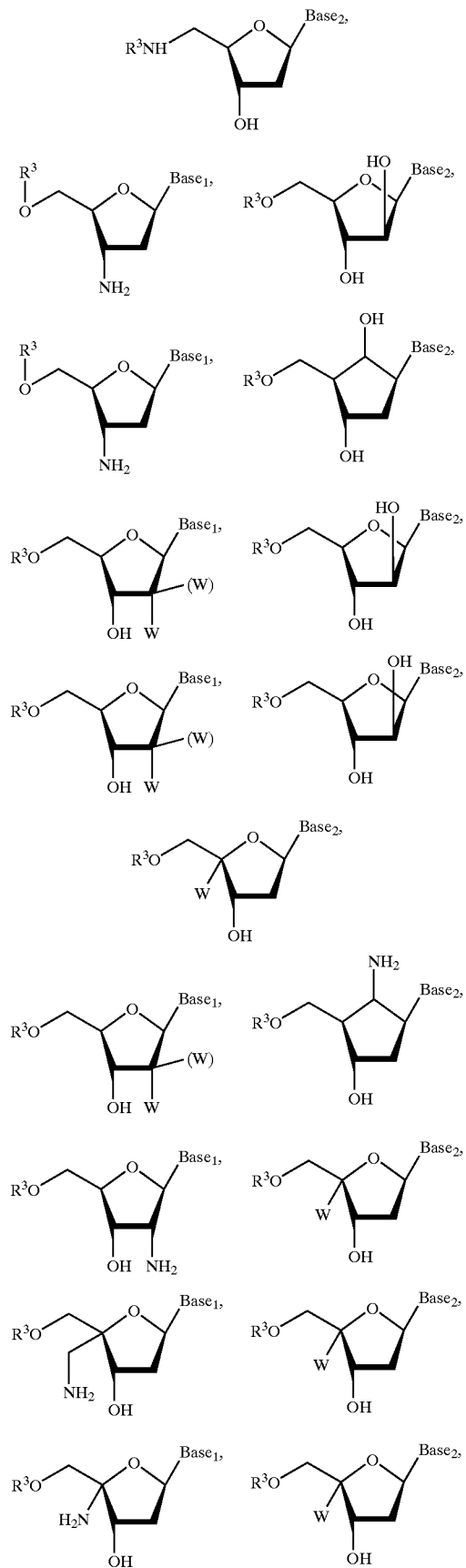
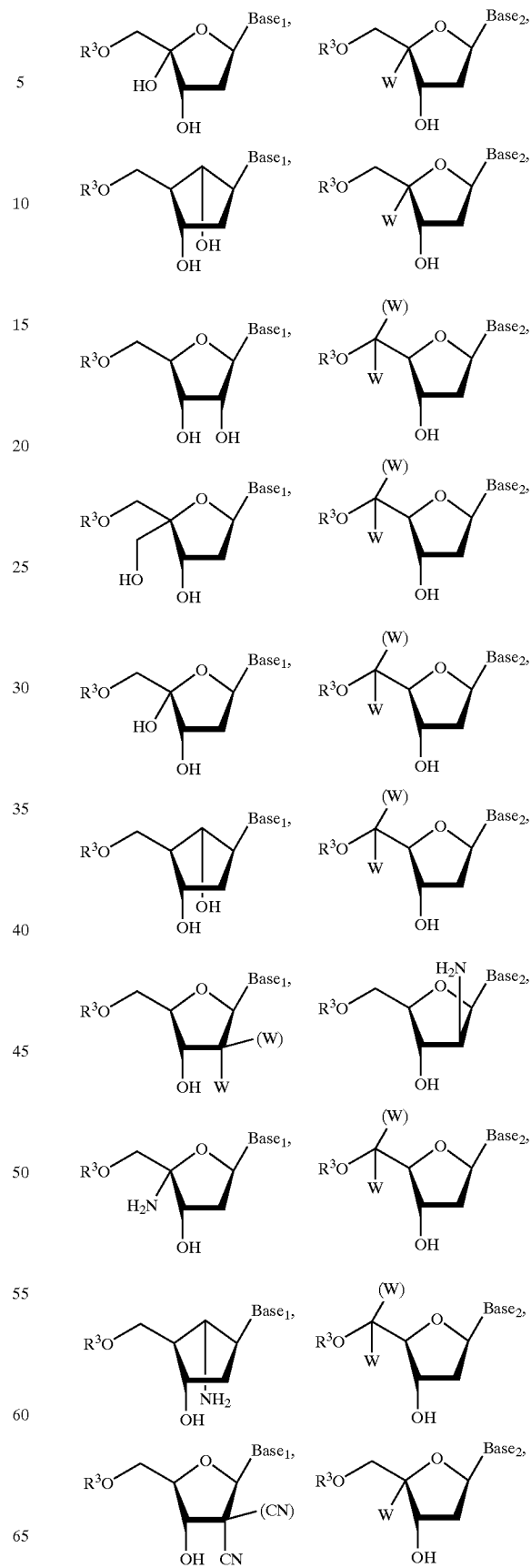

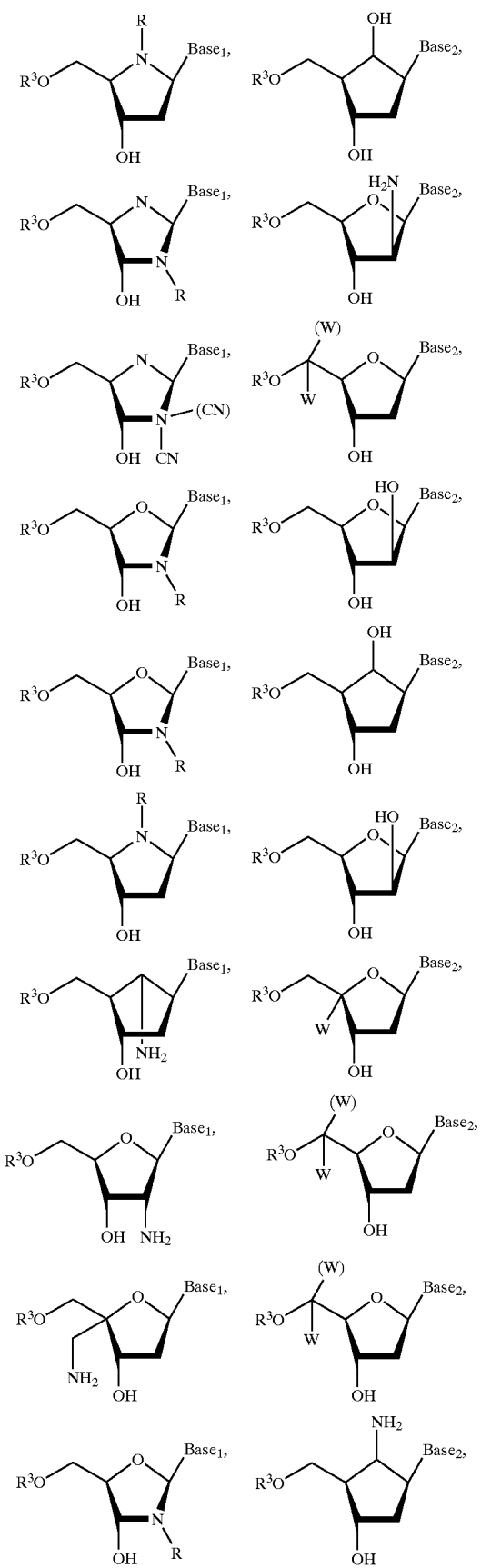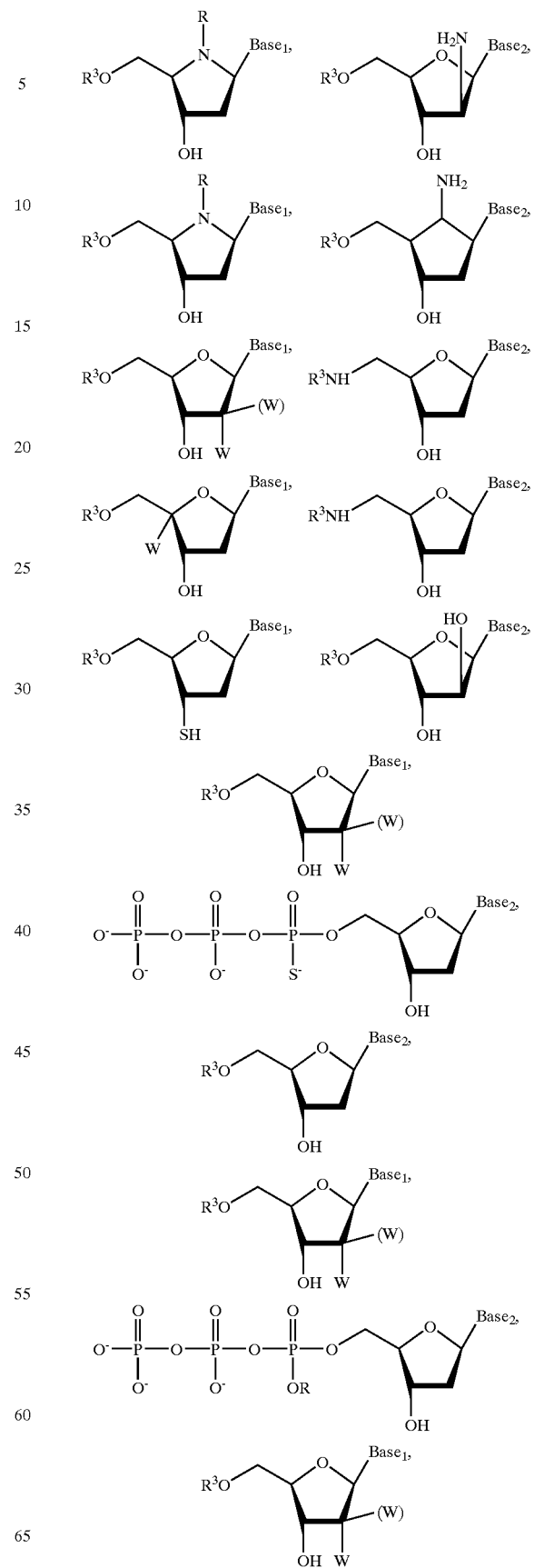

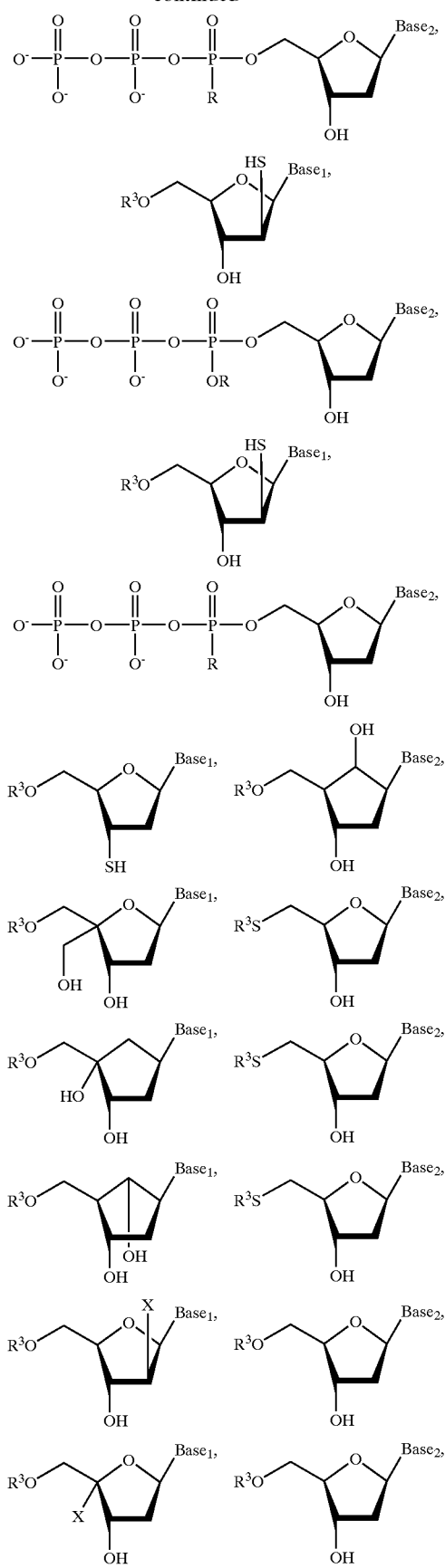
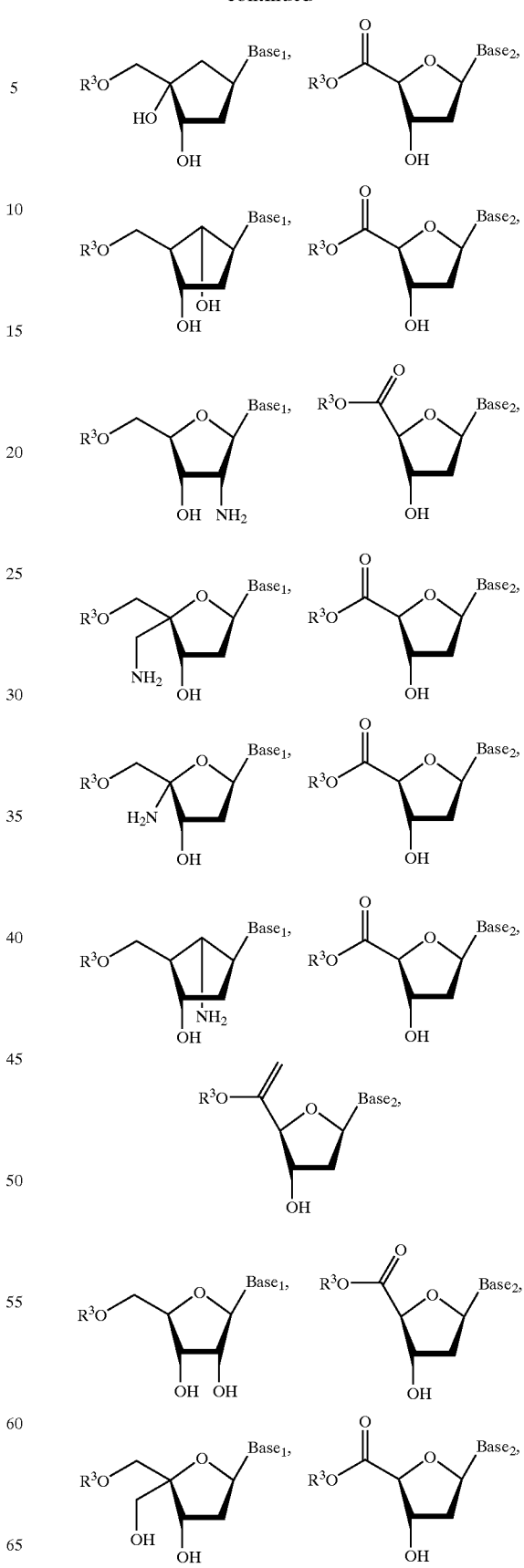

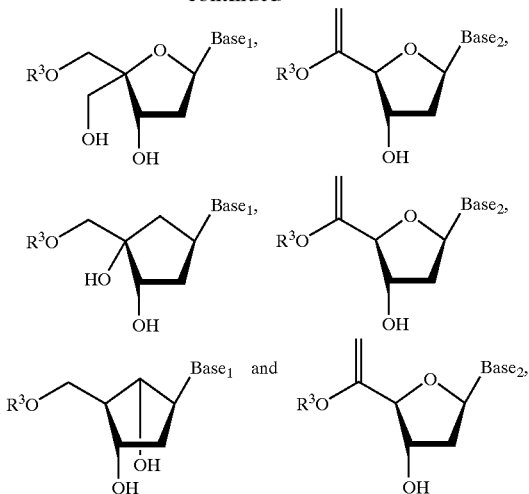

wherein:

Base$_1$ is selected from the group consisting of adenine, cytosine, guanine or inosine, and thymine or uracil;

Base$_2$ is selected from the group consisting of the remaining three bases which are not Base$_1$;

R$^3$ is O$^-$—P(=O)(O$^-$)—O—P(=O)(O$^{31}$ )—O—P(=O)(O$^{31}$ )—O—; and,

W is an electron withdrawing group;

X is leaving group;

a second W or X shown in parentheses on the same carbon atom means that a single W or X group can be in either position on the sugar or both W or both X groups can be present at the same time; and, R is a lower alkyl group;

A final aspect of this invention is a kit, comprising:

one or more modified nucleotides;

one or more polymerases capable of incorporating said one or more modified nucleotides in a polynucleotide to form a modified polynucleotide; and, a reagent or reagents capable of cleaving said modified polynucleotide at each point of occurrence of said one or more modified nucleotides in said polynucleotide.

As used herein, a "chemical method" refers to a combination of one or more modified nucleotides and one or more reagents which, when the modified nucleotide(s) is incorporated into a polynucleotide by partial or complete substitution for a natural nucleotide and the modified polynucleotide is subjected to the reagent(s), results in the selective cleavage of the modified polynucleotide at the point(s) of incorporation of the modified nucleotide(s).

By "analysis" is meant either detection of variance in the nucleotide sequence among two or more related polynucleotides or, in the alternative, the determination of the full nucleotide sequence of a polynucleotide.

By "reagent" is meant a chemical or physical force which causes the cleavage of a modified polynucleotide at the point of incorporation of a modified nucleotide in place of a natural nucleotide; such a reagent may be, without limitation, a chemical or combination of chemicals, normal or coherent (laser) visible or uv light, heat, high energy ion bombardment and irradiation. In addition, a reagent may consist of a protein such as, without limitation, a polymerase.

"Related" polynucleotides are polynucleotides obtained from genetically similar sources such that the nucleotide sequence of the polynucleotides would be expected to be exactly the same in the absence of a variance or there would be expected to be a region of overlap that, in the absence of a variance would be exactly the same, where the region of overlap is greater than 35 nucleotides.

A "variance" is a difference in the nucleotide sequence among related polynucleotides. The difference may be the deletion of one or more nucleotides from the sequence of one polynucleotide compared to the sequence of a related polynucleotide, the addition of one or more nucleotides or the substitution of one nucleotide for another. The terms "mutation," "polymorphism" and "variance" are used interchangeably herein. As used herein, the term "variance" in the singular is to be construed to include multiple variances; i.e., two or more nucleotide additions, deletions and/or substitutions in the same polynucleotide. A "point mutation" refers to a single substitution of one nucleotide for another.

A "sequence" or "nucleotide sequence" refers to the order of nucleotide residues in a nucleic acid.

As noted above, one aspect of the chemical method of the present invention consists of modified nucleotides which can be incorporated into an polynucleotide in place of natural nucleotides.

A "nucleoside" refers to a base linked to a sugar. The base may be adenine (A), guanine (G) (or its substitute, inosine (I)), cytosine (C), or thymine (T) (or its substitute, uracil (U)). The sugar may be ribose (the sugar of a natural nucleotide in RNA) or 2-deoxyribose (the sugar of a natural nucleotide in DNA).

A "nucleoside triphosphate" refers to a nucleoside linked to a triphosphate group:

O$^-$—P(=O)(O$^-$)—O—P(=O)(O$^-$)—O—P(=O)(O$^-$)—O— nucleoside. The triphosphate group has four formal negative charges which require counter-ions, i.e., positively charged ions. Any positively charged ion can be used, e.g., without limitation, Na$^+$, K$^+$, NH$_4^+$, Mg$^{2+}$, Ca$^{2+}$, etc. Na$^+$ is one of the most commonly used counter-ions. It is accepted convention in the art to omit the counter-ion, which is understood to be present, when displaying nucleoside triphosphates and that convention will be followed in this application.

As used herein, unless expressly noted otherwise, the term "nucleoside triphosphate" or reference to any specific nucleoside triphosphate; e.g., adenosine triphosphate, guanosine triphosphate or cytidine triphosphate, refers to the triphosphate made using either a ribonucleoside or a 2'-deoxyribonucleoside.

A "nucleotide" refers to a nucleoside linked to a single phosphate group or, by convention, when referring to incorporation into a polynucleotide, a short-hand for the nucleoside triphosphate which is the species which actually polymerizes in the presence of a polymerase.

A "natural nucleotide" refers to an A, C, G or U nucleotide when referring to RNA and to dA, dC, dG and dT (the "d" referring to the fact that the sugar is a deoxyribose) when referring to DNA. A natural nucleotide also refers to a nucleotide which may have a different structure from the above, but which is naturally incorporated into a polynucleotide sequence by the organism which is the source of the polynucleotide.

As used herein, inosine (I) refers to a purine ribonucleoside containing the base hypoxanthine.

As used herein, a "substitute" for a nucleoside triphosphate refers to a molecule in a different nucleoside may be naturally substituted for A, C, G or T. Thus, inosine is a natural substitute for guanosine and uridine is a natural substitute for thymidine.

As used herein, a "modified nucleotide" is characterized by two criteria. First, a modified nucleotide is a "non-natural" nucleotide. In one aspect, a "non-natural" nucleotide may be a natural nucleotide which is placed in non-natural surroundings. For example, in a polynucleotide, which is naturally composed of deoxyribonucleotides, a ribonucleotide would constitute a "non-natural" nucleotide when incorporated into that polynucleotide. Conversely, in a polynucleotide, which is naturally composed of ribonucleotides, a deoxyribonucleotide incorporated into that polynucleotide would constitute a non-natural nucleotide. In addition, a "non-natural" nucleotide may be a natural nucleotide which has been chemically altered, for example, without limitation, by the addition of one or more chemical substituent groups to the nucleotide molecule, the deletion of one or more chemical substituents groups from the molecule or the replacement of one or more atoms or chemical substituents in the nucleotide for other atoms or chemical substituents. Finally, a "modified" nucleotide may be a molecule that resembles a natural nucleotide little, if at all, but is nevertheless capable of being incorporated by a polymerase into a polynucleotide in place of a natural nucleotide.

The second criterion by which a "modified" nucleotide, as the term is used herein, is characterized is that it alter the cleavage properties of the polynucleotide into which it is incorporated. For example, without limitation, incorporation of a ribonucleotide into an polynucleotide composed predominantly of deoxyribonuclotides imparts a susceptibility to alkaline cleavage which does not exist in natural deoxyribonuclotides. This second criterion of a "modified" nucleotide may be met by a single non-natural nucleotide substituted for a single natural nucleotide (e.g., the substitution of ribonucleotide for deoxyribonucleotide described above) or by a combination of two or more non-natural nucleotides which, when subjected to selected reaction conditions, do not individually alter the cleavage properties of a polynucleotide but, rather, interact with one another to impose altered cleavage properties on the polynucleotide (termed "dinucleotide cleavage").

When reference is made herein to the incorporation of a single modified nucleotide into a polynucleotide and the subsequent cleavage of the modified polynucleotide, the modified nucleotide cannot be a ribonucleotide.

"Having different cleavage characteristics" when referring to a modified nucleotide means that modified nucleotides incorporated into the same modified polynucleotide can be cleaved under reaction conditions which leaves the sites of incorporation of each of the other modified nucleotides in that modified polynucleotide intact.

As used herein, a "stabilizing modified nucleotide" refers to a modified nucleotide that imparts increased resistance to cleavage that the site of incorporation of such a modified nucleotide. Most of the modified nucleotides described herein provide increased lability to cleavage when incorporated in a modified polynucleotide. However, the differential lability of modified nucleotides over natural nucleotides in a modified polynucleotide may not always be sufficient to allow complete cleavage at the modified nucleotide(s) while avoiding any cleavage at the natural nucleotides. Therefore there is a useful role for modified nucleotides that reduce lability (stabilizing nucleotides), in that the presence of stabilizing nucleotides in a polynucleotide which also contains nucleotides that increase lability to a particular cleavage procedure (labilizing nucleotides) can provide increased discrimination between cleaved and noncleaved nucleotides in a cleavage procedure. The preferred way to use stabilizing nucleotides in a polynucleotide is to substitute stabilizing nucleotides for all the nucleotides that are not labilizing nucleotides. In the case of mononucleotide cleavage this would entail use of three stabilizing nucleotides and one labilizing nucleotide; in the case of dinucleotide cleavage this would entail use of two stabilizing nucleotides and two (different) labilizing nucleotides.

As used herein the term "stabilizing nucleotide" refers to a modified nucleotide which, when incorporated in a polynucleotide and subjected to a cleavage procedure, reduces cleavage at the stabilizing nucleotides relative to mono or dinucleotide cleavage at other (nonstabilizing) nucleotides of the polynucleotide, whether said other nucleotides are natural nucleotides or labilizing nucleotides.

As used herein a "destabilizing modified nucleotide" or a "labilizing modified nucleotide refers to a modified nucleotide which imparts greater affinity for cleavage than a natural nucleotide at sites of incorporation of the destabilizing modified nucleotide in a polynucleotide.

As used herein "determining a mass" refers to the use of a mass spectrometer to determine the mass of a molecule. Mass spectrometers generally measure the mass to charge ratio (m/z) of analyte ions, from which the mass can be inferred. When the charge state of the analyte polynucleotide is +1 or −1 the m/z ratio and the mass are numerically the same after making a correction for the proton mass (an extra proton is added to positively charged ions and a proton is abstracted from negatively charged ions) but when the charge is >+1 or <−1 the m/z ratio will usually be less than the actual mass. In some cases the software provided with a mass spectrometer computes the mass from m/z so the user does not need to be aware of the difference.

As used herein, a "label" or "tag" refers to a molecule that, when appended by, for example, without limitation, covalent bonding or hybridization, to another molecule, for example, also without limitation, a polynucleotide or polynucleotide fragment, provides or enhances a means of detecting the other molecule. A fluorescence or fluorescent label or tag emits detectable light at a particular wavelength when excited at a different wavelength. A radiolabel or radioactive tag emits radioactive particles detectable with an instrument such as, without limitation, a scintillation counter.

A "mass-modified" nucleotide is a nucleotide in which an atom or chemical substituents has been added, deleted or substituted but such addition, deletion or substitution does not create modified nucleotide properties, as defined herein, in the nucleotide; i.e., the only effect of the addition, deletion or substitution is to modify the mass of the nucleotide.

A "polynucleotide" refers to a linear chain of nucleotides connected by a phosphodiester linkage between the 3'-hydroxyl group of one nucleoside and the 5'-hydroxyl group of a second nucleoside which in turn is linked through its 3'-hydroxyl group to the 5'-hydroxyl group of a third nucleoside and so on to form a polymer comprised of nucleosides linked by a phosphodiester backbone. The polynucleotide may be, without limitation, single or double stranded DNA or RNA or any other structure known in the art.

A "modified polynucleotide" refers to a polynucleotide in which one or more natural nucleotides have been partially or substantially completely replaced with modified nucleotides.

A "modified DNA fragment" refers to a DNA fragment synthesized under Sanger dideoxy termination conditions with one of the natural nucleotides other than the one which is partially substituted with its dideoxy analog being replaced with a modified nucleotide as defined herein. The result is a set of Sanger fragments; i.e., a set of fragments ending in ddA, ddC, ddG or ddT, depending on the dideoxy nucleotide used with each such fragment also containing modified nucleotides (if, of course, the natural nucleotide corresponding to the modified nucleotide exists in that particular Sanger fragment).

As used herein, to "alter the cleavage properties" of a polynucleotide means to render the polynucleotide differentially cleavable or non-cleavable; i.e., resistant to cleavage, at the point of incorporation of the modified nucleotide relative to sites consisting of other non-natural or natural nucleotides. It is presently preferred to "alter the cleavage properties" by rendering the polynucleotide more susceptible to cleavage at the sites of incorporation of modified nucleotides than at any other sites in the molecule.

As used herein, the use of the singular when referring to nucleotide substitution is to be construed as including substitution at each point of occurrence of the natural nucleotide unless expressly noted to be otherwise.

As used herein, a "template" refers to a target polynucleotide strand, for example, without limitation, an unmodified naturally-occurring DNA strand, which a polymerase uses as a means of recognizing which nucleotide it should next incorporate into a growing strand to polymerize the complement of the naturally-occurring strand. Such DNA strand may be single-stranded or it may be part of a double-stranded DNA template. In applications of the present invention requiring repeated cycles of polymerization, e.g., the polymerase chain reaction (PCR), the template strand itself may become modified by incorporation of modified nucleotides, yet still serve as a template for a polymerase to synthesize additional polynucleotides.

A "primer" is a short oligonucleotide, the sequence of which is complementary to a segment of the template which is being replicated, and which the polymerase uses as the starting point for the replication process. By "complementary" is meant that the nucleotide sequence of a primer is such that the primer can form a stable hydrogen bond complex with the template; i.e., the primer can hybridize to the template by virtue of the formation of base-pairs over a length of at least ten base pairs.

As used herein, a "polymerase" refers, without limitation, to molecules such as DNA or RNA polymerases, reverse transcriptases, mutant DNA or RNA polymerases mutagenized by nucleotide addition, nucleotide deletion, one or more point mutations or the technique known to those skilled in the art as "DNA shuffling" (q.v., infra) or by joining portions of different polymerases to make chimeric polymerases. Combinations of these mutagenizing techniques may also be used. A polymerase catalyzes the polymerization of nucleotides to form polynucleotides. Methods are disclosed herein and are aspects of this invention, for producing, identifying and using polymerases capable of efficiently incorporating modified nucleotides along with natural nucleotides into a polynucleotide. Polymerases may be used either to extend a primer once or repetitively or to amplify a polynucleotide by repetitive priming of two complementary strands using two primers. Methods of amplification include, without limitation, polymerase chain reaction (PCR), NASBR, SDA, 3SR, TSA and rolling circle replication. It is understood that, in any method for producing a polynucleotide containing given modified nucleotides, one or several polymerases or amplification methods may be used.

A "heat stable polymerase" or "thermostable polymerase" refers to a polymerase which retains sufficient activity to effect primer extension reactions after being subjected to elevated temperatures, such as those necessary to denature double-stranded nucleic acids.

The selection of optimal polymerization conditions depends on the application. In general, a form of primer extension may be best suited to sequencing or variance detection methods that rely on dinucleotide cleavage and mass spectrometric analysis while either primer extension or amplification (e.g., PCR) will be suitable for sequencing methods that rely on electrophoretic analysis. Genotyping methods are best suited to production of polynucleotides by amplification. Either type of polymerization may be suitable for variance detection methods of this invention.

A "restriction enzyme" refers to an endonuclease (an enzyme that cleaves phosphodiester bonds within a polynucleotide chain) that cleaves DNA in response to a recognition site on the DNA. The recognition site (restriction site) consists of a specific sequence of nucleotides typically about 4–8 nucleotides long.

As used herein, "electrophoresis" refers to that technique known in the art as gel electrophoresis; e.g., slab gel electrophoresis, capillary electrophoresis and automated versions of these, such as the use of an automated DNA sequencer or a simultaneous multi-channel automated capillary DNA sequencer or electrophoresis in an etched channel such as that which can be produced in glass or other materials.

"Mass spectrometry" refers to a technique for mass analysis known in the art which includes, but is not limited to, matrix assisted laser desorbtion ionization (MALDI) and electrospray ionization (ESI) mass spectrometry optionally employing, without limitation, time-of-flight, quadrupole or Fourier transform detection techniques. While the use of mass spectrometry constitutes a preferred embodiment of this invention, it will be apparent that other instrumental techniques are, or may become, available for the determination of the mass or the comparison of masses of oligonucleotides. An aspect of the present invention is the determination and comparison of masses and any such instrumental procedure capable of such determination and comparison is deemed to be within the scope and spirit of this invention.

As used herein, "FRET" refers to fluorescence resonance energy transfer, a distance dependent interaction between the electronic excited states of two dye molecules in which excitation is transferred from one dye (the donor) to another dye (the acceptor) without emission of a photon. A series of fluorogenic procedures have been developed to exploit FRET. In the present invention, the two dye molecules are generally located on opposite sides of a cleavable modified nucleotide such that cleavage will alter the proximity of the dyes to one another and thereby change the fluorescense output of the dyes on the polynucleotide.

As used herein "construct a gene sequence" refers to the process of inferring partial or complete information about the DNA sequence of a subject polynucleotide by analysis of the masses of its fragments obtained by a cleavage procedure. The process of constructing a gene sequence generally entails comparison of a set of experimentally determined cleavage masses with the known or predicted masses of all possible polynucleotides that could be obtained from the subject polynucleotide given only the constraints of the modified nucleotide(s) incorporated in the polynucleotide and the chemical reaction mechanism(s) utilized, both of which impact the range of possible constituent masses. Various analytical deductions may then be employed to extract the greatest amount of sequence information from the masses of the cleavage fragments. More sequence information can generally be inferred when the subject polynucleotide is modified and cleaved, in separate reactions, by two or more modified nucleotides or sets of modified nucleotides because the range of deductions that may be made from analysis of several sets of cleavage fragments is greater.

As used herein, a "sequence ladder" is a collection of overlapping polynucleotides, prepared from a single DNA or RNA template, which share a common end, usually the 5' end, but which differ in length because they terminate at different sites at the opposite end. The sites of termination coincide with the sites of occurrence of one of the four nucleotides, A,G,C or T/U, in the template. Thus the lengths of the polynucleotides collectively specify the intervals at which one of the four nucleotides occurs in the template DNA fragment. A set of four such sequence ladders, one specific for each of the four nucleotides, specifies the intervals at which all four nucleotides occur, and therefore provides the complete sequence of the template DNA fragment. As used herein, the term "sequence ladder" also refers to the set of four sequence ladders required to determine a complete DNA sequence. The process of obtaining the four sequence ladders to determine a complete DNA sequence is referred to as "generating a sequence ladder."

As used herein, "cell senscence selection" refers to a process by which cells that are susceptible to being killed by a particular chemical only when the cells are actively growing; e.g., without limitation, bacteria which can be killed by antibiotics only when they are growing, are used to find a polymerase which will incorporate a modified nucleotide into a polynucleotide. The procedure requires that, when a particular polymerase which has been introduced into the cell line incorporates a modified nucleotide, that incorporation produces changes in the cells which cause them to senesce, i.e., to stop growing. When cell colonies, some members of which contain the modified nucleotide-incorporating polymerase and some member of which don't, are then exposed to the chemical, only those cells which do not contain the polymerase are killed. The cells are then placed in a medium where cell growth is reinitiated; i.e., a medium without the chemical or the modified nucleotide, and those cells, which grow are separated and the polymerase isolated from them.

As used herein, a "chemical oxidant" refers to a reagent capable of increasing the oxidation state of a group on a molecule. For instance, without limitation, a hydroxyl group (—OH) can be oxidized to a keto group. For example and without limitation, potassium permanganate, t-butyl hypochlorite, m-chloroperbenzoic acid, hydrogen peroxide, sodium hypochlorite, ozone, peracetic acid, potassium persulfate, and sodium hypobromite are chemical oxidants.

As used herein, a "chemical base" refers to a chemical which, in aqueous medium, has a pK greater than 7.0. Examples of chemical bases are, without limitation, alkali (sodium, potassium, lithium) and alkaline earth (calcium, magnesium, barium) hydroxides, sodium carbonate, sodium bicarbonate, trisodium phosphate, ammonium hydroxide and nitrogen-containing organic compounds such as pyridine, aniline, quinoline, morpholine, piperidine and pyrrole. These may be used as aqueous solutions which may be mild (usually due to dilution) or strong (concentrated solutions). A chemical base also refers to a strong non-aqueous organic base; examples of such bases include, without limitation, sodium methoxide, sodium ethoxide and potassium t-butoxide.

As used herein, the term "acid" refers to a substance which dissociates on solution in water to produce one or more hydrogen ions. The acid may be inorganic or organic. The acid may be strong which generally infers highly concentrated, or mild, which generally infers dilute. It is, of course, understood that acids inherently have different strengths; e.g., sulfuric acid is much stronger than acetic acid and this factor may also be taken into consideration when selecting the appropriate acid to use in conjunction with the methods described herein. The proper choice of acid will be apparent to those skilled in the art from the disclosures herein. Preferably, the acids used in the methods of this invention are mild. Examples of inorganic acids are, without limitation, hydrochloric acid, sulfuric acid, phosphoric acid, nitric acid and boric acid. Examples, without limitation, of organic acids are formic acid, acetic acid, benzoic acid, p-toluenesulfonic acid, trifluoracetic acid, naphthoic acid, uric acid and phenol.

An "electron-withdrawing group" refers to a chemical group which, by virtue of its greater electronegativity inductively draws electron density away from nearby groups and toward itself, leaving the less electronegative group with a partial positive charge. This partial positive charge, in turn, can stabilize a negative charge on an adjacent group thus facilitating any reaction, which involves a negative charge, either formal or in a transition state, on the adjacent group. Examples of electron-withdrawing groups include, without limitation, cyano (C≡N), azido (–N≡N), nitro ($NO_2$), halo (F, Cl, Br, I), hydroxy (—OH), thiohydroxy (—SH) and ammonium (—$NH_3^+$).

An "electron withdrawing element," as used herein, refers to an atom which is more electronegative than carbon so that, when placed in a ring, the atom draws electrons to it which, as with an electron-withdrawing group, results in nearby atoms being left with a partial positive charge. This renders the nearby atoms susceptible to nucleophilic attack. It also tends to stabilize, and therefore favor the formation of, negative charges on other atoms attached to the positively charged atom.

An "electrophile" or "electrophilic group" refers to a group which, when it reacts with a molecule, takes a pair of electrons from the molecule. Examples of some common electrophiles are, without limitation, iodine and aromatic nitrogen cations.

An "alkyl" group as used herein refers to a 1 to 20 carbon atom straight or branched, unsubstituted group. Preferably the group consists of a 1 to 10 carbon atom chain; most preferably, it is a 1 to 4 carbon atom chain. As used herein "1 to 20," etc. carbon atoms means 1 or 2 or 3 or 4, etc. up to 20 carbon atoms in the chain.

A "mercapto" group refers to an —SH group.

An "alkylating agent" refers to a molecule which is capable of introducing an alkyl group into a molecule. Examples, without limitation, of alkyl groups include methyl iodide, dimethyl sulfate, diethyl sulfate, ethyl bromide and butyl iodide.

As used herein, the terms "selective," "selectively," "substantially," "essentially," "uniformly" and the like, mean that the indicated event occurs to a particular degree. In particular, the percent incorporation of a modified nucleotide is greater than 90%, preferably greater than 95%, most preferably, greater than 99% or the selectivity for cleavage at a modified nucleotide is greater than 10×, preferably greater than 25×, most preferably greater than 100× that of other nucleotides natural or modified, or the percent cleavage at a modified nucleotide is greater than 90%, preferably greater than 95%, most preferably greater than 99%.

As use herein, "diagnosis" refers to determining the nature of a disease or disorder. The methods of this invention may be used in any form of diagnosis including, without limitation, clinical diagnosis (a diagnosis made from a study of the signs and symptoms of a disease or disorder, where such sign or symptom is the presence of a variance), differential diagnosis (the determination of which of two or more diseases with similar symptoms is the one from which a patient is suffering), etc.

By "prognosis," as used herein, is meant a forecast of the probable course and/or outcome of a disease. In the context of this invention, the methods described herein may be used to follow the effect of a genetic variance or variances on disease progression or treatment response. It is to be noted that, using the methods of this invention as a prognostic tool does not require knowledge of the biological impact of a variance. The detection of a variance in an individual afflicted with a particular disorder or the statistical association of the variance with the disorder is sufficient. The progression or response to treatment of patients with a particular variance can then be traced throughout the course of the disorder to guide therapy or other disorder management decisions.

By "having a genetic component" is meant that a particular disease, disorder or response to treatment is known or suspected to be related to a variance or variances in the genetic code of an individual afflicted with the disease or disorder.

As used herein, an "individual" refers to any higher life form including reptiles and mammals, in particular to human beings. However, the methods of this invention are useful for the analysis of the nucleic acids of any biological organism

BRIEF DESCRIPTION OF THE TABLES

Table 1 is a description of several procedures presently in use for the detection of variance in DNA.

Table 2 shows the molecular weights of the four DNA nucleotide monophosphates and the mass difference between each pair of nucleotides.

Table 3 shows the masses of all possible 2 mers, 3 mers, 4 mers and 5 mers of the DNA nucleotides in Table 2.

Table 4 shows the masses of all possible 2 mers, 3 mers, 4 mers, 5 mers, 6 mers and 7 mers that would be produced by cleavage at one of the four nucleotides and the mass differences between neighboring oligonucleotides.

Table 5 shows the mass changes that will occur for all possible point mutations (replacement of one nucleotide by another) and the theoretical maximum size of a polynucleotide in which a point mutation should be detectable by mass spectrometry using mass spectrometers of varying resolving powers.

Table 6 shows the actual molecular weight differences observed in an oligonucleotide using the method of this invention; the difference reveals a hitherto unknown variance in the oligonucleotide.

Table 7 shows all of the masses obtained by cleavage of an exemplary 20 mer in four separate reactions, each reaction being specific for one of the DNA nucleotide; i.e., at A, C, G and T.

BRIEF DESCRIPTION OF THE FIGURES

FIG. 1 shows one plus strand primer and two minus strand primers used to produce 66 nucleotide (nt) PCR products from the human Replication Factor C (RFC) gene (38 kDA subunit). RFCbio+RFC was used to amplify the RFC sequence in GenBank, while RFCbio+RFCmut was used to amplifu a mutant sequence containing a C in place of a T, 4 nucleotides from the 5' end of RFCmut.

FIG. 2 shows the length and mass of the cleavage products anticipated from incorporation of 7-methyl-dGTP into the extension product followed by cleavage with piperidine. Only one fragment is expected to change in mass; i.e., the 3' terminal 10 mer.

FIG. 4A shows the MALDI-TOF mass spectrum of the fragments of the extension product (T-variant) shown in FIG. 2 after full substitution of 7-methyl-dGTP for dGTP and cleavage with piperidine. The insert is a blow-up of that region of the spectrogram containing the two 10 mers.

FIG. 4B shows the expected masses of the 8 mer and the two 10 mers from FIG. 4A. Although mass accuracy is off by about 20 Da, the differences are very close to the predicted values: 511.97 for the difference between the 8 mer and the invariant 10 mer compared to 512.32 predicted and 15.39 for the difference between the 10 mers compared to 15.02 expected.

FIG. 5A shows the MALDI-TOF mass spectrum of the fragments of the extension product (C-variant) shown in FIG. 2 after full substitution of 7-methyl-dGTP for dGTP and cleavage with piperidine. The primer mass, 6575.79 appears to the right of the spectrum while the two 10 mers and the 8 mer appear to the left and in the insert.

FIG. 5B shows the expected masses of the 8 mer and the two 10 mers from FIG. 5A. The mass difference between the invariant 10 mer and the 8 mer is very close to the predicted value, 512.74 found, 512.32 predicted, while the mass difference between the two 10 mers is far from the predicted value, 319.93 found, 30.04 predicted.

FIG. 6A shows the MALDI-TOF mass spectrum of the RFC and RFCmut primers used to produce the extension products shown in FIGS. 3 and 5.

FIG. 6B shows the expected masses and mass differences of the two primers as well as the expected mass difference of a RFCmut missing a G. The spectrum in 6A suggests that the latter was in fact the case—apparently, the primer received from the commercial source was missing a G, which explains the indicated discrepancies in both FIG. 3 and FIG. 5.

FIG. 7A shows that substitution of 5'-amino-dTTP for dTTP had no ill effect on primer extension (lane 1 is the natural extension product, lane 3 is the extension product with 5'-NH$_2$-dTTP for dTTP substitution). The effect of treatment with glacial acetic acid is shown in lanes 2 (natural extension product, no effect), 4 (nucleotide substitution, 1 hour treatment) and lane 5 (nucleotide substitution, 2 hour treatment).

FIG. 8A shows the result of primer extension of a 7.2 kb M13 template in the presence of 5'-NH$_2$-dTTP and subsequent restriction with Msc I before heat denaturing of the extension product, which results in mostly the 7.2 kb product.

FIG. 8B show the result of restriction with Msc I after heat denaturing, which gives a 1.2 kb product.

FIG. 14A illustrates a hypothetical human DNA sequence modeled after data reported in Martin-Gallardo, et al., *Nature Genetics,* 1992, 1:34–39. The consensus length of the Alu repeat elements is 280 nucleotides. 3The partial L1 element is approximately 850 nucleotides long.

FIG. 14B illustrates the distribution of DNA sequences obtained by shotgun sequencing with 7-fold redundant coverage. Sequences are represented by horizontal black lines while repeat elements are represented by shading behind the sequences to illustrate the fact that many sequence reads start or end in Alu or L1 repeat sequences which hinders definitive assignment of sequence overlaps.

FIG. 14C illustrates the same analysis using the method of this invention with full or partial substitution of a modified nucleotide for a natural nucleotide followed by cleavage and analysis of the fragments. The steps to achieve this result are depicted in FIGS. 15–18.

FIG. 15 illustrates the steps for sequencing a 2.7 kb double stranded DNA using the method of this invention and 5'-amino nucleoside triphosphates as the modified nucleotides. A: linearize pUC19 with Hinell (or can perform primer extension using a circular duplex template); denature duplex DNA. B: primer extend in presence of four dNTPs and one 5'-$NH_2$-dNTP at a ratio that produces partial substitution of the 5'-amino nucleotide for the natural nucleotide; purify extension product. C: digest with Dde I to give fragments shown. D: end label recessed Ddel ends with rhodamine-dUTP (R 110) using polymerase fill-in ends (Klenow exo- polymerase. E: fractionate labeled digestion products; cleave with acid; analyze fragments using, for example capillary electrophoresis.

FIG. 16 shows the separation by HPLC of fragments from Dde I restriction endonuclease digested, rhodamine dUTP end-labeled pUC19 DNA. The fragments were resolved using an HP ZORBAX-Eclipse HPLC column at 45° C. and 0.1 M TEAA, pH 7.0, 0.1 mM EDTA as buffer A and 25% $CH_3CN$, 75% buffer A as buffer B; gradient 60–34% A over 2 minutes, 34–20% A over 22 minutes and 20-0% A over 1 minute.

FIG. 17 shows a comparison of long range sequencing using the method of this invention (5'-amino nucleoside triphosphate modified nucleotides) with dideoxy sequencing. The first row of panels shows the result from the dideoxy chain termination reactions—loss of signal by 1 kb. The second row of panels shows the results using partial substitution with a modified nucleotide followed by chemical cleavage—strong signal to 4 kb. The third row of panels are molecular size markers from 100 nt to 4,000 nt.

FIG. 18 is a comparison of sequencing ladders obtained by chain termination (Sanger) sequencing (the ddA lane) compared to the method of this invention using 5'-amino-A with progressively greater amounts of acid in the cleavage reaction.

Figure 22:
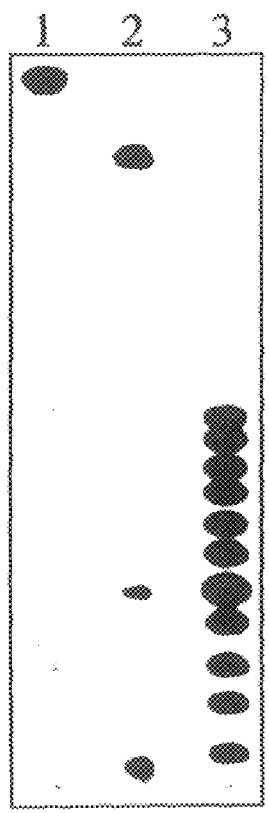

FIG. 22 illustrates dinucleotide cleavage at GT in one allele of the transferrin receptor gene. Primer extension was carried out using RGTP, 5'-aminoTTP, dCTP, dGTP and α-$^{32}$P-dCTP (for body-labeling if DNA fragments). A 1:4 mixture of Klenow (exo-) and E710A Klenow (exo-) was used for extension. Lane 1 is the full length 87 nt fragment extended with natural dNPs, lane 2 is the result of dinucleotide cleavage of the extension product containing rGTP and 5'-aminoTTP and lane 3 are molecular weight markers 12 nt to 32 nt.

Figure 23:
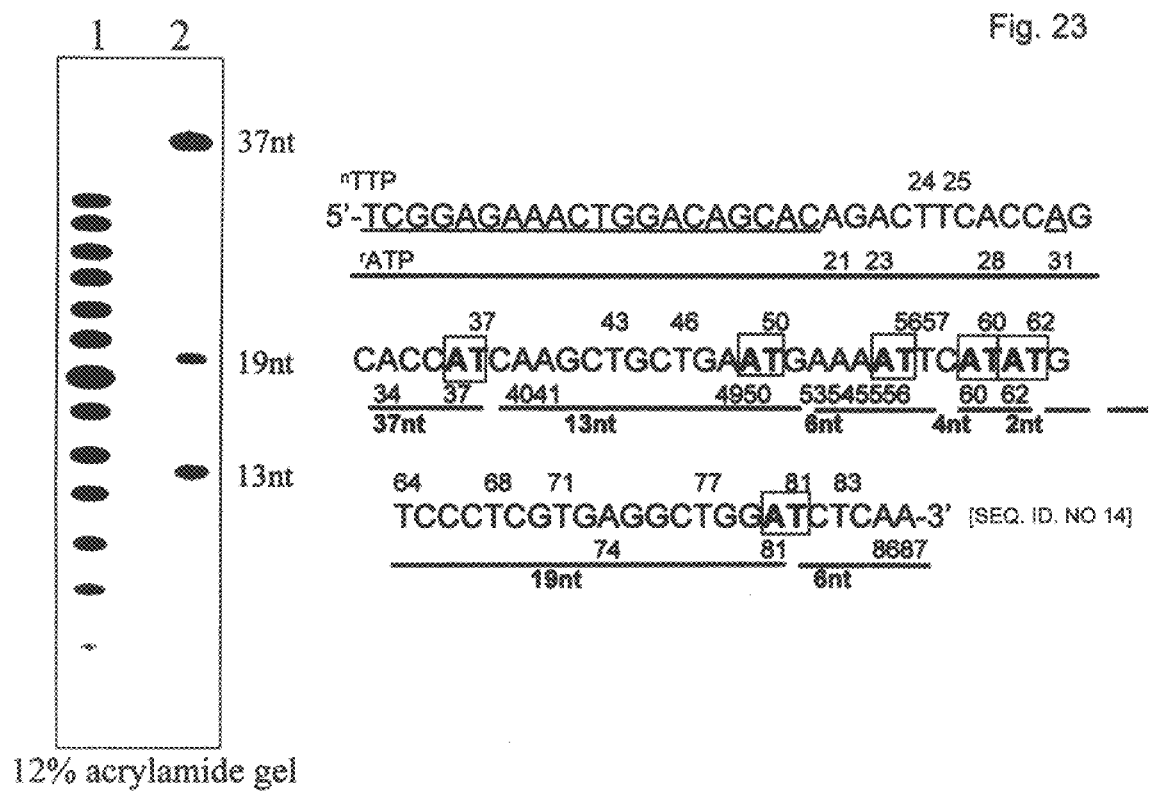

FIG. 23 illustrates dinucleotide cleavage at AT in the serine allele of the transferrin receptor gene. The primer is lightly underlined. The heavy underlining shows the expected fragments from AT dinucleotide cleavage. Lane 1 is the molecular size marker, lane 2 is the result of dinucleotide cleavage at the sites of incorporation of modified A adjacent to modified T.

Figure 24:
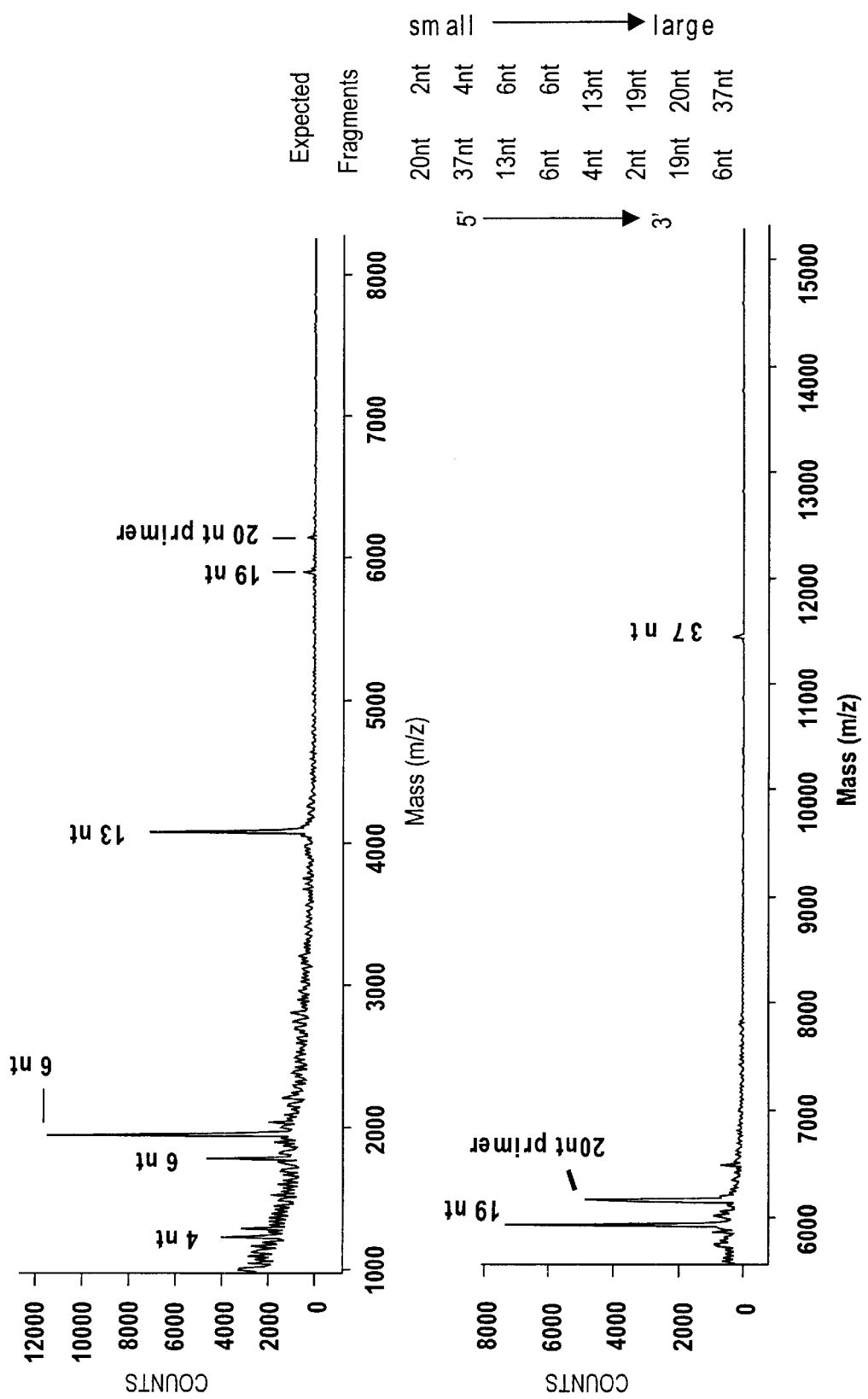

FIG. 24 shows the MALDI-TOF mass spectra of the AT dinucleotide cleavage products from the 87 nt transferrin receptor fragment of FIG. 23. All fragments are observed except for a 2 nt fragment.

Figure 25:
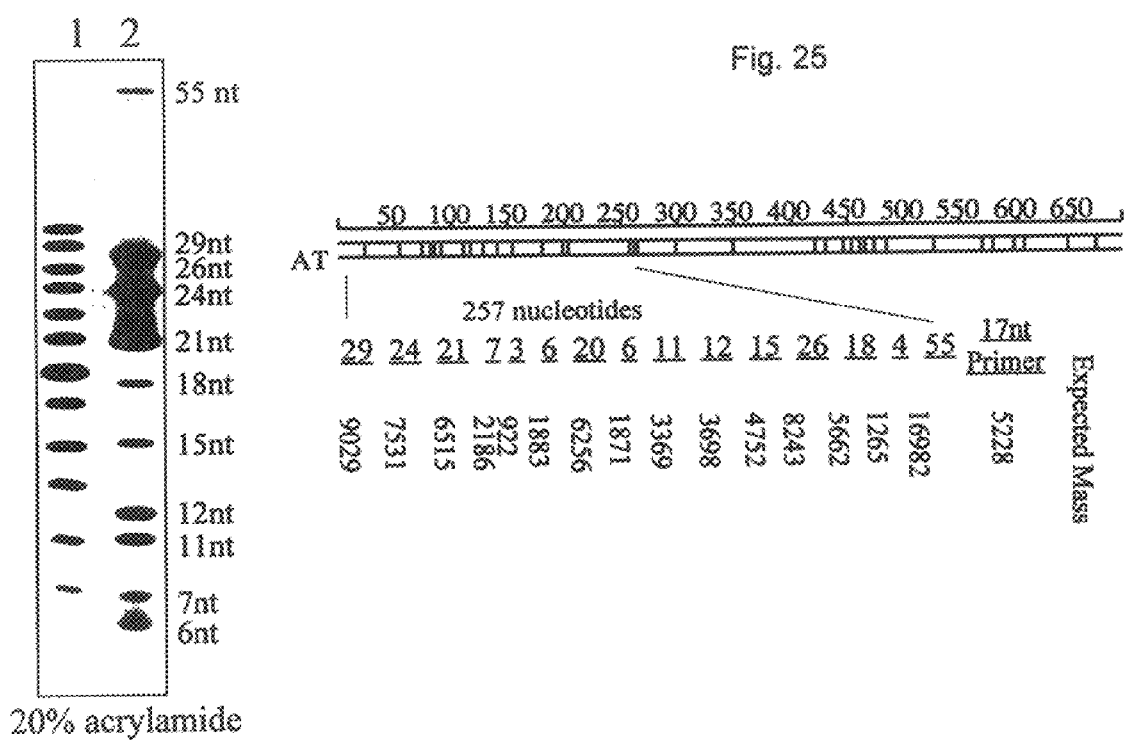

FIG. 25 illustrates the primer extension of M13mp18 DNA followed by dinucleotide cleavage at AT sites. The occurrence of AT dinucleotides is shown for the first 257 nucleotides as are the expected products of AT cleavage. Lane 1 is molecular size markers, lane 2 is the result of dinucleotide cleavage. All expected fragments of 6 nucleotides and greater are observed.

Figure 26:
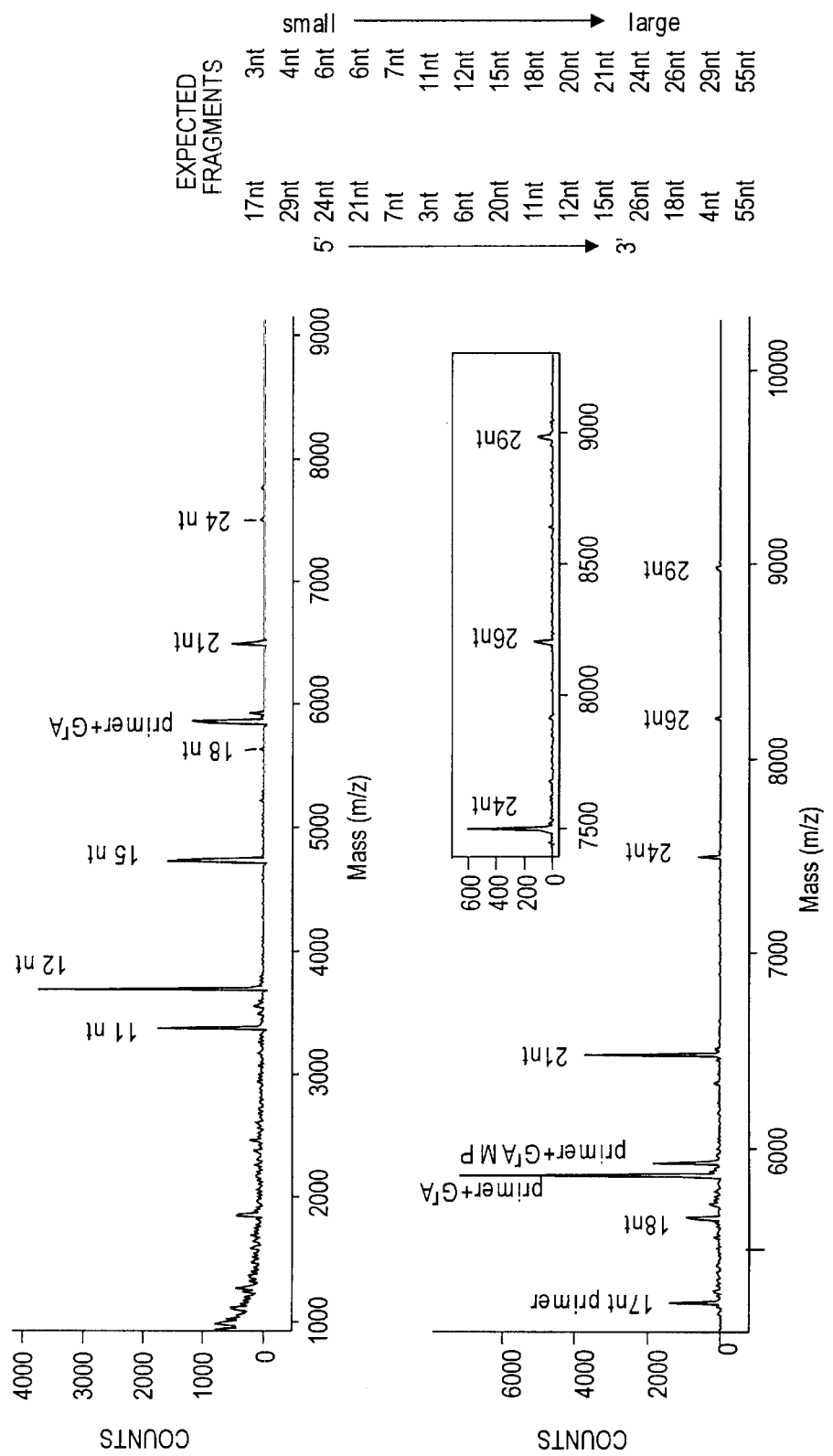

FIG. 26 shows the MALDI-TOF mass spectra of the fragments obtained from AT dinucleotide cleavage of the 257 nt fragment of the M13mp18 DNA shown in FIG. 25.

FIGS. 27–33 demonstrate the application of mononucleotide cleavage to genotyping by mass spectrometry, capillary electrophoresis and FRET.

Figure 27:
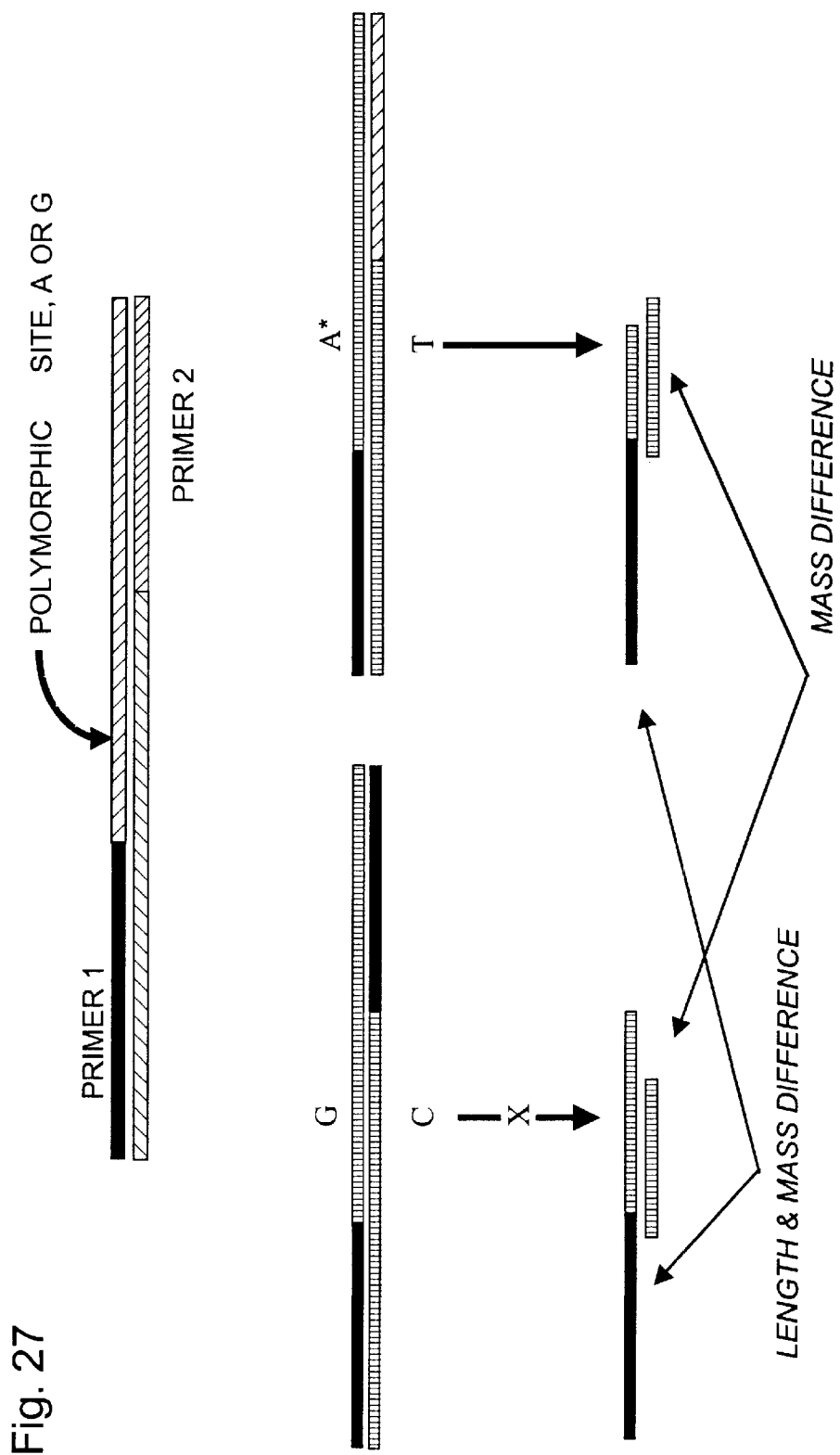

FIG. 27 is a schematic representation of genotyping by chemical restriction. The template is amplified using one cleavable nucleotide analog, dA*TP. The amplicons are chemically restricted to give fragments with the indicated length and mass differences. The fragments obtained can be analyzed by mass spec of electrophoresis.

FIGS. 28A–C show the steps in genotyping a polynucleotide by mass spectrometry: (A) shows the PCR amplification of an 82 bp fragment of transferrin receptor and indicates the site of polymorphism; (B) indicates the amplification in the presence of a modified nucleotide, dA*TP, the structure of which is shown; and, (C) is a gel comparing amplification with unmodified nucleotide and with modified nucleotide and shows that full substitution with modified nucleotide is compatible with efficient PCR amplification.

FIGS. 29A–B illustrate genotyping by detection by mass differences obtained from the amplification and cleavage of the variant forms of transferrin receptor. Only the fragments that illustrate the length and mass differences among the fragments of the same (invariant) and different (variant) alleles are shown.

FIG. 30A is another illustration of genotyping by mass spectrometry. The spectrum is a MALDI-TOF analysis of a chemically restricted DNA fragment. The boxed areas are regions that contain fragments with polymorphism.

FIG. 30B is another illustration of genotyping by mass spectrometry, this time looking as length differences. The spectra constitute a MALDI-TOF comparison of chemically restricted primer fragments of homozygote and heterozygote samples. The figure shows the mass spectra of three genotypes in the region of 7000 Da to 9200 Da.

FIG. 31A illustrates genotyping by mass spectrometry wherein mass differences are detected. The spectrum is the result of a MALDI-TOF analysis of a heterozygote sample that has been chemically restricted in the presence of tris (2-carboxymethyl)phosphine and piperidine.

FIG. 31B shows the proposed chemical structure of the cleavage product obtained under the conditions indicated in FIG. 31A.

FIGS. 32A–B illustrates genotyping by chemical cleavage followed by electrophoresis. In (A) the capillary electrophoresis analysis of a chemically restricted polymorphic DNA fragment is depicted. In (B), the denaturing 20% PAGE analysis of the chemically restricted amplicon is shown.

FIGS. 33 A–D illustrate genotyping by fluorescence resonance energy transfer (FRET): (A) amplify template using one modified, cleavable nucleotide (DA*TP). Primer 1 is modified with a fluor, F1; (B) after cleavage a probe modified with a second fluor, F2, and complementary to primer 1 is added; (C) at elevated temperature, the allele shortened by cleavage is not bound to the probe (and, therefore, no FRET is produced) while the uncleaved allele remains bound giving a FRET. (D) shows a means for positive detection of the short fragment by modifying the probe to contain a hairpin and an additional fluor, F3. The hairpin will open only after binding with the longer, uncleaved fragment resulting in a difference in FRET production.

DETAILED DESCRIPTION OF THE INVENTION

In one aspect, this invention relates to a method for detecting a variance in the nucleotide sequence among related polynucleotides by replacing a natural nucleotide in a polynucleotide at substantially each point of incorporation of the natural nucleotide with a modified nucleotide, cleaving the modified polynucleotide at substantially each point of incorporation of the modified nucleotide, determining the mass of the fragments obtained and then comparing the masses with those expected from a related polynucleotide of known sequence or, if the sequence of a related polynucleotide is unknown, by repeating the above steps with a second related polynucleotide and then comparing the masses of the fragments obtained from the two related polynucleotides. Of course, it is understood that the methods of this invention are not limited to any particular number of related polynucleotides; as many as are needed or desired may be used.

In another aspect, this invention relates to a method for detecting a variance in the nucleotide sequence among related polynucleotides by replacing two natural nucleotides in a polynucleotide with two modified nucleotides, the modified nucleotides being selected so that, under the chosen reaction condition, they individually do not impart selective cleavage properties on the modified polynucleotide. Rather, when the two modified nucleotides are contiguous; i.e., the natural nucleotides being replaced were contiguous in the unmodified polynucleotide, they act in concert to impart selective cleavage properties on the modified polynucleotide. In addition to mere proximity, it may also be necessary, depending on the modified nucleotides and reaction conditions selected, that the modified nucleotides are in the proper spatial relationship. For example, PATENT without limitation, 5'A-3'G might be susceptible to cleavage while 5'G-3'A might not. As above, once substitution of the modified nucleotides for the natural nucleotides has been accomplished, the modified nucleotide pair is cleaved, the masses of the fragments are determined and the masses are compared, either to the masses expected from a related polynucleotide of known sequence or, if the sequence of at least one of the related polynucleotides is not known, to the masses obtained when the procedure is repeated with other related polynucleotides.

In another aspect, this invention relates to methods for detecting mono- or dinucleotide cleavage products by electrophoresis or fluorescence resonance energy transfer (FRET). In FRET-based assays, the presence or absence of fluorescence over a specified wavelength range is monitored. Both these methods are particularly well suited for detecting variance at a single site in a polynucleotide where the variance has been previously identified. Knowledge of the particular variance permits the design of electrophoretic or FRET reagents and procedures specifically suited to the rapid, low cost, automatable determination of the status of the variant nucleotide(s). Examples of electrophoretic and FRET detection of cleavage products are described below and in the —Figures.

The use of the variance detection methods of this invention for the development of and use as diagnostic or prognostic tools for the detection of predisposition to certain diseases and disorders is another aspect of this invention.

In the development of diagnostic tools, the methods of this invention would be employed to compare the DNA of a test subject which is displaying symptoms of a particular disease or disorder known or suspected to be genetically-related or is displaying a desirable characteristic such as a health enhancing or economically valuable trait such as growth rate, pest resistance, crop yield, etc. with the DNA of healthy members of the same population and/or members of the population which exhibit the same disease, disorder or trait. The test subject may be, without limitation, a human, any other mammal such as rat, mouse, dog, cat, horse, cow, pig, sheep, goat, etc., cold-blooded species such as fish or agriculturally important crops such as wheat, corn, cotton and soy beans. The detection of a statistically significant variance between the healthy members of the population and members of the population with the disease or disorder would serve as substantial evidence of the utility of the test for identifying subjects having or at risk of having the disease or disorder. This could lead to very useful diagnostic tests.

Using the methods of this invention as a diagnostic or prognostic tool, it is entirely unnecessary to know anything about the variance being sought; i.e., its exact location, whether it is an addition, deletion or substitution or what nucleotide(s) have been added, deleted or substituted. The mere detection of the presence of the variance accomplishes the desired task, to diagnose or predict the incidence of a disease or disorder in a test subject. In most instances, however, it would be preferable to be able to create a specific genotyping test for a particular variance with diagnostic or prognostic utility.

Particularly useful aspects of the genotyping methods described herein are ease of assay design, low cost of reagents and suitability of the cleavage products for detection by a variety of methods including, without limitation, electrophoresis, mass spectrometry and fluorescent detection.

In another aspect of this invention, the complete sequence of a polynucleotide may be determined by repeating the above method involving the replacement of one natural nucleotide at each point of occurrence of the natural nucleotide with one modified nucleotide followed by cleavage and mass detection. In this embodiment, the procedure is carried out four times with each of the natural nucleotides; i.e., in the case of DNA, for example but without limitation, each of dA, dC, dG and T is replaced with a modified nucleotide in four separate experiments. The masses obtained from the four cleavage reactions can then be used to determine the complete sequence of the polynucleotide. This method is applicable to polynucleotides prepared by primer extension or amplification by, for example, PCR; in the latter case both strands undergo modified nucleotide replacement.

An additional experiment may be necessary should the preceding procedure leave any nucleotide positions in the sequence ambiguous (see, e.g., the Examples section, infra). This additional experiment may be repeating the above procedure using the complementary strand of the DNA being studied if the method involves primer extension. The additional experiment may also be the use of the above described method for replacing two natural nucleotides with two modified nucleotides, cleaving where the modified nucleotides are contiguous and then determining masses of the fragments obtained. Knowledge of the position of contiguous nucleotides in the target polynucleotide may resolve the ambiguity. Another experiment which might be employed to resolve any ambiguity which might occur in the main experiment is one-pass Sanger sequencing followed by gel electrophoresis which is fast and easy but which alone would not afford highly accurate sequencing. Thus, in conjunction with the methods of this invention, an alternative sequencing method known in the art might, in the case of a specific ambiguity, provide the information necessary to resolve the ambiguity. Combinations of these procedures might also be used. The value of using different procedures lies in the generally recognized observation that each sequencing method has certain associated artifacts that compromise its performance but the artifacts are different for different procedures. Thus, when the goal is highly accurate sequencing, using two or more sequencing techniques which would tend to cancel out each other's artifacts should have great utility. Other experiments, which might resolve an ambiguity, will, based on the disclosures herein and the specific sequence ambiguity at issue, be apparent to those skilled in the art and are, therefore, deemed to be within the scope of this invention.

In yet another aspect of this invention, the modified nucleotide cleavage reactions described herein may result in the formation of a covalent bond between one of the cleavage fragments and another molecule. This molecule may serve a number or purposes. It may contain a directly detectable label or a moiety that enhances detection of the cleavage products during mass spectrometric, electrophoretic or fluorogenic analysis. For example, without limitation, the moiety may be a dye, a radioisotope, an ion trap to enhance ionization efficiency, an excitable group which can to desorbtion efficiency or simply a large molecule which globally alter desorbtion and/or ionization characteristics. The labeling reaction may be partial or complete. An example of the use of homogeneously labeled DNA fragments of controllable size is in DNA hybridization such as hybridization probes for DNA on high-density arrays like DNA chips.

An additional aspect of this invention is the replacement of a natural nucleotide with a modified nucleotide at only a percentage of the point of occurrence of that natural nucleotide in a polynucleotide. This percentage may be from about 0.01% to about 95%, preferably it is from about 0.01% to about 50%, more preferably from about 0.01% to about 10% and most preferably from about 0.01% to about 1%. The percent replacement is selected to be complementary to the efficiency of the cleavage reaction selected. That is, if a cleavage reaction of low efficiency is selected, then a higher percentage of substitution is permissible; if a cleavage reaction of high efficiency is selected, then a low percentage of replacement is preferred. The result desired is that, on the average, each individual strand of polynucleotide is cleaved once so that a sequencing ladder, such as that described for the Maxam-Gilbert and Sanger procedures, can be developed. Since the cleavage reactions described herein are of relatively high efficiency, low percentages of replacement are preferred to achieve the desired single cleavage per polynucleotide strand. Low percentages of replacement may also be more readily achieved with available polymerases. However, based on the disclosures herein, other cleavage reactions of varying degrees of efficiency will be apparent to those skilled in the art and, as such, are within the scope of this invention. It is, in fact, an aspect of this invention that, using cleavage reactions of sufficiently low efficiency, which, in terms of percentage cleavage at points of incorporation of a modified nucleotide in a modified polynucleotide may be from about 0.01% to 50%, preferably from about 0.01% to 10% and, most preferably, from about 0.01% to about 1%, a polynucleotide in which a natural nucleotide has been replaced with a modified nucleotide at substantially each point of occurrence may still be used to generate the sequencing ladder. At the most preferred level of efficiency, about 0.01% to about 1%, each strand of a fully modified polynucleotide should, on the average, only be cleaved once.

In another aspect, this invention relates to methods for producing and identifying polymerases with novel properties with respect to incorporation and cleavage of modified nucleotides.

A. Nucleotide Modification and Cleavage (1) Base Modification and Cleavage

A modified nucleotide may contain a modified base, a modified sugar, a modified phosphate ester linkage or a combination of these.

Base-modification is the chemical modification of the adenine, cytosine, guanine or thymine (or, in the case of RNA, uracil) moiety of a nucleotide such that the resulting chemical structure renders the modified nucleotide more susceptible to attack by a reagent than a nucleotide containing the unmodified base. The following are examples, without limitation of base modification. Other such modification of bases will become readily apparent to those skilled in the art in light of the disclosures herein and therefore are to be considered to be within the scope of this invention (e.g., the use of difluorotoluene; Liu, D., at al., *Chem. Biol.*, 4:919–929, 1997; Moran, S., et al., *Proc. Natl. Acad. Sci. USA*, 94:10506–10511,1997).

Some examples, without limitation, of such modified bases are described below.

1. Adenine (1) can be replaced with 7-deaza-7-nitroadenine (2). The 7-deaza-7-nitroadenine is readily incorporated into polynucleotides by enzyme-catalyzed polymerization. The 7-nitro group activates C-8 to attack by chemical base such as, without limitation, aqueous sodium hydroxide or aqueous piperidine, which eventually results in specific strand scission. Verdine, et al., *JACS*, 1996, 118:6116–6120;

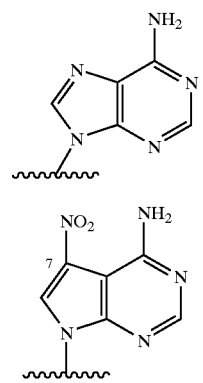

We have found that cleavage with piperidine is not always complete whereas complete cleavage is the desired result. However, when the cleavage reaction is carried out in the presence of a phosphine derivative, for example, without limitation, tris(2-carboxyethyl) phosphine (TCEP) and a base, complete cleavage is obtained. An example of such a cleavage reaction is as follows: DNA modified by incorporation of 7-nitro-7-deaza-2'-deoxyadenosine is treated with 0.2 M TCEP/1 M piperidine/ 0.5 M Tris base at 95° C. for one hour. Denaturing polyacrylamide gel (20%) analysis showed complete cleavage. Other bases such as, without limitation, $NH_4OH$ can be used in place of the piperidine and Tris base. This procedure, i.e., the use of a phosphine in conjunction with a base, should be applicable to any cleavage reaction in which the target polynucleotide has been substituted with a modified nucleotide which is labile to piperidine.

The product of cleavage with TCEP and base is unique. Mass spectrometry analysis was consistent with a structure having a phosphate-ribose-TCEP adduct at 3' ends and a phosphate moiety at 5' ends, i.e. structure 3.

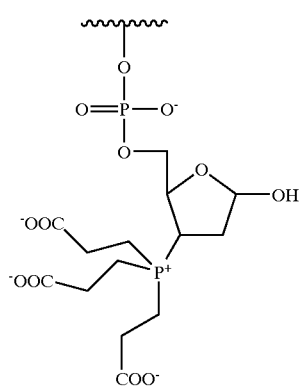

How TCEP participates in the fragmentation of a modified polynucleotide is not presently known; however, without being held to any particular theory, we believe that the mechanism may be the following:

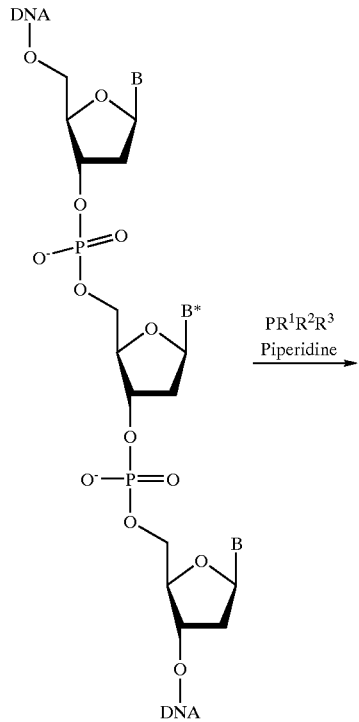

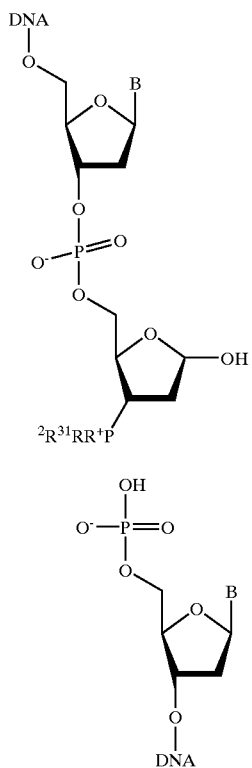

The incorporation of the TCEP (or other phosphine) into the cleavage product should be a very useful method for labeling fragmented polynucleotides at the same time cleavage is being performed. By using an appropriately functionalized phosphine that remains capable of forming an adduct at the 3' end ribose as described above, such functionalities, without limitation, as mass tags, fluorescence tags, radioactive tags and ion-trap tags could be incorporated into a fragmented polynucleotide. Phosphines that contain one or more tags and that are capable of covalently bonding to a cleavage fragment constitute another aspect of this invention. Likewise, the use of such tagged phosphines as a method for labeling polynucleotide fragments is another aspect of this invention.

While other phosphines, which may become apparent to those skilled in the art based on the disclosures herein, may be used to prepare labeled phosphines for incorporation onto nucleotide fragments, TCEP is a particularly good candidate for labeling. For instance, the carboxy (—C(O)OH) groups may be modified directly by numerous techniques, for example, without limitation, reaction with an amine, alcohol or mercaptan in the presence of a carbodiimide to form an amide, ester or mercaptoester as shown in the following reaction scheme:

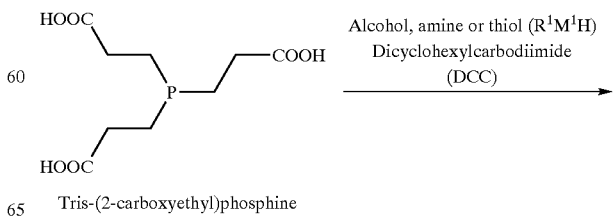

Tris-(2-carboxyethyl)phosphine

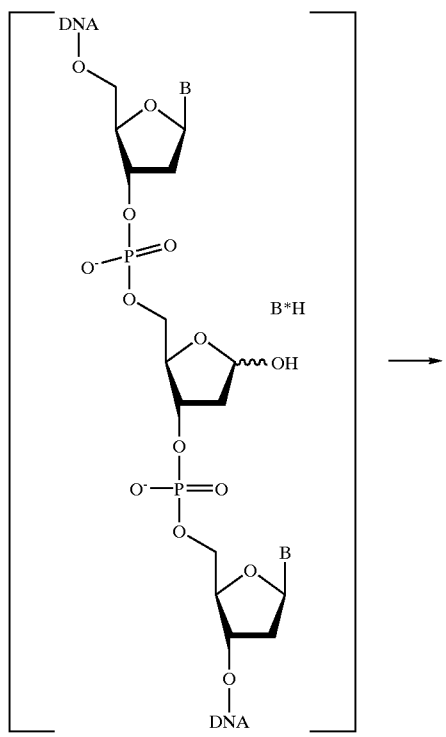

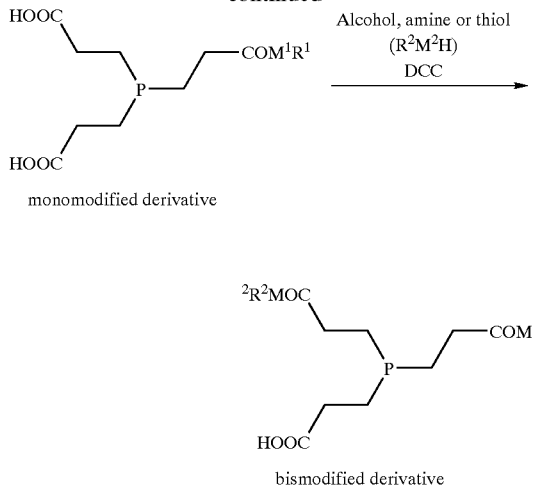

monomodified derivative

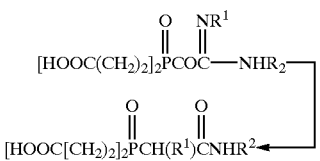

bismodified derivative

When a carboxy group is reacted with a carbodiimide in the absence of a nucleophile (the amine in this case) the adduct between the carbodiimide and the carboxy group may rearrange to form a stable N-acylurea. If the carbodiimide contains a fluorphore, the resultant phosphine will then carry that fluorophore as shown in the following reaction scheme:

$R^1N=C=NR^2$ + P[(CH$_2$)$_2$COOH]$_3$ ⟶

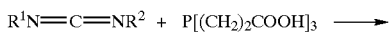

wherein, $M^1$ and $M^2$ are independently O, NH, NR, S.

$R^1$ and $R^2$ are mass tags, fluorescent tags, radioactive tags, ion trap tags or combinations thereof.

Amino group-containing fluorophores such as fluoresceinyl glycine amide (5-(aminoacetamido)fluorescein, 7-amino-4-methylcoumarin, 2-aminoacridone, 5-aminofluorescein, 1-pyrenemethylamine and 5-aminoeosin may be used to prepare the labeled phosphines of this method. Amino derivatives of lucifer yellow and Cascade Blue may also be used as can amino derivatives of biotin. In addition, hydrazine derivatives such as rhodamine and Texas Red hydrazine may be useful in this method.

Fluorescent diazoalkanes, such as, without limitation, 1-pyrenyl-diazomethane, may also be used to form esters with TCEP.

Fluorescent alkyl halides may also react with the anion of the carboxy group, i.e., the C(O)O$^-$ group, to form esters. Among the halides which might be used are, without limitation, panacyl bromide, 3-bromoacetyl-7-diethylamino-coumarin, 6-bromoacetyl-2-diethylaminonaphthalene, 5-bromomethylluorescein, BODIPY® 493/503 methyl bromide, monobromobimanes and iodoacetamides such as coumarin iodoacetamide may serve as effective label-carrying moieties which will covalently bond with TCEP.

Naphthalimide sulfonate ester reacts rapidly with the anions of carboxylic acids in acetonitrile to give adducts which are detectable by absorption at 259 nm down to 100 femtomoles and by fluorescence at 394 nm down to four femtomoles.

There are, furthermore, countless amine-reactive fluorescent probes available and it is possible to covert TCEP into an primary amine by the following reaction:

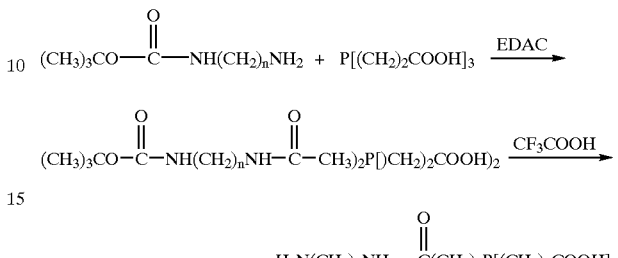

The aminophospine can then be used to form label-containing aminophosphines for use in the cleavage/labeling method described herein.

The above dyes and procedures for covalently bonding them to TCEP are but a few examples of the possible adducts which can be formed. A valuable source of additional such reagents and procedures is the catalog of Molecular Probes, Inc. Based on the disclosures herein and resources such as the Molecular Probes catalog, many others way to modify phosphines, in particular TCEP, will be apparent to those skilled in the art. Those other ways to modify phosphines for use in the incorporation of labels into polynucleotide fragments during chemical cleavage of the polynucleotide are within the scope of this invention.

2. Cytosine (4) can be replaced with 5-azacytosine (5). 5-Azacytosine is likewise efficiently incorporated into polynucleotides by enzyme catalyzed polymerization. 5-Azacytosine is susceptible to cleavage by chemical base, particularly aqueous base, such as aqueous piperidine or aqueous sodium hydroxide. Verdine, et al., *Biochemistry*, 1992, 31:11265–11273;

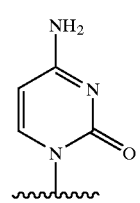

4

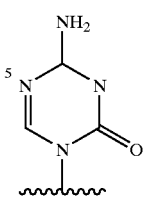

5

3(a). Guanine (6) can be replaced with 7-methylguanine (7) and can likewise be readily incorporated into polynucleotides by polymerases (Verdine, et al., *JACS*, 1991, 113:5104–5106 ) and is susceptible to attack by chemical base, such as, without limitation, aqueous piperidine (Siebenlist, et al.,*Proc. Natl. Acad. Sci. USA*, 1980, 77:122); or,

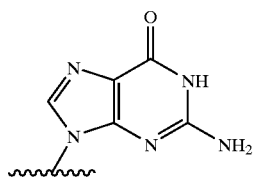

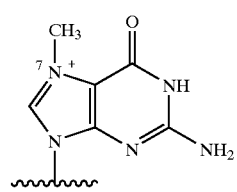

3(b). Gupta and Kool, Chem. Commun. 1997, pp 1425–26 have demonstrated that $N^6$-allyl-dideoxyadenine, when incorporated into a DNA strand, will cleave on treatment with a mild electrophile, $E^+$, in their case iodine. The proposed mechanism is shown in Scheme 1:

A similar procedure might be employed with guanine using the previously unreported 2-allylaminoguanine derivative 8, which can be prepared by the procedure shown in Scheme 2:

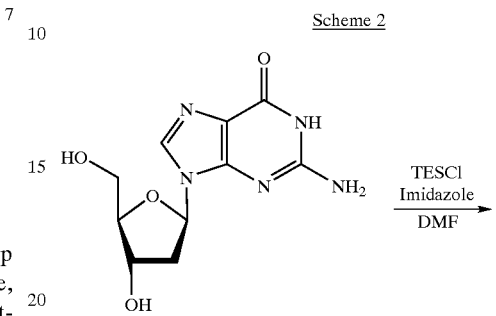

Scheme 2

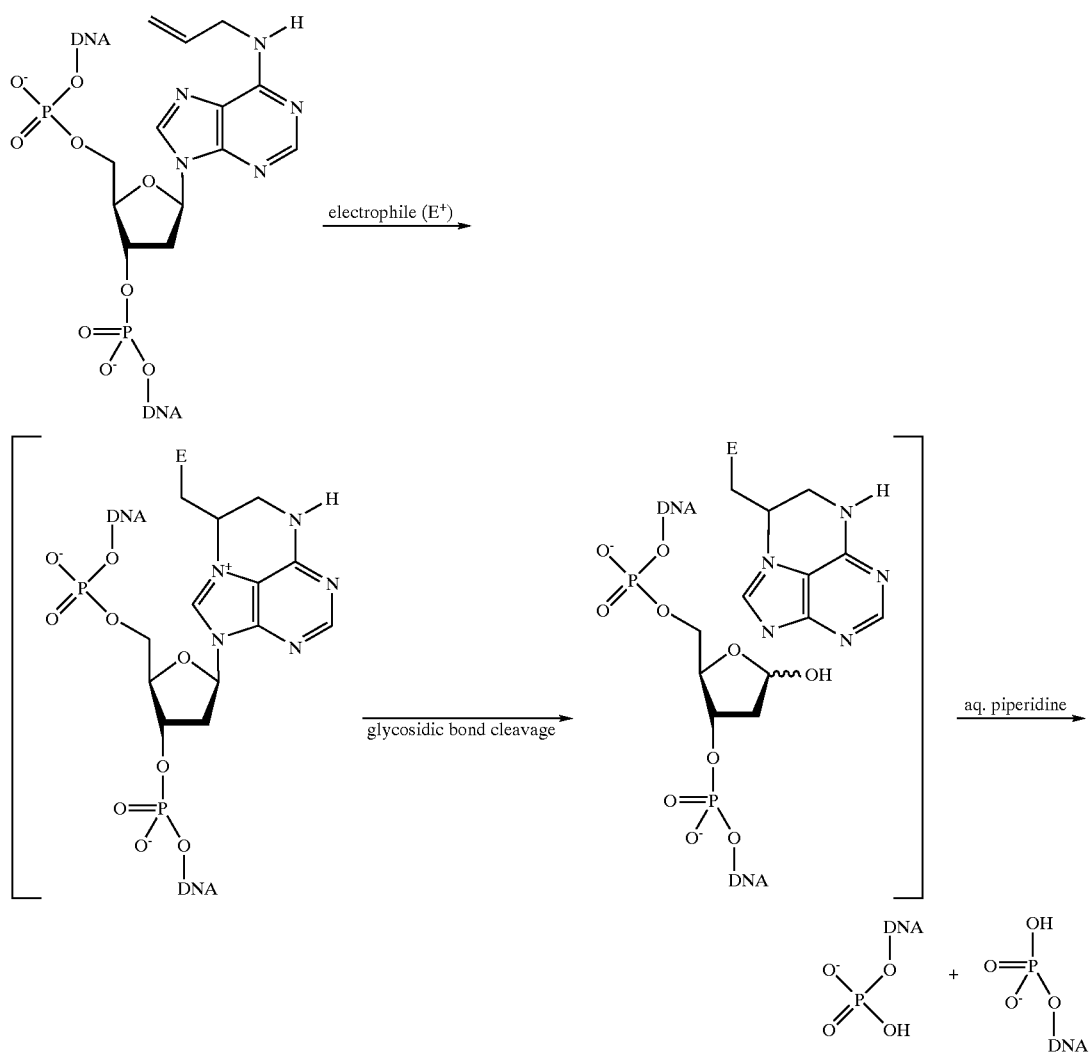

Scheme 1

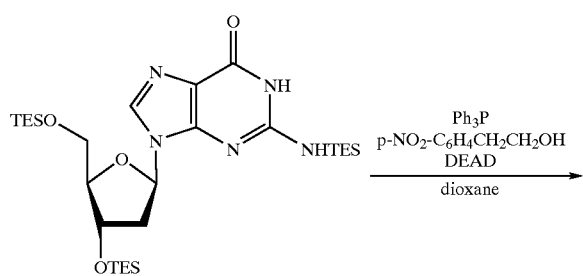
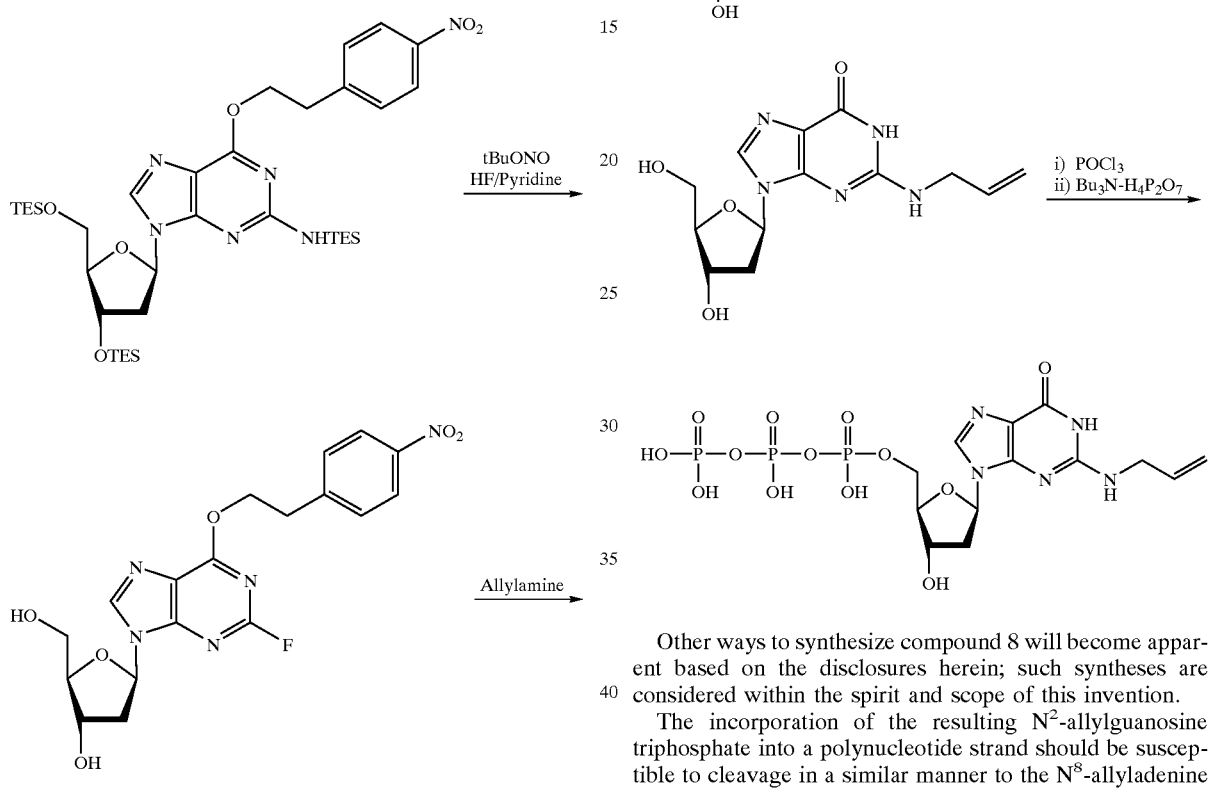

Other ways to synthesize compound 8 will become apparent based on the disclosures herein; such syntheses are considered within the spirit and scope of this invention.

The incorporation of the resulting $N^2$-allylguanosine triphosphate into a polynucleotide strand should be susceptible to cleavage in a similar manner to the $N^8$-allyladenine nucleotide of Gupta, i.e. by the mechanism shown in Scheme 3:

Scheme 3

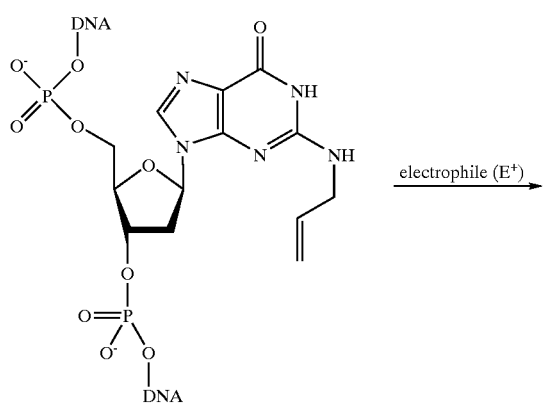

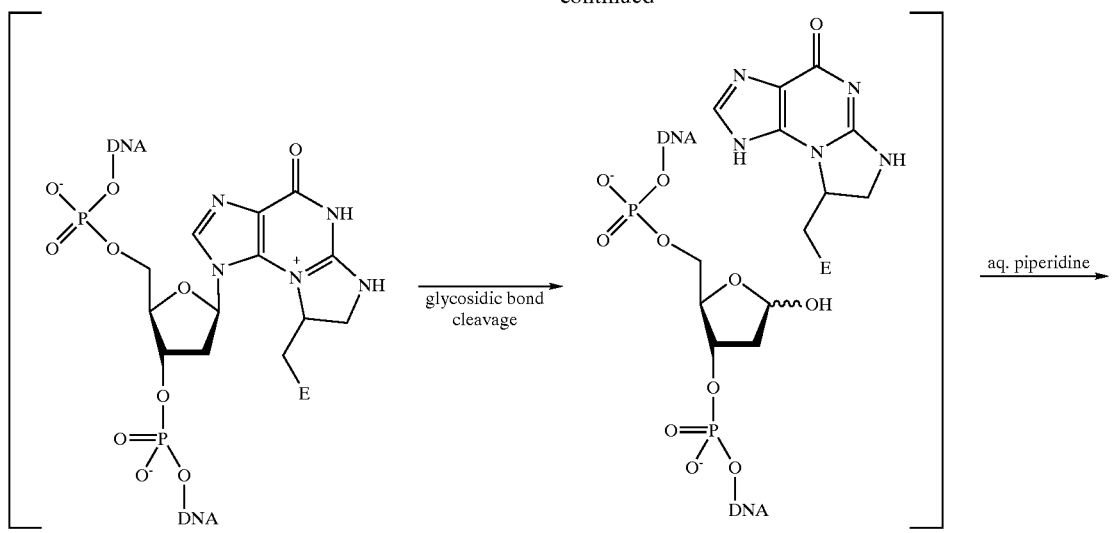

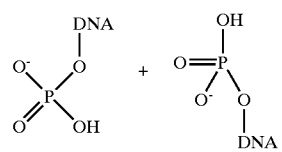

4. Either thymine (p9) or uracil (to0) may be replaced with 5-hydroxyuracil (11) (Verdine, *JACS*, 1991, 113:5104). As with the above modified bases, the nucleotide prepared from 5-hydroxyuracil can also be incorporated into a polynucleotide by enzyme-catalyzed polymerization. Verdine, at. al., *JACS* 93,115:374–375. Specific cleavage is accomplished by first treating the 5-hydroxyuracil with an oxidizing agent, for instance, aqueous permanganate, and then with a chemical base such as, without limitation, aqueous piperidine (Verdine, ibid.).

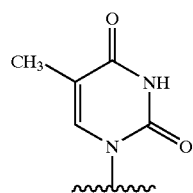

9

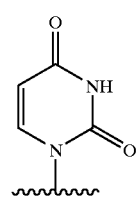

10

-continued

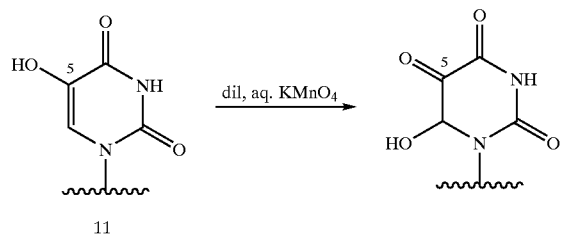

11

5. Pyrimidines substituted at the 5-position with an electron withdrawing as, group such as, without limitation, nitro, halo or cyano, should be susceptible to nucleophilic attack at the 6-position followed by base-catalyzed ring opening and subsequent degradation of the phosphate ester linkage. An example, which is not be construed as limiting the scope of this technique in any manner, is shown in Scheme 4 using 5-substituted cytidine. If the cleavage is carried out in the presence of tris(carboxyethyl)phosphine (TCEP), the adduct 10 may be obtained and, if the TCEP is functionalized with an infra), labeled polynucleotide fragments may be 91 92
Scheme 4
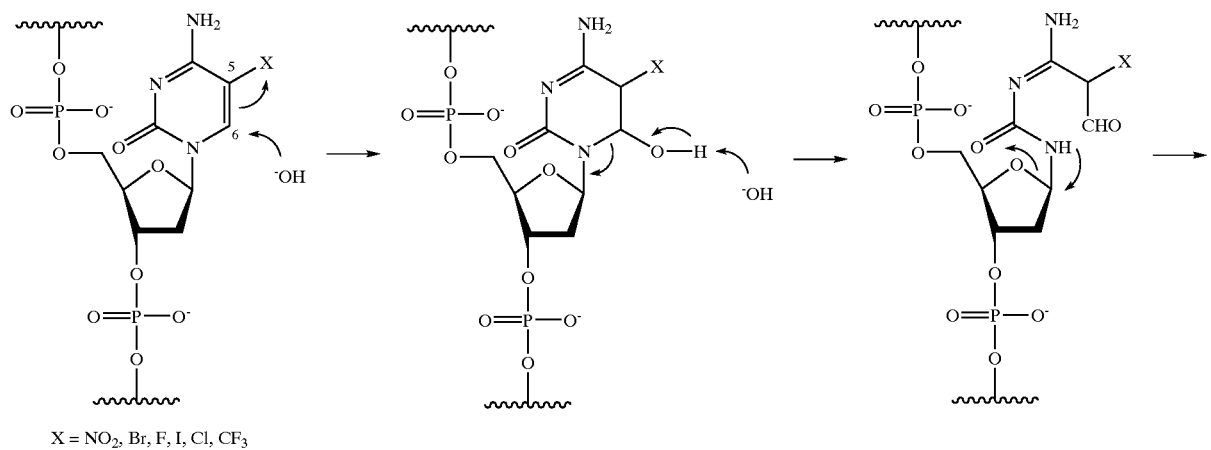
X = NO₂, Br, F, I, Cl, CF₃
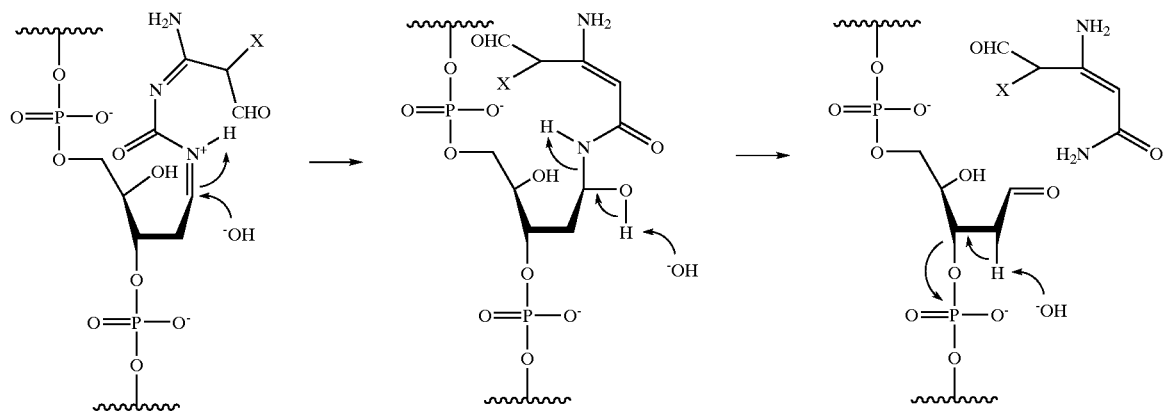
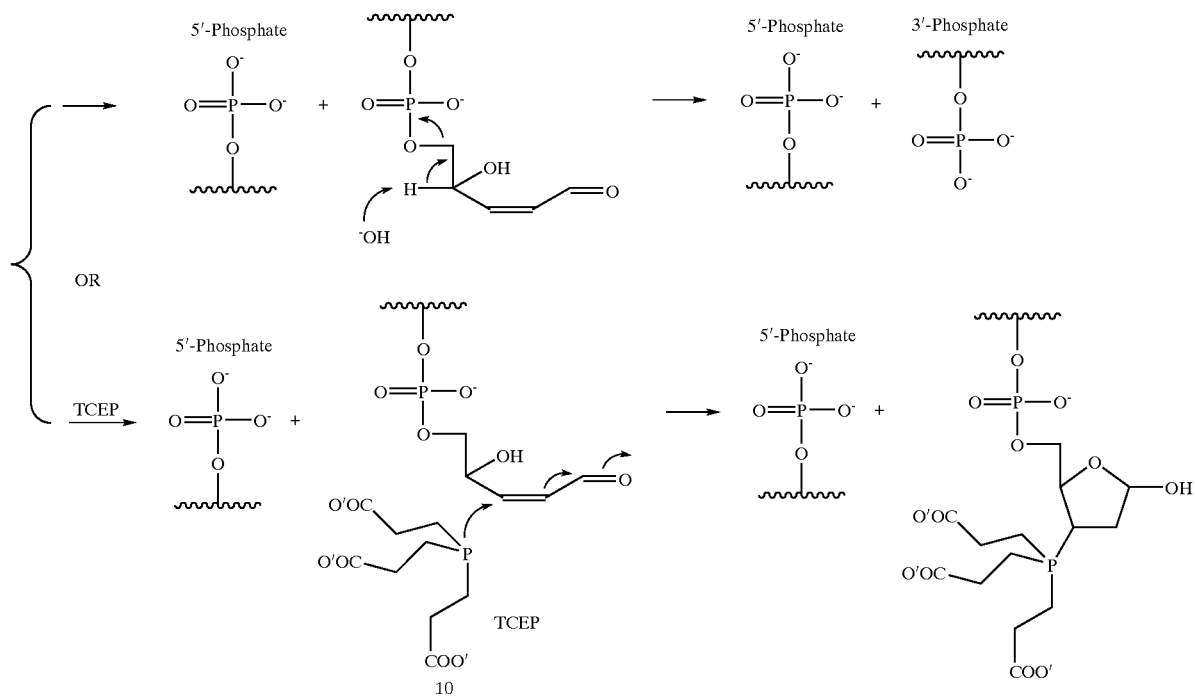

(2) Sugar Modification and Cleavage

Modification of the sugar portion of a nucleotide may also afford a modified polynucleotide which is susceptible to selective cleavage at the sites(s)of incorporation of such modification. In general, the sugar is modified to include one more functional groups which renders the 3' and/or 5' phosphate ester linkage more labile; i.e. susceptible to cleavage, than the 3' and/or 5' phosphate ester linkage of a natural nucleotide. The following are examples, without limitation, of such sugar modifications. Other sugar modifications will become readily apparent to those skilled in the art in light of the disclosures herein and are therefore deemed to be within the scope of this invention. In the formulas which follow, B and B' refer to any base and they may be the same or different.

1. In a deoxyribose-based polynucleotide, replacement of one or more of the deoxyribonucleosides with a ribose analog; e.g., without limitation, substituting adenosine (12) for deoxyadenosine (13) renders the resultant modified polynucleotide susceptible to selective cleavage by chemical bases such as, without limitation, aqueous sodium hydroxide or concentrated ammonium hydroxide, at each point of occurrence of adenosine in the modified polynucleotide (Scheme 5);

Scheme 5

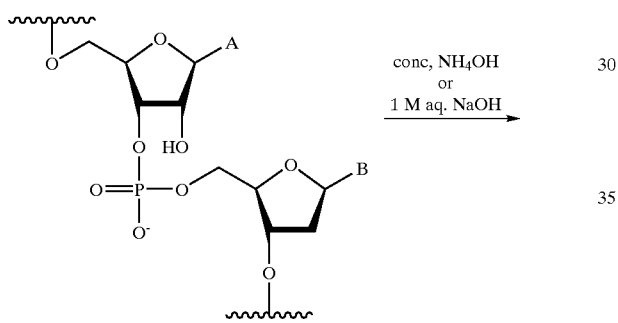

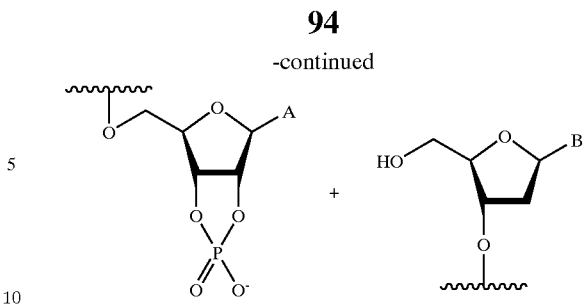

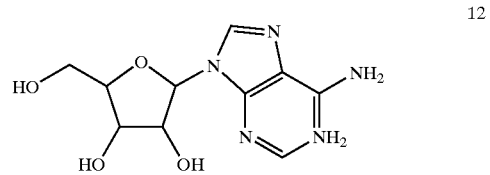

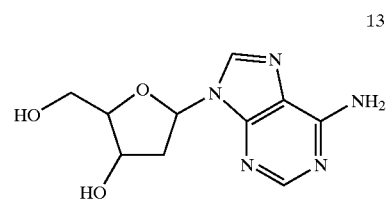

2. A 2'-ketosugar (14, synthesis: *JACS,* 1967, 89:2697) may be substituted for the sugar of a deoxynucleotide; upon treatment with chemical base such as, without limitation, aqueous hydroxide, the keto group equilibrates with its ketal form (15) which then attacks the phosphate ester linkage effecting cleavage (Scheme 6);

Scheme 6

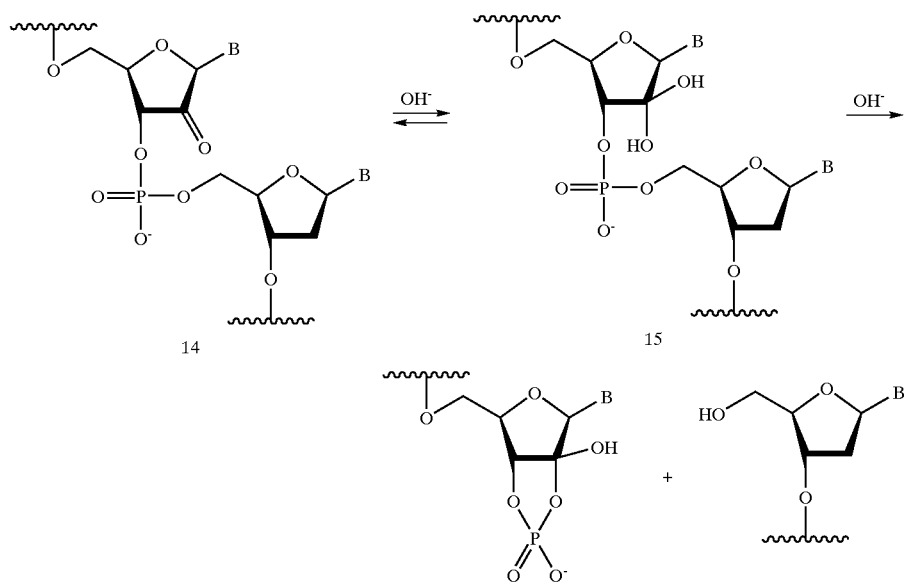

3. A deoxyribose nucleotide can be replaced with its arabinose analog; i.e., a sugar containing a 2"-hydroxy group (16). Again, treatment with mild (dilute aqueous) chemical base effects the intermolecular displacement of a phosphate ester linkage resulting in cleavage of the polynucleotide (Scheme 7):

Scheme 7

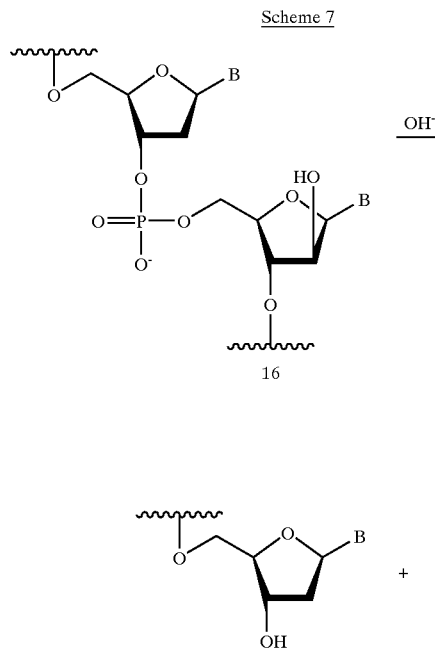

4. A deoxyribose nucleotide can be replaced by its 4'-hydroxymethyl analog (17, synthesis: *Helv. Chim. Acta,* 1966, 79:1980) which, on treatment with mild chemical base such as, without limitation, dilute aqueous hydroxide, likewise displaces a phosphate ester linkage causing cleavage of the polynucleotide (Scheme 8):

Scheme 8

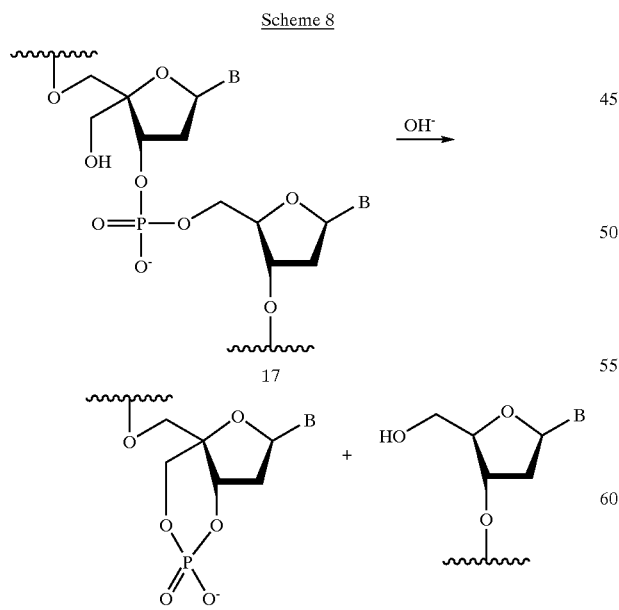

5. A deoxyribose nucleotide can be replaced by its 4'-hydroxy carbocyclic analog; i.e., a 4-hydroxymethylcyclopenane derivative (18) which, on treatment with aqueous base, results in the cleavage of the polynucleotide at a phosphate ester linkage (Scheme 9):

Scheme 9

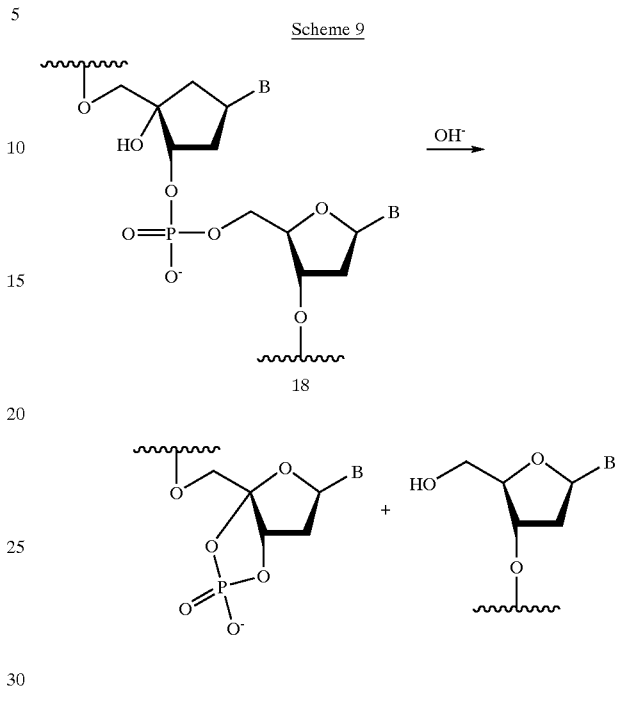

6. A sugar ring may be replaced with its carbocyclic analog which is further substituted with a hydroxyl group (19). Depending on the stereochemical positioning of the hydroxyl group on the ring, either a 3' or a 5' phosphate ester linkage can be selectively cleaved on treatment with mild chemical base (Scheme 10):

Scheme 10

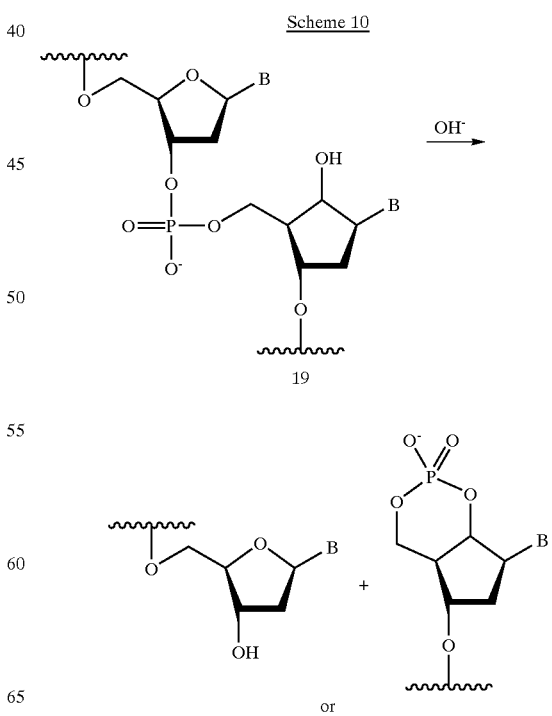

or

97

-continued

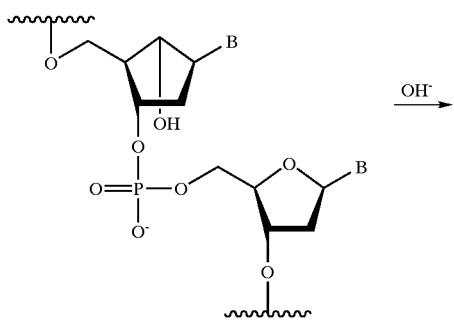

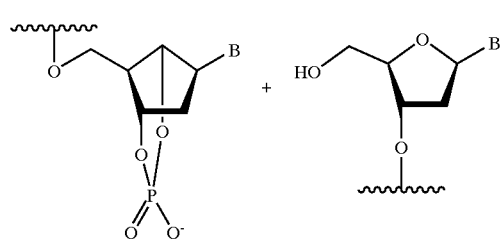

7. In each of examples 1, 3, 4, 5 and 6, above, the hydroxy group which attacks the phosphate ester cleavage may be replaced with an amino group (—NH$_2$). The amino group may be generated in situ from the corresponding azidosugar by treatment with tris(2-carboxyethyl)phosphine (TCEP) after the azide-modified polynucleotide has been formed (Scheme 11). The amino group, once formed, spontaneously attacks the phosphate ester linkage resulting in cleavage.

Scheme 11

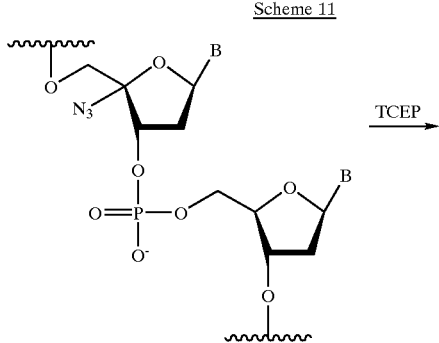

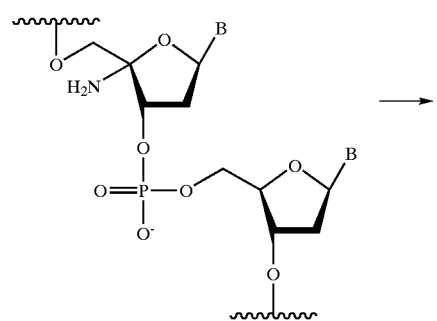

98

-continued

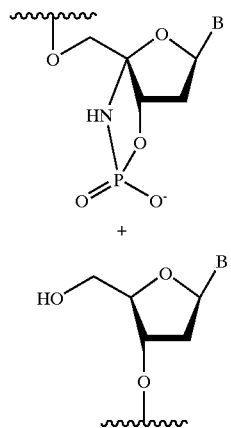

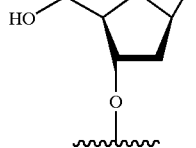

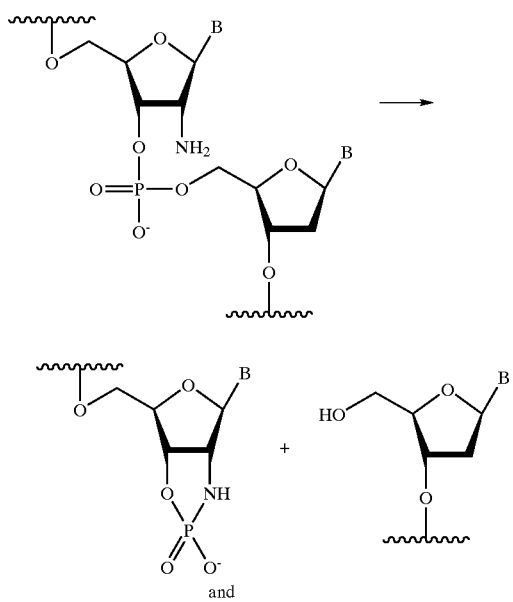

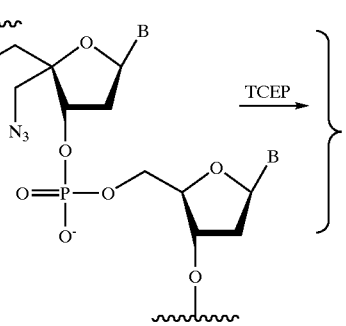

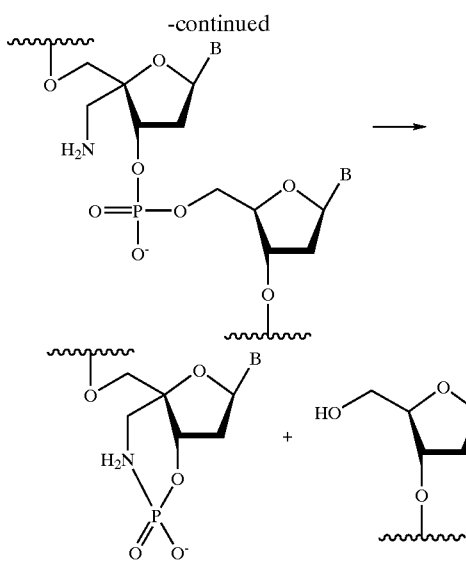

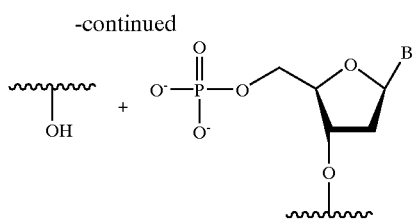

9. An electron-withdrawing group may be incorporated into the sugar such that the nucleotide is either rendered susceptible to β-elimination (when W is cyano (a "cyanosugar," 20)) or the oxyanion formed by the hydrolysis of the 3'-phosphate ester linkage is stabilized and thus hydrolysis with mild chemical base will be preferred at the modified sugar; such electron-withdrawing groups include, without limitation, cyano (—C≡N), nitro (—$NO_2$), halo (in particular, fluoro), azido (—$N_3$) or methoxy (—$OCH_3$) (Scheme 13):

8. A sugar may be substituted with a functional group which is capable of generating a free radical such as, without limitation, a phenylselenyl (PhSe—) or a t-butyl ester group ($^t$BuC(=O)—) (*Angew. Chem. Int. Ed. Engl.* 1993, 32:1742–43). Treatment of the modified sugar with ultraviolet light under anaerobic conditions results in the formation of a $C_4^{1'}$ radical whose fragmentation causes the excision of the modified nucleotide and thereby the cleavage of the polynucleotide at the modified nucleotide (Scheme 12). The free radicals may be generated either prior to or during the laser desorption/ionization process of MALDI mass analysis. Modified nucleotides with other photolabile 4' substitutents such as, without limitation, 2-nitrobenzyl groups or 3-nitrophenyl groups (*Synthesis*, 1980, 1–26) and bromo or iodo groups may also be used as precursors to form a $C_4'$ radical.

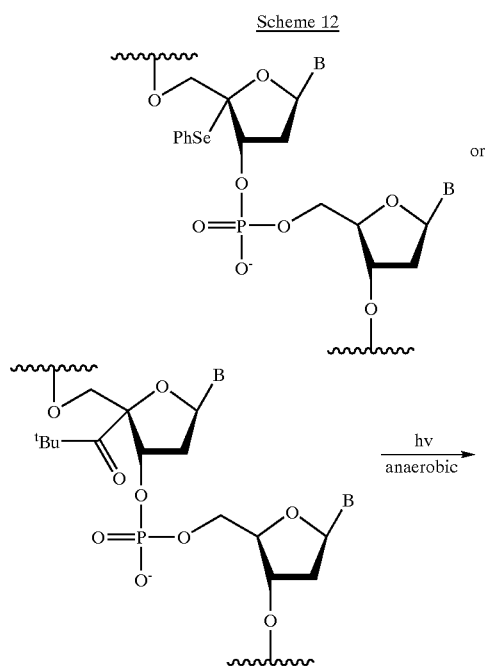

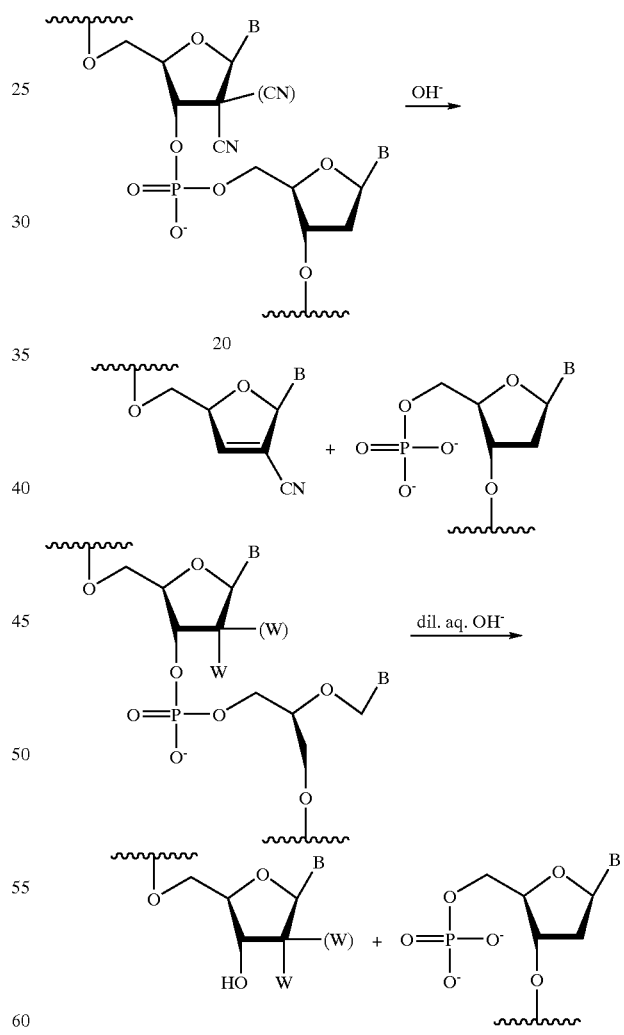

A cyano sugar can be prepared by a number of approaches, one of which is shown in (Scheme 14). Other methods will no doubt be apparent to those skilled in the art based on the disclosures herein; such alternate approaches to cyano (or other electron withdrawing group substituted sugars) are within the spirit and scope of this invention.

Scheme 14

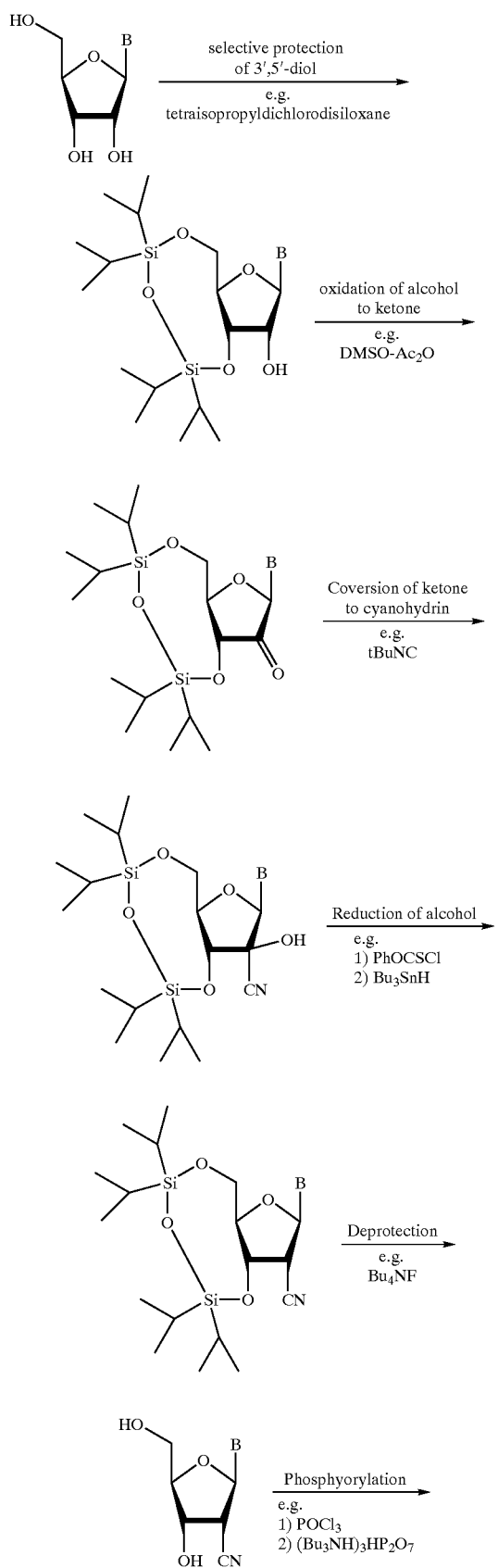

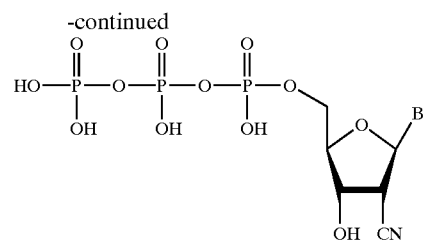

10. The ring oxygen of a sugar may be replaced with another atom; e.g., without limitation, a nitrogen to form a pyrrole ring (21). Or, another heteroatom may be placed in the sugar ring in place of one of the ring carbon atoms; for example, without limitation, a nitrogen atom to form an oxazole ring (22). In either case, the purpose of the different or additional heteroatom is to render the phosphate ester linkage of the resulting non-natural nucleotide more labile than that of the natural nucleotide (Scheme 15):

Scheme 15

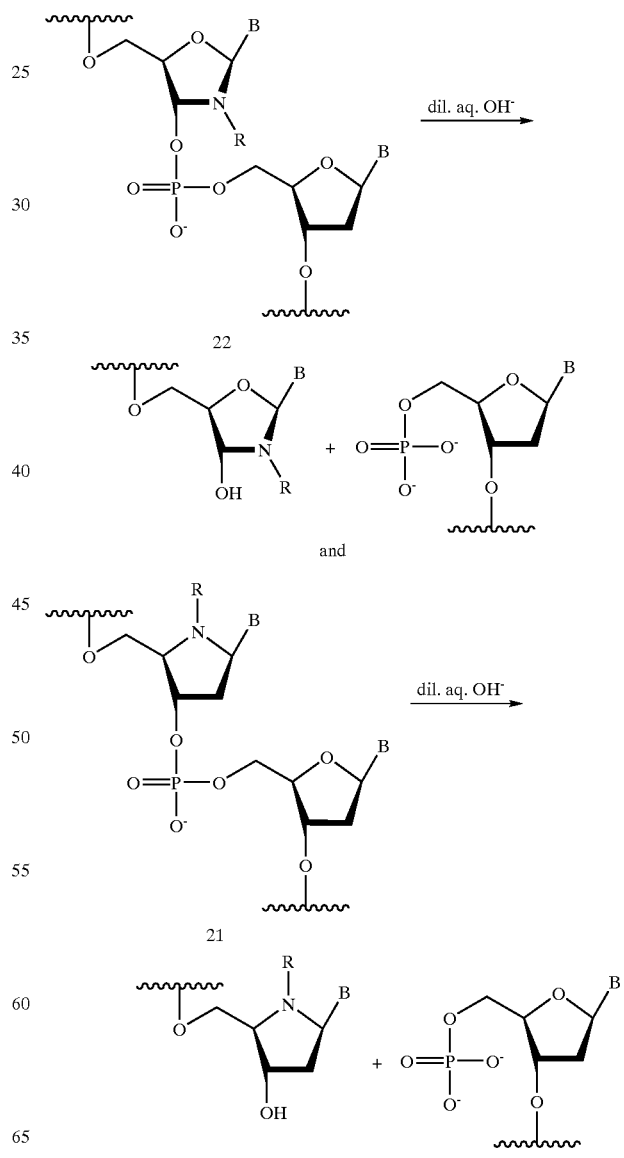

11. A group such as, without limitation, a mercapto group may be incorporated at the 2" position of a sugar ring which group, on treatment with mild chemical base, forms a ring by elimination of the 3'-phosphate ester (Scheme 16).

Scheme 16

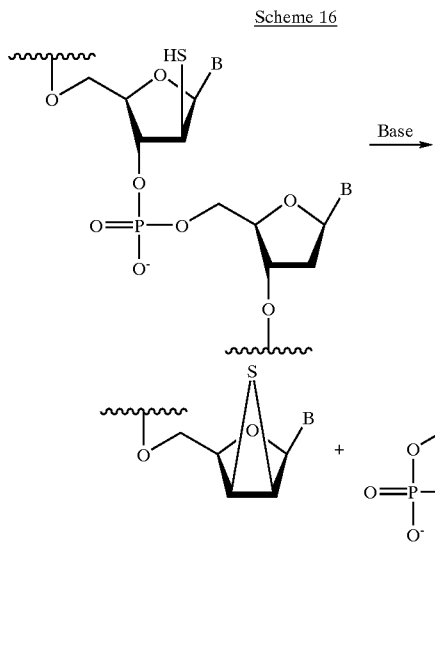

12. A keto group can be incorporated at the 5' position such that the resulting phosphate has the lability of an anhydride, i.e., structure 23. A nucleotide triphosphate such as 23 may be synthesized by the procedure shown in Scheme 17. It is recognized that other routes to such nucleotide triphosphates may become apparent to those skilled in the art based on the disclosures herein; such syntheses are within the spirit and scope of this invention.

Scheme 17

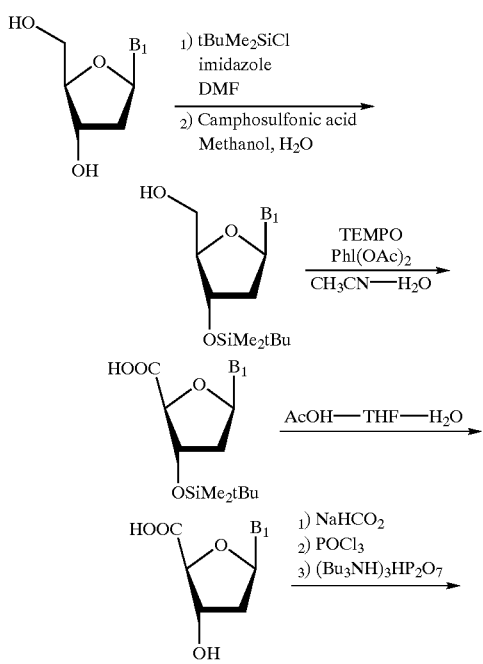

-continued

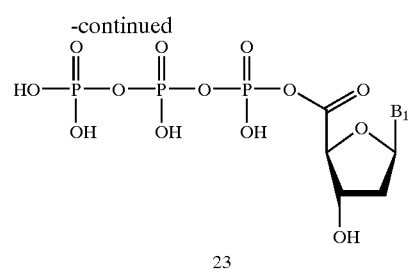

23

Polynucleotides into which nucleotide triphosphates of structure 23 have been incorporated should, like analogous mixed anhydrides, be susceptible to alkaline hydrolysis (Scheme 18):

Scheme 18

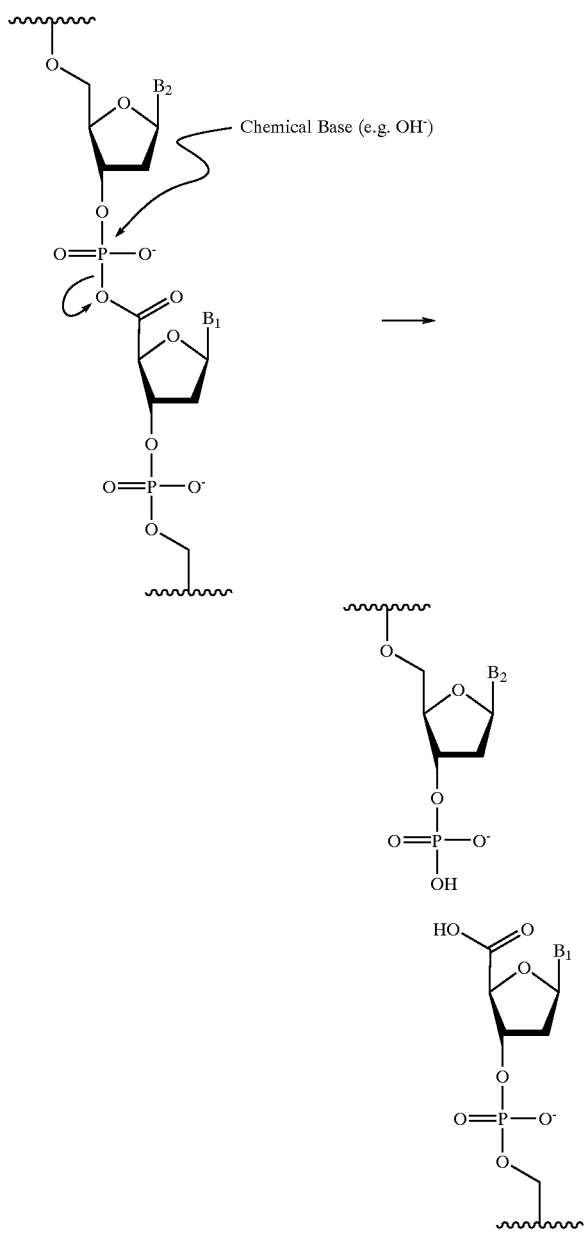

13. The phosphate ester linkage could be turned into the relatively more labile enol ester linkage by the incorporation of a double bond at the 5' position, that is, a nucleotide triphosphate of structure 24 could be used. A nucleotide triphosphate of structure 24 can be prepared by the procedure shown in Scheme 19. It is again understood that other ways to produce structure 24 may be apparent to those skilled in the art based on the disclosures herein, as before, these alternate syntheses are well within the spirit and scope of this invention.

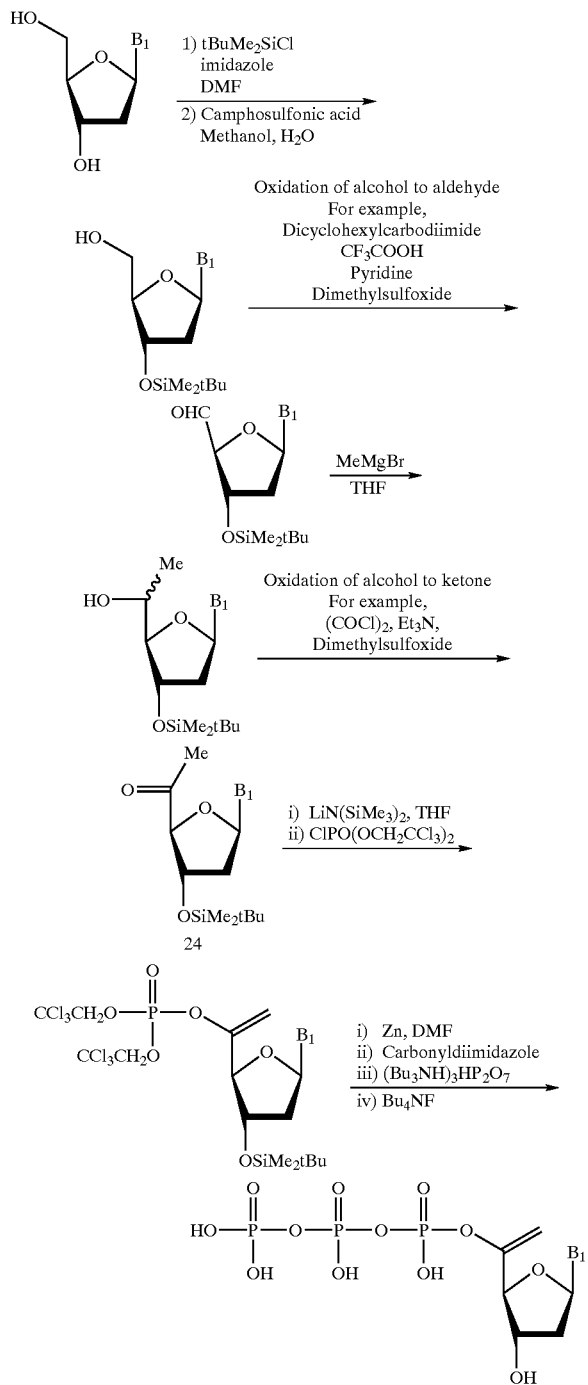

Scheme 19

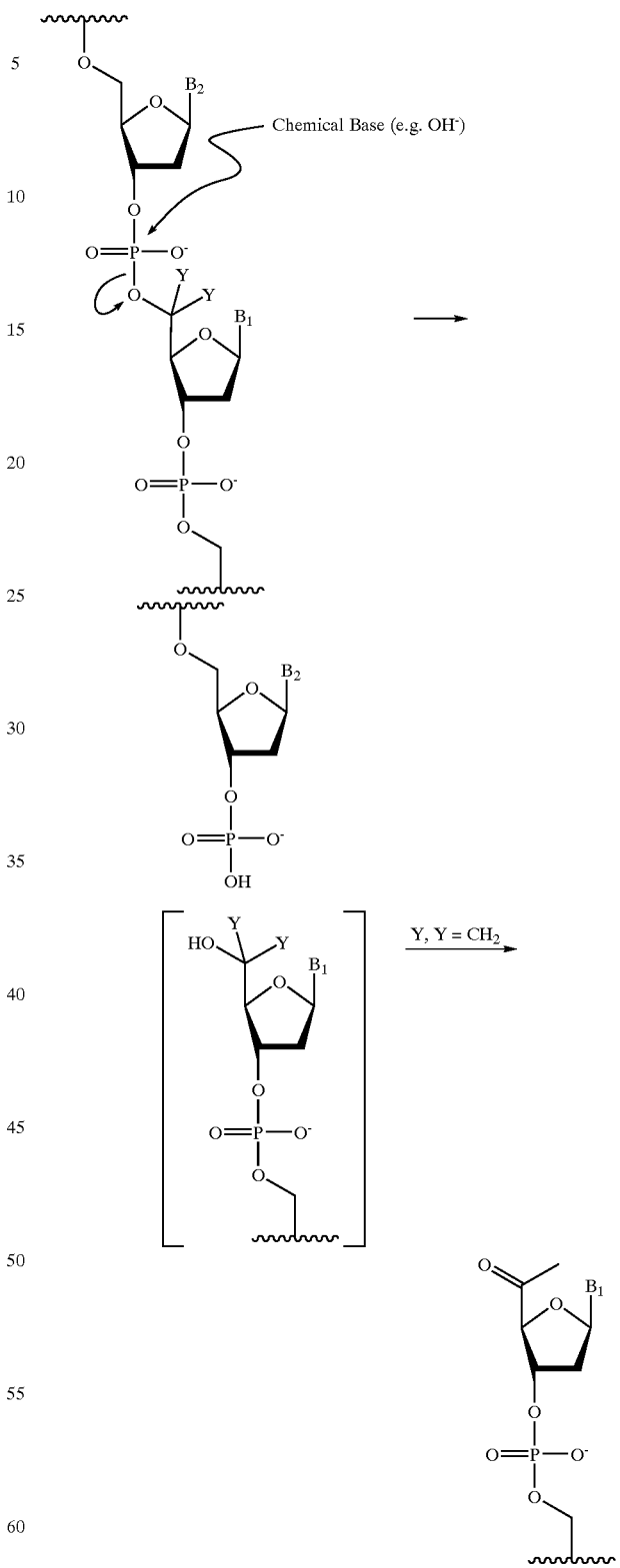

Scheme 20

The enol ester would be susceptible to alkaline cleavage (Scheme 20).

14. Difluoro substitution at the 5' position would increase the lability of the phosphate ester linkage and would also push the reaction to completion by virtue of the hydrolysis of the intermediate difluorohydroxy group to an acid group (Scheme 22). The dihalo derivative could be synthesized by the procedure shown in Scheme 21. Once again, the route shown in Scheme 21 is not the only way possible to make the difluoronucleotide triphosphate. However, as above, these other routes would be apparent based on the disclosures herein and would be within the spirit and scope of this invention.

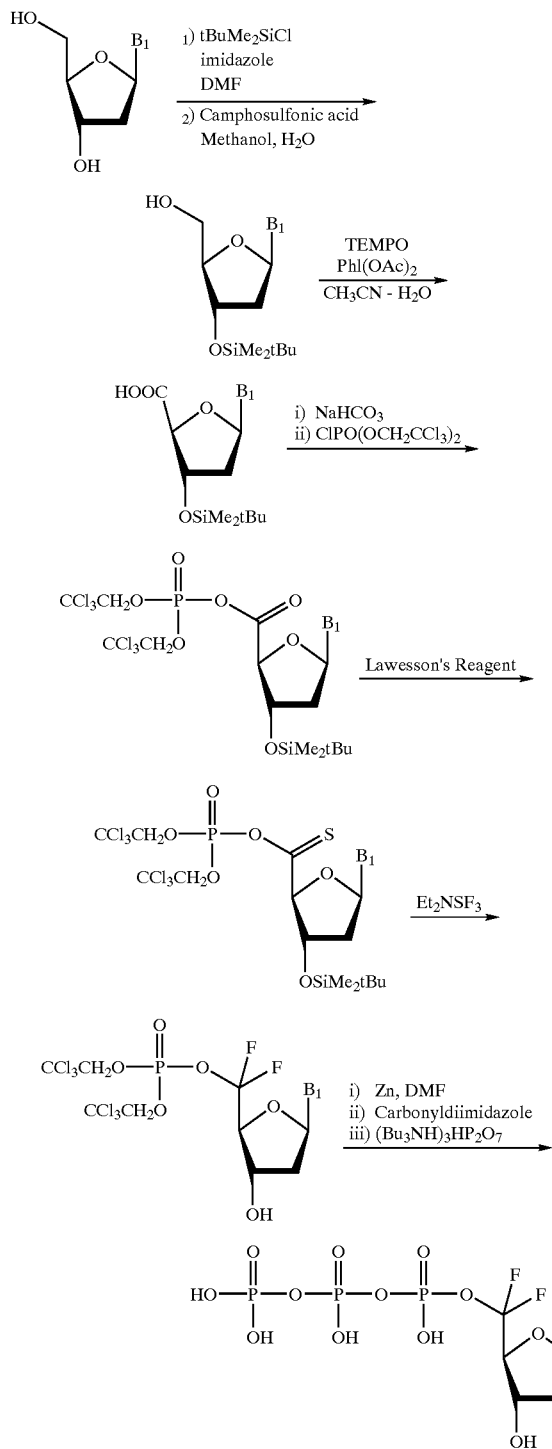

Scheme 21

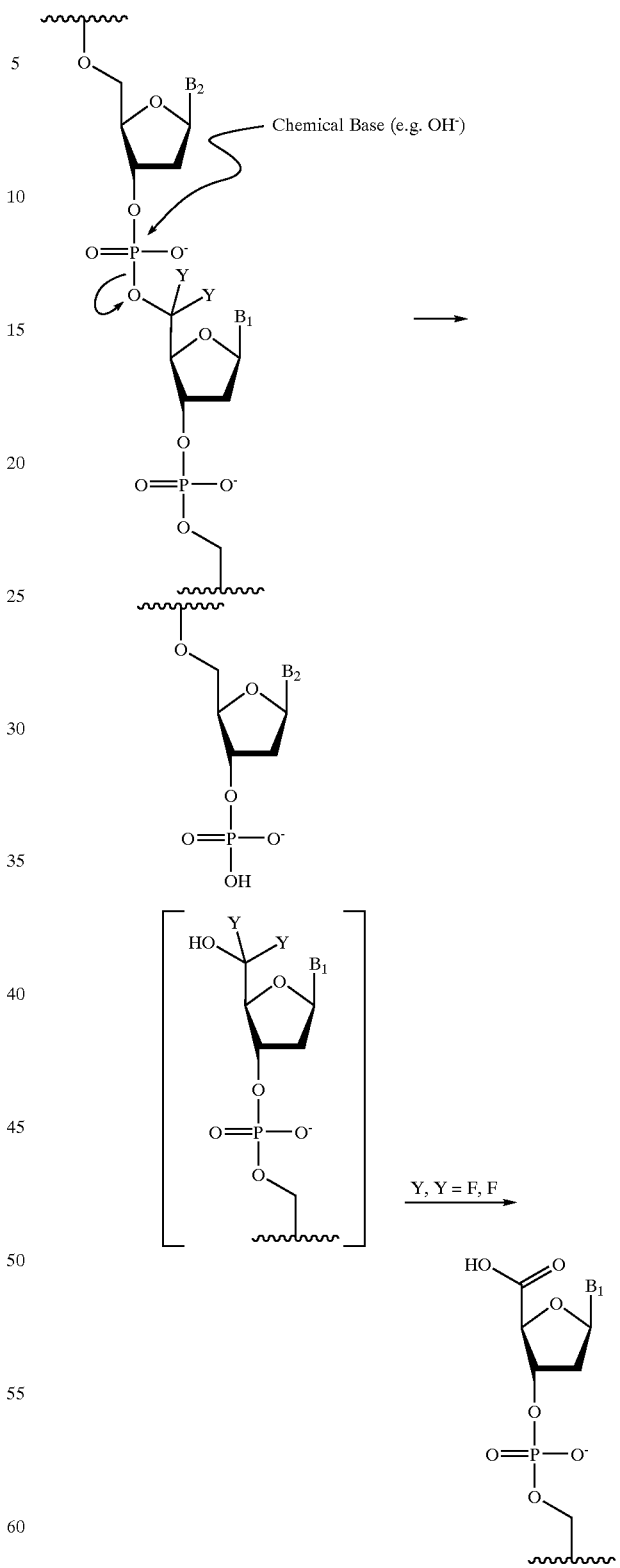

Scheme 22

(3) Phosphate Ester Modification and Cleavage

Modification of the phosphate ester of a nucleotide results in modification of the phosphodiester linkages between the 3'-hydroxy group of one nucleotide and the 5'-hydroxy group of the adjacent nucleotide such that one or the other of the modified 3' or 5' phosphate ester linkages is rendered substantially more susceptible to cleavage than the corresponding unmodified linkage. Since the phosphodiester linkage forms the backbone of a polynucleotide, this modification method will, herein, be referred to alternatively as "backbone modification." The following are non-limiting examples of backbone modification. Other such modifications will become apparent to those skilled in the art based on the disclosures herein and therefore are deemed to be within the scope of this invention.

1. Replacement of an oxygen in the phosphate ester linkage with a sulfur; i.e., creation of a phosphorothiolate linkage ( structures 25a, 25b, 25c) which either directly on treatment with mild base (Schemes 23(a) and 23(b)) or on treatment with an alkylating agent, such as, for instance, methyl iodide, followed by treatment with strong non-aqueous organic base, for example, methoxide (Scheme 23(c)), results in the selective cleavage of the phosphothioester linkage. Alternatively, phosphorothiolate linkages such as those in Formula 14 may also be selectively cleaved through laser photolysis during MALDI mass analysis. This in-source fragmentation procedure (*Internat'l J. of Mass Spec. and Ion Process,* 1997, 169/170:331–350) consolidates polynucleotide cleavage and analysis into one step;

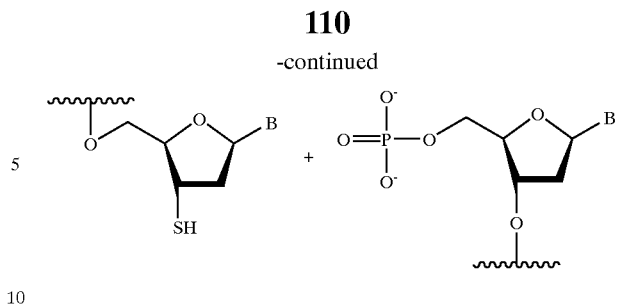

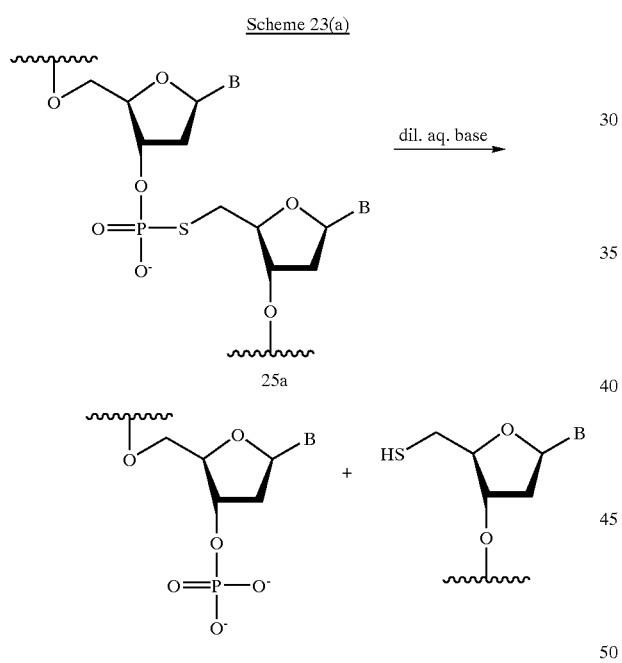

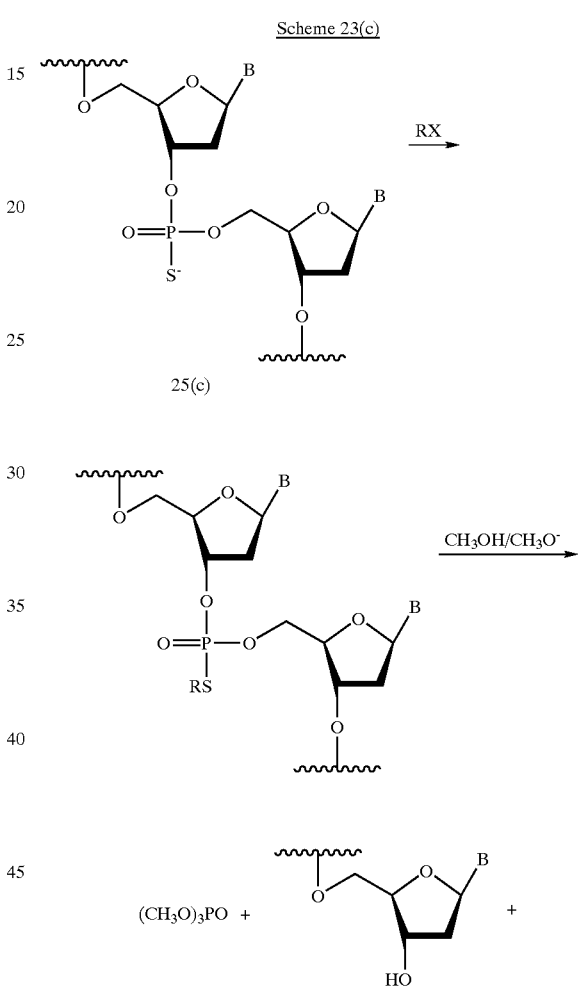

2. Replacement of an oxygen in the phosphate ester linkage with a nitrogen creating a phosphoramidate linkage (26) which, on treatment with, for instance and without limitation, dilute aqueous acid, will result in selective cleavage (Scheme 24);

Scheme 24

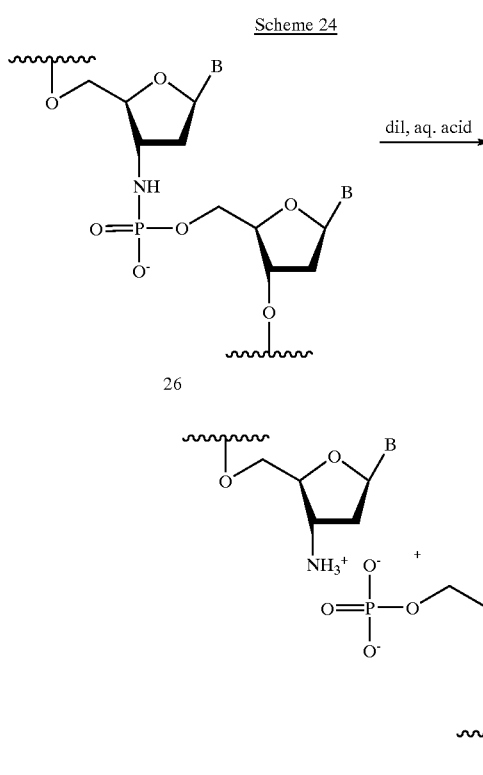

3. Replacement of one of the free oxygen atoms attached to the phosphorus of the phosphate backbone with an alkyl group, such as, without limitation, a methyl group, to form a methylphosphonate linkage, which, on treatment with strong non-aqueous organic base, such as without limitation, methoxide, will likewise result in selective cleavage (Scheme 25).

Scheme 25

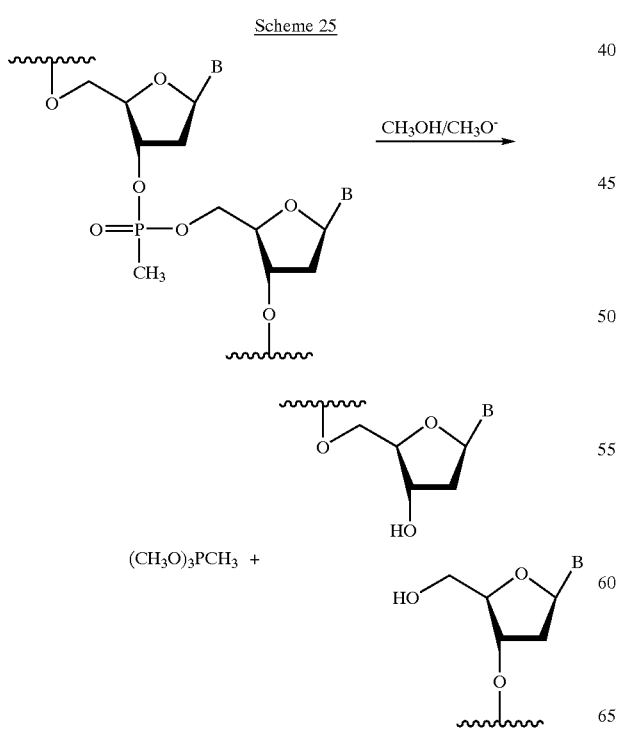

4. Alkylation of the free oxyanion of a phosphate ester linkage with an alkyl group such as, without limitation, a methyl group will, on treatment with strong non-aqueous organic base such as without limitation, methoxide, result in the selective cleavage of the resulting alkylphosphorotriester linkage (Scheme 26).

Scheme 26

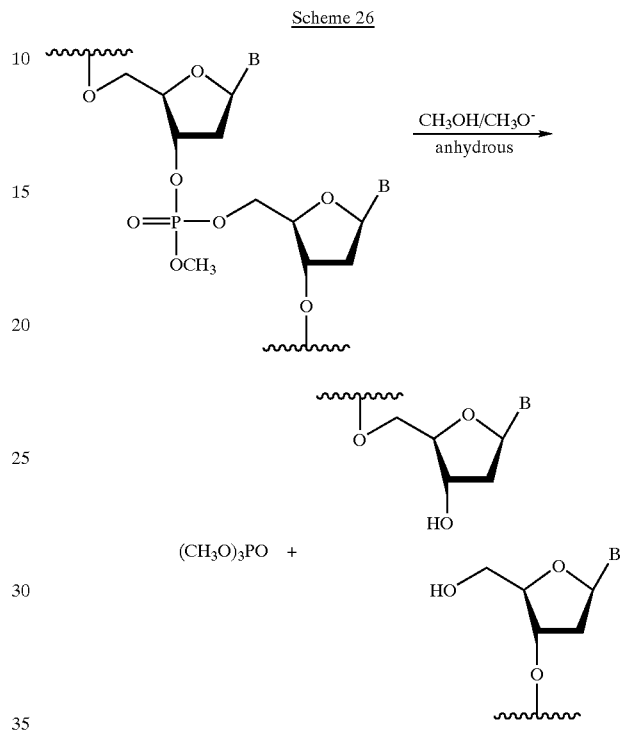

5. Treatment of a phosphorothioate with β-mercaptoethanol in a strong, base such as, without limitation, methanolic sodium methoxide, in which the mercaptoethanol exists primarily as the disulfide, could result in the formation of a mixed disulfide, which would then degrade, with or without rearrangement, to give the cleavage products shown in Scheme 27.

Scheme 27

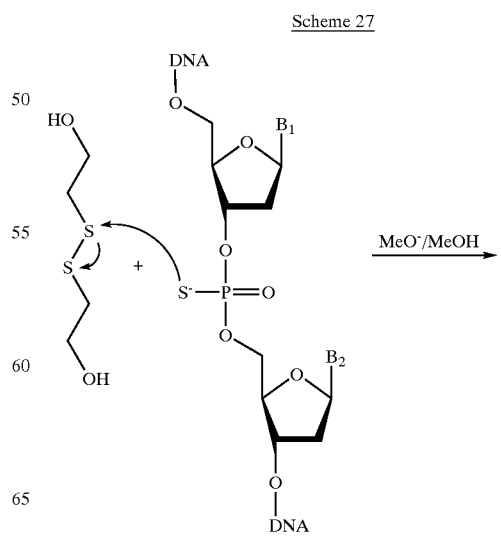

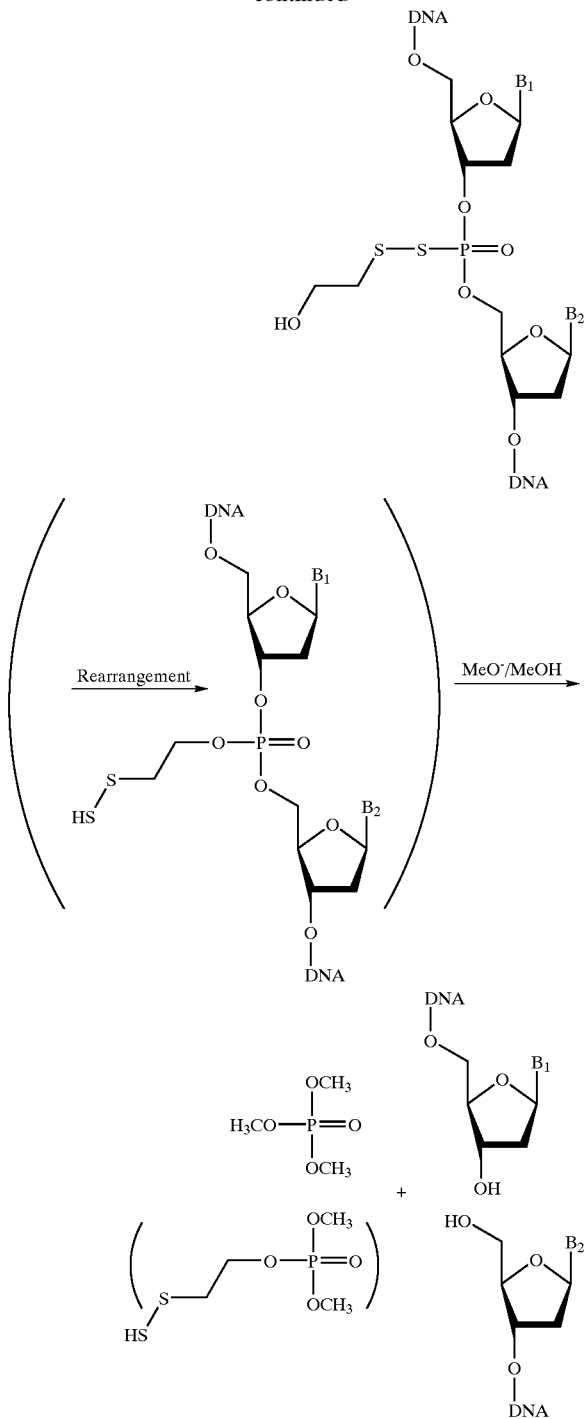

(4) Dinucleotide Modification and Cleavage

The previous substitutions are all single substitutions; that is, one modified nucleotide is substituted for one natural nucleotide wherever the natural nucleotide occurs in the target polynucleotide or, if desired, at a fraction of such sites. In an additional aspect of this invention, multiple substitutions may be used. That is, two or more different modified nucleotides may be substituted for two or more different natural nucleotides, respectively, wherever the natural nucleotides occur in a subject polynucleotide. The modified nucleotides and cleavage conditions are selected such that, under the proper cleavage conditions, they do not individually confer selective cleavage properties on a polynucleotide. When, however, the proper cleavage conditions are applied and the modified nucleotides are incorporated into the polynucleotide in a particular spatial relationship to one another, they interact to jointly render the polynucleotide selectively cleavable. Preferably, two modified nucleotides are substituted for two natural nucleotides in a polynucleotide, thus, this method is referred to herein as "dinucleotide modification." It is important to note that, individually, each of the two modified nucleotides may elecit specific and selective cleavage of a polynucleotide albeit under quite different, typically more vigorous chemical conditions.

As used herein, "spatial relationship" refers to the 3-dimensional relationship between two or more modified nucleotides after substitution into a polynucleotide. In a preferred embodiment of this invention, two modified nucleotides must be contiguous in a modified polynucleotide in order to impart altered cleavage properties on the modified polynucleotide. By employing two modified nucleotides in this manner, and then cleaving the modified polynucleotide, the relationship between two natural nucleotides in a target polynucleotide can be established depending on the nature of the multiple substitution selected. That is, the natural nucleotides being replaced would also have been adjacent to one another in the natural nucleotide. For example, without limitation, if a modified A and modified G are replaced at every point of occurrence of the corresponding natural A and natural G, respectively, the modified polynucleotide will be rendered selectively cleavable only where the natural A and G were directly adjacent, i.e., AG or GA (but not both), in the naturally-occurring polynucleotide. As shown below, proper choice of the modified polynucleotides will also reveal the exact relationship of the nucleotides, i.e., in the example above, whether the nucleotide sequence in the natural polynucleotide was AG or GA. The following are non-limiting examples of multiple substitutions. Other multiple substitutions will become apparent to those skilled in the art based on the disclosures set forth herein and therefore are deemed to be within the scope of this invention.

1. One modified nucleotide may contain a functional group capable of effecting nucleophilic substitution while the companion modified nucleotide is modified so as to render it a selective leaving group. The nucleophile and the leaving group may be in a 5'–3' orientation or in a 3'–5'orientation with respect to one another. A non-limiting example of this is shown in (Scheme 28). The 2' or 2" hydroxy group on one modified nucleotide, when treated with mild chemical base becomes a good nucleophile. The other modified nucleotide contains a 3' or 5' thiohydroxy (—SH) group which forms a 3' or 5' phosphorothioate linkage when incorporated into the modified polynucleotide. This phosphorothiolate linkage is selectively more labile than a normal phosphodiester linkage. When treated with mild base, the oxyanion formed from the hydroxy group of one modified nucleotide selectively displaces the thiophosphate linkage to the other modified nucleotide resulting in cleavage. As shown in Scheme 28(a) and 2(b), depending on the stereochemical relationship between the hydroxy group and the thiophosphate linkage, cleavage will occur either to the 3' or the 5' side of the hydroxy-containing modified nucleotide. Thus, the exact relationship of the natural nucleotides in the naturally occurring polynucleotide is revealed.

Scheme 28(a)

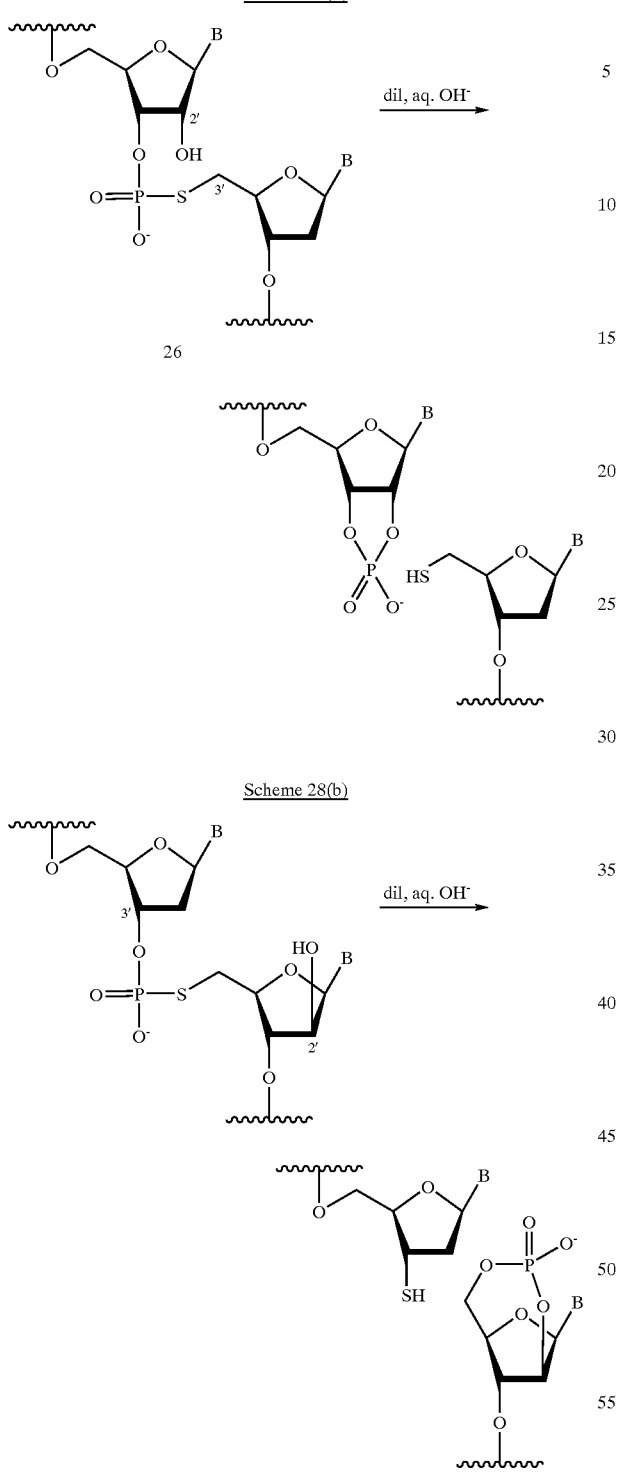

Scheme 28(b)

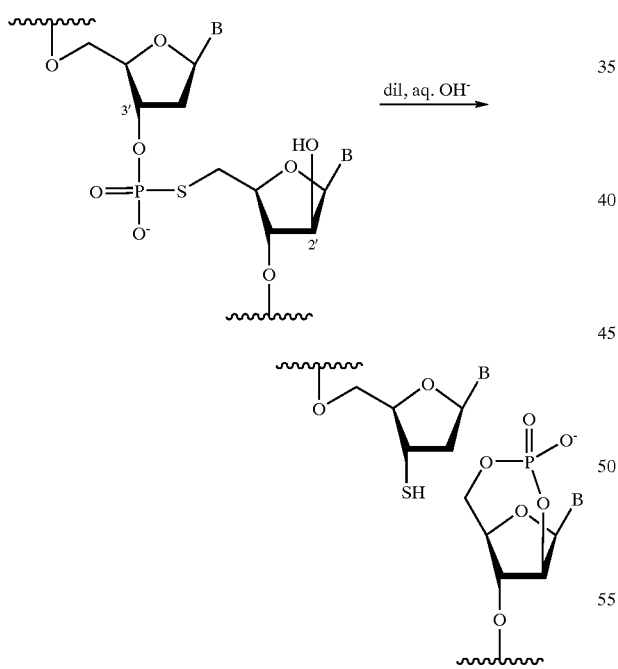

the exact relationship of the nucleotides in the naturally-occurring polynucleotide can be determined as shown in Schemes 29(a) and 29(b).

Scheme 29(a)

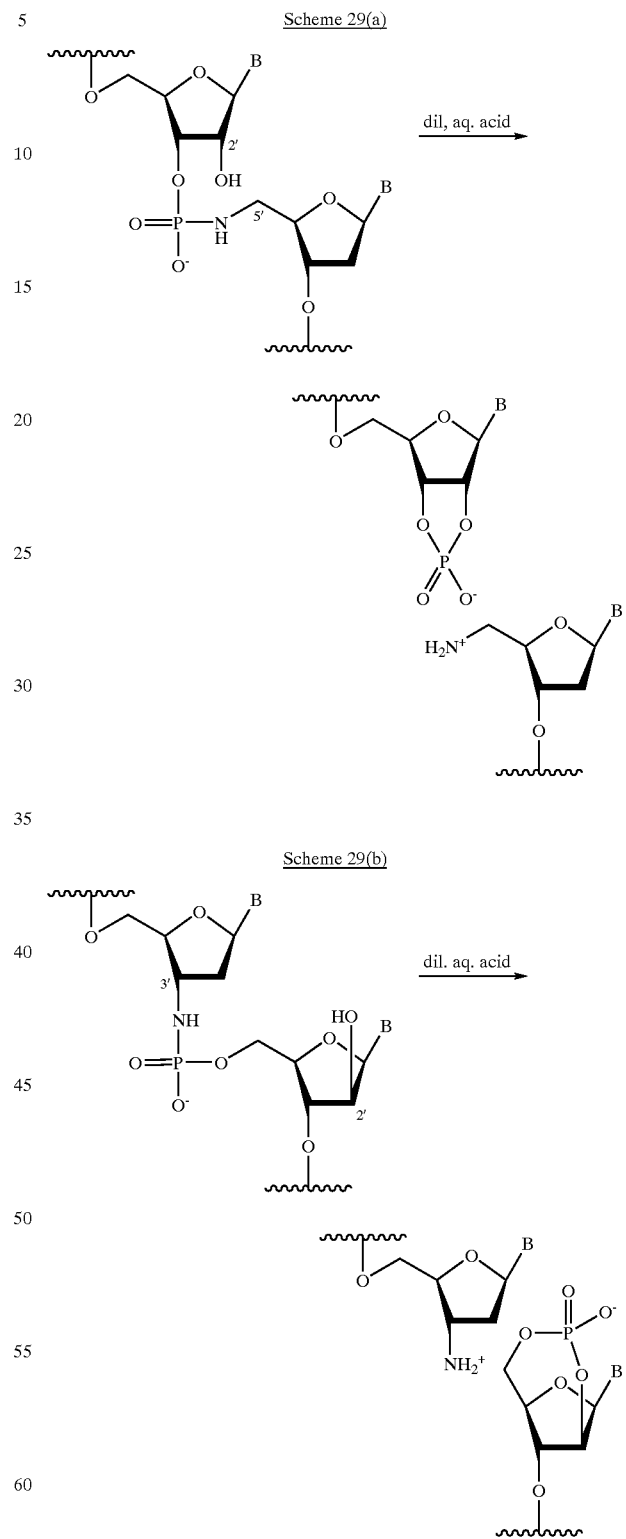

Scheme 29(b)

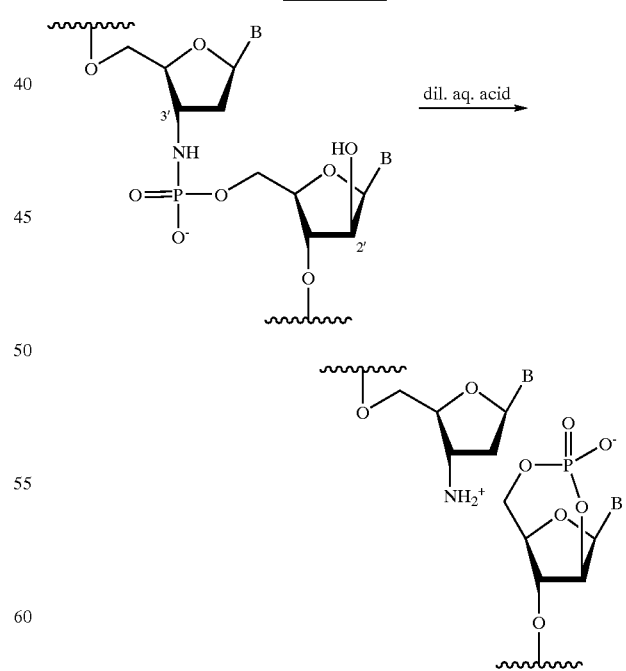

2 (a). If one modified nucleotide contains a 3' or 5' amino (—$NH_2$) group and the other modified nucleotide contains a 5' or 3' hydroxy group, respectively, treatment of the resulting phosphoroamidate-linked polynucleotide with mild acid results in the protonation of the amino group of the phosphoroamidate linkage which then becomes a very good leaving group. Once again, depending on the spatial relationship between the hydroxy group of one modified nucleotide and the amino group of the other modified nucleotide, Dinucleotide cleavage of a ribonucleotide/ 5'-aminonucleotide 5'-3' linkage is presently a preferred embodiment of this invention. Examples of this method are shown in FIGS. 21–26.

2(b). When the amino group of the modified nucleotide is 5', a ribonucleotide/5'-amino 2',5'-dideoxynucleotide pair may be cleaved during the polymerization process. For example, without limitation, cleavage occurs during the incorporation of adenine ribonucleotide and 5'-aminodideoxythymine nucleotide into a polynucleotide using a combination of wild type Klenow (exo-) and mutant E710 A Klenow (exo-) polymerases. E710A is a mutant Klenow (exo-) polymerase in which a glutamate at residue 710 has been replace by alanine. The E710A mutant is more efficient at incorporating both ribonucleotides and deoxyribonucleotides into a single nascent polynucleotide strand than Klenow (exo-). Other polymerases with similar properties will be apparent to those skilled in the art based on the disclosures herein and their use for the incorporation of ribonucleotide and 5'-amino-2',5'-dideoxynucleotide into a polynucleotide with subsequent cleavage during the polymerization reaction is within the scope of this invention.

When a 5'-end radiolabeled primer was extended using a mixture of Klenow (exo-) and E710A Klenow (exo-), only one fragment (the 5'-end fragment) was observed indicating complete cleavage at the ribonucleotide-5'-aminonucleotide sites. We have shown (FIGS. 21–26) that the polymerization and cleavage occur in the same step. That is, cleavage is induced during protein-DNA contact. The figures show that the polymerases continue to extend the template even after cleavage, which also suggests that the cleavage is the result of protein-DNA contact. While USB brand Klenow polymerase (Amersham) was also able to incorporate the two nucleotides, it was not as efficient as the mixture of polymerases and, furthermore, multiple product bands were observed indicating incomplete cleavage at the AT sites.

The above is, of course, a specific example of a general concept. That is, other wild type polymerases, mutant polymerases or combinations thereof should likewise be capable of cleaving, or facilitating cleavage of, modified nucleotides or dinucleotides during the polymerization procedure. The procedure for determining the exact combinations of polymerase(s) and nucleotide modifications that result in cleavage, based on the disclosures herein, will be apparent to those skilled in the art. For instance, as is described below, it may be useful to generate a library of mutant polymerases and select specifically for those which induce dinucleotide cleavage. Thus, a polymerase or a combination of polymerases which cause the cleavage of a forming modified polynucleotide during the polymerization process is yet another aspect of this invention, as are the method of cleaving a modified polynucleotide during the polymerization process using a polymerase or combination of polymerases and the modified nucleotide(s) necessary for the cleavage to occur.

3. An electron-withdrawing group can be placed on a sugar carbon adjacent to the carbon which is bonded to the hydroxy group participating in the ester linkage of a methylphosphonate (Scheme 30(a)) or methylphosphotriester (Scheme 30(b)) backbone. This will result in increased stability of the oxyanion formed when the phosphate group is hydrolyzed with mild chemical base and thus selective hydrolysis of those phosphate ester linkages compared to phosphate ester linkages not adjacent to such hydroxy groups.

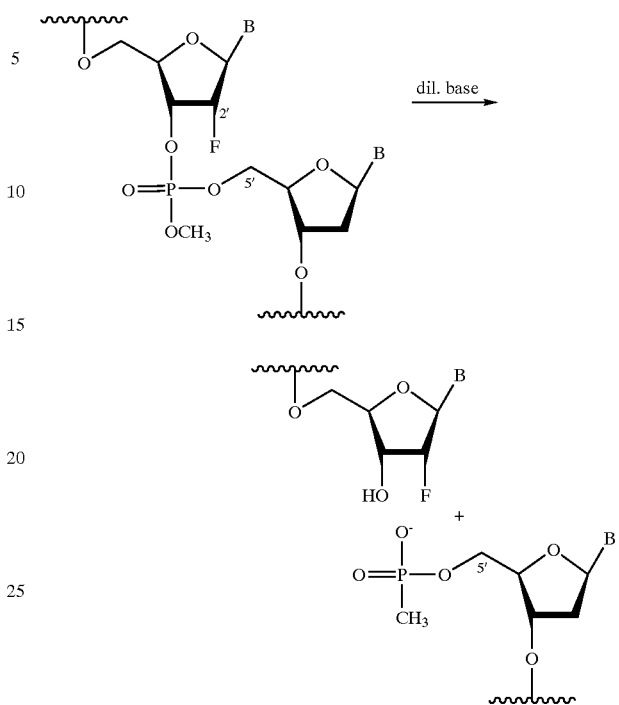

Scheme 30(a)

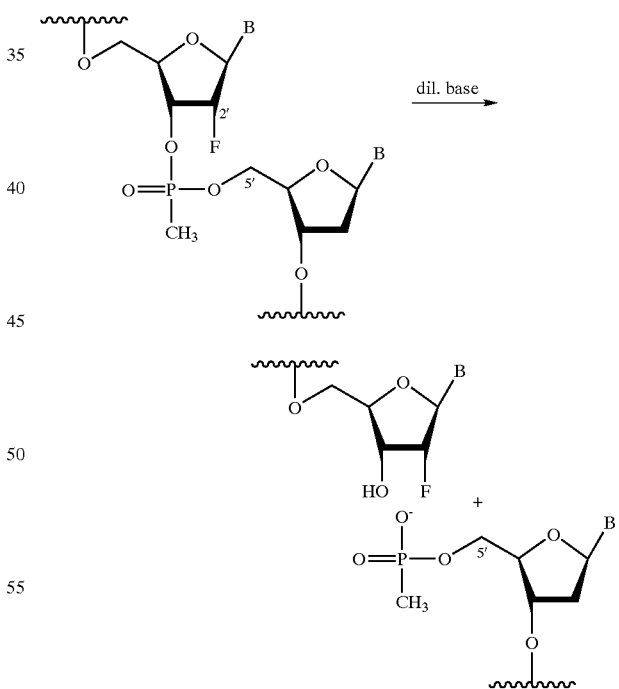

Scheme 30(b)

4. An electron-withdrawing group can be placed on the 4' carbon of a nucleotide which is linked through its 5'-hydroxy group to the 3'-hydroxy group of an adjacent ribonucletoide. Treatment with dilute base will result in cleavage (Scheme 31).

Scheme 31
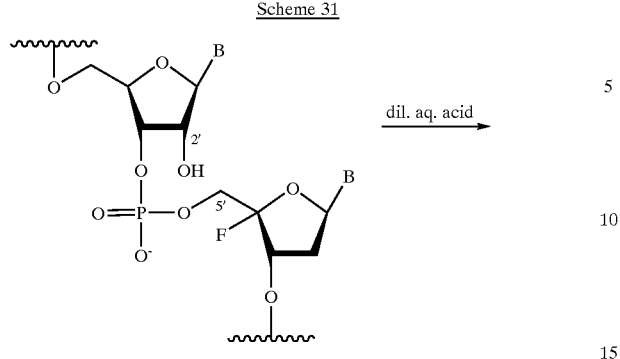
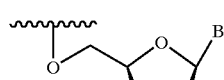
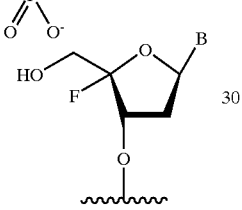
5. A 2' or 4' leaving group in a sugar may be susceptible to attack by the sulfur of a phosphorothioate (Schemes 32 and 33) to afford the desired cleavage:
Scheme 32
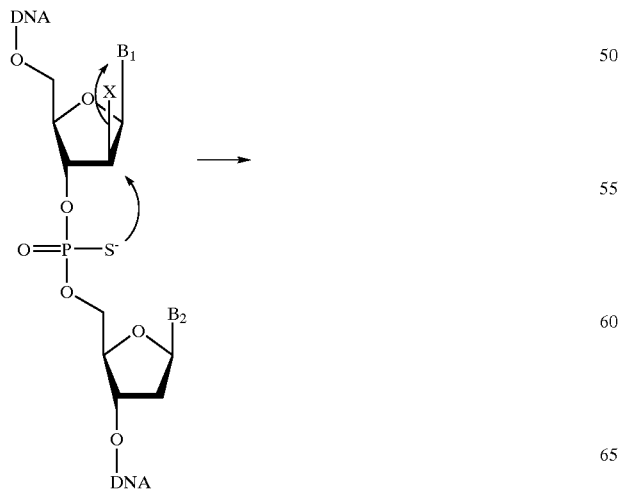
-continued
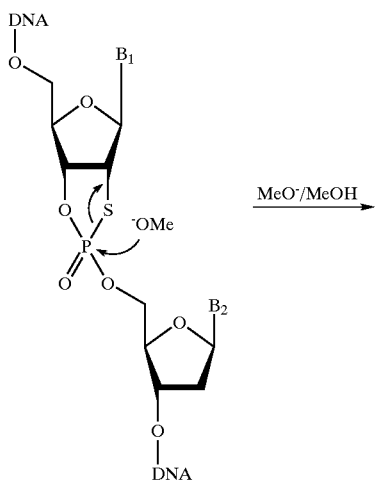
Scheme 33
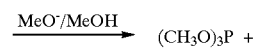
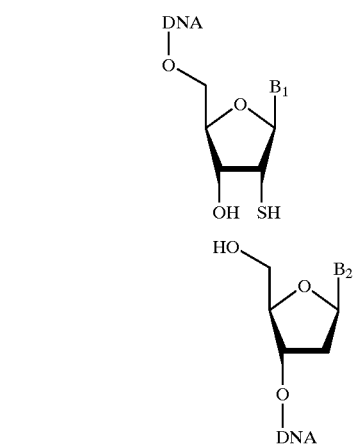

121
-continued
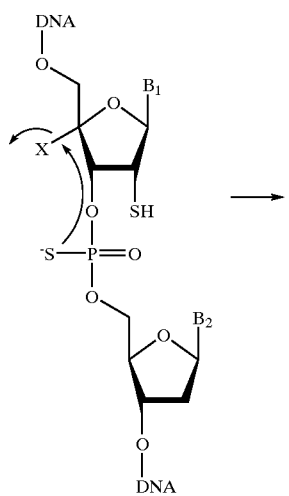
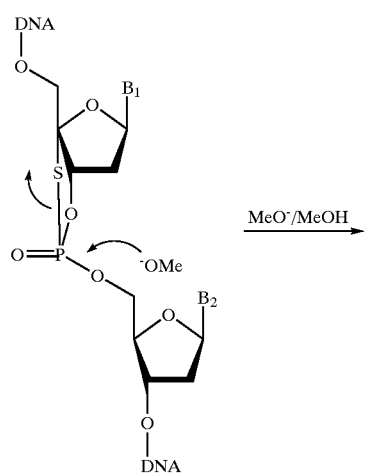
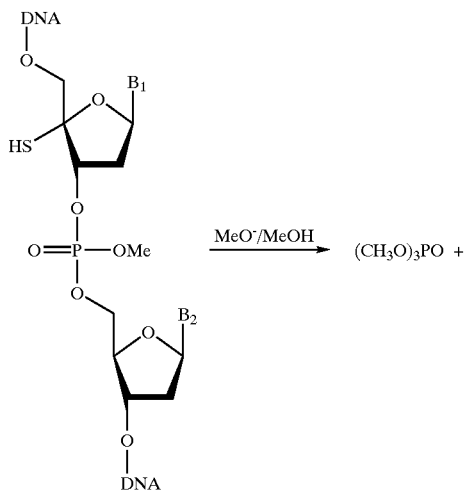
122
-continued
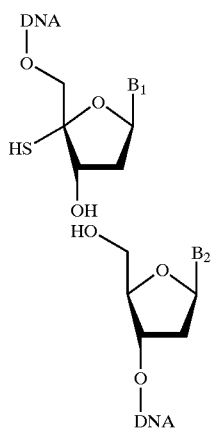
6. Ethylene sulfide could effect the cleavage of a 2' fluoro derivative of a sugar next to a phosphorothioate (Scheme 34):
Scheme 34
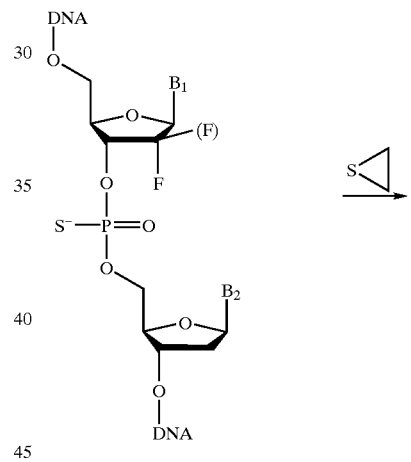
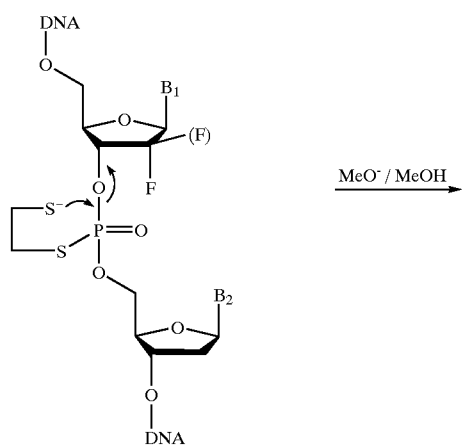

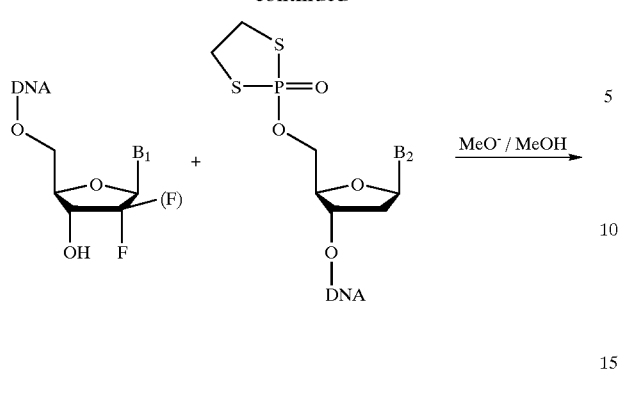

β-Mercaptoethanol or a similar reagent may be substituted for the ethylene sulfide.

7. A phosphorothioate might coordinate with a metal oxidant such as, without limitation, $Cu^{II}$ or $Fe^{III}$, which would be held in close proximity to the 2' hydroxy group of an adjacent ribonucleotide. Selective oxidation of the 2' hydroxy group to a ketone should render the adjacent phosphate ester linkage more susceptible to cleavage under basic conditions than the corresponding ribonucleotides or deoxyribonucleotides (Scheme 35):

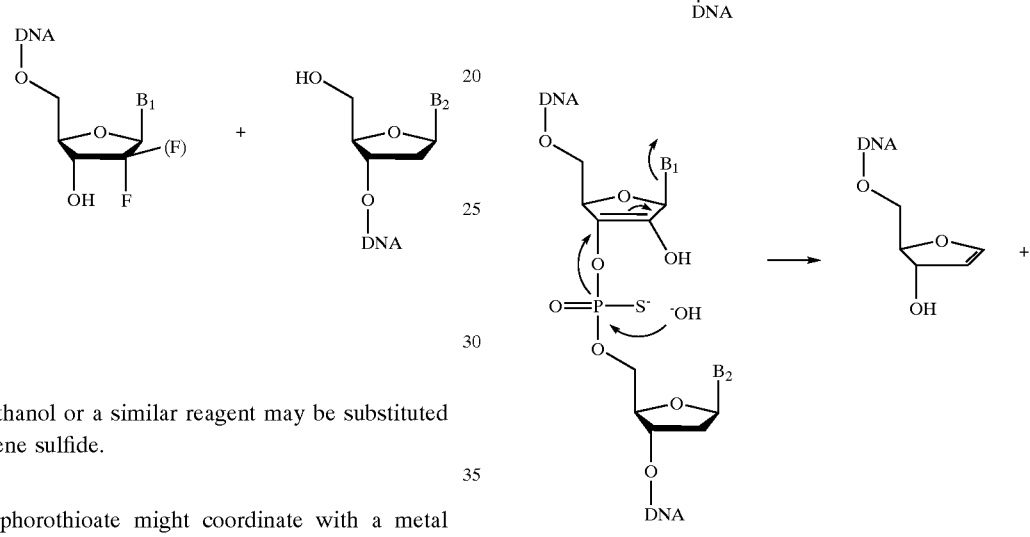

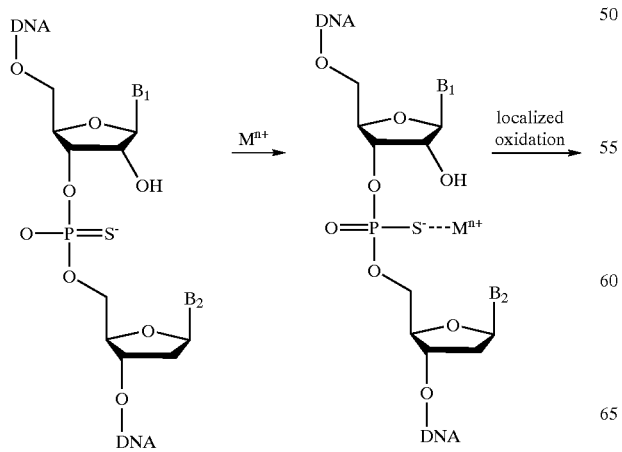

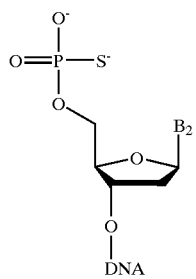

The preceding cleavage reactions may be carried out in such a manner as to cause cleavage at substantially all points of occurrence of the modified nucleotide or, in the case of multiple substitutions, all points of occurrence of two or more modified nucleotides in the proper spatial relationship. On the other hand, by controlling the amount of cleaving reagent and the reaction conditions, cleavage can be partial; i.e., cleavage will occur at only a fraction of the points of occurrence of a modified nucleotide or pairs of modified nucleotides.

B. Fragmenting Modified Polynucleotides in Mass Spectrometers

The preceding discussion relates to chemical methods for cleaving polynucleotides at sites where modified nucleotides have been incorporated. However, besides fragmenting polynucleotide molecules chemically in solution, it is a further aspect of this invention that fragmentation is accomplished within a mass spectrometer using chemical or physical means. Further, by manipulating the conditions within the mass spectrometer, the extent of fragmentation can be controlled. The ability to control degree of fragmentation of chemically modified oligonucleotides can be very useful in determining relationships between adjacent sequences. This is because, while mass spectrometric (MS) analysis of a completely cleaved polynucleotide provides the masses and therefore the nucleotide content of each fragment polynucleotide, determining the order in which these fragment polynucleotides are linked together in the original (analyte) polynucleotide is a difficult problem. By relaxing the stringency of cleavage one can generate fragments that correspond to two or more fragments from the complete cleavage set. The mass of these compound fragments provides the information that permits the inference that the two component fragments are adjacent in the original polynucleotide. By determining that multiple different pairs or triplets of complete cleavage fragments are adjacent to each other, eventually a much larger sequence can be pieced together than if one must rely solely on analysis of complete cleavage fragments. The ability to control the conditions of fragmentation by manipulation in the mass spectrometer is particularly advantageous because, in contrast to the iterative generation and subsequent testing of partial cleavages in a test tube, the effect of various partial cleavage conditions can be directly observed in real time and instantaneously manipulated to provide the optimal partial cleavage data set(s). For some purposes, use of several partial cleavage conditions may be very useful as successive levels of partial cleavage will provide a cumulative picture of the relationships between ever larger fragments. Specific mechanisms for fragmentation of modified polynucleotides are described below.

First, by choice of appropriate ionization methods, fragmentation can be induced during the ionization process. Alternatively, in the tandem mass spectrometry (MS/MS) approach, ions with mass-to-charge ratios (m/z) of interest can be selected and then activated by a variety of procedures including collision with molecules, ions or electrons, or the absorption of photons of various wavelength, leading to the fragmentation of the ions. In one aspect, ionization and fragmentation of the polynucleotide molecules can be achieved with fast atom bombardment (FAB). In this approach, modified polynucleotide molecules are dissolved in a liquid matrix such as glycerol, thioglycerol, or other glycerol analogs. The solution is deposited on a metallic surface. Particles with thousands of electron volts of kinetic energy are directed at the liquid droplet. Depending on the modification of the polynucleotides, partial fragmentation or complete fragmentation at every modified nucleotide can be achieved.

In another aspect, ionization and fragmentation can be effected by matrix-assisted laser desorption ionization mass spectrometry (MALDI-MS). In MALDI-MS a solution of modified polynucleotide molecules is mixed with a matrix solution, e.g., 3-hydroxypicolinic acid in aqueous solution. An aliquot of the mixture is deposited on a solid support, typically a metallic surface with or without modification. Lasers, preferably with wavelength between 3 $\mu$m and 10.6 $\mu$m, are used to irradiate the modified polynucleotide/matrix mixture. To analyze in-source fragmentation (ISF) products, delayed extraction can be employed. To analyze post-source decay (PSD) products, an ion reflector can be employed.

In another approach, ionization and fragmentation can be accomplished by electrospray ionization (ESI). In this procedure, the solution of modified DNA is sprayed through the orifice of a needle with a few kilovolts of voltage applied. Fragmentation of the modified polynucleotide molecules would occur during the desolvation process in the nozzle-skimmer (NS) region. The degree of the fragmentation will depend on the nature of the modification as well as factors such the voltage between the nozzle and skimmer, the flow rate as well as the temperature of the drying gas. If a capillary is used to assist the desolvation, then it is the voltage between the exit of the capillary and the skimmer and the temperature of the capillary that need to be controlled to achieved the desired degree of fragmentation.

In yet another technique, modified polynucleotide molecules can be selectively activated and dissociated. Activation can be accomplished by accelerating precursor ions to a kinetic energy of a few hundred to a few million electron volts and then causing them to collide with neutral molecules, preferably of noble gas. In the collision some of the kinetic energy of the precursor ions is converted into internal energy and causes fragmentation. Activation can be also accomplished by allowing accelerated precursor ions to collide onto a conductive or semi-conductive surface. Activation can also be accomplished by allowing accelerated precursor ions to collide with ions of opposite polarity. In another approach, activation can be accomplished by electron capturing. In this technique, the precursor ions are allowed to collide with thermalized electrons. Activation can also be accomplished by irradiating the precursor ions with photons of various wavelengths, preferably in the range of 193 nm to 10.6 $\mu$m. Activation can also be accomplished by heating vacuum chambers for trapped ions; the heating of vacuum chamber walls causes blackbody IR irradiation (Williams, E. R., *Anal. Chem.*, 1998, 70:179A-185A). The presence of modified nucleotides in a polynucleotide could also increase the rate constant of the fragmentation reaction, shortening the 10–1000 second duration required by the blackbody IR irradiation approach for unmodified polynucleotides.

As noted previously, tandem mass spectrometry is another tool that may be beneficially employed with the methods of this invention. In tandem mass spectrometry, precursor ions with m/z of interest are selected and subjected to activation. Depending on the activation technique employed, some or all of the precursor ions can be fragmented to give product ions. When this is done inside a suitable mass spectrometer (e.g., Fourier-transform ion cyclotron resonance mass spectrometer and ion trap mass spectrometers), the product ions with m/z of interest can be further selected and subjected to activation and fragmentation, giving more product ions. The mass of both precursor and product ions can be determined.

To control the degree of fragmentation at different stages of activation, two or more different types of modified nucleotides which, for purposes of discussion will be called Type I and Type II, with different sensitivity to different activation techniques could be incorporated (complete replacement of the natural nucleotide) into a target polynucleotide. Such a polynucleotide can be fragmented with high efficiency by type I activation technique at every position where type I modified nucleotides are incorporated. The resulting fragment ions, which still contain type II modified nucleotides can then be selected and fragmented by a type II activation technique to generate a set of sub-fragments from which nucleotide content can be more readily inferred. Such an approach can be useful for variance detection. For example, a 500-mer polynucleotide can be first fragmented into 10–50 fragments using a type I fragmentation technique. The m/z of each fragment (when compared to the predicted set of fragment masses) will reveal if a variance is present. Once fragments containing a variance are identified, the rest of the fragment ions are ejected from the ion-trapping device, while the fragment ions of interest are subjected to activation. By controlling the degree of fragmentation of these fragment ions, a set of smaller DNA fragments can be generated, allowing the order of the nucleotides and the position of the variance to be determined. Compared to the approach involving one type of modified nucleotide and one stage fragmentation, such an approach has the advantage in that the number of experimental steps and the amount of data that needs to be processed is significantly reduced. Compared to the approach involving one type of modified nucleotide but two stages of partial fragmentation, this approach has the advantage in that the fragmentation efficiency at the second stage is more controllable, hence reducing the chance of sequence gaps.

Although the aforementioned schemes of activation can be applied to all kinds of mass spectrometers, ion-trap mass spectrometers (ITMS) and Fourier-transform ion cyclotron resonance mass spectrometers (FT-ICRMS) are particularly suited for the electron capturing, photon activation, and blackbody IR irradiation approaches.

C. Modified Nucleotide Incorporation

Several examples of the polymerase catalyzed incorporation of a modified nucleotide into polynucleotides are described in the Example section, below. It may be, however, that one particular polymerase will not incorporate all the modified nucleotides described above, or others like them which are within the scope of this invention, with the same ease and efficiency. Also, while a particular polymerase may be capable of incorporating one modified nucleotide efficiently, it may be less efficient in incorporating a second modified nucleotide directly adjacent to the first modified nucleotide. Furthermore, currently available polymerases may not be capable of inducing or facilitating cleavage at modified nucleotides or nucleotide pairs, an extremely convenient way to achieve cleavage (see above). There are, however, several approaches to acquiring polymerases that are capable of incorporating the modified nucleotides and contiguous pairs of modified nucleotides of this invention and, potentially, inducing or facilitating specific cleavage at that modified nucleotide or those modified nucleotides.

One approach to finding polymerases with the proper capabilities is to take advantage of the diversity inherent among naturally-occurring polymerases including, without limitation, RNA polymerases, DNA polymerases and reverse transcriptases. Naturally occurring polymerases are known to have differing affinities for non-natural nucleotides and it is likely that a natural polymerase, which will perform the desired incorporation, can be identified. In some cases, use of a mixture of two or more naturally occurring polymerases having different properties regarding the incorporation of one or more non-natural nucleotides may be advantageous. For example, W. Barnes has reported (*Proc. Natl. Acad. Sci. USA,* 1994, 91:2216–2220) the use of two polymerases, an exonuclease-free N-terminal deletion mutant of Taq DNA polymerase and a thermostable DNA polymerase having 3'-exonuclease activity, to achieve improved polymerization of long DNA templates. Naturally occurring polymerases from thermophilic organisms are preferred polymerases for applications in which amplification by thermal cycling, e.g., PCR, is the most convenient way to produce modified polynucleotides.

Another approach is to employ current knowledge of polymerase structure-function relationships (see, e.g., Delarue, M., et al., *Protein Engineering,* 1990, 3:461467; Joyce, C. M., *Proc. Natl. Acad. Sci. USA,* 1997, 94:1619–1622) to identify or aid in the rational design of a polymerase which can accomplish a particular modified nucleotide incorporation. For example, the amino acid residues of DNA polymerases that provide specificity for deoxyribo-NTPs (dNTPs, deoxyribo Nucleotide TriPhosphates), while excluding ribo-NTPs (rNTPs), have been examined in some detail. Phenylalanine residue 155 or Moloney Murine Leukemia Virus reverse transcriptase appears to provide a steric barrier that blocks entry of ribo-NTPs. A similar role is played by phenylalanine residue 762 of the Klenow Fragment of *E. Coli* DNA polymerase 1, and tyrosine residue 115 of HIV-1 reverse transcriptase. Mutation of this latter amino acid, or its equivalent, in several different polymerases has the effect of altering polymerase fidelity and sensitivity to nucleotide inhibitors.

The corresponding site in RNA polymerases has also been investigated and appears to play a similar role in discriminating ribo- from deoxyribo- nucleotides. For example, it has been shown that mutation of tyrosine 639 of T7 RNA polymerase to phenylalanine reduces the specificity of the polymerase for rNTPs by about 20-fold and almost eliminates the $K_m$ difference between rNTPs and dNTPs. The result is that the mutant T7 RNA polymerase can polymerize a mixed dNTP/rNTP chain. See, e.g., Huang, Y., *Biochemistry,* 1997, 36:13718–13728. These results illustrate the use of structure-function information in the design of polymerases that will readily incorporate one or more modified nucleotides.

In addition, chemical modification or site directed mutagenesis of specific amino acids or genetic engineering can be used to create truncated, mutant or chimeric polymerases with particular properties. For example, chemical modification has been used to modify T7 DNA polymerase (Sequenase®, Amersham) to increase its processivity and affinity for non-natural nucleotides (Tabor, S., et al., *Proc. Natl. Acad. Sci. USA,* 1987, 84:47674771). Likewise, site directed mutagenesis has been employed to examine how *E. coli* DNA polymerase I (Klenow fragment) distinguishes between deoxy and dideoxynucleotides (Astake, M., et al., *J. Mol. Biol.,* 1998, 278:147–165).

Furthermore, development of a polymerase with optimal characteristics can be accomplished by random mutagenesis of one or more known polymerases coupled with an assay which manifests the desired characteristics in the mutated polymerase. A particularly useful procedure for performing such mutagenesis is called "DNA shuffling " (see Harayama, S., *Trends Biotechnol.,* 1998, 16:76–82). For example, using only three rounds of DNA shuffling and assaying for β-lactamase activity, a variant with 16,000-fold higher resistance to the antibiotic cefotaxime than the wild-type gene was created (Stemmer, W. P. C., *Nature,* 1994, 370:389–391).

A novel procedure, which is a further aspect of this invention, for creating and selecting polymerases capable of efficiently incorporating a modified nucleotide or contiguous pair of modified polynucleotides of this invention is described in the Examples section, below.

D. Fragment Analysis

Once a modified nucleotide or nucleotides has been partially or completely substituted for one or more natural nucleotides in a polynucleotide and cleavage of the resultant modified polynucleotide has been accomplished, analysis of the fragments obtained can be performed. If the goal is complete sequencing of a polynucleotide, the above-mentioned partial incorporation of modified nucleotides into a polynucleotide or partial cleavage of a completely modified-nucleotide-substituted polynucleotide may be used to create fragment ladders similar to those obtained when using the Maxam-Gilbert or Sanger procedures. In such case, a sequencing ladder can then be constructed using slab, capillary or miniaturized gel electrophoresis techniques. The advantages of the method of this invention over the Maxam-Gilbert procedure is that the placement of the modified nucleotides in the modified polynucleotide is precise as is cleavage whereas post-synthesis modification of a full-length polynucleotide by the Maxam-Gilbert reactions is susceptible to error. For example, the wrong nucleotides might be modified and thus the wrong cleavage may occur or the intended nucleotides may not be modified at all such that there may be insufficient, perhaps even no cleavage where cleavage would be expected to occur. The advantages over the Sanger procedure are several. First, the full-length clone can be purified after extension and prior to cleavage so that prematurely terminated fragments due to stops caused by polymerase error or template secondary structure can be removed before gel electrophoresis resulting in cleaner cleavage bands. In fact, it may not even be necessary to perform such clean up in that the prematurely terminated polymerase extension fragments themselves will be cleaved if they contain a modified nucleotide and those correctly cleavage fragments will simply augment the other fragments obtained from the cleavage of the full length clone (although such augmentation is confined to fragments shorter than the site of premature termination). Second, the chemical method produces equal intensity sequence ladder products in contrast to dye-terminator sequencing where substantial differences in the characteristics of different dye terminator molecules or in the interaction of dye modified dideoxynucleotides with polymerase template complexes results in an uneven signal intensity in the resulting sequence ladders. Such differences can lead to errors and make heterozygote identification difficult. Third, the chemical methods described herein allow production of homogeneous sequence ladders over distances of multiple kb, in contrast to the Sanger chain terminating method, which generate usefully labeled fragments over a substantially shorter interval. This is demonstrated in FIGS. 17 and 18. The production of long sequence ladders can be coupled with restriction endonuclease digestion to accomplish 1× sequencing of long templates.

Figure 14:
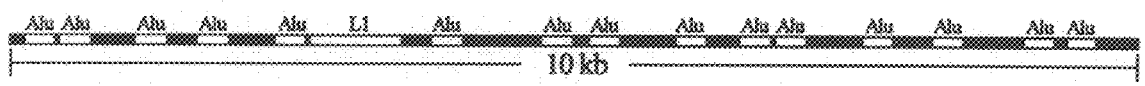
FIGS. 14 through 18 show various aspects of long range DNA sequencing using chemically cleavable modified nucleotides.
Figure 14:
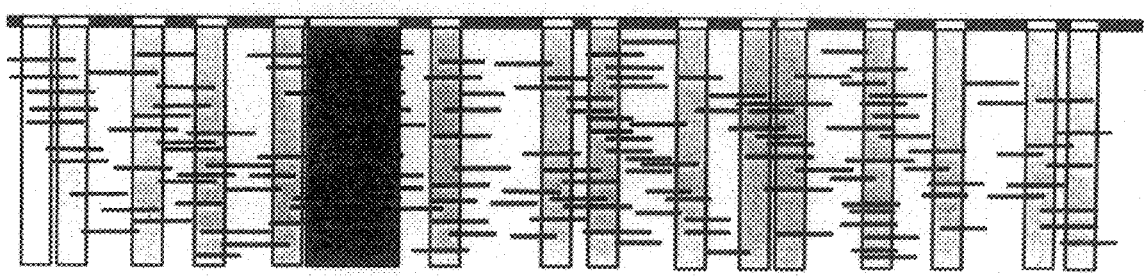
Figure 14:
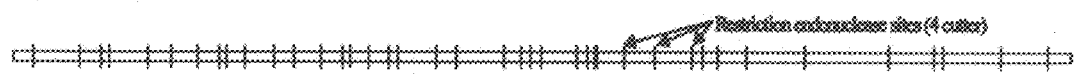
Figure 15:
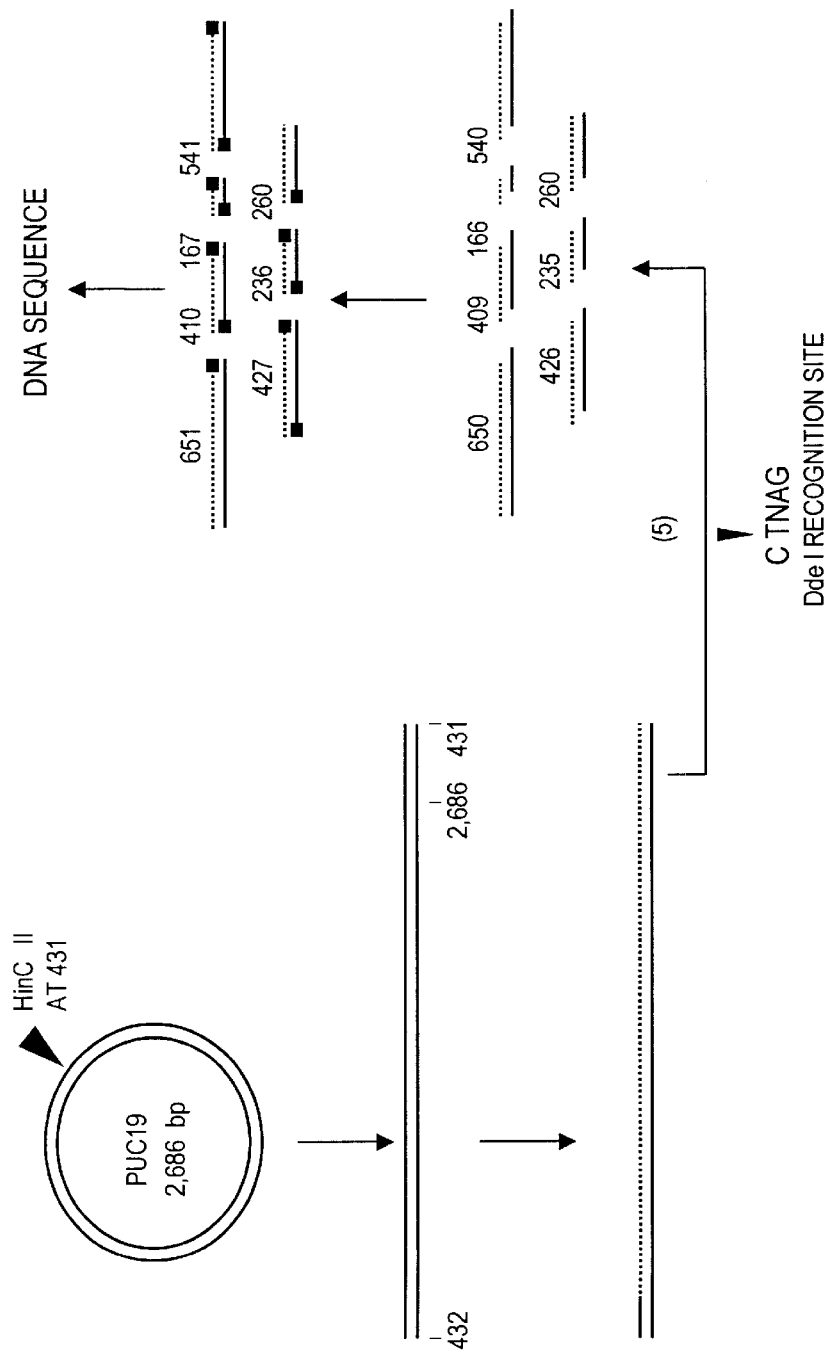
Figure 16:
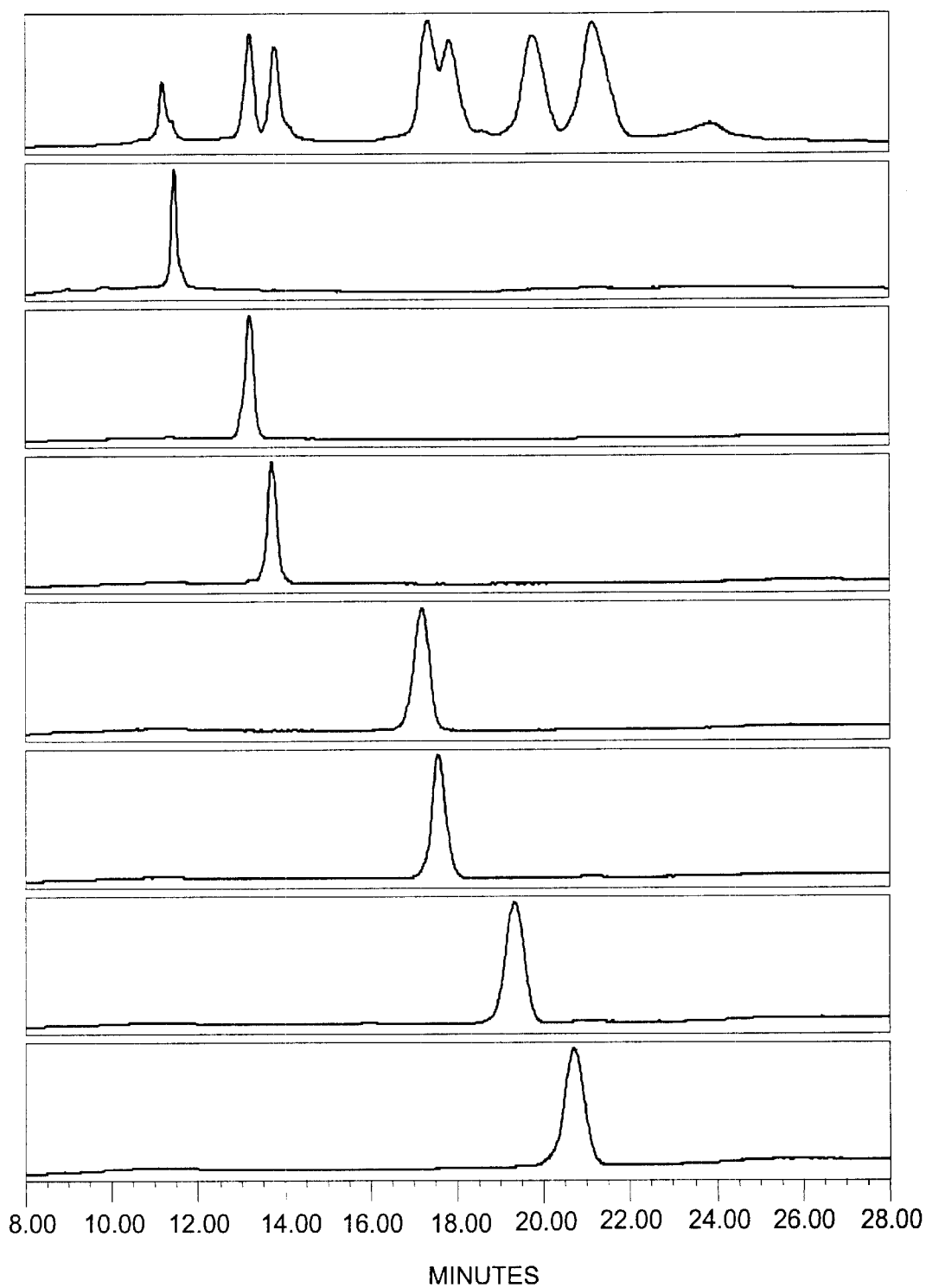

The utility of this approach to sequencing genomic DNA is exemplified in FIGS. 14, 15 and 16. These methods have particular utility in the sequencing of repeat-rich genomes such as, without limitation, the human genome.

A particular advantage of the methods described herein for the use of mass spectrometry for polynucleotide sequence determination is the speed, reproducibility, low cost and automation associated with mass spectrometry, especially in comparison to gel electrophoresis. See, e.g., Fu, D. J., et al., *Nature Biotechnology*, 1998, 16:381–384. Thus, although some aspects of this invention may employ gel analysis, those that use mass spectroscopy are preferred embodiments.

When detection of variance between two or more related polynucleotides is the goal, the ability of mass spectrometry to differentiate masses within a few or even one atomic mass unit (amu) of each other permits such detection without the need for determining the complete nucleotide sequences of the polynucleotides being compared; i.e., the masses of the oligonucleotides provide the nucleotide content. The use of mass spectrometry in this manner constitutes yet another aspect of this invention.

This use of mass spectrometry to identify and determine the chemical nature of variances is based on the unique molecular weight characteristics of the four deoxynucleotides and their oligomers.

Table 2 shows the mass differences among the four deoxynucleotide monophosphates. Table 3A then shows the calculated masses of all possible 2-mers, 3-mers, 4-mers and 5-mers by nucleotide composition alone; that is, without consideration of nucleotide order. As can be seen, only two of the 121 possible 2 mer through 5 mer oligonucleotides have the same mass. Thus, the nucleotide composition, of all 2 mers, 3 mers, 4 mers and all but two 5 mers created by cleavage of a polynucleotide can be immediately determined by mass spectrometry using an instrument with sufficient resolving power. For the masses in Table 3A, an instrument with a resolution (full width at half-maximal height) of 1500 to 2000 would be sufficient; mass spectrometers with resolution up to 10,000 are commercially available. However, when cleavage is performed at all sites of modified nucleotide substitution, it is not necessary to consider the masses of all possible 2 mers, 3 mers, 4 mers, etc. This is because there can be no internal occurrences of the cleavage nucleotide in any cleavage fragment. That is, if G is the cleavage nucleotide, then all resulting cleavage fragments will have 0 or 1 G, depending on the cleavage mechanism and, if it is 1 G, that G must occur at either the 3' or the 5' end of the fragment depending on the cleavage mechanism. Put another way, there cannot be a G internal to a fragment because, if there were, that fragment would necessarily be refragmented at the internal G. Thus, if the cleavage chemistry does leave a G on either end of all G-cleavage fragments, then the mass of G can be subtracted from the mass of each fragment and the resulting masses can be compared. The same can be done with A, C and T. Table 4 shows the masses of all 2 mers through 7 mers lacking one nucleotide. This calculation has been performed for polynucleotides up to 30 mers and it has been shown that there are only 8 sets of isobaric oligonucleotides (oligonucleotides with masses within 0.01% of each other) below a mass of 5000 Da. The eight sets of isobaric oligonucleotides are shown in Table 3B. Inspection of Table 3B reveals that every set except Set 2 involves a polynucleotide with multiple G residues. Thus, cleavage at G would eliminate all isobaric masses except one, $d(T_8)$ vs $d(C_3A_5)$ which could not be resolved by mass spectrometry with a resolution of 0.01%. However, either C or A cleavage would remove the latter polynucleotide.

Table 4 shows that cleavage at A or T consistently produces fragments with larger mass differences between the closest possible cleavage fragments. Cleavage at A produces mass differences of 5, 10, 15, 20 or 25 Da between the closest fragments while cleavage at T affords mass differences of 8, 18 or 24 Da, albeit at the expense of a few more isobaric fragments.

TABLE 2

|  | dAMP | DCMP | dGMP | dTMP | 2-chloroadenineMP |
|---|---|---|---|---|---|
| Panel A |  |  |  |  |  |
| Mol. wt. | 313.2 | 289.2 | 329.2 | 304.2 |  |
| vs. dAMP | — | 24 | 16 | 9 |  |
| vs. dCMP |  | — | 40 | 15 |  |
| vs. dGMP |  |  | — | 25 |  |
| Panel B |  |  |  |  |  |
| Mol. wt. | 313.2 | 289.2 | 329.2 | 304.2 | 347.7 |
| vs. dTMP |  |  |  |  | 42.3 |

TABLE 2-continued

|  | dAMP | DCMP | dGMP | dTMP | 2-chloro-adenineMP |
|---|---|---|---|---|---|
| vs. dAMP | — | 24 | 16 | 9 | — |
| vs. dCMP |  | — | 40 | 15 | 57.3 |
| vs. dGMP |  |  | — | 25 | 17.3 |

In Table 2, Panel A shows the masses of the four deoxynucleotide residues are shown across the top, and calculated molecular weight differences between each pair of nucleotide residues are shown in the table. Note that chemically modified nucleotides will generally have masses different than those shown above for the natural nucleotides. The mass difference between a particular modified nucleotide and the other nucleotides will vary depending on the modification. See description of specific nucleotide modifications and cleavage mechanisms for details of cleavage products. Panel B shows that the mass differences between the natural nucleotides and 2-chloroadenine are shown (far right column). The smallest mass difference is 17.3 Da instead of 9 Da as in panel A, providing advantageous discrimination of nucleotides using mass spectrometry.

TABLE 3a shows the masses of all possible compositions of 2mers, 3mers, 4mers and 5mers in order of mass in Daltons (Da), rounded to the nearest whole number for ease of presentation. (Other nucleotide orders are possible for many of the oligonucleotides.) The 5mers column is continued on the left under the 2mers. Note that two 5mers with different nucleotide content have the same mass (AAAAA and CCGGG, shaded at bottom right, both weigh 1504). The molecular masses are provided; ionization will change the masses. More generally, these masses are illustrative; actual masses will differ depending on the chemical modification, cleavage mechanism and polarity of ionization.

| 2mer | mass | 3 mer | Mass | 4mer | mass | 5mer | mass |
|---|---|---|---|---|---|---|---|
| CC | 596 | CCC | 885 | CCCC | 1174 | CCCCC | 1463 |
| CT | 611 | CCT | 900 | CCCT | 1189 | CCCCT | 1478 |
| AC | 620 | CCA | 909 | CCCA | 1198 | CCCCA | 1487 |
| TT | 626 | CTT | 915 | CCTT | 1204 | CCCTT | 1493 |
| AT | 635 | CTA | 924 | CCTA | 1213 | CCCTA | 1502 |
| CG | 636 | CCG | 925 | CCCG | 1214 | CCCCG | 1503 |
| AA | 644 | TTT | 930 | CTTT | 1219 | CCTTT | 1508 |
| GT | 651 | CAA | 933 | CCAA | 1222 | CCCAA | 1511 |
| AG | 660 | TTA | 939 | CTTA | 1228 | CCTTA | 1517 |
| GG | 676 | CTG | 940 | CCTG | 1229 | CCCTG | 1518 |
|  |  | TAA | 948 | TTTT | 1234 | CTTTT | 1523 |
|  |  | CGA | 949 | CAAT | 1237 | CCTAA | 1526 |
|  |  | TTG | 955 | CCAG | 1238 | CCCGA | 1527 |
|  |  | AAA | 957 | TTTA | 1243 | CTTTA | 1532 |
|  |  | TGA | 964 | CTTG | 1244 | CCTTG | 1533 |
|  |  | CGG | 965 | CAAA | 1246 | CCAAA | 1535 |
|  |  | AAG | 973 | TTAA | 1252 | TTTTT | 1538 |
|  |  | TGG | 980 | CTAG | 1253 | CTTAA | 1541 |
|  |  | GGA | 989 | CCGG | 1254 | CCTGA | 1542 |
|  |  | GGG | 1005 | TTTG | 1259 | CCCGG | 1543 |
|  |  |  |  | TAAA | 1261 | TTTTA | 1547 |
|  |  |  |  | CAAG | 1262 | CTTTG | 1548 |
|  |  |  |  | TTAG | 1268 | CAATA | 1550 |
|  |  |  |  | CTGG | 1269 | CCAGA | 1551 |
|  |  |  |  | AAAA | 1270 | TTTAA | 1556 |
|  |  |  |  | TAAG | 1277 | CTTGA | 1557 |
|  |  |  |  | CAGG | 1278 | CCTGG | 1558 |
|  |  |  |  | TTGG | 1284 | CAAAA | 1559 |
|  |  |  |  | AAAG | 1286 | TTTTG | 1563 |
|  |  |  |  | TAGG | 1293 | TTAAA | 1565 |
|  |  |  |  | CGGG | 1294 | CTAGA | 1566 |
|  |  |  |  | AAGG | 1302 | CCGGA | 1567 |
|  |  |  |  | TGGG | 1309 | TTTGA | 1572 |
|  |  |  |  | AGGG | 1318 | CTTGG | 1573 |
|  |  |  |  | GGGG | 1334 | TAAAA | 1574 |
|  |  |  |  |  |  | CAAAG | 1575 |
|  |  |  |  |  |  | TTAAG | 1581 |
|  |  |  |  |  |  | CTGGA | 1582 |
|  |  |  |  |  |  | AAAAA | 1583 |
|  |  |  |  |  |  | CCGGG | 1583 |

Continued from right

| 5mer | mass |
|---|---|
| TTTGG | 1588 |
| TAAAG | 1590 |
| CAAGG | 1591 |
| ATTGG | 1597 |
| CTGGG | 1598 |
| AAAAG | 1599 |
| TAAGG | 1606 |
| ACGGG | 1607 |
| TTGGG | 1613 |
| AAAGG | 1615 |
| ATGGG | 1622 |
| CGGGG | 1623 |
| AAGGG | 1631 |
| TGGGG | 1638 |
| AGGGG | 1647 |
| GGGGG | 1663 |

TABLE 3b

|  | Polynucleotides | Masses |
|---|---|---|
| Set 1 | $d(C_2G_3)$ | 1566.016 |
|  | $d(A_5)$ | 1566.068 |
| Set 2 | $d(C_5G_3)$ | 2433.584 |
|  | $d(T_8)$ | 2433.603 |
|  | $d(C_3A_5)$ | 2433.636 |
| Set 3 | $d(A_1G_7)$ | 2617.707 |
|  | $d(C_8T_1)$ | 2617.711 |
| Set 4 | $d(C_{10}T_1)$ | 3196.090 |
|  | $d(G_{10})$ | 3196.137 |

TABLE 3b-continued

|  | Polynucleotides | Masses |
|---|---|---|
| Set 5 | $d(C_6T_1A_4)$ | 3292.134 |
|  | $d(C_{13})$ | 3292.190 |
| Set 6 | $d(C_{13})$ | 3759.457 |
|  | $d(T_7A_1G_4)$ | 3759.472 |
| Set 7 | $d(C_5T_9)$ | 4183.751 |
|  | $d(A_6G_7)$ | 4183.779 |
| Set 8 | $d(T_7G_7)$ | 4433.899 |
|  | $d(C_{11}A_4)$ | 4433.936 |

TABLE 4

| Cleavage at G | | | Cleavage at C | | | Cleavage at A | | | Cleavage at T | | |
|---|---|---|---|---|---|---|---|---|---|---|---|
| 2 mer | mass | mass Δ | 2 mer | Mass | mass Δ | 2 mer | mass | mass Δ | 2 mer | Mass | mass Δ |
| CC | 517 |  | TT | 547 |  | CC | 517 |  | CC | 517 |  |
| CT | 532 | 15 | AT | 556 | 9 | CT | 532 | 15 | AC | 541 | 24 |
| AC | 541 | 9 | AA | 565 | 9 | TT | 547 | 15 | CG | 557 | 16 |
| TT | 547 | 6 | GT | 572 | 7 | CG | 557 | 10 | AA | 565 | 8 |
| AT | 556 | 9 | AG | 581 | 9 | GT | 572 | 15 | AG | 581 | 16 |
| AA | 565 | 9 | CG | 597 | 16 | CG | 597 | 25 | CG | 597 | 16 |
| 3 mer | mass | mass Δ | 3 mer | Mass | mass Δ | 3 mer | mass | mass Δ | 3 mer | mass | massΔ |
| CCC | 806 |  | TTT | 851 |  | CCC | 806 |  | CCC | 806 |  |
| CCT | 821 | 15 | TTA | 860 | 9 | CCT | 821 | 15 | CCA | 830 | 24 |
| CCA | 830 | 9 | TAA | 869 | 9 | CTT | 836 | 15 | CCG | 846 | 16 |
| CTT | 836 | 6 | TTG | 876 | 7 | CCG | 846 | 10 | CAA | 854 | 8 |
| CTA | 845 | 9 | AAA | 878 | 2 | TTT | 851 | 5 | CGA | 870 | 16 |
| TTT | 851 | 6 | TGA | 885 | 7 | CTG | 861 | 10 | AAA | 878 | 8 |
| CAA | 854 | 3 | AAG | 894 | 9 | TTG | 876 | 15 | CGG | 886 | 8 |
| TTA | 860 | 6 | TGG | 901 | 7 | CGG | 886 | 10 | AAG | 894 | 8 |
| TAA | 869 | 9 | GGA | 910 | 9 | TGG | 901 | 15 | GGA | 910 | 16 |
| AAA | 878 | 9 | GGG | 926 | 16 | GGG | 926 | 25 | GGG | 926 | 16 |
| 4 mer | mass | mass Δ | 4 mer | mass | mass Δ | 4 mer | mass | mass Δ | 4 mer | mass | mass Δ |
| CCCC | 1095 |  | TTTT | 1155 |  | CCCC | 1095 |  | CCCC | 1095 |  |
| CCCT | 1110 | 15 | TTTA | 1164 | 9 | CCCT | 1110 | 15 | CCCA | 1119 | 24 |
| CCCA | 1119 | 9 | TTAA | 1173 | 9 | CCTT | 1125 | 15 | CCCG | 1135 | 16 |
| CCTT | 1125 | 6 | TTTG | 1180 | 7 | CCCG | 1135 | 10 | CCAA | 1143 | 8 |
| CCTA | 1134 | 9 | TAAA | 1182 | 2 | CTTT | 1140 | 5 | CCAG | 1159 | 16 |
| CTTT | 1140 | 6 | TTAG | 1189 | 7 | CCTG | 1150 | 10 | CAAA | 1167 | 8 |
| CCAA | 1143 | 3 | AAAA | 1191 | 2 | TTTT | 1155 | 5 | CCGG | 1175 | 8 |
| CTTA | 1149 | 6 | TAAG | 1198 | 7 | CTTG | 1165 | 10 | CAAG | 1183 | 8 |
| TTTT | 1155 | 6 | TTGG | 1205 | 7 | CCGG | 1175 | 10 | AAAA | 1191 | 8 |
| CAAT | 1158 | 3 | AAAG | 1207 | 2 | TTTG | 1180 | 5 | CAGG | 1199 | 8 |
| TTTA | 1164 | 6 | TAGG | 1214 | 7 | CTGG | 1190 | 10 | AAAG | 1207 | 8 |
| CAAA | 1167 | 3 | AAGG | 1223 | 9 | TTGG | 1205 | 15 | CGGG | 1215 | 8 |
| TTAA | 1173 | 6 | TGGG | 1230 | 7 | CGGG | 1215 | 10 | AAGG | 1223 | 8 |
| TAAA | 1182 | 9 | AGGG | 1239 | 9 | TGGG | 1230 | 15 | AGGG | 1239 | 16 |
| AAAA | 1191 | 9 | GGGG | 1255 | 16 | GGGG | 1255 | 25 | GGGG | 1255 | 16 |
| 5 mer | mass | mass Δ | 5 mer | mass | mass Δ | 5 mer | mass | mass Δ | 5 mer | mass | mass Δ |
| CCCCC | 1384 |  | TTTTT | 1459 |  | CCCCC | 1384 |  | CCCCC | 1384 |  |
| CCCCT | 1399 | 15 | TTTTA | 1468 | 9 | CCCCT | 1399 | 15 | CCCCA | 1408 | 24 |
| CCCCA | 1408 | 9 | TTTAA | 1477 | 9 | CCCTT | 1414 | 15 | CCCCG | 1424 | 16 |
| CCCTT | 1414 | 6 | TTTTG | 1484 | 7 | CCCCG | 1424 | 10 | CCCAA | 1432 | 8 |
| CCCTA | 1423 | 9 | TTAAA | 1486 | 2 | CCTTT | 1429 | 5 | CCCGA | 1448 | 16 |
| CCTTT | 1429 | 6 | TTTGA | 1493 | 7 | CCCTG | 1439 | 10 | CCAAA | 1456 | 8 |
| CCCAA | 1432 | 3 | TAAAA | 1495 | 2 | CTTTT | 1444 | 5 | CCCGG | 1464 | 8 |
| CCTTA | 1438 | 6 | TTAAG | 1502 | 7 | CCTTG | 1454 | 10 | CCAGA | 1472 | 8 |
| CTTTT | 1444 | 6 | AAAAA | 1504 | 2 | TTTTT | 1459 | 5 | CAAAA | 1480 | 8 |
| CCTAA | 1447 | 3 | TTTGG | 1509 | 5 | CCCGG | 1464 | 5 | CCGGA | 1488 | 8 |
| CTTTA | 1453 | 6 | TAAAG | 1511 | 2 | CTTTG | 1469 | 5 | CAAAG | 1496 | 8 |

TABLE 4-continued

| Cleavage at G | | | Cleavage at C | | | Cleavage at A | | | Cleavage at T | | |
|---|---|---|---|---|---|---|---|---|---|---|---|
| CCAAA | 1456 | 3 | ATTGG | 1518 | 7 | CCTGG | 1479 | 10 | AAAAA | 1504 | 8 |
| TTTTT | 1459 | 3 | AAAAG | 1520 | 2 | TTTTG | 1484 | 5 | CCGGG | 1504 | 0 |
| CTTAA | 1462 | 3 | TAAGG | 1527 | 7 | CTTGG | 1494 | 10 | CAAGG | 1512 | 8 |
| TTTTA | 1468 | 6 | TTGGG | 1534 | 7 | CCGGG | 1504 | 10 | AAAAG | 1520 | 8 |
| CAATA | 1471 | 3 | AAAGG | 1536 | 2 | TTTGG | 1509 | 5 | ACGGG | 1528 | 8 |
| TTTAA | 1477 | 6 | ATGGG | 1543 | 7 | CTGGG | 1519 | 10 | AAAGG | 1536 | 8 |
| CAAAA | 1480 | 3 | AAGGG | 1552 | 9 | TTGGG | 1534 | 15 | CGGGG | 1544 | 8 |
| TTAAA | 1486 | 6 | TGGGG | 1559 | 7 | CGGGG | 1544 | 10 | AAGGG | 1552 | 8 |
| TAAAA | 1495 | 9 | AGGGG | 1568 | 9 | TGGGG | 1559 | 15 | AGGGG | 1568 | 16 |
| AAAAA | 1504 | 9 | GGGGG | 1584 | 16 | GGGGG | 1584 | 25 | GGGGG | 1564 | 16 |

| 6 mer | mass | mass Δ | 6 mer | mass | mass Δ | 6 mer | mass | mass Δ | 6 mer | mass | mass Δ |
|---|---|---|---|---|---|---|---|---|---|---|---|
| CCCCCC | 1673 | | TTTTTT | 1763 | | CCCCCC | 1673 | | CCCCCC | 1673 | |
| CCCCCT | 1688 | 15 | TTTTTA | 1772 | 9 | CCCCCT | 1688 | 15 | CCCCCA | 1697 | 24 |
| CCCCCA | 1697 | 9 | TTTTAA | 1781 | 9 | CCCCTT | 1703 | 15 | CCCCCG | 1713 | 16 |
| CCCCTT | 1703 | 6 | TTTTTG | 1788 | 7 | CCCCCG | 1713 | 10 | CCCCAA | 1721 | 8 |
| CCCCTA | 1712 | 9 | TTTAAA | 1790 | 2 | CCCTTT | 1718 | 5 | CCCCAG | 1737 | 16 |
| CCCTTT | 1718 | 6 | TTTTAG | 1797 | 7 | CCCCTG | 1728 | 10 | CCCAAA | 1745 | 8 |
| CCCCAA | 1721 | 3 | TTAAAA | 1799 | 2 | CCTTTT | 1733 | 5 | CCCCGG | 1753 | 8 |
| CCCTTA | 1727 | 6 | TTTAAG | 1806 | 7 | CCCTTG | 1743 | 10 | CCCAAG | 1761 | 8 |
| CCTTTT | 1733 | 6 | TAAAAA | 1808 | 2 | TTTTTC | 1748 | 5 | CCAAAA | 1769 | 8 |
| CCCTAA | 1736 | 3 | TTTTGG | 1813 | 5 | CCCCGG | 1753 | 5 | CCCGGA | 1777 | 8 |
| CCTTTA | 1742 | 6 | TTAAAG | 1815 | 2 | CCTTTG | 1758 | 5 | CCAAAG | 1785 | 8 |
| CCCAAA | 1745 | 3 | AAAAAA | 1817 | 2 | TTTTTT | 1763 | 5 | CCCGGG | 1793 | 8 |
| TTTTTC | 1748 | 3 | TTTGGA | 1822 | 5 | CCCTGG | 1768 | 5 | CAAAAA | 1793 | 0 |
| CCTTAA | 1751 | 3 | AAAAGT | 1824 | 2 | TTTTCG | 1773 | 5 | CCAAGG | 1801 | 8 |
| CTTTTA | 1757 | 6 | TTAAGG | 1831 | 7 | CCTTGG | 1783 | 10 | CAAAAG | 1809 | 8 |
| CCAAAT | 1760 | 3 | AAAAAG | 1833 | 2 | TTTTTG | 1788 | 5 | CCGGGA | 1817 | 8 |
| TTTTTT | 1763 | 3 | TTTGGG | 1838 | 5 | CCGGGG | 1793 | 5 | AAAAAA | 1817 | 0 |
| CTTTAA | 1766 | 3 | AAAGGT | 1840 | 2 | TTTCGG | 1798 | 5 | AAACGG | 1825 | 8 |
| CCAAAA | 1769 | 3 | ATTGGG | 1847 | 7 | CCTGGG | 1808 | 10 | AAAAAG | 1833 | 8 |
| TTTTTA | 1772 | 3 | AAAAGG | 1849 | 2 | TTTTGG | 1813 | 5 | CCGGGG | 1833 | 0 |
| CTTAAA | 1775 | 3 | TAAGGG | 1856 | 7 | TTCGGG | 1823 | 10 | AACGGG | 1841 | 8 |
| TTTTAA | 1781 | 6 | TTGGGG | 1863 | 7 | CCGGGG | 1833 | 10 | AAAAGG | 1849 | 8 |
| TAAAAC | 1784 | 3 | AAAGGG | 1865 | 2 | TTTGGG | 1838 | 5 | ACGGGG | 1857 | 8 |
| TTTAAA | 1790 | 6 | AGGGGT | 1872 | 7 | TGGGGC | 1848 | 10 | AAAGGG | 1865 | 8 |
| CAAAAA | 1793 | 3 | AAGGGG | 1881 | 9 | TTGGGG | 1863 | 15 | GGGGGC | 1873 | 8 |
| TTAAAA | 1799 | 6 | GGGGGT | 1888 | 7 | GGGGGC | 1873 | 10 | AAGGGG | 1881 | 8 |
| TAAAAA | 1808 | 9 | AGGGGG | 1897 | 9 | GGGGGT | 1888 | 15 | AGGGGG | 1897 | 16 |
| AAAAAA | 1817 | 9 | GGGGGG | 1913 | 16 | GGGGGG | 1913 | 25 | GGGGGG | 1913 | 16 |

| 7 mer | mass | mass Δ | 7 mer | mass | mass Δ | 7 mer | mass | mass Δ | 7 mer | mass | mass Δ |
|---|---|---|---|---|---|---|---|---|---|---|---|
| CCCCCCC | 1962 | | TTTTTTT | 2067 | | CCCCCCC | 1962 | | CCCCCCC | 1962 | |
| CCCCCCT | 1977 | 15 | TTTTTTA | 2076 | 9 | CCCCCCT | 1977 | 15 | CCCCCCA | 1986 | 24 |
| CCCCCCA | 1986 | 9 | TTTTTAA | 2085 | 9 | CCCCCTT | 1992 | 15 | CCCCCCG | 2002 | 16 |
| CCCCCTT | 1992 | 6 | TTTTTTG | 2092 | 7 | CCCCCCG | 2002 | 10 | CCCCCAA | 2010 | 8 |
| CCCCCTA | 2001 | 9 | TTTTAAA | 2094 | 2 | CCCCTTT | 2007 | 5 | CCCCCGA | 2026 | 16 |
| CCCCTTT | 2007 | 6 | TTTTTGA | 2101 | 7 | CCCCCTG | 2017 | 10 | CCCCAAA | 2034 | 8 |
| CCCCCAA | 2010 | 3 | TTTAAAA | 2103 | 2 | CCCTTTT | 2022 | 5 | CCCCCGG | 2042 | 8 |
| CCCCTTA | 2016 | 6 | TTTTAAG | 2110 | 7 | CCCCTTG | 2032 | 10 | CCCCAAG | 2050 | 8 |
| CCCTTTT | 2022 | 6 | TTAAAAA | 2112 | 2 | CCTTTTT | 2037 | 5 | CCCAAAA | 2058 | 8 |
| CCCCTAA | 2025 | 3 | GGTTTTT | 2117 | 5 | CCCCCGG | 2042 | 5 | CCCCGGA | 2066 | 8 |
| CCCTTTA | 2031 | 6 | TTTAAAG | 2119 | 2 | CCCTTTG | 2047 | 5 | CCCAAAG | 2074 | 8 |
| CCCCAAA | 2034 | 3 | TAAAAAA | 2121 | 2 | CTTTTTT | 2052 | 5 | CCAAAAA | 2082 | 8 |
| CCTTTTT | 2037 | 3 | TTTTGGA | 2126 | 5 | CCCCTGG | 2057 | 5 | CCCCGGG | 2082 | 0 |
| CCCTTAA | 2040 | 3 | TTAAAGA | 2128 | 2 | CCTTTTG | 2062 | 5 | CCCGGAA | 2090 | 8 |
| CCTTTTA | 2046 | 6 | AAAAAAA | 2130 | 2 | TTTTTTT | 2067 | 5 | CCAAAGG | 2098 | 8 |
| CCCAAAT | 2049 | 3 | TTTGGAA | 2135 | 5 | CCCTTGG | 2072 | 5 | CCCGGGA | 2106 | 8 |
| CTTTTTT | 2052 | 3 | AAAAAGT | 2137 | 2 | CTTTTTG | 2077 | 5 | CAAAAAA | 2106 | 0 |
| CCTTAAA | 2055 | 3 | GGGTTTT | 2142 | 5 | CCCCGGG | 2082 | 5 | CCAAAGG | 2114 | 8 |
| CCCAAAA | 2058 | 3 | TTAAAGG | 2144 | 2 | CTTTCGG | 2087 | 5 | CAAAAAG | 2122 | 8 |
| TTTTCA | 2061 | 3 | AAAAAAG | 2146 | 2 | GTTTTTT | 2092 | 5 | CCCGGGG | 2122 | 0 |
| CCTTAAA | 2064 | 3 | TTTGGGA | 2151 | 5 | CCCTGGG | 2097 | 5 | CCGGGAA | 2130 | 8 |
| TTTTTTT | 2067 | 3 | AAAAGGT | 2153 | 2 | CTTTTGG | 2102 | 5 | AAAAAAA | 2130 | 0 |
| TTTAAC | 2070 | 3 | AATTGGG | 2160 | 7 | CCTTGGG | 2112 | 10 | AAAACGG | 2138 | 8 |
| TAAAACC | 2073 | 3 | AAAAAGG | 2162 | 2 | GGTTTTT | 2117 | 5 | AAAAAAG | 2146 | 8 |
| ATTTTTT | 2076 | 3 | GGGGTTT | 2167 | 5 | CCCGGGG | 2122 | 5 | CCGGGGA | 2146 | 0 |
| TTTAAAC | 2079 | 3 | TAAAGGG | 2169 | 2 | CTTTGGG | 2127 | 5 | AAACGGG | 2154 | 8 |
| CCAAAAA | 2082 | 3 | TTGGGGA | 2176 | 7 | TGGGGCC | 2137 | 10 | AAAAAGG | 2162 | 8 |
| AATTTTT | 2085 | 3 | AAAAGGG | 2178 | 2 | GGGTTTT | 2142 | 5 | CCGGGGG | 2162 | 0 |
| CTTAAAA | 2088 | 3 | AAGGGGT | 2185 | 7 | CTTGGGG | 2152 | 10 | AACGGGG | 2170 | 8 |
| AAATTTT | 2094 | 6 | GGGGGTT | 2192 | 7 | GGGGGCC | 2162 | 10 | AAAAGGG | 2178 | 8 |
| CTAAAAA | 2097 | 3 | AAAGGGG | 2194 | 2 | GGGGTTT | 2167 | 5 | AGGGGGC | 2186 | 8 |
| AAAATTT | 2103 | 6 | AGGGGGT | 2201 | 7 | GGGGGTC | 2177 | 10 | AAAGGGG | 2194 | 8 |
| CAAAAAA | 2106 | 3 | AAGGGGG | 2210 | 9 | GGGGGTT | 2192 | 15 | CGGGGGG | 2202 | 8 |

TABLE 4-continued

| Cleavage at G | | | Cleavage at C | | | Cleavage at A | | | Cleavage at T | | |
|---|---|---|---|---|---|---|---|---|---|---|---|
| AAAAATT | 2112 | 6 | GGGGGGT | 2217 | 7 | CGGGGGG | 2202 | 10 | AAGGGGG | 2210 | 8 |
| AAAAAAT | 2121 | 9 | AGGGGGG | 2226 | 9 | GGGGGGT | 2217 | 15 | AGGGGGG | 2226 | 16 |
| AAAAAA | 2130 | 9 | GGGGGG | 2242 | 16 | GGGGGGG | 2242 | 25 | GGGGGGG | 2242 | 16 |

Table 4 shows the masses resulting from cleavage of oligonucleotides at specific nucleotides. Cleavage at G produces fragments with no internal G residues; certain cleavage mechanisms may leave a G at the 5' or 3' end of a fragment. In the table, G has been omitted from the G cleavage fragments for ease of representation. The mass of one phosphate group, 61 daltons, was subtracted from each fragment since most cleavage reactions result in the loss of one phosphate group. Note that the two 5 mers with the same T cleavage mass (part 1) continue to propagate through the T cleavage masses.

Thus, for a given target analyte polynucleotide, if its sequence is known, it is possible to determine whether cleavage at one or more of the base nucleotides would produce any of the above confounding artifacts and then, by judicious choice of experimental conditions, it is possible to avoid or resolve them.

Based on the preceding analysis, it can be seen that any difference in the nucleotide sequence among two or more similar polynucleotides from different members of a population will result in a difference in the pattern of fragments obtained by cleavage of the polynucleotides and thus a difference in the masses seen in the mass spectrogram. Every variance will result in two mass changes, the disappearance of a mass and the appearance of a new mass. In addition, if a double-stranded polynucleotide is being analyzed or if two strands are being analyzed independently, the variance will result in a change in mass of the two complementary strands of a target DNA resulting in four mass changes altogether (a mass disappearance and a mass appearance in each strand). The presence of a second strand displaying mass changes provides a useful internal corroboration of the presence of a variance. In addition, the sets of mass changes in fragments from complementary strands can provide additional information regarding the nature of the variance. FIGS. 27–30 exemplify the detection of a mass difference on both strands of a polynucleotide after full substitution and cleavage at modified dA, a variant position in the transferrin receptor gene. Table 5 shows the sets of mass changes expected on complementary strands for all possible point mutations (transitions and transversions). Once the mass spectrogram is obtained, it will be immediately apparent whether the variance was an addition of one or more nucleotides to a fragment (an approximately 300+a.u. increase in fragment mass), deletion of one or more nucleotides from a fragment (approximately a 300+a.u. decrease in fragment mass) or a substitution of one or more nucleotides for one or more other nucleotides (differences as shown in Table 5). Furthermore, if the variance is a substitution, the exact nature of that substitution can also be ascertained.

TABLE 5

| | | Resolving Power of MS Instrument (FWHM) | | | |
|---|---|---|---|---|---|
| | | 1,000 | 1,500 | 2,000 | 10,000 |
| Nucleotide substitution | Δ(Da) | Maximum fragment in which Δ at left is resolvable | | | |
| C <-> G | 40 | 123 nt | 184 nt | 246 nt | 1,230 |
| G <-> T | 25 | 77 nt | 116 nt | 154 nt | 770 |
| A <-> C | 24 | 74 nt | 111 nt | 148 nt | 740 |
| A <-> G | 16 | 49 nt | 74 nt | 98 nt | 490 |
| C <-> T | 15 | 46 nt | 69 nt | 92 nt | 460 |
| A <-> T | 9 | 27 nt | 41 nt | 55 nt | 270 |

Table 5 summarizes the relation between mass spectrometer resolution and nucleotide changes in determining the maximum size fragment in which a given base change can be identified. The maximum size DNA fragment (in nucleotides; nt) in which a base substitution can theoretically be resolved is provided in the four columns at right (bottom 6 rows) for each possible nucleotide substitution, listed in column at left. As is evident from the table, the mass difference created by each substitution (Δ, measured in Daltons) and the resolving power of the mass spectrometer determine the size limit of fragments that can be successfully analyzed. Commercially available MALDI instruments can resolve between 1 part in 1,000 to 1 part in 5,000 (FWHM) while available ESI instruments can resolve 1 part in 10,000. Modified ESI MS instruments are capable of at least 10-fold greater mass resolution. (The theoretical resolution numbers in the table do not take into consideration limitations on actual resolution imposed by the isotopic heterogeneity of molecular species and the technical difficulty of efficiently obtaining large ions.) FWHM: full width at half-maximal height, is a standard measure of mass resolution. (For further information on resolution and mass accuracy in MS see, for example: Siuzdak, G. *Mass Spectrometry for Biotechnology*, Academic Press, San Diego, 1996.)

E. Serial Cleavage

The preceding discussion focuses primarily on the use of one cleavage reaction with any given modified polynucleotide. However, it is also possible and it is a further aspect of this invention, to serially cleave a polynucleotide in which two or more natural nucleotides have been replaced with two or more modified nucleotides, which have different cleavage characteristics. That is, a polynucleotide that contains two or more types of modified nucleotides, either fully or partially substituted, can be cleaved by serial exposure to different cleavage conditions, either chemical, physical or both. One preferred embodiment of this approach is tandem mass spectrometry, where fragmented molecular species produced by one procedure can be retained in a suitable mass spectrometer (e.g. Fourier-transform ion cyclotron resonance mass spectrometer or ion trap mass spectrometer), for subsequent exposure to a second physical/chemical procedure that results in activation and cleavage at a second modified nucleotide. The product ions may be subjected to a third and even a fourth cleavage condition directed to specific modifications on a third and fourth nucleotide to enable observation of precursor-product relationships between the input (precursor) ions and those generated during each round of cleavage. The use of a continuous or stepwise gradient of cleavage conditions of increasing efficiency may be used to enhance the elucidation of precursor-product relationships between ions.

Figure 21:
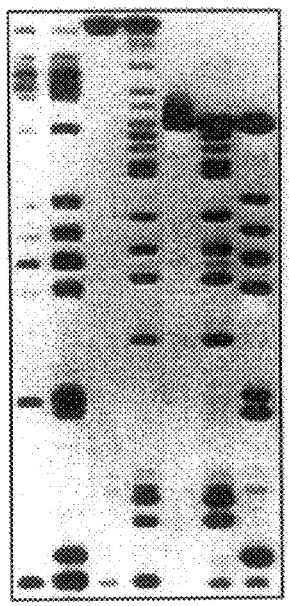
FIG. 21 illustrates the method of this invention involving incorporation of two different modified nucleotides in the same DNA strand and cleavage by two different chemical means to produce two different sequence ladders. The primer sequence is underlined. T nucleotides are numbered above the sequence and G nucleotides are numbered below the sequence. In the ladder lane 1 is the extension product using ribo-GTP, lane 2 is the result of cleavage of the lane 1 product with chemical base, lane 3 is the extension product incorporation 5'-aminoTTP, lane 4 is the result of cleavage of the lane 3 product with acid, lane 5 is the extension product containing both ribo-GTP and 5'-aminoTTP, lane 6 is the result of cleavage of the lane 5 product with acid and lane 7 is the result of cleavage of the lane 5 product with chemical base.

The production of a polynucleotide containing multiple modified nucleotides reduces the need to perform multiple polymerizations on the same template to produce a set of polynucleotides each with a different single modified nucleotide; i.e., one for cleavage at A, one for G, one for T and one for C. Also, the serial application of cleavage procedures specific for different nucleotides of a single polynucleotide enhances detection of precursor-product relationships, which is useful for determining DNA sequence. FIG. 21 shows the production of a polynucleotide modified by complete substitution of riboGTP for dGTP and 5'-amino-TTP for dTTP followed by cleavage with base, which results in cleavage at G, or cleavage with acid, which results in cleavage at T. Subsequent treatment of the base cleaved fragments with acid or visa-versa results in further fragmentation into double (G and T) cleaved fragments. This would be useful, for example and without limitation, for identifying a variance at position 27 (dA) of the sequence (FIG. 21). That is, as can be seen in FIG. 21, cleavage at G alone produces the fragment ACTTCACCG (position 27 is highlighted), which contains two dA residues. A change in mass of this fragment of −24 Da, indicating an A to C change, would not permit determination of which of the two dA residues changed to dC. Similarly, cleavage at T alone to give the fragment TCACCGGCACCA [SEQ. ID 17], which contains three dA residues also prevents determination of which dA was changed. However, double cleavage at G and T produces the fragment TCACCG which undergoes the −24 Da mass shift and, because it only contains one dA, allows definitive assignment of the variant nucleotide. Schemes using this approach to precisely detect variances at other nucleotides will be apparent to those skilled in the art based on the disclosures herein and are within the scope of this invention.

A further aspect of this invention is a algorithm or algorithms which permit the use of computers to directly infer DNA sequence or the presence of variances from mass spectrometry.

F. Parallel Cleavage

It is likewise possible, and it is a further aspect of this invention that a polynucleotide which has been substituted with two or more modified nucleotides each if which is susceptible to a different cleavage procedure, may be analyzed in parallel fashion. That is, one can divide the polynucleotide into aliquots and expose each aliquot to a cleavage procedure specific for one of the modified nucleotides. This saves the effort of performing independent polymerization reactions for each of the modified nucleotides. This approach can be used to generate sequence ladders, or to generate complete cleavage products for variance detection. As shown in Example 5, complete cleavage at two different nucleotides (performed independently), followed by mass spectrometry, substantially increases the efficiency of variance detection compared to cleavage at a single nucleotide.

For example, consider a single polynucleotide substituted with ribo-A, 5'-amino-C, and 5'-(bridging) thio-G nucleotides. All three modified nucleotides are known to be incorporated by polymerases. Sequence ladders can be produced from such a modified polynucleotide by exposure of one aliquot to acid, resulting in cleavage at C; exposure of a second aliquot to base, resulting in cleavage at A; and exposure of a third aliquot to silver or mercury salts, resulting in cleavage at G. It is possible that a polynucleotide produced with the three above modified nucleotides plus 4'-C-acyl T could also (separately) be exposed to UV light to produce cleavage at T, resulting in a complete set of sequencing reactions from a single polymerization product.

G. Combination of Modified Nucleotide Cleavage and Chain Termination

Another application of modified nucleotide incorporation and cleavage is to combine it with a chain termination procedure. By incorporating one or more modified nucleotides in a polymerization procedure (for example but without limitation, modified A) with a different chain terminating nucleotide, such as a dideoxy-G, a Sanger-type ladder of fragments terminating at the dideoxy-nucleotide can be generated. Subsequent exposure of this ladder of fragments to a chemical that cleaves at the modified A will result in further fragmentation, with the resulting fragments terminating 5' to A and 3' to either A (most of the time) or G (in one fragment per chain termination product). Comparison of the resulting fragment set with a fragment set produced solely by substitution and cleavage at the modified nucleotide (A) will provide an instructive comparison: all the fragments will be the same except for the presence of extra fragments in the chain terminating set which end at 3' G, which, on mass spectrometric analysis would provide the mass (and by inference the nucleotide content) of all fragments in which an A is followed (directly or after some interval) by a G, without an intervening A. Derivation of similar data using other chain terminating nucleotides and other cleavage nucleotides will cumulatively provide a set of data useful for determining the sequence of the polymerization products.

H. Cleavage Resistant Modified Nucleotide Substitution and Mass Shifting Nucleotides The preceding embodiments of this invention relate primarily to the substitution into a polynucleotide of one or more modified nucleotides which have the effect of enhancing the susceptibility of the polynucleotide to cleavage at the site(s) of incorporation of the modified nucleotide(s) in comparison to unmodified nucleotides. It is entirely possible, however, and it is yet another aspect of this invention, that a modified nucleotide which, when incorporated into a polynucleotide, reduces susceptibility to cleavage at the site of incorporation of the modified nucleotide compared to unmodified sites. In this scenario, cleavage would then occur at unmodified sites in the polynucleotide. Alternatively, a combination of cleavage-resistant and cleavage-sensitive modified nucleotides may be incorporated into the same polynucleotide to optimize the differential between cleavable and non-cleavable sites.

An example of a modified nucleotide which imparts this type of resistance to cleavage is the 2'-fluoro derivative of any natural nucleotide. The 2'-fluoro derivative has been shown to be substantially less susceptible to fragmentation in a mass spectrometer than unsubstituted natural nucleotides.

As shown in Table 2, the mass differences between the naturally occurring nucleotides range from 9 to 40 Da and are sufficient for resolving single nucleotide differences in all fragments of 25 mer size and under. However, it may be desirable to increase the mass difference between the four nucleotides or between any pair of nucleotides to simplify their detection by mass spectrometry. This is illustrated for dA and its 2-chloroadenine analog in Table 2. That is, substitution with 2-chloroadenine, mass 347.7, increases the A-T mass difference from 9 Da to 42.3 Da, the A-C difference from 24 to 57.3 Da and the A-G difference from 16 to 17.3 Da. Other mass-shifting nucleotide analogs are known in the art and it is an aspect of this invention that they may be used to advantage with the mass spectrometric methods of this invention.

I. Applications

A number of applications of the methods of the present invention are described below. It is understood that these descriptions are exemplary only and are not intended to be, or are they to be construed as being, limiting on the scope of this invention in any manner whatsoever. Thus, other applications of the methods described herein will become apparent to those skilled in the art based on the disclosures herein; such applications are within the scope of this invention.

a. Full Substitution, Full Extension and Complete Cleavage.

In one aspect of the present invention at least one of the four nucleotides of which the target polynucleotide is composed is completely replaced with a modified polynucleotide (either on one strand using primer extension, or on both strands using a DNA amplification procedure), a full length polynucleotide is made and substantially complete cleavage is effected. The result will be cleavage of modified polynucleotides into fragments averaging four nucleotides in length. This is so because the abundance of A, T, G and C nucleotides is roughly equal in most genomes and their distribution is semi-random. Therefore a particular nucleotide occurs approximately once every four nucleotides in a natural polynucleotide sequence. There will, of course, be a distribution of sizes, with considerable deviation from the average size due to the non-random nature of the sequence of biological polynucleotides, and the unequal amounts of A:T vs. G:C base pairs in different genomes. The extended primer (whether primer extension or amplification) will not be cleaved until the first occurrence of a modified nucleotide after the end of the primer, resulting in fragments of greater than 15 nt (i.e., greater than the length of the primer). Often, these primer-containing fragments will be the largest or among the largest produced. This can be advantageous in the design of genotyping assays. That is, primers can be designed so that the first occurrence of a polymorphic nucleotide position is after the primer. After cleavage, the genotype can be determined from the length of the primer-containing fragment. This is illustrated in FIGS. 27–32. Due to this variation in the. size of analyte masses it is essential that the mass spectrometer be capable of detecting polynucleotides ranging up to 20 mers, or even 30 mers, with a level of resolution and mass accuracy consistent with unambiguous determination of the nucleotide content of each mass. As discussed below, this requirement has different implications depending on whether the nucleotide sequence of the analyte polynucleotide is already known (as will generally be the case with variance detection or genotyping) or not (as will be the case with de novo DNA sequencing).

i. Applications to Variance Detection

Variance detection is usually performed on an analyte DNA or cDNA sequence for which at least one reference sequence is available. The concern of variance detection is to examine a set of corresponding sequences from different individuals (sample sequences) in order to identify sequence differences between the reference and sample sequences or among the sample sequences. Such sequence variances will be identified and characterized by the existence of different masses among the cleaved sample polynucleotides.

Depending on the scope of the variance detection procedure, analyte fragments of different lengths may be optimal. For genotyping, it is desirable that one primer be close to the known variant site.

Generally an analyte fragment of at least 50 nucleotides, more preferably at least 100 nucleotides and still more preferably at least 200 nucleotides will be produced by polymerase incorporation of modified nucleotides (either A, G, C or T), followed by cleavage at the sites of modified nucleotide incorporation, and mass spectrometric analysis of the resulting products. Given the frequency of nucleotide variances (estimated at one in 200 to one in 1000 nucleotides in the human genome), there will generally be zero or only one or two cleavage fragments that differ among any two samples. The fragments that differ among the samples may range in size from a monomer to a 10 mer, less frequently up to a 20 mer or, rarely, a fragment of even greater length; however, as noted above, the average cleavage fragment will be about 4 nucleotides. Knowledge of the reference sequence can be used to avoid cleavage schemes that would generate very large cleavage products, and more generally to enhance the detectability of any sequence variation that may exist among the samples by computing the efficiency of variance detection at each nucleotide position for all possible cleavage schemes, as outlined below. However, large sequences are not really a problem when a reference sequence is available and the analyte fragment length is only several hundred nucleotides. This is because it is extremely unlikely that any analyte fragment will contain two large cleavage masses that are close in size. In general, if there are only a few large fragments they can be easily identified and, as Table 5 shows, even with a MALDI instrument capable of mass resolution of only 1000, the most difficult substitution, an A←→T change resulting in a 9 amu shift can be detected in a 27 mer.

In order to select experimental conditions for variance detection that maximize the likelihood of success, one can use the reference sequence to predict the fragments that would be produced by cleavage at A, G, C or T in advance of experimental work. Based on such an analysis, the optimal modified nucleotide substitution and cleavage scheme can be selected for each DNA or cDNA sequence that is to be analyzed. Such an analysis can be performed as follows:

For each nucleotide of the test polynucleotide, substitute each of the three other possible nucleotides and generate an associated mass change. For example, if at position 1 the test polynucleotide begins with A, then generate hypothetical polynucleotides beginning with T, G and C. Next move to position two of the test sequence and again make all three possible substitutions, and so forth for all positions of the test polynucleotide. If the test polynucleotide is 100 nucleotides in length then altogether 300 new hypothetical fragments will be generated by this procedure on one strand and another 300 on the complementary strand. Each set of three substitutions can then be analyzed together.

Generate the masses that would be produced by cleaving at T, C, G or A each of the three new hypothetical test fragments obtained by the substitutions of T, C or G for A at position 1. Compare these mass sets with the set of masses obtained from the reference sequence (which in our example has A at position 1). For each of the four cleavages (T, C, G, A), determine whether the disappearance of an existing mass or the generation of a new mass would create a difference in the total set of masses. If a difference is created, determine whether it is a single difference or two differences (i.e. a disappearance of one mass and an appearance of another). Also determine the magnitude of the mass difference compared to the set of masses generated by cleavage of the reference sequence. Perform this same analysis for each of the 100 positions of the test sequence, in each case examining the consequences of each of the four possible base-specific cleavages, i.e., for DNA, at A, C, G and T.

Generate a correlation score for each of the four possible base-specific cleavages. The correlation score increases in proportion to the fraction of the 300 possible deviations from the reference sequence that produce one or more mass changes (i.e., a higher correlation score for two mass differences), and in proportion to the extent of the mass differences (greater mass differences score higher than small ones).

In the case of primer extension, the analysis is performed for one strand; in the case of amplfication, the computation is carried out on the products of cleavage of both strands.

The above method can be extended to the use of combinations of substitution and cleavage. For example, T cleavage on each of the strands of the analyte polynucleotide (either independent or simultaneous cleavage of both strands at T), or cleavage at T and A on one strand (again, either independent or simultaneous cleavage of both strands), or cleavage of one strand with T and cleavage of the complementary strand with A, and so forth. Based on the generated correlation scores for each of the different schemes, an optimal scheme can be determined in advance of experimental work.

A computer program can be constructed to accomplish the above task. Such a program can also be extended to encompass the analysis of experimental cleavage masses. That is, the program can be constructed to compare all the masses in the experimentally determined mass spectrum with the cleavage masses expected from cleavage of the reference sequence and to flag any new or missing masses. If there are new or missing masses, the experimental set of masses can be compared with the masses generated in the computational analysis of all the possible nucleotide substitutions, insertions or deletions associated with the experimental cleavage conditions. However, nucleotide substitutions are about ten times more common than insertions or deletions, so an analysis of substitutions alone should be useful. In one embodiment, the computational analysis data for all possible nucleotide insertions, deletions and substitutions can be stored in a look-up table. The set of computational masses that matches the experimental data then provides the sequence of the new variant sequence or, at a minimum, the restricted set of possible sequences of the new variant sequence. (The location and chemical nature of a substitution may not be uniquely specified by one cleavage experiment.) To resolve all ambiguity concerning the nucleotide sequence of a variant sample may require, in some cases, another substitution and cleavage experiment (see Section E, Serial Cleavage and DNA sequencing applications described below), or may be resolved by some other sequencing method (e.g. conventional sequencing methods or sequencing by hybridization). It may be advantageous to routinely perform multiple different substitution and cleavage experiments on all samples to maximize the fraction of variances, which can be precisely assigned to a specific nucleotide.

A computational analysis of natural polynucleotides of 50, 100, 150, 200 and 250 nucleotides has been performed and it was discovered that combinations of two nucleotide cleavages (for example cleave at A on one strand and G on the complementary strand) result in 99–100% detection efficiency, considering all possible substitutions up to 250 nt. Potentially useful but sometimes less than 100% sensitive analyses can be performed on longer fragments up to 1000 nt. See Example 5 for details of this analysis.

ii. Applications to DNA Sequencing

A still further aspect of this invention utilizes the chemical methods disclosed herein together with mass spectrometry to determine the complete nucleotide sequence of a polynucleotide de novo. The procedure involves the same reactions described above for variance detection; i.e., total replacement of one of the four nucleotides in a polynucleotide with a modified nucleotide followed by substantially complete cleavage of the modified polynucleotide at each and every point of occurrence of the modified nucleotide and then determination of the masses of the fragments obtained. In this case, however, it may be necessary to routinely perform four sets of cleavage reactions, a different natural nucleotide being replaced with a modified nucleotide in each reaction so that all four natural nucleotides are in turn replaced with modified nucleotides and the resultant modified polynucleotides are cleaved and the masses of the cleavage products determined. It may also be necessary to employ one or more multiple nucleotide substitutions, as discussed above, to resolve sequencing ambiguities that may arise. While the number of reactions necessary per sequence determination experiment is thus similar to that required for Maxam-Gilbert or Sanger sequencing, the method of this invention has the advantages of eliminating radiolabels or dyes, providing superior speed and accuracy, permitting automation and eliminating artifacts, including compressions, associated with Maxam-Gilbert and Sanger sequencing or any other gel-based methods. This latter consideration may be of preeminent importance as mass spectrometry will currently allow analysis of cleavage reactions in a matter of seconds to minutes (and, in the future, milliseconds), compared to hours for current gel electrophoretic procedures. Furthermore, the inherent accuracy of mass spectrometry, together with the control over the construction of the modified polynucleotide that can be achieved using the methods of this invention will sharply reduce the need for sequencing redundancy. A representative total sequencing experiment is set forth in the Examples section, below.

The process of inferring DNA sequence from the pattern of masses obtained by cleavage of analyte molecules is considerably more complicated than the process for detecting and inferring the chemical nature of sequence variances. In the case of sequencing by complete cleavage and mass analysis the following must be accomplished:

Determine the length of the sequence. From the experimentally determined masses infer the nucleotide content of each cleavage fragment as discussed elsewherein herein. This analysis is performed for each of the four sets of experimental cleavage masses. The shortcomings of this analysis are that two or more fragments (particularly short ones) may have identical mass, and therefore may be counted as one, leading to an undercounting of the length of the sequence. However, this is not a serious experimental problem in that the fragment masses can be summed and compared for all four cleavages; if they do not correspond then there must be two or more overlapping masses among the fragments. Thus, the determination of all fragment masses in all four cleavage reactions essentially eliminates this source of potential error. First, the set of cleavage masses that gives the greatest length can be taken as a starting point. Next, the nucleotide content of all of the masses in the other three cleavage reactions can be tested for whether they are compatible with the nucleotide content of any of the masses associated with the greatest length cleavage set. If they are not compatible, then there must be undercounting even in the set associated with the greatest length.

Comparison of sequence contents will generally allow the uncounted bases to be identified and the full length of the sequence to thus be determined.

The next aspect of the analysis may include: (a) determining the intervals at which A, C, G and T nucleotides must occur based on the sizes of respective cleavage products; (b) analyze the nucleotide content of the largest fragments from each cleavage set to identify sets of nucleotides that belong together; (c) compare nucleotide content of fragments between the different sets to determine which fragments are compatible (i.e. one could be subsumed within the other or they could overlap) or incompatible (no nucleotides in common); (d) begin to integrate the results of these different analyses to restrict the number of ways in which fragments can be pieced together. The elimination of possibilities is as useful as the identification of possible relationships. A detailed illustration of the logic required to work out the sequence of a short oligonucleotide is provided in Example 4.

One way to provide additional information about local sequence relationships is to reduce the extent of nucleotide substitution or the completeness of cleavage (see below) in order to obtain sets of incompletely (but still substantially) cleaved fragments. The mass analysis of such fragments may be extremely useful, in conjunction with the completely cleaved fragment sets, for identifying which fragments are adjacent to each other. A limited amount of such information is needed to complete the entire puzzle of assembling the cleavage fragments into a continuous sequence.

Three additional ways to augment the inference of DNA sequence from analysis of complete substitution and cleavage masses are: (a) analysis of dinucleotide cleavage masses (see below), which can provide a framework for compartmentalizing the small masses associated with mononucleotide substitution and cleavage into fewer intermediate size collections. Dinucleotide cleavage also provides the location of dinucleotides sequences at intervals along the entire sequence in fact, dinucleotide cleavage at all possible dinucleotides is an alternate DNA sequencing method; (b) mononucleotide substitution and cleavage of the complementary strand using one or more modified nucleotides which can provide valuable complementary information on fragment length and overlaps; (c) combination substitution and cleavage schemes employing simultaneous di- and mononucleotide cleavages or two different simultaneous mononucleotide cleavages can provide unambiguous information on sequence order.

In the foregoing descriptions, it has been assumed that the modified nucleotide is selectively more susceptible to chemical cleavage under appropriate conditions than the three unmodified nucleotides. However, an alternative approach to effecting mononucleotide cleavage is to use three modified nucleotides that are resistant to cleavage under chemical or physical conditions sufficient to induce cleavage at an unmodified, natural nucleotide. Thus, in another aspect of the present invention, mononucleotide cleavage may be effected by selective cleavage at an unmodified nucleotide. One chemical modification of nucleotides which has been shown to make them more stable to fragmentation during mass spectrometric analysis is the 2'-fluoro modification. (Ono, T., et al., *Nucleic Acids Research*, 1997, 25: 4581–4588.) The utility of 2'-fluoro substituted DNA for extending the accessible mass range for Sanger sequencing reactions (which is generally limited by fragmentation) has been recognized, but it is an aspect of the present invention that this chemistry also has utility in effecting nucleotide specific cleavage by fully substituting three modified nucleotides that are resistant to a specific physical or chemical cleavage procedure. Another chemical modification that has been shown to increase the stability of nucleotides during MALDI-MS is the 7-deaza analog of adenine and guanine. (Schneider, K. and Chait, B. T., *Nucleic Acids Research*, 1995, 23: 1570–1575.)

In another aspect of this invention, cleavage-resistant modified nucleotides may be used in conjunction with cleavage-sensitive modified nucleotides to effect a heightened degree of selectivity in the cleavage step.

iii. Applications to Genotyping

As DNA sequence data accumulates from various species there is increasing demand for accurate, high throughput, automatable and inexpensive methods for determining the status of a specific nucleotide or nucleotides in a biological sample, where variation at a specific nucleotide (either polymorphism or mutation) has previously been discovered. This procedure—the determination of the nucleotide at a particular location in a DNA sequence—is referred to as genotyping. Genotyping is in many respects a special case of DNA sequencing (or variance detection where only one position is being queried), but the sequence of only one nucleotide position is determined. Because only one nucleotide position must be assayed, genotyping methods do not entirely overlap with DNA sequencing methods. The methods of this invention provide the basis for novel and useful genotyping procedures. The basis of these methods is polymerization of a polynucleotide spanning the polymorphic site. The polymerization may be either by the PCR method or by primer extension, but is preferably by PCR. The polymerization is performed in the presence of three natural nucleotides and one chemically modified nucleotide, such that the chemically modified nucleotide corresponds to one of the nucleotides at the polymorphic or mutant site. For example if an A/T polymorphism is to be genotyped the cleavable nucleotide could be either A or T. If a G/A polymorphism is to be genotyped the cleavable nucleotide could be either A or G. Conversely the assay could be set up for the complementary strand, where T and C occur opposite A and G. Subsequently the polymerization product is chemically cleaved by treatment with acid, base or other cleavage scheme. This results in two products from the two possible alleles, one longer than the other as a result of the presence of the cleavable nucleotide at the polymorphic site in one allele but not the other. A mass change, but not a length change, also occurs on the opposite strand. One constraint is that one of the primers used for producing the polynucleotide must be located such that the first occurrence of the cleavable nucleotide after the end of the primer is at the polymorphic site. This usually requires one of the primers to be close to the polymorphic site. An alternative method is to simultaneously incorporate two cleavable nucleotides, one for a polymorphic nucleotide on the (+) strand, one for a polymorphic site on the (−) strand. For example, one might incorporate cleavable dA on the (+) strand (to detect an A-G polymorphism) and cleavable dC on the (−) strand (to positively detect the presence of the G allele on the (+) strand. In this case, it may be advantageous to have both primers close to the variant site. The two allelic products of different size can be separated by electrophoretic means, such as, without limitation, capillary electrophoresis. They could also be separated by mass using, without limitation, mass spectrometry. In addition, a FRET assay can be used to detect them, as described below. Any of these three assay formats is compatible with multiplexing by means known in the art.

Figure 32:
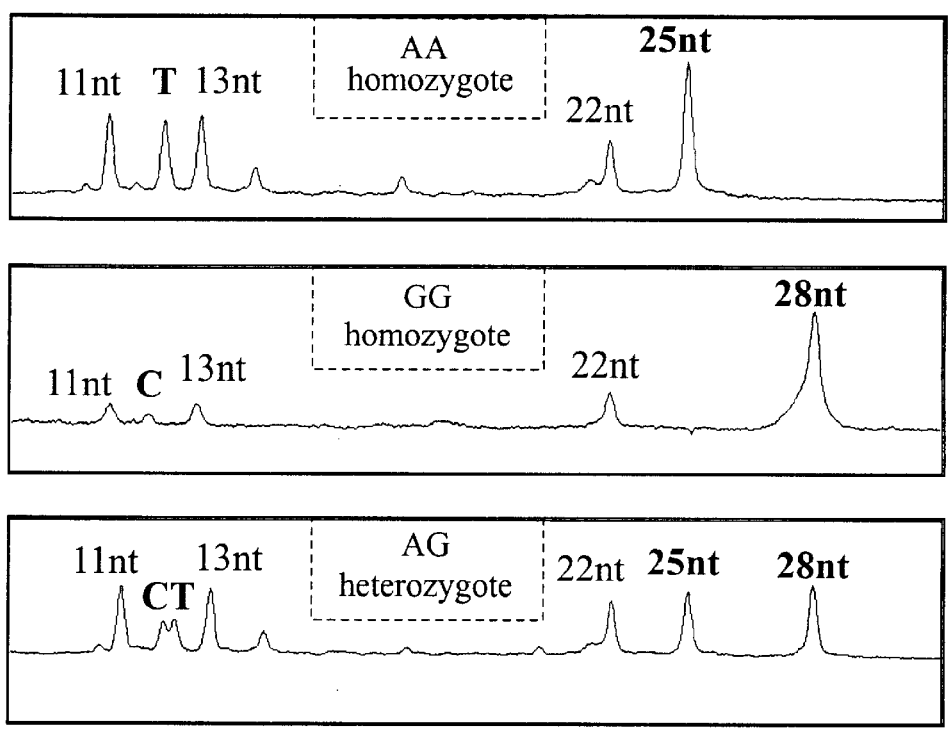
Figure 32:
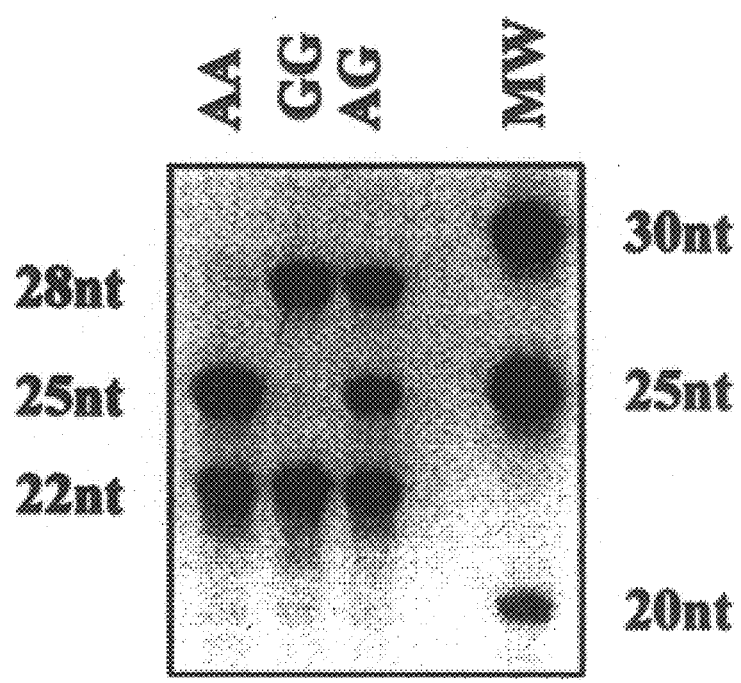

One way to perform a FRET detection for the presence or absence of the allelic cleavage product is to introduce a probe with a fluor or a quencher moiety such that the probe hybridizes differentially to the cleaved strand (representing one allele) vs the non-cleaved strand (representing the other allele; see FIG. 2 for illustration of several possible schemes). Such differential hybridization is readily achievable because one strand is longer than the other by at least one, and often several nucleotides. If a fluor or quenching group is also placed on the primer used to produce the cleavable polynucleotide (by PCR or primer extension) such that an appropriate FRET interaction between the moiety on the probe and the moiety on the primer exists, i.e., the absorbing and emitting wavelengths of the two moieties are matched, and the distance and orientation between the two moieties is optimized by methods known to those skilled in the art, then a powerful signal will be present with one allele but not the other when the probe and primer are heated at the temperature that affords maximal hybridization discrimination. Ideally the probe is synthesized in a manner that takes maximal advantage of the different length of the cleaved and non-cleaved alleles. For example the primer should hybridize to the region that is removed by cleavage in one allele but is present in the other allele. When selecting primers for the PCR or primer extension one experimental design consideration would be to locate the primer so as to maximize the length difference between the two alleles. Other means of maximizing the discrimination would include the use of a "molecular beacon" strategy where the ends of the probe are complementary, and form a stem, except in the presence of the non-cleaved allele where the non-cleaved segment is complementary to the stem of the probe and therefore effectively competes with the formation of intramolecular stems in the probe molecule (FIGS. 32 and 33).

The above FRET methods can be performed in a single tube, for example, as follows: (1) PCR; (2) addition of cleavage reagent (and heat if necessary); (3) addition of the probe; and (4) temperature ramping if necessary in an instrument such as the ABI Prism which is capable of excitation and fluorescence detection in 96 wells.

Another way to produce a FRET signal that discriminates the two variant alleles is to incorporate a nucleotide with a dye that interacts with the dye on the primer. The key to achieving differential FRET is that the dye modified nucleotide must first occur (after the 3' end of the primer) beyond the polymorphic site so that, after cleavage, the nucleotide dye of one allele (cleaved) will no longer be in within the requisite resonance producing distance of the primer dye while, in the other (uncleaved) allele, the proper distance will be maintained and FRET will occur. The only disadvantage of this method is that it requires a purification step to remove unincorporated dye molecules that can produce a background signal, which might interfere with the FRET detection. A non-limiting example of the experimental steps involved in carrying out this method are: (1) PCR with dye-labeled primer and either a cleavable modified nucleotide with also carrier a dye or one cleavable modified nucleotide and one dye-labeled nucleotide. The dye can be on the cleavable nucleotide if the cleavage mechanism results in separation of the dye from the primer as, for instance, in the case of 5'-amino substitution which results in cleavage proximal to the sugar and base of the nucleotide; (2) cleavage at the cleavable modified nucleotide; (3) purification to remove free nucleotides; and (4) FRET detection.

Figure 28:
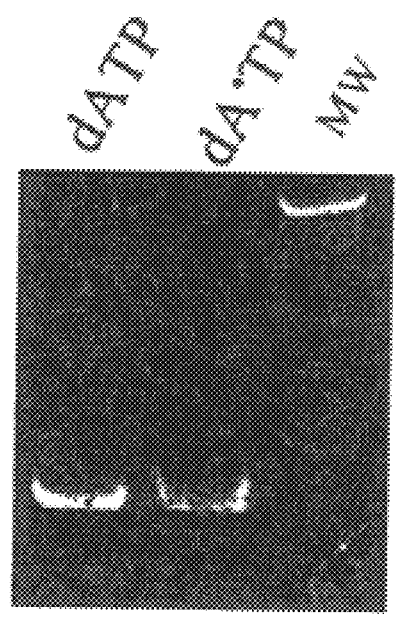
Figure 30:
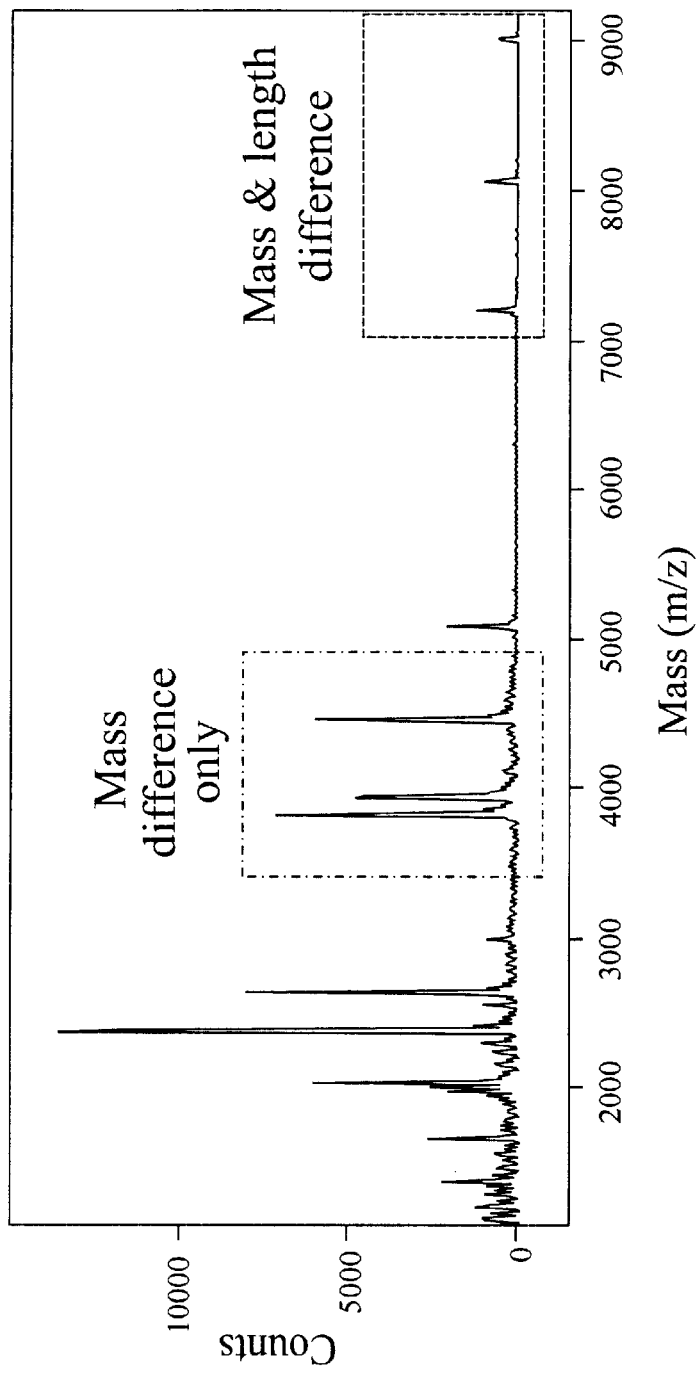
Figure 30:
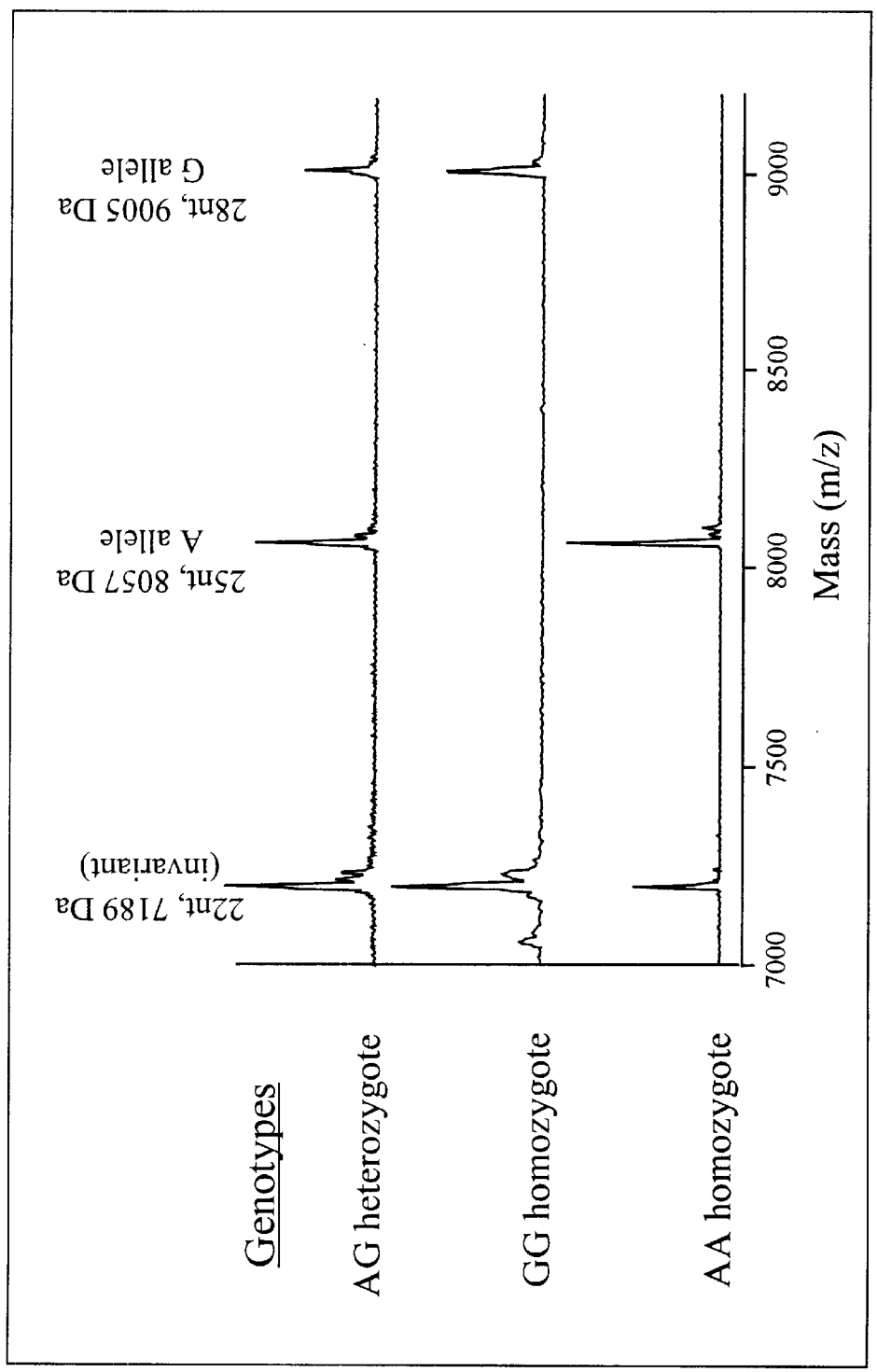
Figure 31:
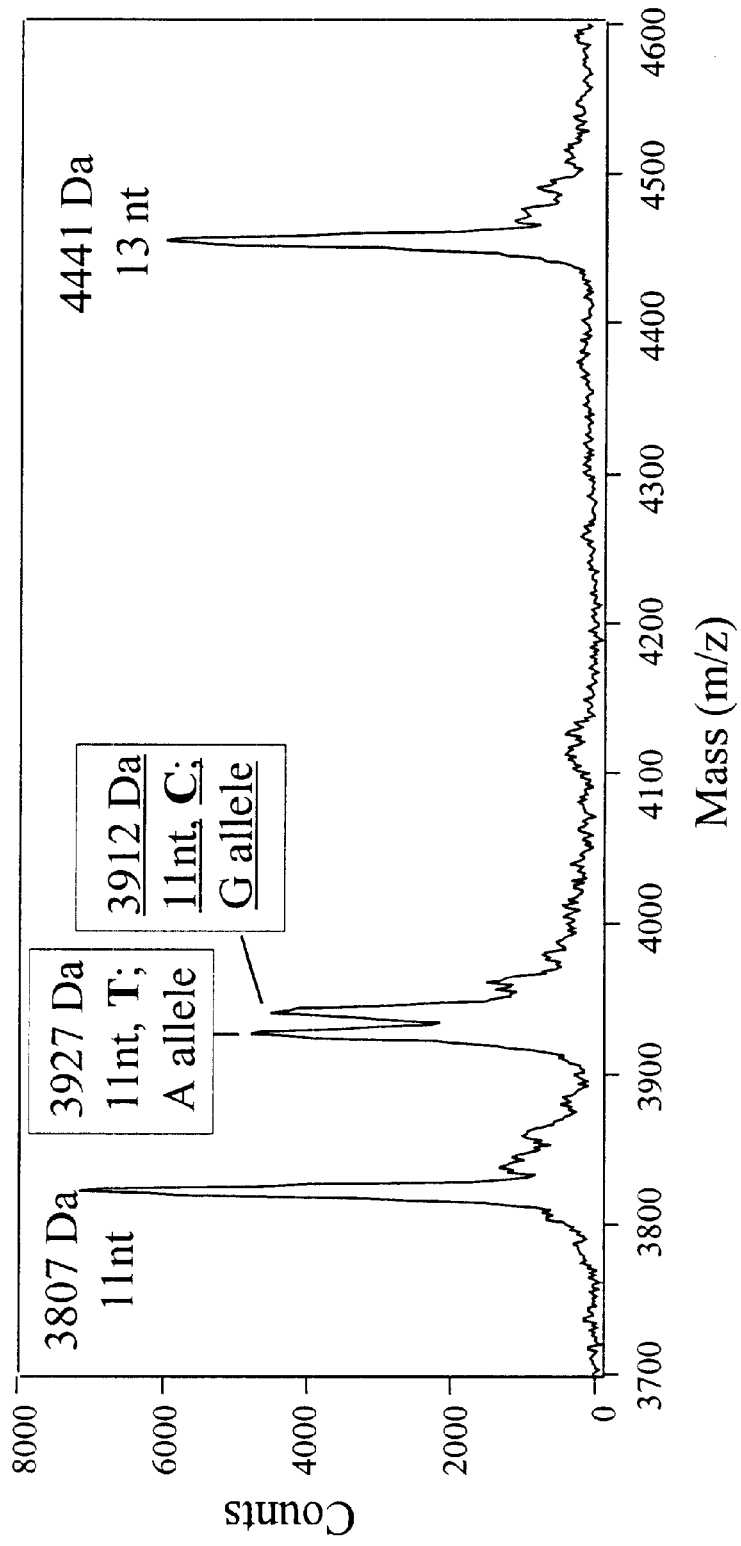
Figure 31:
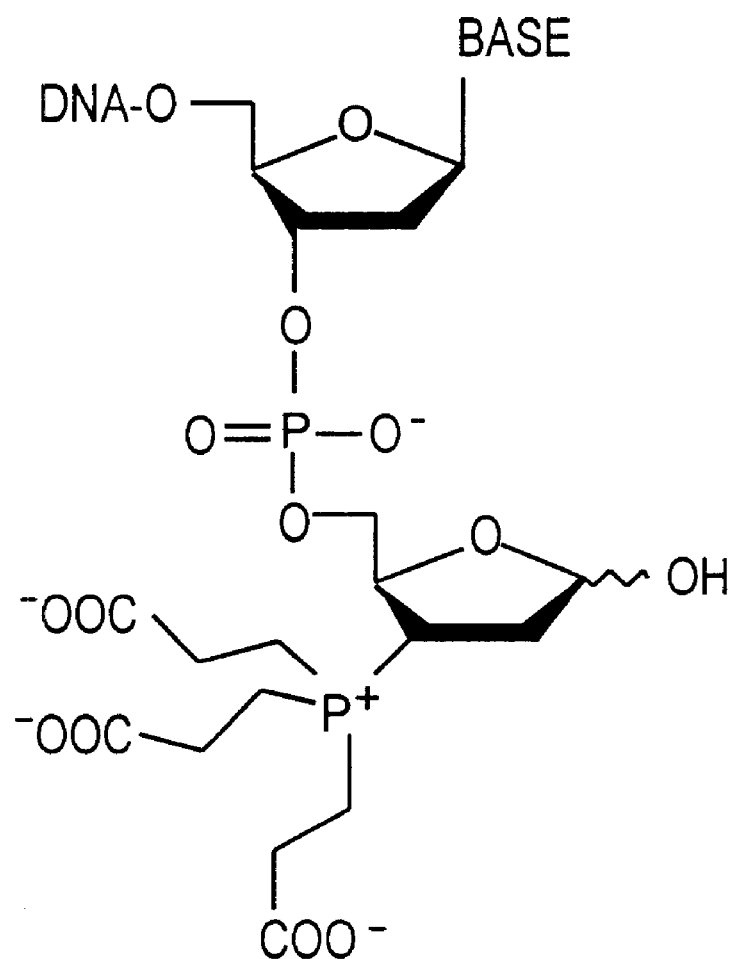

As noted earlier in this disclosure, we have demonstrated that polynucleotides containing 7-nitro-7-deaza-2'-deoxyadenosine in place of 2'-deoxyadenosine may be specifically and completely cleaved using piperidine/TCEP/Tris base. There are many other examples of chemistries where such PCR amplification and chemical cleavage may be possible. In a putative genotyping assay, a PCR reaction is carried out with one cleavable nucleotide analogue along with three other nucleotides. The PCR primers may be designed such that the polymorphic base is near one of the primers (P) and there is no cleavable base between the primer and the polymorphic base. If the cleavable base is one of the polymorphic bases, the P-containing cleavage product from this allele is expected to be shorter than the product from the other allele. The schematic presentation (FIG. 27) and experimental data (FIGS. 28 to 31) are examples of this arrangement. If the cleavable base is different from either of the polymorphic bases, the P-containing fragment would have the same length, but different molecular weight for the two alleles. In this case, Mass Spectrometry would be the preferred analytical tool; although we had observed that oligonucleotides with one single base difference may migrate differently when analyzed by capillary electrophoresis. In one specific example, a 82 bp fragment of Transferrin Receptor gene was amplified by PCR using 7-nitro-7-deaza-2'-deoxyadenosine in place of 2'-deoxyadenosine. The polymorphic base pair is A:T to G:C. The PCR amplification generated fully substituted product in similar yields to that of natural DNA (FIG. 28). MALDI-TOF Mass Spectrometry analysis revealed the polymorphism in two regions of the spectra. The first between 7000 Da and 9200 Da and the second between 3700 Da and 4600 Da (FIG. 30, panel A). The first region demonstrated the difference in primer-containing fragments of different lengths (FIG. 30. panel B). The second region showed the opposite strand of DNA containing the polymorphism that have the same length but different mass (FIG. 30, panel C). The common fragments between the two alleles may serve as mass references. Capillary electrophoresis analysis may also be used (FIG. 31). Mobility difference between the two fragments of different length was easily detected in the test sample, as expected. In addition, mobility difference between two polymorphic fragments (11 nt) of same length but one different base (C vs. T) was observed, providing supporting evidence from the opposite strand. FIG. 32 illustrates schemes for FRET detection of the same polymorphic site.

b. Full Substitution, Full Extension and Complete Cleavage at Dinucleotides

In another aspect of the present invention, two of the four nucleotides of which the subject polynucleotide is composed are completely replaced with modified nucleotides (either on one strand using primer extension, or on both strands using a DNA amplification procedure) and substantially complete cleavage is then effected preferentially at the site of dinucleotides involving the two different modified nucleotides. Generally, given the steric constraints of most cleavage mechanisms, the two modified nucleotides will be cleaved only when they occur in a specific order. For example if T and C are modified, the sequence 5' TpC 3' would be cleaved but 5° CpT 3' would not (5' and 3' indicate the polarity of the polynucleotide strand and p indicates an internal phosphate group).

The rationale for dinucleotide cleavage is that mononucleotide cleavage is not ideally suited to the analysis of polynucleotides longer than 300 to 400 nucleotides because the number of fragments that must be detected and resolved by the mass spectrometer may become limiting and the likelihood of coincidental occurrence of two or more cleavage fragments with the same mass increases and begins to limit the efficiency of the method. This latter problem is especially acute with respect to the occurrence of mono, di, tri, and tetranucleotides of the same composition which can mask the appearance or disappearance of fragments because MS is not quantitative. In contrast, capillary electrophoresis, while not providing mass and thereby nucleotide content, is a quantitative method that allows detection of variation in the numbers of di-, tri- and tetranucleotides.

Cleavage at modified dinucleotides should result in fragments averaging sixteen nucleotides in length. This is because the abundance of any dinucleotide, given four nucleotides, is $4^2$, which equals 16, assuming nucleotide frequencies are equal and there is no biological selection imposed on any class of dinucleotides (i.e. their occurrence is random). Neither of these assumptions is completely accurate, however, so there will in actuality be a wide size distribution of cleavage masses, with considerable deviation in the average size mass depending on which nucleotide pair is selected for substitution and cleavage. However, available information concerning the frequency of various dinucleotides in mammalian, invertebrate and prokaryotic genomes can be used to select appropriate dinucleotides. It is well known, for example, that 5' CpG 3' dinucleotides are under-represented in mammalian genomes; they can be avoided if relatively frequent cleavage intervals are desired.

I. Applications to Variance Detection

If the sequence of the analyte polynucleotide is known, then an optimal dinucleotide cleavage scheme can be selected based on analysis of the masses of predicted cleavage fragments. For example, cleavage fragments that fall within the size range optimal for analysis by mass spectrometry can be selected by analysis of the fragment sizes produced by all possible dinucleotide cleavage schemes. Further, the theoretical efficiency of variance detection associated with all possible dinucleotide cleavage schemes can be determined as described above for full mononucleotide substitution and cleavage—that is, by determining the detectability of every possible nucleotide substitution in the entire analyte fragment. In some cases two or more independent dinucleotide cleavage reactions may produce complementary results, or a second dinucleotide cleavage experiment may be run to provide corroboration.

Given the length of dinucleotides (16 mers on the average), it will often not be possible to determine with precision the location of a variant nucleotide based on one dinucleotide cleavage experiment. For example, if a 15 Dalton mass difference between samples is detected in a 14 mer then there must be a C ←→T variance (Table 2) in the 14 mer, with the heavier alleles containing T at a position where the lighter alleles contain C. However, unless there is only one C in the lighter variant fragment, or only one T in the heavier variant fragment, it is impossible to determine which, C or T, is the variant one. This ambiguity regarding the precise nucleotide that varies can be resolved in several ways. First, a second mono- or dinucleotide substitution and cleavage experiment, or a combination of such cleavage experiments, may be designed so as to divide the original variant fragment into pieces that will allow unambiguous assignment of the polymorphic residue. Second, an alternative sequencing procedure may be used as an independent check on the results, such as Sanger sequencing or sequencing by hybridization.

ii. Applications to DNA Sequencing

As a stand alone procedure, dinucleotide substitution and cleavage can provide useful information concerning nucleotide content of DNA fragments averaging about 16 nucleotides in length, but ranging up to 30, 40 or even 50 or more nucleotides. However, as described above, the main applications of dinucleotide cleavage to DNA sequencing occur in conjunction with mononucleotide cleavage. The comparatively large DNA fragments produced by dinucleotide cleavage can be very useful in assorting the smaller fragments produced by mononucleotide cleavage into sets of fragments which must fit together. The additional constraints imposed by these groupings can be sufficient to allow complete sequence to be determined from even relatively large fragments.

In Example 4 the steps required to infer a nucleotide sequence from a 20 mer using four mononucleotide substitution and cleavage reactions are shown. The procedures described in Example 4 could be carried out on a series of 10–30 mers, the sequence content of which was initially defined, or at least constrained, by a dinucleotide cleavage procedure. Thereby, the sequence of a much larger fragment can be obtained. Note that as nucleotide length increases the relationship between fragment mass and sequence content becomes more ambiguous; that is, there are more and more possible sequences that could produce the given mass. However, if the number of nucleotides comprising the mass are known the number of possible nucleotide contents falls significantly (Pomerantz, S. C., et al., *J. Am. Soc. Mass Spectrom.*, 1993, 4: 204–209). Further, sequence constraints, such as the lack of internal dinucleotide sequences of a particular type, further reduce the number of possible nucleotide contents as illustrated in Table 4 for mononucleotide sets.

C. Full substitution with modified nucleotide and partial cleavage
   Partial substitution with modified nucleotide and full cleavage Partial substitution with modified nucleotide and partial cleavage These applications provide partially cleaved polynucleotides by different strategies; each of these procedures has utility in specific embodiments of the invention. However, full substitution with a modified nucleotide and partial cleavage is the preferred method of producing partial cleavage products for mass spectrometric analysis. The reason is that with full substitution one can vary the degree of partial cleavage over a very wide spectrum, from cleavage of 1 in 100 nucleotides to cleavage of 99 in 100 nucleotides. Partial substitution, even with full cleavage, does not allow this range of cleavage completeness. However, for modified nucleotides, which are not efficiently incorporated by polymerases, lesser degrees of substitution are preferred. As the completeness of cleavage is reduced the relationship between cleavage fragments over a longer and longer range becomes evident. On the other hand as the completeness of cleavage is increased the ability to obtain precise mass data and unambiguous assignment of nucleotide content is increased. The combination of slight, intermediate and substantial cleavage provides an integrated picture of an entire polynucleotide, whether the application is variance detection or sequencing. The small polynucleotides of defined nucleotide content can be joined into larger and larger groups of defined order.

Partial substitution with full cleavage and partial substitution with partial cleavage are useful for the preparation of sequencing ladders. If a modified nucleotide is not efficiently incorporated into polynucleotides by available polymerases then a low ratio of partial substitution may be optimal for efficient production of polynucleotides containing the modified nucleotide. However a low degree of substitution may then require complete cleavage in order to produce sufficient cleavage fragments for ready detection.

Figure 17:
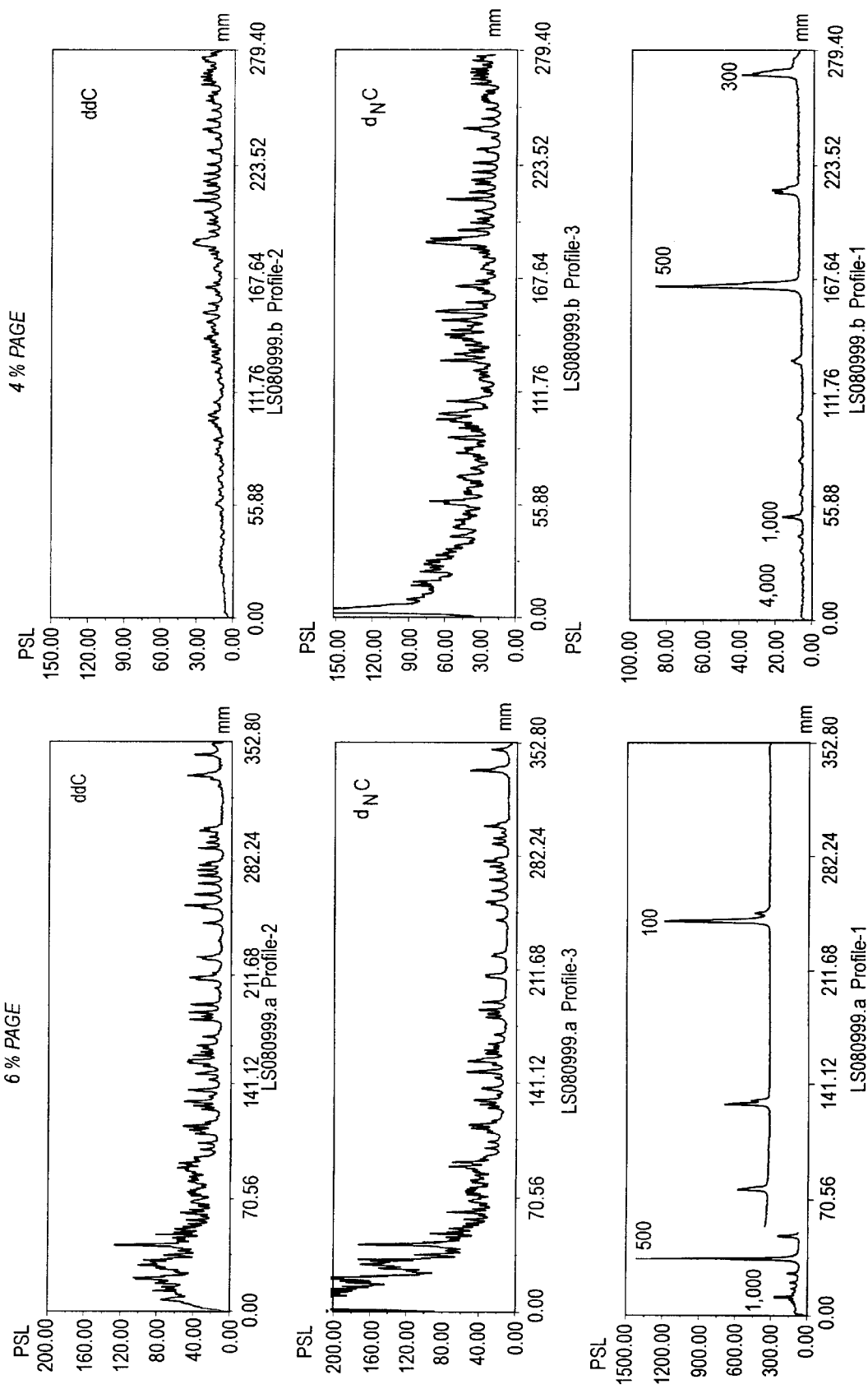
Figure 18:
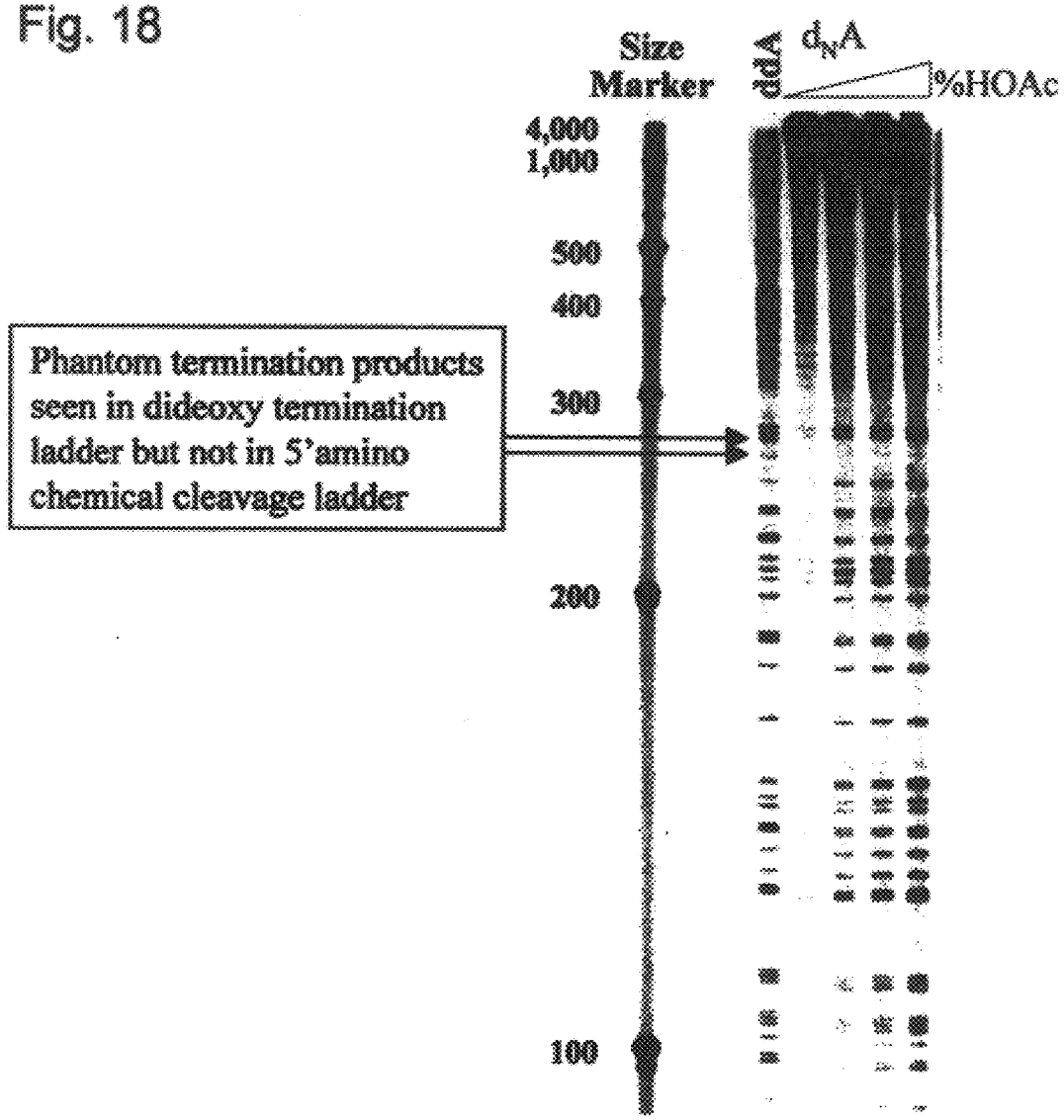

Partial substitution with partial cleavage is generally a preferred approach as conditions for complete cleavage may be harsh and thereby result in some nonspecific cleavage or modification to polynucleotides. Also, partial substitution at relatively high levels (i.e. at 5% or more of the occurrences of the nucleotide) allows a range of partial cleavage efficiencies to be analyzed. As with MS analysis, there are advantages to being able to test multiple degrees of cleavage. For example, it is well known in Sanger sequencing that there are tradeoffs to production of very long sequence ladders: generally the beginning of the ladder, with the shortest fragments, is difficult to read as is the end of the ladder with the longest fragments. Similarly, the ability to manipulate partial cleavage conditions with the polynucleotides of this invention will allow a series of sequencing ladders to be produced from the same polynucleotide that provide clear sequence data close to the primer or at some distance from the primer. As shown in FIG. 17, sequence ladders produced by chemical cleavage have a much better distribution of labeled fragments than dideoxy termination over distances up to 4 kb and beyond.

Partial cleavage may also be obtained by the substitution of cleavage-resistant modified nucleotides, described above, for all but one natural nucleotide, which then provides the cleavage sites. In addition, as described previously, combinations of cleavage resistant modified nucleotides and cleavage-sensitive modified nucleotides may be used.

While any technique which permits the determination of the mass of relatively large molecules without causing non-specific disintegration of the molecules in the process may be used with the methods of this invention, a preferred technique is MALDI mass spectroscopy since it is well suited to the analysis of complex mixtures of analyte. Commercial MALDI instruments are available which are capable of measuring mass with an accuracy on the order of 0.1% to .05%. That is, these instruments are capable of resolving molecules differing in molecular weight by as little as one part in two thousand under optimal conditions. Advances in MALDI MS technology will likely increase the resolution of commercial instruments in the next few years. Considering the smallest difference that can occur between two strands containing a variance (an A-T transversion, a molecular weight difference of 9; see Table 5), and given a MALDI apparatus with a resolution of 2,000 (that is, a machine capable of distinguishing an ion with an m/z (mass/charge) of 2,000 from an ion with an m/z of 2,001), the largest DNA fragment which the A-T transversion would be detectable is approximately 18,000 Daltons (a 'Dalton' is a unit of molecular weight used when describing the size of large molecules; for all intents and purposes it is equivalent to the molecular weight of the molecule). In the experimental setting, the practical resolving power of an instrument may be limited by the isotopic heterogeneity of carbon; i.e., carbon exists in nature as Carbon-12 and Carbon-13, as well as other factors. Assuming an approximately even distribution of the four nucleotides in the DNA fragment, this translates to detection of an A-T transversion in an oligonucleotide containing about 55 nucleotides. At the other end of the spectrum, a single C-G transversion, which results in a molecular weight difference of 40, could be detected using MALDI mass spectroscopy in an oligonucleotide consisting of about 246 nucleotides. The size of an oligonucleotide in which an A-T transversion would be detectable could be increased by substituting a heavier non-natural nucleotide for either the A or the T; for example, without limitation, replacing A with 7-methyl-A, thus increasing the molecular weight change to 23. Table 5 shows the approximate size of an oligonucleotide in which each possible single point mutation could be detected for mass spectrometers of different resolving powers without any modification of molecular weight.

A variety of chemical modifications of nucleotides have been described with respect to their utility in increasing the detectability of mass differences during MS analysis. A particularly useful mass modification for use with the methods of this invention is the purine analog 2-chloroadenine, which has a mass of 364.5. As shown in Table 2, Panel B, this has a favorable effect on mass differences between all the nucleotides and A. Most important, it changes the T-A difference from 9 Da to 42.3 Da. Further, it has been shown that 2-chloradenine can be incorporated in polynucleotides by DNA polymerase from Thermus aquaticus. Full substitution on one strand has been described. (Hentosh, P. *Anal. Biochem.*, 1992, 201: 277–281.)

E. EXAMPLES

1. Polymerase Development

A variety of mutant polymerases have bee shown to have altered catalytic properties with respect to modified nucleotides. Mutant polymerases with reduced discrimination between ribonucleotides and deoxyribonucleotides have been extensively studied. Human DNA polymerase β mutants that discriminate against azidothymidine (AZT) incorporation have been isolated by genetic selection. Thus, it is highly likely that mutant polymerases capable of incorporating any of the modified nucleotides of this invention better than natural polymerases can be produced and selected.

The following procedure can be employed to obtain an optimal polymerase for incorporation of a particular modified nucleotide or nucleotides into a polynucleotide. It is understood that modifications of the following procedure will be readily apparent to those skilled in the art; such modifications are within the scope of this invention.

a. A starting polymerase is selected. Alternatively, multiple polymerases that have different sequences and/or different capabilities with regard to incorporation of a modified nucleotide or nucleotides into a polynucleotide might be selected. For example, without limitation, two polymerases, one of which efficiently incorporates a nucleotide having a sugar modification and the other of which efficiently incorporates a nucleotide having a phosphate backbone modification, might be selected. The coding sequences of the polymerase(s) is then cloned into a prokaryotic host.

It may be advantageous to incorporate a protein tag in the polymerase during cloning, the protein tag being selected for its ability to direct the polymerase into the periplasmic space of the host. An example, without limitation of such a tag is thioredoxin. Proteins in the periplasmic space can be obtained in a semi-pure state by heat shock (or other procedures known in the art) and are less likely to be incorporated into inclusion bodies.

b. Several (preferably three or more) rounds of shuffling (Stemmer, supra) are then performed.

c. After each round of shuffling, the shuffled DNA is transformed into a host. The library of transformants obtained is then plated and pools of transformants (approximately 10–1000 colonies per pool) are prepared from the host cell colonies for screening by sib selection. A lysate is then made from each pool. The host may be prokaryotic such as, without limitation, bacteria or a single-celled eukaryote such as a yeast. The following description assumes the use of a bacterial prokaryotic host but other possible prokaryotic hosts will be apparent to those skilled in the art and are within the scope of this invention.

d. The lysates are subjected to dialysis using a low molecular weight cut-off membrane to remove substantially all natural nucleotides. This is necessary because the assay for polymerase with the desired characteristics entails polymerase extension of a primer in the presence of modified nucleotides. The presence of the corresponding natural nucleotides will result in a high background in the assay that might obscure the results. An alternative procedure is degradation of all natural nucleotides with a phosphatase such as shrimp alkaline phosphatase.

e. Add the following to the dialyzed lysate: a single stranded DNA template, a single stranded DNA primer complementary to one end of the template, the modified nucleotide or nucleotides whose incorporation into the DNA is desired and the natural nucleotides which are not being replaced by the modified nucleotides. If the desired polymerase is to have the capability of incorporating two contiguous modified nucleotides, then the template should be selected to contain one or more complementary contiguous sequences. For example, without limitation, if a polymerase which is capable of incorporating a modified-C-modified-T sequence is desired 5' to 3', the template should contain one or more G-A or A-G sequences 3' to 5'. Following (that is, 5' to) the segment of the template strand designed to test the ability of the polymerase to incorporate the modified nucleotide or nucleotides is segment of template strand that produces a detectable sequence when copied by the polymerase. The sequence can be detected in several ways. One possibility is to use a template having a homopolymeric segment of nucleotides complementary to one of the natural nucleotides. Then, if the goal is, for example, identification of a polymerase that incorporates modified C, then detection might entail polymerization of a consecutive series of A, G or T providing, however, that the nucleotide used for detection does not occur earlier in the polymerized sequence complementary to the template sequence. The detection nucleotide could be a radiolabeled or dye-labeled nucleotide that would only be incorporated by mutant polymerase that had already traversed the segment of template requiring incorporation of the modified nucleotide(s). Another way to detect the homopolymer would be to make a complementary radiolabeled or dye-labeled probe that could be hybridized to the homopolymer produced only in those pools containing a polymerase capable of incorporating the modified nucleotide(s). Hybridization could then be detected by, for example, spotting the primer extension products from each pool on a nylon filter, followed by denaturing, drying and addition of the labeled homopolymeric probe that would hybridize to the complementary strand of the polymerization product. Of course, a homopolymer or other sequence not present in the host cell genome or an episomes should be used to minimize background hybridization to host sequences present in all the pools.

Yet another detection procedure would be to incorporate a sequence corresponding to an RNA polymerase promoter, such as, without limitation, the T7 promoter, followed by a reporter sequence into the template. These sequences should be located downstream (3' to) the primer and template sequence requiring incorporation of modified nucleotides. The T7 promoter will be inactive until it becomes double-stranded as a consequence of the polymerization; however, polymerization of the T7 promoter sequence will only occur if the mutant polymerase being tested is capable of incorporating the modified nucleotide or sequence of modified nucleotides which lie upstream of the T7 promoter sequence. The reporter sequence may include a homopolymeric sequence of a nucleotide (e.g., T) the complement of which (in this case, A) is labeled with a dye or radioactive label. In this manner, high levels of T7 polymerase mediated transcription will result in large quantities of high molecular weight (i.e., capable of precipitation by trichloroacetic acid), labeled polymer. An alternative reporter sequence might be a ribozyme capable of cleaving an exogenously added marker oligonucleotide which permits easy distinction of cleaved from non-cleaved products. For example, again without limitation, one end of the oligonucleotide might be biotinylated and the other end might contain a fluorescent dye. Such systems are capable of 1000-fold or greater amplification of a signal. In this approach it would first be necessary to demonstrate that the function of the promoter is not disturbed by the presence of modified nucleotide or to create a version of the promoter that lacks the nucleotide being modified.

f. Any pool of lysed bacterial colonies which contains a polymerase capable of incorporating the selected modified nucleotide or contiguous modified nucleotides will produce detectable homopolymer or will contain double-stranded T7 RNA polymerase promoter upstream of a marker sequence as the result of the polymerization across the modified nucleotide or contiguous nucleotides, across the T7 promoter and across the marker sequence. Addition of T7 RNA polymerase to the mixture (or, alternatively, expression of T7 RNA polymerase from a plasmid) will result in transcription of the marker sequence that then can be detected by an appropriate method depending on the marker system selected. It may not be necessary to select or design a promoter which either lacks the modified nucleotide(s) or which can function effectively with the modified nucleotide (s).

g. Bacterial colonies containing a polymerase having the desired properties are then identified and purified from pools of bacterial colonies by sib selection. In each round of selection the pool or pools with the desired properties are split into sub-pools and each sub-pool is tested for activity as set forth above. The sub-pool displaying the highest level of activity is selected and separated into a second round of subpools and the process repeated. This is repeated until there is only one colony remaining which contains the desired polymerase. That polymerase can then be re-cloned into a protein expression vector and large amounts of the polymerase can be expressed and purified.

Another approach to polymerase development involves the well-known propensity for some antibiotics to kill only growing cells, e.g., penicillin and related drugs which kill by interfering with bacterial cell wall synthesis of growing cells but do not affect quiescent cells.

The approach would be to introduce a modified nucleotide into bacterial cells which have been genetically altered to express one or more mutant polymerases, preferably a library of mutant polymerases. An ideal host strain would be one in which the endogenos polymerase has been inactivated but is complemented by a plasmid-encoded polymerase. A library of polymerases could than be created on a second plasmid with a different selectable marker, e.g., antibiotic resistance. The library would then be introduced into the host cell in the presence of negative selection against the first (non-mutated) polymerase-encoding plasmid, leaving cells with only the mutant polymerases. If one or more of the mutant polymerases is capable of incorporating the modified nucleotide into the genetic material of the cells, the expression of the modified gene(s) will be altered and/or a series of host cell responses will be elicited such as the SOS response which affects cell growth. The effect sought would be reversible growth arrest, i.e., a cytostatic rather than cytocidal effect. The cells would then be treated with an antibiotic that only kills actively growing cells. The cells are then removed from the presence of the antibiotic and placed in fresh growth medium. Any cells whose growth was arrested by the incorporation of the modified nucleotide into their genetic material and therefore which were unaffected by the antibiotic would form colonies. Plasmids containing the code for the polymerase which catalyzed the incorporation of the modified nucleotide into the cells' genetic material are then isolated and the procedure repeated for additional rounds of selection. Once a sufficient number of selection rounds have been performed, the polymerase is isolated and characterized. An exemplary, but by no means limiting, experimental procedure that might be employed to accomplish the foregoing is as follows:

1. Select a polymerase or set of polymerases for mutagenesis. The starting polymerase(s) may include, without limitation, a mutant polymerase such as Klenow E710A, wild type polymerases, thermostable or thermolabile polymerases or polymerases known to complement *E. coli* DNA Pol 1, etc.

2. Prepare a library of mutant polymerases using techniques such as "dirty PCR," shuffling, site-directed mutatgenesis or other diversity generating procedures.

3. Clone the library into a plasmid vector.

4. Transform bacteria with the plasmid library and isolate transfectants by selection on an appropriate antibiotic. Preferably, the host strain has an inactivated chromosomal polymerase and selection can be applied to insure that only the mutant polymerases are expressed in the host cells, as described above. The only cells harboring plasmids encoding functional polymerases will survive this step.

5. Add the modified nucleotide triphosphate to the media. It may be necessary to use a cell permeabilizing procedure such as electroporation, addition of calcium or rubidium chloride, heat shock, etc. to facilitate entrance of the modified nucleotide into the cells. The cells are then grown in the presence of the modified nucleotide triphosphate until incorporation of the modified nucleotide(s) induces arrest of cell growth in selected cells.

6. Add penicillin, ampicillin, nalidixic acid or any other antibiotic that selectively kills actively dividing cells. Continue growing the cells for a selected time.

7. Spin the cells out, suspend them in fresh LB media and plate them. Grow for an empirically determined time.

8. Select colonies, isolate the plasmids and repeat steps 4 to 7 for additional rounds of selection or, in the alternative, use a biochemical assay for incorporation of the modified nucleotide to examine individual colonies or pools of colonies. Such an assay might entail polymerization of a template in the presence of radiolabelled modified nucleotide on individual clones or on pools of clones in a sib selection scheme.

Further characterize the polymerase(s) determined to have the desired activity by the assay of step 8.

10. Remutagenize the polymerase(s) obtained in Step 8 and repeat the selection procedure from Step 3.

11. When an acceptable level of ability to incorporate the modified nucleotide is achieved, isolate and characterize the polymerase.

Another method for selecting active polymerases for incorporation of modified nucleotide involves use of a bacteriophage which has been described for selection of an active enzyme (Pedersen et. al., *Proc. Natl. Acad. Sci. USA*, 1998, 95:10523–8). A modification of that procedure might be used for mutant polymerase selection. That is, oligonucleotides which are covalently attached to phage surfaces can be extended by mutant polymerases expressed on the surface of the phage. Dye-labeled modified nucleotides would be used for primer extension. After removal of unincorporated nucleotides, the phage bearing dye-modified nucleotide could be identified using fluorescence-activated cell sorting procedures. Alternatively, using an appropriate template design, the fluorescence label can be attached to another nucleotide that would only be incorporated downstream of a stretch of modified nucleosides.

Yet another approach to identifying active polymerases for modified nucleotide incorporation would use available X-ray crystal structures of polymerases bound to template DNA and nucleotide substrate. Based on observed or predicted interactions within the polymerase/substrate complex, rational amino acid changes could be created to accommodate the structural deviation of a given modified nucleotides. For example, based on the structural information on a complex of T7 polymerase and its substrates for which the X-ray crystal structure shows the amino acids that are in the polymerase active site (Doublie et. al., *Nature*, 1998, 391:251–258), site-directed mutagenesis might be designed for structurally similar protein Klenow to increase its specific activity for incorporation of ribonucleotides (rNTPs) and/or 5'-amino-nucleotides (5'-aminodNTPs).

The E710A mutant of Klenow (Astatke et. al., *Proc. Nat Acad. Sci. USA*, 1998, 95:3402–3407) has an increased capacity to incorporate rNTPs as compared to wild type Klenow, probably because the mutation removes the steric gate against the 2'-hydroxyl group of rNTPs. This mutation, however, decreased the mutant's activity for incorporation of natural dNTPs and 5'-aminodNTPs. In this case, use of the E710S mutation might lead to improved activity because E710S might possibly H-bond with the 2'-OH of rNTPs substrates. The E710A or E710S mutation might also be used in combination with Y766F, a previously described mutant which by itself has little effect on polymerase activity (Astatke et al., *J. Biol. Chem.*, 1995, 270: 1945–54). The crystal structure of Y766 reveals that its hydroxyl forms hydrogen bonds with the side chain of E710, which might affect polymerase activity when E710 is truncated to Ala. On the other hand, E710 mutations in combination with F762A might improve activity by holding the sugar ring in a defined position. Similarly, better incorporation of the 5'-aminoanalogs might be achieved by relaxing the binding of the polymerase on the nucleotide substrate since the 5'-nitrogen changes the conformation of the nucleotide and thus the alignment of the alpha-phosphorous atom. Initially, the focus could be on mutagenesis on a limited number of residues that engage the sugar and phosphates of the nucleotide substrate such as residues R668, H734, and F762. The H881 residue might also work. Although It is further from the dNTP binding site, an Ala substitution at this position influences the fidelity of dNTP incorporation (Polesky et al., *J. Biol. Chem.*, 1990, 265:14579–91). These residues could be targeted for cassette mutagenesis to ascertain the amino acid residue with maximized effect, followed by selection for active polymerases as described. R668K substitution is particularly interesting, because it should eliminate contact to the dNTP while preserving the minor groove interaction with the primer 3'-NMP. On the other hand, Although R754 and K758 contact the beta and alpha phosphates, changes at these positions are likely to severely impair catalysis. Histidine or lysine at these positions could preserve interactions with the phosphates and might retain activity.

Another method for selecting active polymerases for incorporation of modified nucleotides involves use of the phage display system, which allows foreign proteins to be expressed on the surface of bacteriophage as fusions with phage surface proteins. Kay, B. K., Winter, J. and J. McCafferty (Editors) Phage Display of Peptides and Proteins: A Laboratory Manual. Academic Press, 1996. Establishing an experimental system for detection of a mutant polymerase would entail expressing mutant polymerases on the surface of a library of phage, and subsequently isolating phage-bearing polymerases with the desired polymerase activity. Aspects of such a system have been described for selection of an active enzyme nuclease (Pedersen et. al., Proc. Natl. Acad. Sci. USA, 1998, 95:10523–8). A modification of that procedure might be used for mutant polymerase selection. That is, oligonucleotides which are covalently attached to proteins on the phage surfaces surface can be extended by mutant polymerases expressed on the surface of the same phage. The oligonucleotides must fold up to provide a primer-template complex recognizable by the polymerase, or alternatively a primer complementary to the oligonucleotide can be provided separately. In either event, the portion of the oligonucleotide serving as a template for polymerization will contain nucleotides complementary to the modified nucleotide(s) for which an efficient polymerase is being sought. The template oligonucleotide may also be designed so that the extension product is easily detectable as a result of templated incorporation of a labeled nucleotide, which occurs only after polymerization across the segment of template requiring incorporation of the modified nucleotide (s). One method for selectively enriching phage-bearing polymerases with the desired catalytic properties involves use of a fluorescence activated cell sorter (FACS). Dye-labeled modified nucleotides would be used for incorporated in a primer extension reaction only after incorporation of the test modified nucleotide(s). After removal of unincorporated nucleotides, the phage bearing with attached dye modified nucleotides (which must encode mutant polymerases capable of incorporating the modified nucleotide or nucleotides) can be identified enriched in one or more rounds using fluorescence activated cell sorting procedures (Daugherty P. S., et al., Antibody affinity maturation using bacterial surface display. Protein Eng., 11:825–32, 1998). Alternatively, the modified nucleotide(s) themselves can be labelled with dye and detection will similarly be accomplished by FACS sorting of dye labeled phage. This procedure has the disadvantage that the dye may interfere with polymerization; however one skilled in the art will recognize that the dye can be attached to the modified nucleotide via a linkage that is unlikely to inhibit polymerization using an appropriate template design, the fluorescence label can be attached to another nucleotide which would only be incorporated downstream of a stretch of modified nucleosides.

Yet another approach to identifying active polymerases for modified nucleotide incorporation would be to use available X-ray crystal structures of polymerases bound to template DNA and nucleotide substrate. Based on observed or predicted interactions within the polymerase/substrate complex, rational amino acid changes could be created to accommodate the structural deviation of a given modified nucleotides. For example, based on the structural information on a complex of T7 polymerase and its substrates for which the X-ray crystal structure shows the amino acids that are in the polymerase active site (Doublie et. al., *Nature*, 1998, 391:251–258), site-directed mutagenesis might be designed for structurally similar protein Klenow to increase its specific activity for incorporation of ribonucleotides (rNTPs) and/or 5'-amino-nucleotides (5'-aminodNTPs).

The E710A mutant of Klenow (Astatke et. al., *Proc. Nat. Acad. Sci. USA,* 1998, 95:3402–3407) has an increased capacity to incorporate rNTPs as compared to wild type Klenow, probably because the mutation removes the steric gate against 2'-hydroxyl group of rNTPs. This mutation, however, decreased the mutant's activity for incorporation of natural dNTPs and 5'-aminodNTPs. In this case, use of the E710S mutation might lead to improved activity because E710S might possibly H-bond with the 2'-OH of rNTPs substrates. The E710A or E710S mutation might also be used in combination with Y766F, a previously described mutant which by itself has little effect on polymerase activity (Astatke et al., *J. Biol. Chem.,* 1995, 270: 1945–54). The crystal structure of Y766 reveals that its hydroxyl forms hydrogen bonds with the side chain of E710, which might affect polymerase activity when E710 is truncated to Ala. On the other hand, E710 mutations in combination with F762A might improve activity by holding the sugar ring in a defined position. Similarly, better incorporation of the 5'-amino-analogs might be achieved by relaxing the binding of the polymerase on the nucleotide substrate since the 5'-nitrogen changes the conformation of the nucleotide and thus the alignment of the alpha-phosphorous atom. Initially, the focus could be on mutagenesis on a limited number of residues that engage the sugar and phosphates of the nucleotide substrate such as residues R668, H734, and F762. The H881 residue might also work. Although It is further from the dNTP binding site, an Ala substitution at this position influences the fidelity of dNTP incorporation (Polesky et al., *J. Biol. Chem.,* 1990, 265:14579–91). These residues could be targeted for cassette mutagenesis to ascertain the amino acid residue with maximized effect, followed by selection for active polymerases as described. R668K substitution is particularly interesting, because it should eliminate contact to the dNTP while preserving the minor groove interaction with the primer 3'-NMP. On the other hand, Although R754 and K758 contact the beta and alpha phosphates, changes at these positions are likely to severely impair catalysis. Histidine or lysine at these positions could preserve interactions with the phosphates and might retain activity.

One skilled in the art will recognize that the collection of preferred amino acid modifications to Klenow polymerase described above may be applied to other polymerases to produce useful mutant versions of those polymerases. This can be accomplished by aligning the amino acid sequences of the other polymerases with that of Klenow polymerase to determine the location of the corresponding amino acids in the other polymerases, and/or, where crystal structures are available, comparing three dimensional structures of other polymerases with that of Klenow polymerase to identify orthologous amino acids. Methods for performing site directed mutagenesis and expressing mutant polymerases in procaryotic vectors are known in the art (Ausubel, F. M., et al., *Current Protocols in Molecular Biology,* John Wiley & Sons, 1998).

In addition to producing and screening for mutant polymerases capable of incorporating modified nucleotides it may also be useful in some instances to screen for other polymerase properties. In general the additional desirable polymerase properties described below are more difficult to assay than incorporation of modified nucleotides, so assays for these additional properties may be conducted as a second screen of mutant polymerases with demonstrated capacity to incorporate modified nucleotides. One aspect of this invention is that cleavage at modified nucleotides may be caused or enhanced by contact between the modified nucleotides and a polymerase (see Example and FIGS. 20–26). This is a preferred cleavage mode as it obviates a separate cleavage step. Thus it is useful to assay mutant polymerases for cleavage-enhancing properties. One simple assay for such properties is a primer extension where the extension sequence following the primer includes the cleavable nucleotide(s) followed by the first occurrence of a different nucleotide that is detectably labeled. In the event of polymerase assisted cleavage the labeled molecule will be separated from the primer resulting in a smaller labeled molecule, which can be detected by electrophoretic or other methods. A second useful property of mutant polymerases is the ability to recognize a modified nucleotide or nucleotides in a template strand and catalyze incorporation of the appropriate complementary nucleotide (natural or modified) on the nascent complementary strand. This property is a necessary condition for a polymerase to be used in a cycling procedure such as PCR, where newly synthesized polynucleotides serve as templates in successive rounds of amplification. A simple assay for such properties is a short primer extension where the template strand is synthesized with the modified nucleotide or nucleotides occurring shortly after the end of the primer, such that a primer extension reaction will soon encounter the modified nucleotide(s). Successful polymerization across the template, indicating use of the modified nucleotide(s) as templates, will result in a longer extension product than failure to utilize the modified nucleotides as templates. The extension product can be made easily detectable by synthesizing the template so as to cause templated incorporation of a labeled nucleotide only after traversing the modified nucleotide(s). The sequence of the extension product can subsequently be determined to confirm that the nucleotides incorporated on the extension strand opposite the modified nucleotides are correct. Still other attractive properties of polymerases include high fidelity, thermostability and processivity. Assays for these properties are known in the art.

EXAMPLE 2

Variance Detection by Mononucleotide Restriction

The following procedure is an example of nucleotide sequence variance detection in a polynucleotide without the necessity of obtaining the complete sequence of the polynucleotide. While the modified nucleotide used in this example is 7-methylguanine (7-methylG) and the polynucleotide under analysis is a 66 base-pair fragment of a specific DNA, it is understood that the described technique may be employed using any of the modified nucleotides discussed above or any other modified nucleotides which, as noted above, are within the scope of this invention. The polynucleotide may be any polynucleotide of any length that can be produced by a polymerase.

A 66 base pair region of the 38 Kda subunit of replication factor C (RFC) cDNA was amplified by PCR (polymerase chain reaction). Three primers were used in two separate amplification reactions. The forward primer (RFC bio) was biotinylated. This allows the isolation of a single-stranded template using streptavidin-coated beads which can then be extended using the Klenow exo- fragment of E. Coli DNA polymerase to incorporate the 7-methylG. This also permits cleanup of the modified 7-methylG DNA after extension and prior to cleavage.

Two reverse primers were used in a separate amplification reaction; one matched the natural sequence for the RFC gene (RFC), the other (RFC mut) introduced a base mutation (T to C) into the 66 base pair RFC sequence. The primers and corresponding products are also labelled RFC 4.4 and RFC 4.4 Mut in some of the Figures herein.

Using PCR and the above two primers, 66 base pair fragments were produced (FIG. 1). The two fragments differ at one position, a T to C change in the biotinylated strand and an A to G change in the complementary strand (encoded by the two reverse primers). The PCR products were purified using streptavidin agarose and the non-biotinylated strand from each PCR product was eluted and used as a template for primer extension. The biotinylated primer RFC bio was extended on these templates in the presence of dATP, dCPT, dTTP and 7-methyl dGTP.

The streptavidin agarose-bound single-stranded DNA was then incubated with piperidine for 30 minutes at 90° C. to cleave at sites of incorporation of 7-methylG into the modified DNA fragment. This treatment also resulted in the separation of the biotinyated fragment from streptavidin. The reaction mixture was subjected to centrifugation and the polynucleotide-containing supernatant was transferred to a new tube. The DNA was dried in a speed vac and re-suspended in deionized water. This sample was then subjected to MALDI mass spectrometry.

FIG. 2 shows the molecular weights of the expected fragments of interest as a result of the cleavage of the biotinylated DNA strand at each site of incorporation of 7-methylG. These fragments and their molecular weights are: a 27-mer (8772.15), a 10-mer (3069.92), an 8-mer (2557.6), and one of the following 10-mers depending on the reverse primer used in the PCR reaction, RFC (3054.9) or RFC mut (3039.88). The biotinylated 20-mer primer is also present because it was provided in excess in the extension reaction. The 10-mer fragments for RFC and RFC mut, which differ by 15 daltons, are the ones that should be detected and resolved by mass spectrometry, thus revealing the point mutation.

Figure 3:
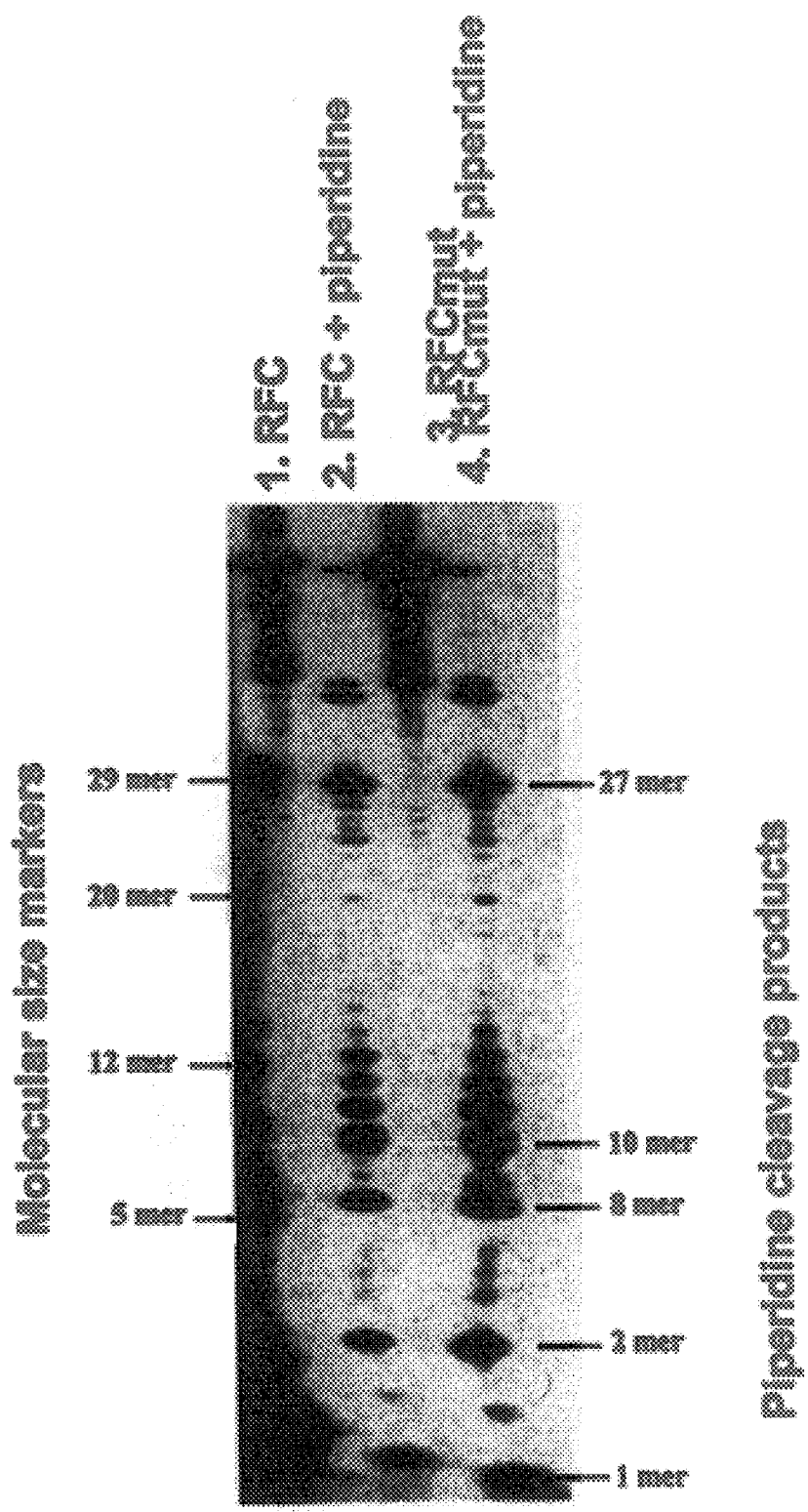
FIG. 3 shows a 10% polyacrylamide gel analysis of the primer extension products shown in FIG. 2 after full substitution of 7-methyl-dGTP for dGTP and cleavage with piperidine for one hour at 90° C. The cleavage products (lanes 2 and 4) correspond with those predicted in FIG. 2, albeit the two 10 mers overlap and cleavage is incomplete, possibly due to partial cleavage at the three consecutive G residues adjacent to the variant 10 mer. A 9 mer is seen in lane 4 (RFCmut) that is absent in lane 2 (RFC).

FIG. 3 shows a denaturing polynucleotide sequencing gel analysis of the RFC and RFC mut Klenow polymerase extension fragments before and after cleavage with piperidine. All the expected fragments were present in both cases. Most of the additional minor bands are the result of incomplete cleavage of the DNA strand by piperidine. Complete cleavage may be achieved through two cycles of piperidine treatment using freshly distilled piperidine for 30 minutes at 90° C. with each cycle being followed by drying and washing of the samples (data not shown). The band from the RFC mut cleavage (lane 4 of FIG. 3) which runs between the 8-mer and the 10-mer is the only band not explained by complete or incomplete cleavage.

FIG. 4 is the RFC mass spectrogram of the RFC sample. The peak on the far right is the biotinylated primer band that was used as a standard to calculate the molecular weights of all other bands. The left side of the spectrogram reveals all three expected cleavage bands (two 10-mers and an 8-mer). The insert in FIG. 4 is a magnified view of the region surrounding the two 10-mers and the 8-mer. The molecular weights in this region were all uniformly off by about 20 daltons because the primer used for calibration was off by 20 daltons. However, the mass differences between the peaks were all exactly as predicted.

FIG. 5 shows the mass spectrogram and a magnified portion thereof from the RFC mut sample. Two peaks should remain the same between the RFC and RFC mut samples, one of the 10-mers (3089.67) and the 8-mer (2576.93). The molecular weight of the remaining 10-mer should be decreased in the RFC-mut 10-mer by 15.02 Da (from 3054.9 to 3039.88) due to the single T to C switch and the mass difference between it and the unchanged RFC 10-mer should be 30.04 (3039.88 vs. 3069.92). However, the mass difference actually obtained from the RFC mut was 319.73 Da. This might be due to a deletion of a C from the 10-mer corresponding to nucleotides 57–66. This would also explain the anomolous 9-mer on the RFC mut sequencing gel (FIG. 3). For this to be so, the commercially obtained primer used in the amplification reaction would have to have been missing a G. The expected molecular weights for the RFC primer, the RFC mut primer and the RFC mut primer with a single G deletion are shown in Table 6. To test the hypothesis that an error had occurred in the synthesis of RFC mut oligonucleotide primer, the RFC and RFC mut oligonucleotides were then combined and subjected to mass spectrometry. As can be seen from the mass differences obtained (FIG. 6 and Table 6), the hypothesis was correct, the RFC mut primer was indeed missing one G.

The power of the method of this invention is dramatically revealed in the above experiment. What began as a controlled test of the method using a known sequence and a known nucleotide variance actually detected an unknown variance in an unexpected place—the RFC mut primer.

EXAMPLE 3

Variance Detection by Dinucleotide Restriction

Figure 19:
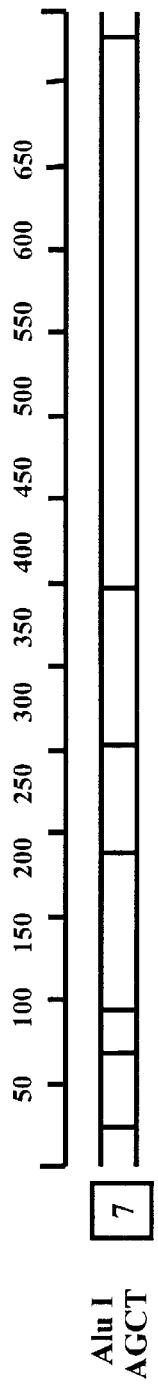
FIG. 19A shows the results of digestion of a 700 nt DNA fragment with Alu I, the vertical marks indicating the sites of cleavage.
FIG. 19B shows the results of cleavage using the dinucleotide method of this invention with 12 possible dinucleotide pairs. Dinucleotide cleavage produces a median fragment size of 16 nucleotides
Figure 19:
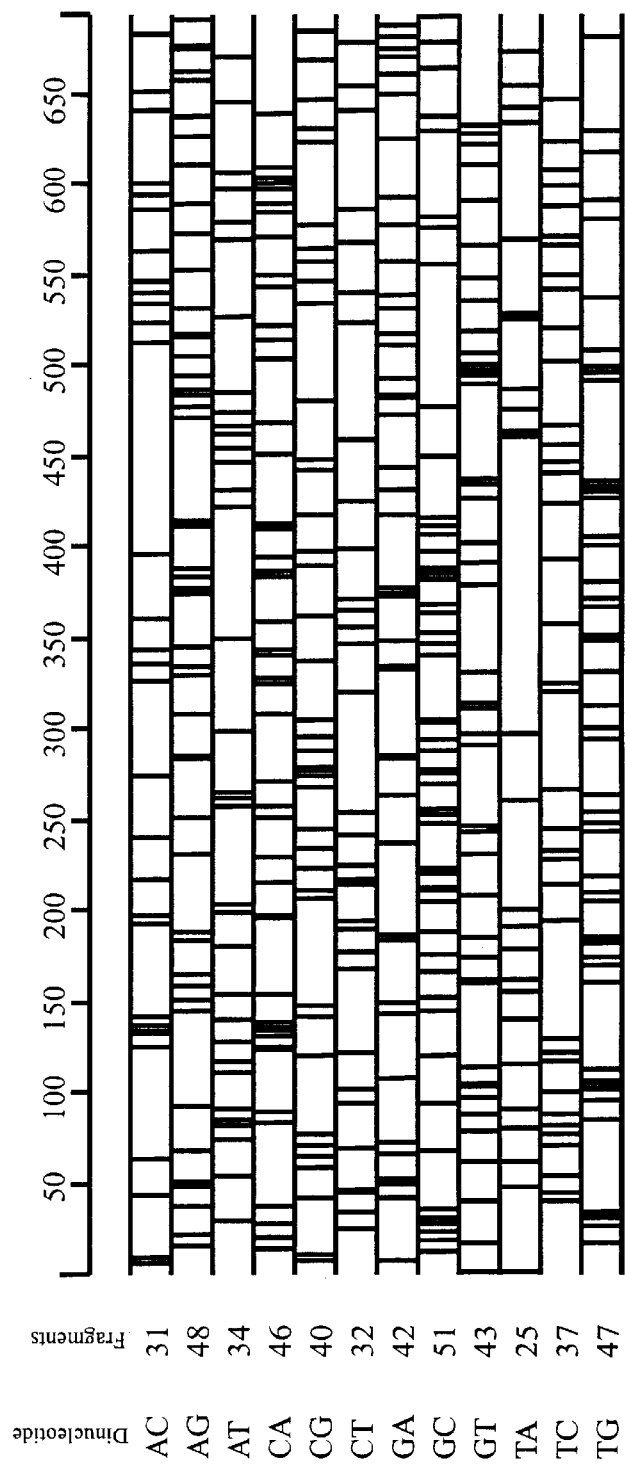

A restriction enzyme that has a four base pair recognition site will cleave DNA specifically with a statistical frequency of one cleavage every 256 ($4^4$) bases, resulting in fragments that are often too large to be analyzed by mass spectrometry (FIG. 19A). Our chemical dinucleotide restriction strategy, on the other hand, would result in much smaller fragments of the same polynucleotide. The average size of the fragments obtained is 16 ($2^4$) bases (FIG. 19B) which is quite amenable to mass spectrometry analysis.

Figure 20:
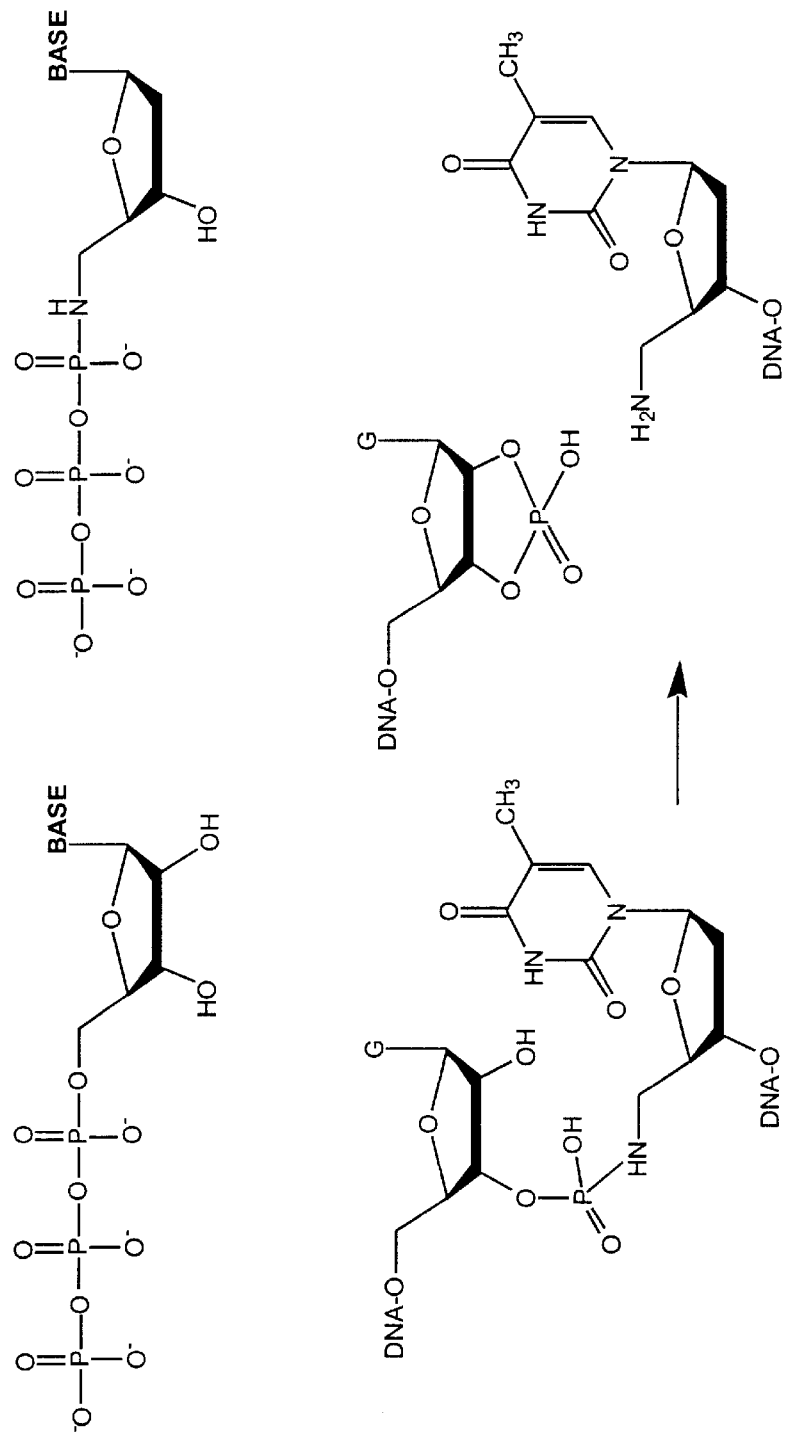
FIG. 20 illustrates the dinucleotide cleavage method of this invention using a ribonucleotide and a 5'-amino nucleotide in a 5' to 3' orientation. The products of cleavage are shown.

An example of this chemical restriction principle is illustrated in FIG. 20. Depicted in this figure is a dinucleotide pair having a ribonucleotide and 5'-aminonucleotides connected in 5' to 3' orientation, thereby positioning the 2'-hydroxyl group of the ribonucleotide in close proximity to the phosphoramidate linkage. The chemical lability of the phosphoramidate linker is enhanced since the hydroxyl group can attack the phosphorous atom to form a 2', 3'-cyclic phosphate, resulting in the cleavage of DNA at this particular dinucleotide site.

Shown in FIG. 21 is an actual application of this approach. A 5'-$^{32}$P labeled 20 nt primer was extended with a mixture of Klenow (exo-) and E710A Klenow (exo-) polymerases using an 87 nt single stranded template in a Tris buffer at pH9. The primer extension was performed with riboGTP (lane 1), 5'-aminoTTP (lane 3), or riboGTP/5'-aminoTTP (lane 5) in place of the corresponding natural nucleotides. After the extension, the reaction mixtures were purified on a G25 column. The riboG-containing extension product was cleaved with aqueous base to generate a G sequencing ladder (lane 2). The 5'-aminoT-containing product was, on the other hand, acid labile and was cleaved to afford a T sequencing ladder (lane 4). Under the conditions of the extension reaction with riboGTP/5'-aminoTTP (lane 5), a 64 nt product was obtained instead of the expected 87 nt. Interestingly, the 64 nt fragment is one of the dinucleotide cleavage products expected for GT restriction and the only one that should be visible by autoradiography. Acid cleavage of this product produced a T ladder (lane 6) whereas base cleavage generated a G ladder (lane 7), indicating the successful incorporation of both riboGTP and 5'-aminoTTP into the polynucleotide. From these results it can be concluded that GT restriction cleavage had occurred during the extension and/or workup procedures, most likely due to the synergized lability of the two modified nucleotides.

In order to visualize all three expected restriction fragments, the same extension-cleavage experiment was performed in the presence of $\alpha$-$^{32}$P-dCTP. As shown in FIG. 22, three GT restriction fragments were observed with the expected relative mobility and specific radioactivity.

The versatility of this dinucleotide restriction approach is demonstrated by AT restriction of the same DNA. Specific AT restriction was observed by polyacrylamide gel electrophoresis (PAGE) analysis (FIG. 23). A similarly generated non-radioactive product was analyzed by MALDI-TOF mass spectrometry (FIG. 24). All the expected restriction fragments were observed except for a 2 nt fragment that is lost during G25 column purification.

The general applicability of this technology is further demonstrated when a longer, different DNA template was used (FIGS. 25 and 26). Primer extension with riboATP and 5'-aminoTTP followed by AT restriction generated expected oligonucleotides as observed by PAGE analysis (FIG. 25) or MALDI-TOF mass analysis (FIG. 26).

EXAMPLE 4

Genotyping by Complete Substitution/Complete Cleavage

The following genotyping procedure by chemical restriction is an attractive alternative to other genotyping methods with many advantages including increased accuracy and speed. In general, this method involves PCR amplification of genomic DNA using chemically modified nucleotides followed by chemical cleavage at the modified bases with the resulting amplicons. Shown in FIG. 27 is a schematic presentation of this technique. One of the primers (Primer 1) is designed to be close to the polymorphic site of interest so that one of the polymorphic bases (e.g., A) may be selected as the first cleavable nucleotide. After PCR amplification with the chemically modified nucleotide (supplemented with the other three natural nucleotides), only one of the two alleles would be cleavable at the polymorphic site. Treatment with chemical reagents would afford cleavage products comprising Primer 1, whose length can reveal the genotype of the sample. Analysis by either mass spectrometry or electrophoresis can be implemented for identifying the expected length difference. Furthermore, mass spectrometry analysis may unmask the single base difference on the complementary strand of DNA that contains the polymorphism, providing a built-in redundancy and higher accuracy.

Illustrated in FIGS. 28 to 31 is the chemical cleavage and analysis procedures utilized to genotype transferrin receptor (TR) gene. A 82 bp DNA sequence of TR gene was selected based on the location of polymorphism and efficiency of amplification (FIG. 28). The polymorphic base (A or G) is positioned 3 bases from the 3' end of Primer 1. For A allele it is the first modified nucleotide to be incorporated; for G allele, the first cleavable base is 6 bases from the primer. As a result, fragments of different lengths are produced from chemical cleavage. The PCR amplification reactions (50 µl each) were carried out in standard buffer with polymerase AmpliTaq Gold (0.1 unit/µl Cycler (MJ Research PTC-200) using 35 cycles of amplification (1 min denaturation, 1.5 min annealing, and 5 min extension). Analysis of the PCR products on a 5% non-denaturing polyacrylamide gel (stained with Stains-All from Sigma) showed that 7-deaza-7-nitro-dATP can replace dATP for efficient PCR amplification (FIG. 28).

To the PCR products from 7-deaza-7-nitro-dATP were directly added piperidine, tris-(2-carboxylethyl)phosphine (TCEP), and Tris base to a final concentration of 1 M, 0.2 M, and 0.5 M, respectively, in a total volume of 100 1. After incubation at 95° C. for 1 hour, 1 ml of 0.2 M triethylammonium acetate (TEAA) was added to each reaction mixture and the resulting solution purified on an OASIS column (Waters). The eluted products were concentrated to dryness on Speedvac and the residue analyzed by mass spectrometry or electrophoresis. FIG. 29 shows the sequences of selected fragments expected from cleavage at 7-deaza-7-nitro-dA. The sequences are grouped according to lengths and molecular weights. The first group contains longer fragments that are extended from primers. The 22 nt is an invariant fragment which may be used as an internal reference. The 25 nt or 28 nt fragment is expected from A or G allele, respectively. The shaded group of sequences are from the complementary strand of DNA, including invariant 13 nt and 11 nt fragments that can be used as internal references and a pair of 11 nt fragments expected from two allelic forms of TR gene with a 15 Da mass difference. Shown in FIG. 30(a) is a MALDI-TOF spectrum of chemically cleaved products from a 82 bp heterozygote TR DNA sample. Highlighted in the spectrum are the two regions that contain fragments depicted in FIG. 29.

Each purified cleavage sample was mixed with 3-hydroxypicolinic acid and subjected to MALDI-TOF analysis on a Perceptive Biosystems Voyager-DE mass spectrometer. Mass spectra in the region of 7000–9200 daltons were recorded and the results for the three TR genotypes are shown in FIG. 30(b). The spectra were aligned using the peak representing invariant 22 nt fragment (7189 Da). Two additional peaks were observed for AG heterozygote sample with one corresponding to A allele (8057 Da) and the other G allele (9005 Da). As expected, only one additional peak was observed for GG or M homozygote samples, each with the molecular weight of cleavage fragments from G or A allele. FIG. 31(a) shows a mass spectrum of AG heterozygote sample in the region of 3700–4600 Da. With 3807 Da and 4441 Da fragments as internal references, the genotype of this sample was confirmed through the observation of two peaks in the middle of the spectrum with 15 Da mass difference. The molecular weights observed by mass spectrometry indicated that phosphate-deoxyribose-TCEP adducts were uniformly formed during the cleavage reaction, resulting in fragments that are modified at 3' end (FIG. 31(b)). The data shown in FIG. 30 and FIG. 31 also illustrated that the combination of chemical restriction with mass spectrometry can provide corroborating genotyping information from both strands of DNA, thereby assuring the accuracy of the analysis.

Alternatively, the chemically restricted samples may be analyzed by electrophoresis to detect the diagnostic length difference resulting from the two alleles. Capillary electrophoresis (CE) analyses were performed using a homemade instrument with a UV detector and a capillary containing denaturing linear polyacrylamide gel. FIG. 32(a) shows the CE chromatogram obtained from TR samples of various genotypes. As predicted, each genotype showed distinguished elution pattern corresponding with the lengths of expected cleavage products. Whereas M homozygote produced a 25 nt fragment and GG homozygote generated a 28 nt fragment, AG heterozygote sample afforded both 25 nt and 28 nt products. After being labeled at 5' end by $^{32}$P, the cleavage samples were subjected to PAGE analysis. The resulting autoradiogram in FIG. 32(b) demonstrates that the cleavage is specific with little or no background and the genotyping results are unambiguous.

Another alternative detection method involves the application of fluorescence resonance energy transfer (FRET). FRET has been successfully applied for polymorphism detection by TaqMan assays (Todd J. A. et al. 1995, Nature Genetics, 3:341–342) and Molecular Beacons (Tyagi, S. et al. 1998, Nature Biotechnology, 16:49–53). However, when longer probes are necessary to achieve their hybridization to target sequences (e.g., AT rich sequences), it becomes increasingly difficult to distinguish the vanishingly small difference resulted from a single nucleotide mismatch. The advantage of chemical restriction in this regard is illustrated in FIG. 33. Similar to the aforementioned example, a modified nucleotide analog of one of the polymorphic base (e.g., A) is used in place of its natural counterpart in the PCR amplification. Primer 1 is designed to be close to the polymorphic site so that the polymorphic base A would be the first cleavable nucleotide for A allele. Primer 1 is also labeled with a fluorescent group (F1) positioned close to 3' end (FIG. 33(a)). After amplification and chemical restriction, a probe covalently attached to another fluor F2 (shown in FIG. 3(b)) can be added and the FRET effect between the two fuorophores measured. Because one of alleles was cleaved closer to the 3' end of primer 1 than the other, the difference between them in hybridization is expected to be greater than a single nucleotide mismatch, and may be exploited to distinguish the two allelic targets. As depicted in FIG. 33(c), the experimental temperature can be attenuated so that only the longer fragment from G allele can hybridize with the probe, resulting in FRET. Since in this system a "NO FRET" result could be interpreted either as allele A or failed PCR amplification, it is necessary to measure the fluorescence of each sample at various temperatures to ensure the positive detection of the shorter fragment from allele A at a lower temperature. Alternatively, this positive detection may be achieved through the use of a hairpined probe depicted in FIG. 33(d). The probe has a 5' end tail that folds back to form a hairpin, in addition to a fluro F3 at the 5' end. With the short cleavage fragment from A allele, the hairpin probe can form a bridging duplex as depicted, generating detectable FRET between F1 and F3. Only with the longer fragment from G allele can the interstrand hybridization compete with the stability of the hairpin and result in loss of FRET between F1 and F3.

EXAMPLE 5

Complete Sequencing by Partial Substitution/Partial Cleavage

Using the following procedure, it is entirely possible to sequence, in one set of sequencing reactions, a polynucleotide consisting of 10,000, 20,000 or even more bases by polymerization in the presence of modified nucleotides, enzymatic restriction of polymerization products, purification of restriction fragments and chemical degradation to produce sequence ladders from each fragment. The procedure is limited only by the size of the template and the processivity (the ability to continue the polymerization reaction) of the polymerase used to extend the primer. Unlike a shotgun cloning library in which there is a normal distribution of sequence inserts requiring highly redundant sequencing, using the method describe herein results in each nucleotide being sampled once and only once. Repeating the procedure using a second or even a third restriction enzyme cocktail will provide the sequence information needed to reassemble the sequences determined from the initial restriction in the proper order to reconstruct the full length polynucleotide sequence while also supplying the redundancy necessary to ensure the accuracy of the results. In the description which follows a variety of options for carrying out each step are provided. As before, it is understood that other modifications to the procedure described will be readily apparent to those skilled in the art; such other modifications are within the scope of this invention.

TABLE 6

| Primer | Molecular Weight | Mass Difference |
|---|---|---|
| RFCC | 6099.6 | |
| RFC mut | 6115.9 | +16 |
| RFC mut | 5786.7 | −313.2 | a. Anneal Primer and Template

The template used may be a small or a large insert cloning vector or an amplification product such as a PCR fragment; it may also be single- or double-stranded. For example, without limitation, the template may be a plasmid, phagemid, cosmid, P1, PAC, BAC or YAC clone. The template is ideally rendered linear before extension to ensure that all extension products terminate at the same place. This can be accomplished by restricting the template with a restriction endonuclease. For example, the templates may be prepared in a vector that has restriction sites for one or more rare cutters on either side of the cloning site so that a linear template can be routinely prepared by restriction using the rare cutter enzyme (i.e., an enzyme that cleaves, for example, a 7 or 8 nucleotide motif). Many plasmid vectors such as, without limitation, Bluescript (Stratagene, Inc.) have these features. A primer can be selected which will anneal to a sequence in the vector, for example, the M13 universal primer sequences. This allows the sequencing of a library of clones using only one or two primers (one from each side of the insert). Alternative, a series of insert-specific primers may be used (at approximately 5–20 kb intervals) in a version of primer walking.

b. Extend Primer in Presence of all Four Natural Deoxyribonucleotides and a Modified Nucleotide Corresponding to one of the Natural Nucleotides.

Figure 7B:
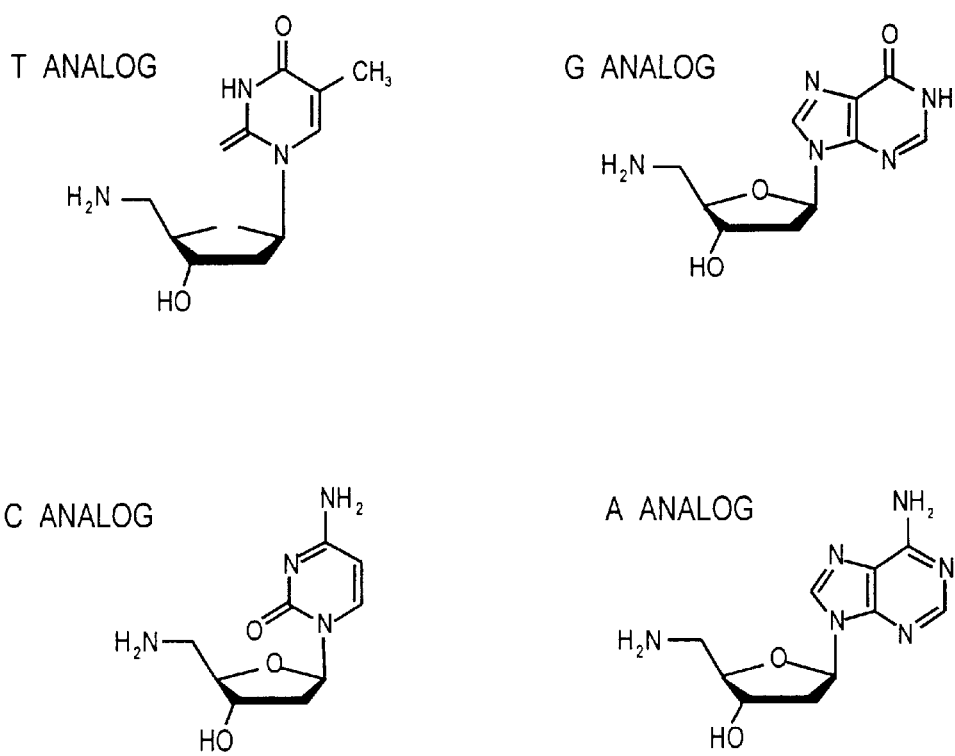
FIG. 7B shows the chemical structure of 5'-amino-DT, dG, dC and dA.
Figure 9:
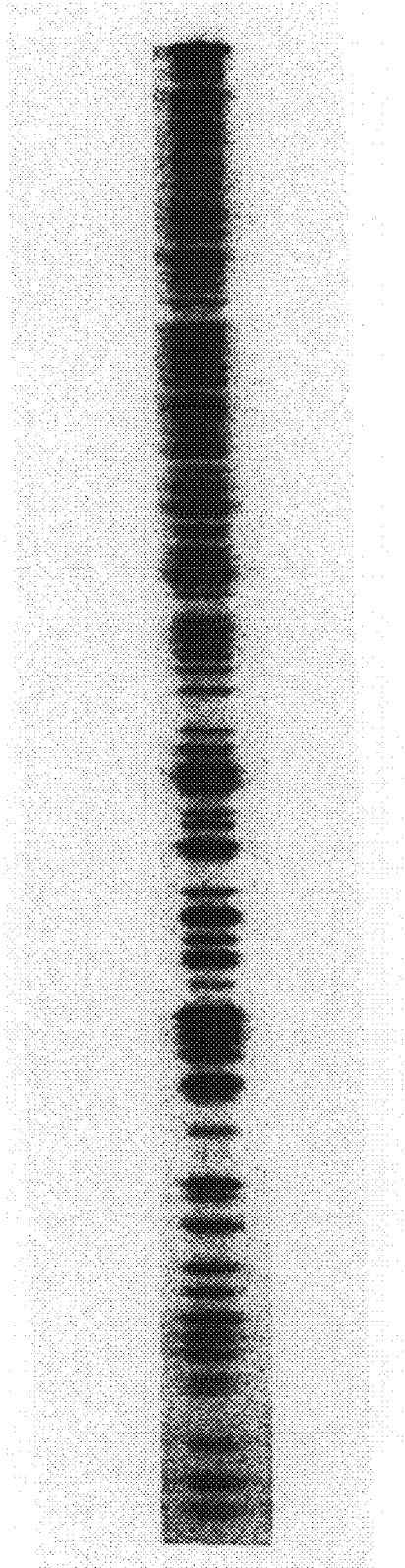
FIG. 9 is an autoradiogram showing the result of cleavage of the 1.2 kb Msc I restriction product at the sites of incorporation of 5'-amino-d-TTP with acetic acid and resolution of the fragments by denaturing acrylamide gel electrophoresis.

The procedures discussed above are used to extend the primer over the entire length of the template using one of the modified nucleotides described above or any other modified nucleotide which is capable of imparting selective cleavage properties to the modified polynucleotide. In general, the ratio of modified nucleotide to its natural counterpart can vary over a considerable range from very little (approximately 1%) to complete ($\geq$99%) substitution. The controlling factor is the efficiency of the subsequent chemical cleavage reaction. The more efficient the cleavage reaction, the lower the level of incorporation can be. The goal is to have approximately one modified nucleotide per restriction fragment so that, after cleavage, each molecule in the reaction mixture contributes to the sequencing ladder. FIG. 7 shows one such modified polynucleotide, a linearized, single-stranded M13 template extended to 87 nucleotides in the presence of the modified nucleotide, 5'-amino dTTP using the exo-minus Klenow fragment of *E. coli* DNA polymerase. FIG. 9 shows a 7.2 Kb extension product, again produced from an M13 template in the presence of 5'-amino-dTTP and dTTP at a molar ratio of 100:1 (Panel A, extension product).

c. Purify the Full Length Primer Extension Product (Optional)

Figure 8C:
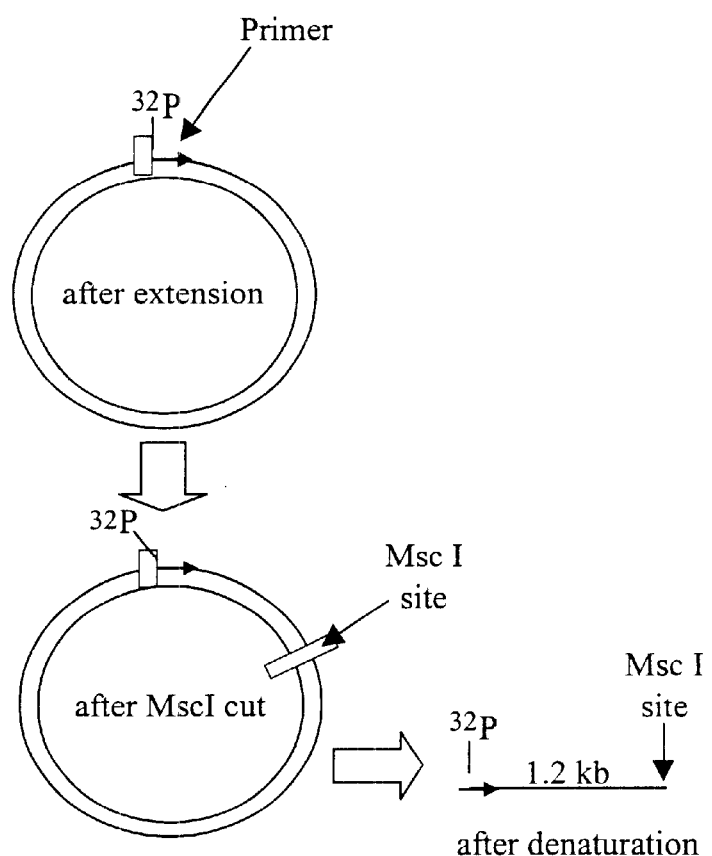
FIG. 8C shows a proposed mechanism that would afford the 1.2 kb product by restriction after heat denaturing.

In order to eliminate prematurely terminated (i.e., less than full length) polymerase extension products, thereby assuring a homogeneous sequencing ladder on electrophoresis after cleavage, it may be desirable to purify the full length or substantially full length extension products. It is noted, however, that the purification of the restriction fragments after digestion (step f, below) achieves essentially the same goal and, in most instances, is likely to suffice. In any event, the elimination of short extension products can be accomplished by numerous procedures known in the art such as spun column chromatography or high performance liquid chromatography (HPLC). FIG. 8 shows a purified full-length extension product before (Panel A) and after (Panel B) chemical cleavage with acid.

d. Cleave the Primer Extension Product with one or More Restriction Enzymes.

As noted previously, the optimal size for DNA sequencing templates (in this case, of restriction products) is approximately 300 to about 800 nucleotides when gel electrophoresis is to be used for the creation of the sequencing ladder. Thus restriction endonucleases must be employed to reduce the full-length extension product of 10 Kb or more to manageable size. Numerous such endonucleases are known in the art. For example, many four-base restriction endonucleases are known and these will generally yield restriction products in the desired range. Shorter restriction fragments; e.g., less than 300 nucleotides, can also be sequenced, but to make the most efficient use of gel runs, it is desirable to separate the restriction fragments into sets according to their length. The shorter fragments will then require relatively brief sequencing run times while the longer fragments will require a longer gel and/or longer run times. Two or more restriction endonuclease cocktails, each containing one or more restriction endonucleases and a compatible buffer, can be used to provide the overlapping sequence information necessary to re-assemble the complete sequence of the polynucleotide from the restriction fragments. FIG. 9 shows an exemplary restriction endonuclease digestion of a primer/template complex extended in the presence of dTTP and the modified nucleotide 5'-amino dTTP. As can be seen in FIG. 9, complete cleavage was obtained using the restriction endonuclease Msc I. Other MSC I restriction products are not seen because only the 5' end of the primer extension product was labelled with $^{32}$p.

e. Label the Restriction Endonuclease Products.

To visualize the DNA sequencing ladder generated by this method, it is necessary to label the restriction endonuclease products with a detectable label. Many such labels are known in the art; any of them may be used with the methods of this invention. Among these are, without limitation, radioactive labels and chemical fluorophors. For instance, $^{35}$SdATP (Amersham Phamacia Biotech, Inc) or rhodamine-dUTP (Molecular Probes) can be incorporated at the primer extension step. Alternatively, the DNA can be labeled after restriction by modification of the restriction fragments ends by, without limitation, T4 polynucleotide kinase or filling recessed ends with a DNA polymerase and a labeled nucleotide. Such end-labeling is well known in the art (see, for example, Ausubel, F. M., et al., *Current Protocols in Molecular Biology*, John Wiley & Sons, 1998). End labeling has the advantage of putting one molecule of label on each DNA fragment that will afford homogenous sequencing ladders. Labeling of the template strand is of no consequence since it will not be cleaved during the chemical cleavage reaction due to the absence of modified nucleotide in its sequence. Thus, no sequencing ladder will be produced for the template strand.

f. Separate the Labeled Restriction Endonuclease Products

Figure 10:
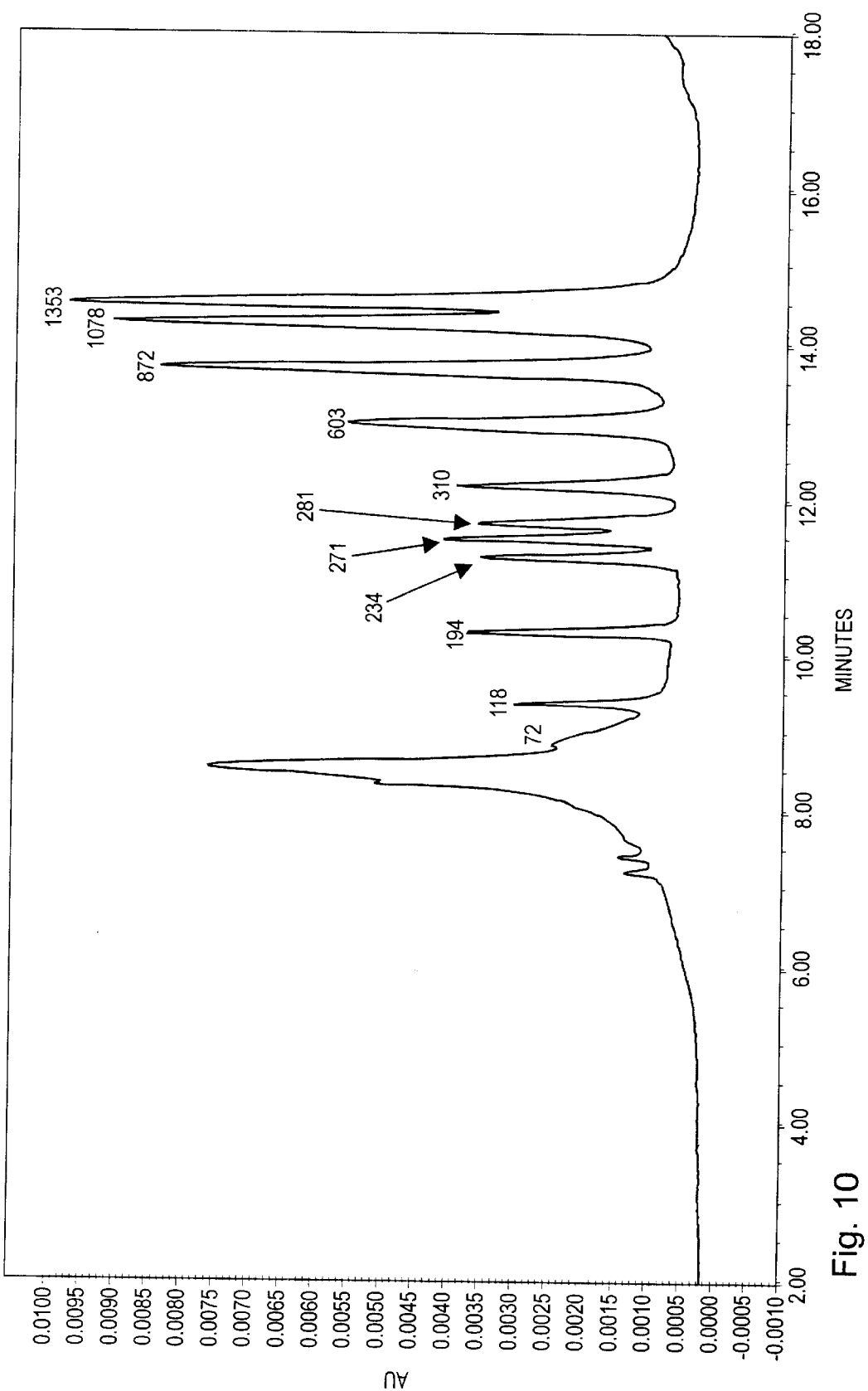
FIG. 10 shows the result of ion pair reverse phase HPLC separation of Hac III DNA restriction fragments from PhiX174. The fragment lengths are shown above the peaks. Resolution was performed on a Micra Scientific NPS C18 1.5 μm column at 63° C. using 0.1 M TEM, pH 8.3 as buffer A and 50% $CH_3CN$, 0.1 M TEM, pH 8.3, as buffer B.

The restriction fragments must be separated prior to chemical cleavage. Numerous methods are known in the art for accomplishing this (see, for example, Ausubel, F. M., op. cit.). A particularly useful technique is HPLC, which is rapid, simple, effective and automatable. For example, FIG. 10 shows the resolution obtained by HPLC on Hae III restricted PhiX174 DNA. Ion reverse pair phase HPLC and ion exchange HPLC are two preferred methods of separation.

g. Cleave the Separated Labeled Restriction Endonuclease Fragments at Sites of Modified Nucleotide Incorporation.

Depending on the modified nucleotide incorporated, use one of the cleavage reactions previously described herein or any other cleavage reaction which will selectively cleave at the site of incorporation of the modified nucleotide, such other cleavage reactions being within the scope of this invention.

h. Determine the Sequence of the Fragment

Figure 11A:
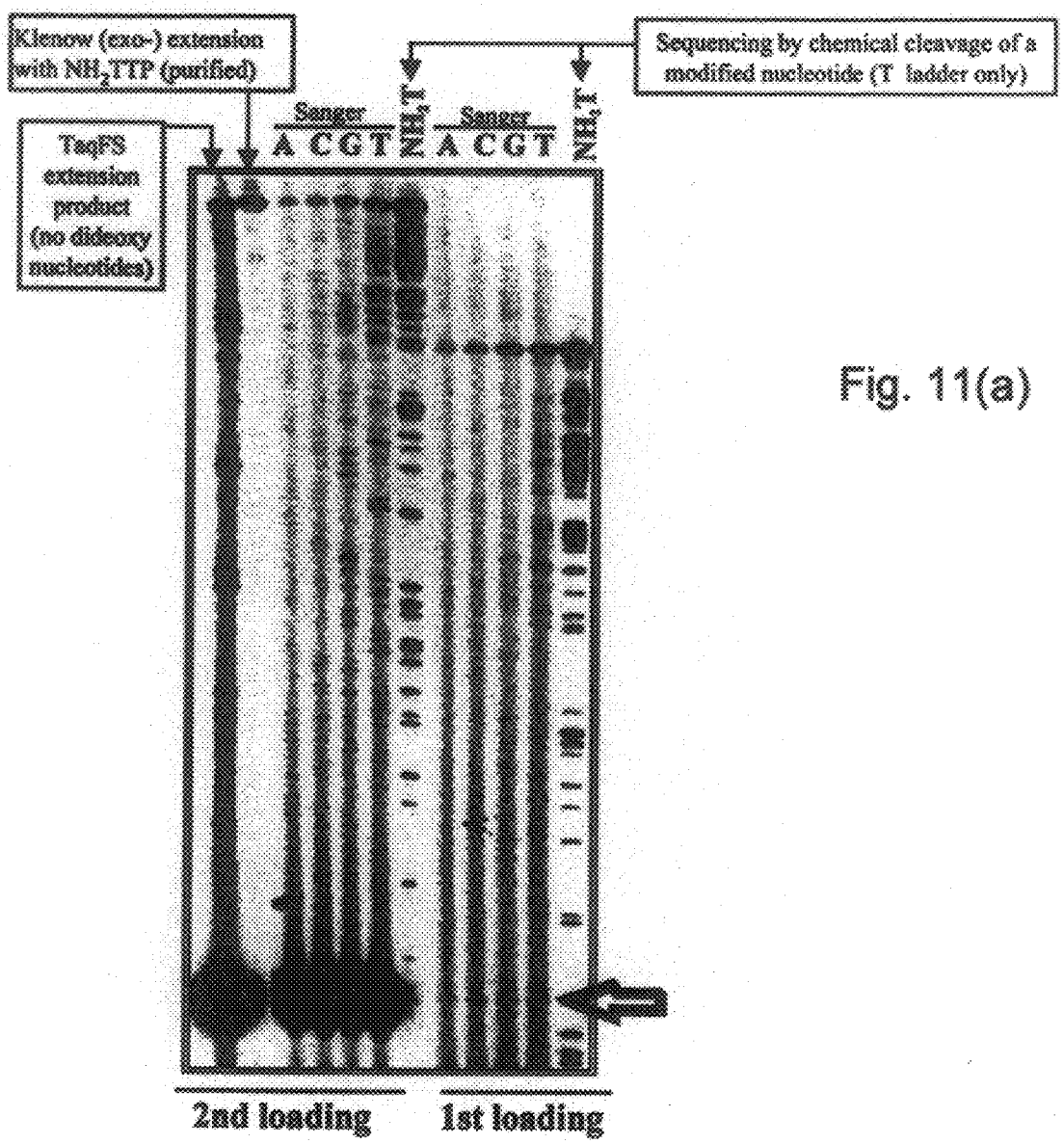
FIG. 11A is a comparison of Sanger-type sequencing with the modified nucleotide incorporation/cleavage procedure of the present invention. Lane 1 is the TaqFS extension product with no dideoxynucleotides. Lane 2 is the purified Klenow (exo-) extension product substituting 5'-$NH_2$-dTTP for dTTP. Lanes 3, 4, 5, 6, 8, 9 10 and 11 are the Sanger fragment ladders. Lanes 7 and 12 are the ladders obtained by the chemical cleavage method of this invention (T ladder only).
Figure 11B:
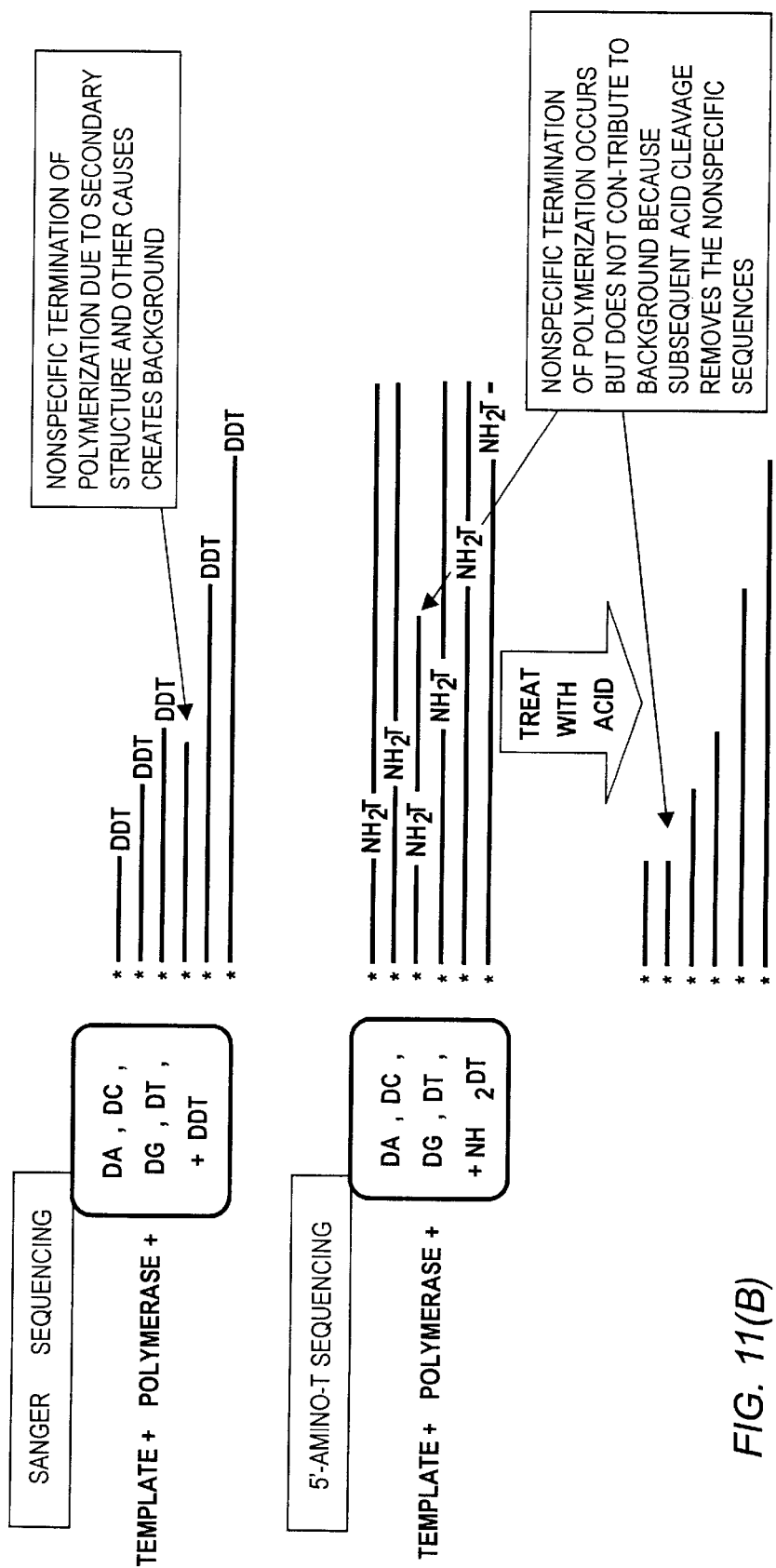
FIG. 11B is a schematic representation of the present invention using modified nucleotide incorporation/cleavage to sequence DNA compared to the Sanger sequencing method. The asterisk (*) represents a dye or isotopic label. The $4^{th}$ sequence, which has no ddT at the end signifies non-specific polymerization termination caused by secondary structure and/or other phenomena that result in background noise. The same non-specific polymerization termination in the method of the present invention (the short extension product) does not contribute to background because subsequent acid cleavage removes the non-specific sequences, as shown.
Figure 12:
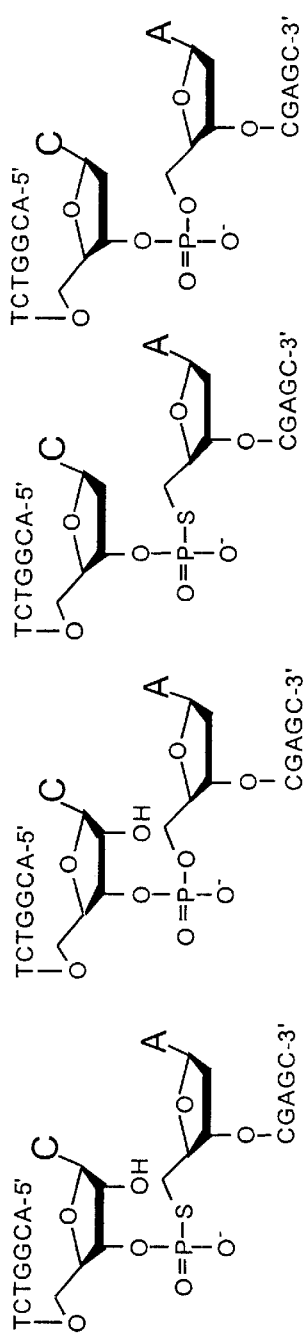
FIG. 12 demonstrates the dinucleotide cleavage method of the present invention. As can be seen, cleavage only occurs when the ribo-C and the thio-A are adjacent to one another (column 1). If either of the modified nucleotides is not positioned properly, very little (column 2) or no (columns 3 and 4) cleavage results.
Figure 13:
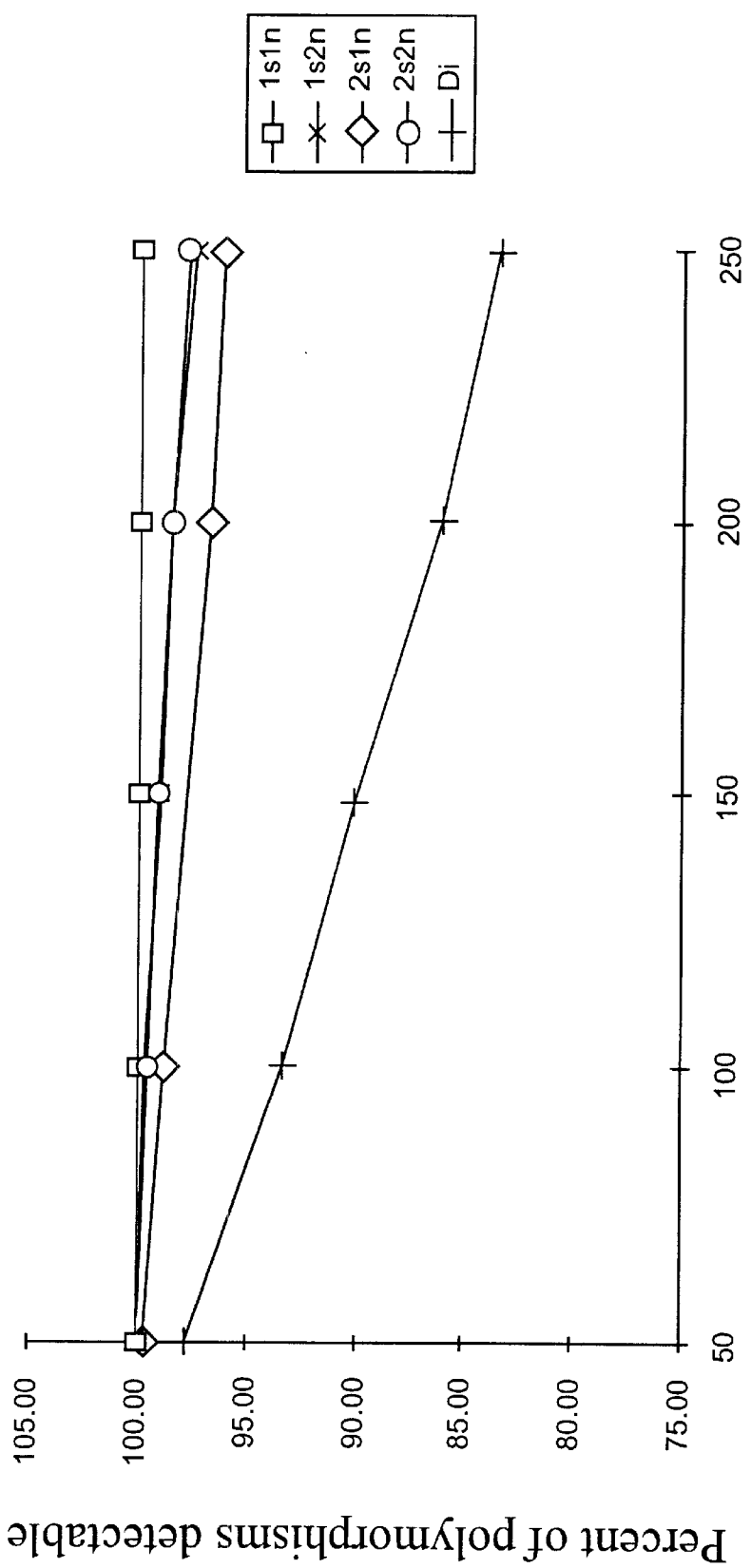
FIG. 13 is a graph depicting the efficiency of variance detection as a function of polynucleotide length. 1s1n refers to single strand, one modified nucleotide, 1 s2n to single strand, two different nucleotides in separate reactions, 2s1n to two strands analyzed separately with the same nucleotide in each, 2s2n to two strands, two different nucleotides and Di to dinucleotide cleavage (all possible dinucleotide combinations). As can be seen, even single strand, single nucleotide cleavage is up to 85% efficient at detecting all variances in a 250 mer polynucleotide.

FIG. 11 shows the sequence ladder obtained from a polynucleotide in which T has been replaced with 5-amino T. This ladder, of course, only reveals where T occurs in the complete sequence of the target polynucleotide. To obtain the entire sequence, the above procedure would be repeated three more times, in each case one of the remaining nucleotides, A, C and G would be replaced with a corresponding modified nucleotide; e.g., 5'-amino-dATP, 5'-amino-dCTP or 5'-amino-dGTP. When all four individual fragment ladders are in hand, the complete sequence of the polynucleotide can easily be re-constructed by analysis and comparison of gel sequencing data.

EXAMPLE 6

Complete Sequencing by Substantially Complete Substitution/substantially Complete Cleavage Combined with Mass Spectrometry.

The preceding procedure for complete sequencing of a polynucleotide still requires the use of gel electrophoresis for creating fragment ladders from which the sequence is read. As noted previously, gel electrophoresis is a time and labor intensive process which also requires a fair degree of skill to carry out in such a manner as to have a reasonable assurance of reproducible and accurate results. It is an aspect of this invention that the use of gel electrophoresis can be eliminated completely and replaced with relatively simple to use, fast, sensitive, accurate, automated mass spectrometry. The basis for this aspect of this invention is the previously discussed uniqueness in the molecular weights of virtually all 2-mers through 14-mers with the exception of the 8 fragment pairs described above (and other fragment pairs that are based on addition of identical sets of nucleotides to the 8 fragment pairs. The following is an example of how this procedure would be carried out. While the example is described in terms of human intervention and specific analyses at each step, it will be readily apparent to those skilled in the art that a computer program could be devised to completely automate the analytic procedure and further increase the speed of this aspect of this invention. The use of such a computer program is, therefore, within the scope of this invention.

The procedure for determining complete nucleotide sequences by mass spectroscopy would entail the following steps:

a. substantially complete replacement of a natural nucleotide in a polynucleotide with a modified nucleotide to form a modified polynucleotide. This would be accomplished by an amplification procedure or by primer extension employing the polymerase reaction discussed above. Optionally, the procedure disclosed above could be used to arrive at the optimal polymerase or set of polymerases for preparing the desired modified polynucleotide;

b. cleavage of the modified polynucleotide under conditions that favor substantially complete cleavage at and essentially only at the points of incorporation of the modified nucleotide in the modified polynucleotide; and, c. determination of the masses of the fragments obtained in the preceding cleavage reaction.

The above three steps are then repeated three more times, each time a different modified nucleotide corresponding to each of the remaining natural nucleotides is used. The result will be a series of masses from which all or most of the sequence of the entire original polynucleotide can be ascertained. Any sequence ambiguity which remains after the main analysis is done should be readily resolved by using one more reactions involving a contiguous dinucleotide substitution/cleavage reaction or by a conventional DNA sequencing procedure. The following is an example of how the analysis of a fragment would proceed.

Given the following 20 nucleotide natural oligomer extended from a 16 mer primer:

5'-primer-TTACTGCATCGATATTAGTC-3' (SEQ. ID. NO. 1) polymerization in the presence of dTTP, dCTP, dGTP and a modified dATP will result, after substantially complete cleavage, in five fragments whose masses are shown in Table 7. Carrying out the procedure three more times for the remaining three natural nucleotides will result in three more sets of fragments, the masses of which are also shown in Table 7. From these masses, the nucleotide content (but not sequence, yet) of all the fragments can be uniquely determined. The actual sequence is determined by analyzing all four cleavage results together.

For example, looking at the masses of all the fragments in Table 1, it is readily discernable that only one mass in each cleavage set comprises more than 16 nucleotides, that all the other fragments are 3' of the primer (since the fragment containing the primer must be at least 16 nt) and that there are two nucleotides after the primer in the A cleavage column, three in the C column, five in the G column and none in the T column. Therefore, the sequence must begin with TT followed by an A, then a C, an unknown nucleotide and then a G. The sequence must start with 2 T residues because neither A, C nor G cleavage occurs in this initial interval. Also, by adding the masses of the fragments in the different cleavage sets, it can be seen that the length the unsequenced region is 20 nucleotides. The number of nucleotides in of the four cleavage sets are also readily ascertainable—set A: (primer +2) +5+4+3+2=16; set C:( primer+3)+10+3+3+1=20; set G: primer+5)+7+5+3=20; set T:4+3+3+2+2+1=15. From this information it is clear that there must be overlapping fragments in the A and T sets.

Subtracting the known mass of the primer from those fragments containing the primer reveals the nucleotide content of the sequence immediately following the primer. Thus, in lane A, the residual mass of 608 Daltons which, from Table 3, is seen to correspond to TT which therefore must be the first two nucleotides in the unknown fragment sequence. The sequence following the primer is thus already known to be TTAC_G. From the mass of the 5 mer in the G lane (1514 Daltons), it can be seen that the 5-mer contains three Ts, an A and a C. Thus, the missing nucleotide must be a T; the leading sequence is TTACTG.

TABLE 7

5'-Primer-TTACTGCATCGATATTAGTC-3' [SEQ.ID.No. 1]

| Cleave at modified: | A | Mass | C | Mass | G | Mass | T | Mass |
|---|---|---|---|---|---|---|---|---|
| Cleavage fragments listed in 5'—3' order | Primer-TT ACTGC ATCG AT ATT AGTC | 608+ primer 1463 1174 556 860 1174 | primer-TTA CTG CAT CGATATTAGT C | 921+ primer 861 845 3041 289 | primer-TTACT GCATC GATATTA GTC | 1514+ primer 1463 2119 861 | primer T TAC TGCA TCGA TA T TAG TC | primer only 304 845 1174 1174 556 304 885 532 |

Table 7 shows the nucleotide-specific cleavage patterns for the sequence shown at top, which consists of a primer of known sequence and length (not specified) followed by 20 nucleotides of 'unknown' sequence. Cleavages in this example occur via a mechanism that breaks the phosphodiester bond 5' of the modified nucleotide. Each cleavage set includes one fragment containing the primer plus however many nucleotides after the primer until the first occurrence of the modified nucleotide. The known mass of the primer can be subtracted from this (largest) mass to obtain the difference, which gives the mass and therefore the nucleotide content of the sequence immediately 3' of the primer. The masses provided in the table reflect the presence of one external phosphate group in each cleavage mass, however it should be recognized that, depending on the chemical nature of the nucleotide modification and the cleavage reaction, actual masses will likely differ from those shown in the table. However, such differences are expected to be systematic and therefore do not invalidate the analysis.

Turning now to the masses shown in the T lane of Table 7, the 906 Dalton mass must contain a T, an A and a C. Since there already is a TAC sequence known, it may tentatively be held that this is a confirming sequence, part of the overlap of the A and T cleavages. It, of course, cannot yet be ruled out that another 3-mer containing T, A and C exist in the fragment which is why this assignment must remain tentative at this point.

The next T cleavage fragment must, at a minimum, contain a T and a G. Two T cleavage masses permit this: 946 and 1235. Thus, the additional sequence must be either G followed by T (if the 946 mass is the next mass) or G followed by a C and an A, order not known, and then T. The sequence is now known to be either TTACTGGT or TTACTG(C, A)T (the parentheses and comma between nucleotides will be used to indicate unknown order).

Going back to the A cleavage reaction, it can be seen that the next cleavage mass after the TT must contain ACTG. Two masses, 1235 Da and 1524 Da, meet this criterion. If 1235 Da is correct, the seventh nucleotide in the sequence is A because cleavage has to have occurred at that nucleotide. If 1524 Da is correct, then the sequence is CA. CA is consistent with one of the two possibilities discussed above; thus the overall sequence so far is TTACTGCAT.

Looking next at the masses from the C cleavage reaction, it can be seen that the first mass after the initial TTA must be CTG(C,A). Since cleavage will occur 5' of any C, the possibilities are CTG or CTGA; only the first of these is supported by the masses in the C lane. Thus the second mass fragment in the C lane must be CTG followed by another C (because cleavage has occurred at that point). The third mass in the C lane (906 Da) must contain a C, an A and a T which confirms the previous sequence of CAT. This leaves only two possibilities for the remaining sequences, a C followed by the 10 mer or the 10 mer followed by a terminal C. However, if the former were the case, then a cleavage fragment from one of the other lanes, A, G, or T, should show a 3 mer, 4 mer or 5 mer which contains 2 Cs. Since none of the masses permit such an oligomer, the lone C must be at the 3' end of the unknown fragment and the 10 mer is next after CAT giving the following sequence TTACTGCATC_____C.

Turning once again to the G cleavages, it is now known that a fragment must exist which contains at least GCATC. From the masses available this may be GCATC itself (1524 Da) or the 7 mer (2180 Da). However, if the mass of the 5 mer is substracted from the mass of the 7 mer, the remaining mass, 656 Da, does not correspond to any known oligonucleotide. Thus, the 7 mer cannot be next, GCATC is the correct sequence and the next nucleotide must be a G (since cleavage has occurred to give the 5 mer). The sequence is now TTACTGCATCG_____C.

The next mass in the T cleavage series must begin with TCG. The only T cleavage mass which permits such a combination is 1235 Da which corresponds to a TCGA sequence. This sequence must be followed by a T since cleavage has occurred at that point. The overall sequence is, therefore, TTACTGCATCGAT_____C.

There is only one mass among the available T cleavage series which contains a C, the 593 Da TC. Thus the nucleotide preceding the terminal C must be a T. Likewise, the only TC-containing mass in the A cleavage series that does not contain 2 Cs, which is now known to be not permissible, is 1235 or (A,G)TC. The 1235 mass has already been used once (nucleotides 8–11) but it is also known that there is fragment overlap since the A series only accounts for a total of 16 nucleotides. The sequence is now known to be TTACTGCATCGAT____(A,G)TC. However, if the terminal sequence is ATC, there should be a 906 Da mass among the A cleavages; there is not. On the other hand, if the terminal sequence is GTC, a mass of 922 Da should be found among the G cleavage fragments and there is. Thus, the sequence can now be established as TTACTGCATCGAT____AGTC.

There is only one available T cleavage mass containing AG but no C, the 946 Da mass consisting of T(A,G). This mass must account for the AG in positions 17 and 18. Therefore, position 16 must be a T; the sequence is now known to be TTACTGCATCGAT___TAGCT.

Only two masses are still available in the A cleavage group, 617 (AT) and 921 (ATT). These complete the overall sequence in two ways, ATATT or ATTAT. None of the masses permits the resolution of this ambiguity. However, all 20 nucleotides in the target oligonucleotide have, in a single experiment, been unambiguously identified and 18 of the 20 have been unambiguously sequenced.

With regard to ambiguity generally, be it be one, as in the above example, or more than one, as might be the case when sequencing longer fragments, depending on the nature of the ambiguity and the environment it which it exists; i.e., the nucleotides on either side of it, an additional experiment using any one of several available procedures should readily resolve the matter. For instance, an experiment using the dinucleotide cleavage method of this invention might provide the additional information necessary to resolve the ambiguity. Alternatively, some relaxation of the substantially complete cleavage conditions might result in a ladder of masses in which a known mass is joined with an adjacent ambiguous mass in a manner that clarifies the position and order of the ambiguous mass with respect to the known mass. Or, low accuracy, single pass Sanger sequencing might be employed. Alone, this relatively easy and rapid version of Sanger sequencing would not provide much valuable information but, as a complement to the method of this invention, it would likely provide sufficient information to resolve the ambiguity (and, to the extent the sequencing ladder obtained is unambiguously readable it would provide a partial redundancy verifying the mass spec data.

CONCLUSION

Thus, it will be appreciated that the method of the present invention provides versatile tools for the detection of variance in polynucleotides, for the determination of complete nucleotide sequences in polynucleotides and for genotyping of DNA.

Although certain embodiments and examples have been used to describe the present invention, it will be apparent to those skilled in the art that changes in the embodiments and examples shown may be made without departing from the scope of this invention.

Other embodiments are within the following claims.

What is claimed:

1. A method for synthesizing a polynucleotide comprising mixing a compound having the chemical structure:

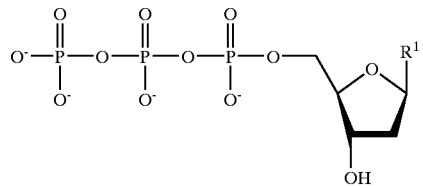

wherein $R^1$ is selected from the group consisting of:

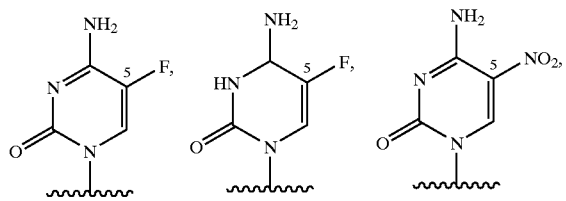

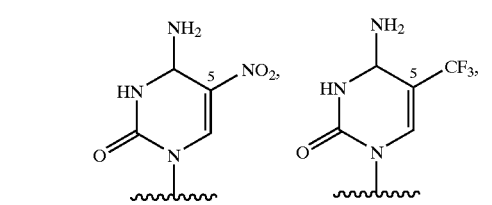

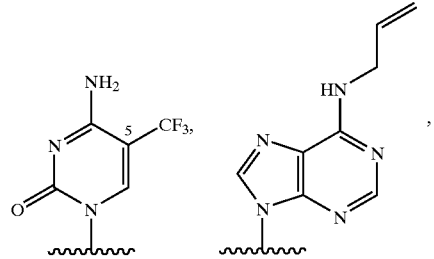

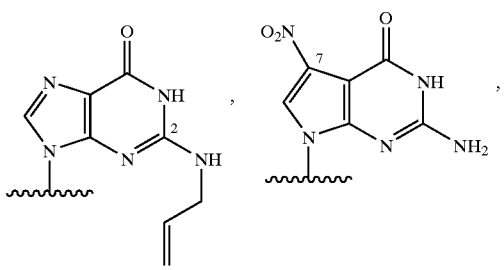

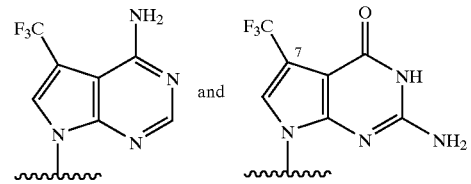

with adenosine triphosphate, guanosine triphosphate, and thymidine or uridine triphosphate in the presence of one or more polymerases.

2. A method for synthesizing a polynucleotide comprising mixing a compound having the chemical structure:

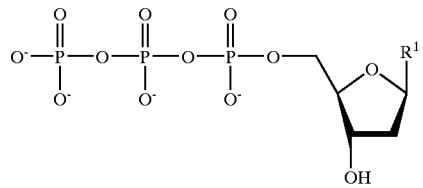

wherein $R^1$ is selected from the group consisting of:

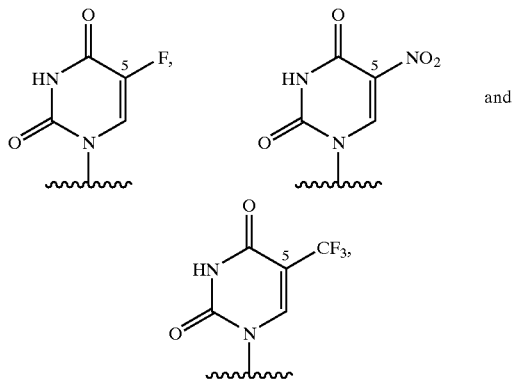

with adenosine triphosphate, cytidine triphosphate and guanosine triphosphate in the presence of one or more polymerases.

3. A method for synthesizing a polynucleotide, comprising mixing a compound having the chemical structure:

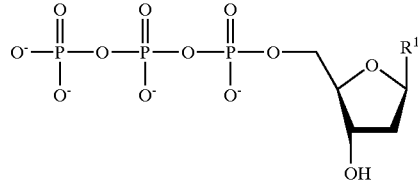

wherein $R^1$ is selected from the group consisting of:

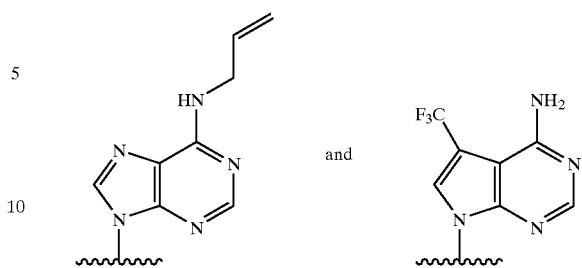

with cytidine triphosphate, guanosine triphosphate, and thymidine triphosphate in the presence of one or more polymerases.

4. A method for synthesizing a polynucleotide, comprising mixing a compound having the chemical structure:

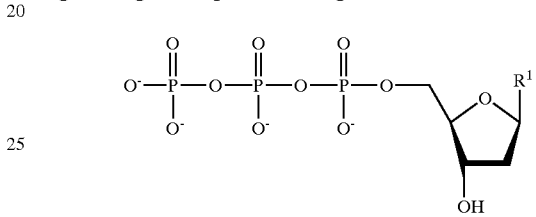

wherein $R^1$ is selected from the group consisting of:

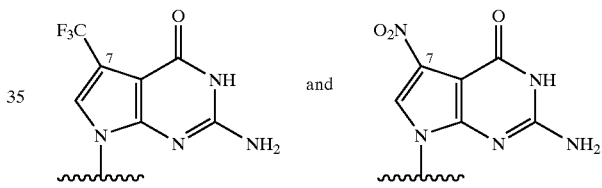

with adenosine triphosphate, cytidine triphosphate and thymidine triphosphate in the presence of one or more polymerases.

* * * * *

```
                         SEQUENCE LISTING

<160> NUMBER OF SEQ ID NOS: 17

<210> SEQ ID NO 1
<211> LENGTH: 20
<212> TYPE: DNA
<213> ORGANISM: Artificial Sequence
<220> FEATURE:
<223> OTHER INFORMATION: hypothetical sequence to demonstrate
      application

<400> SEQUENCE: 1
ttactgcatc gatattagtc                                                   20

<210> SEQ ID NO 2
<211> LENGTH: 20
<212> TYPE: DNA
<213> ORGANISM: Artificial Sequence
<220> FEATURE:
<223> OTHER INFORMATION: Hypothetical sequence to demonstrate
      application.

<400> SEQUENCE: 2
gaaggctgta tgagcttcta                                                   20

<210> SEQ ID NO 3
<211> LENGTH: 16
<212> TYPE: DNA
<213> ORGANISM: Artificial Sequence
<220> FEATURE:
<223> OTHER INFORMATION: Hypothetical sequence to demonstrate
      application.

<400> SEQUENCE: 3
ttcccggaag agagtc                                                       16

<210> SEQ ID NO 4
<211> LENGTH: 16
<212> TYPE: DNA
<213> ORGANISM: Artificial Sequence
```

-continued

```
<220> FEATURE:
<223> OTHER INFORMATION: Hypothetical sequence to demonstrate
      application.

<400> SEQUENCE: 4
ttcccggaag agggtc                                                    16

<210> SEQ ID NO 5
<211> LENGTH: 66
<212> TYPE: DNA
<213> ORGANISM: Artificial Sequence
<220> FEATURE:
<223> OTHER INFORMATION: Hypothetical sequence to demonstrate
      application.

<400> SEQUENCE: 5
gaaggctgta tgagcttcta actcattgta ttcctcctga gataataatg aagggccttc    60
tctcag                                                               66

<210> SEQ ID NO 6
<211> LENGTH: 66
<212> TYPE: DNA
<213> ORGANISM: Artificial Sequence
<220> FEATURE:
<223> OTHER INFORMATION: Hypothetical sequence to demonstrate
      application.

<400> SEQUENCE: 6
gaaggctgta tgagcttcta actcattgta ttcctcctga gataataatg aagggccttc    60
tcccag                                                               66

<210> SEQ ID NO 7
<211> LENGTH: 10
<212> TYPE: DNA
<213> ORGANISM: Artificial Sequence
<220> FEATURE:
<223> OTHER INFORMATION: Hypothetical sequence to demonstrate
      application.

<400> SEQUENCE: 7
tattcctcct                                                           10

<210> SEQ ID NO 8
<211> LENGTH: 10
<212> TYPE: DNA
<213> ORGANISM: Artificial Sequence
<220> FEATURE:
<223> OTHER INFORMATION: Hypothetical sequence to demonstrate
      application.

<400> SEQUENCE: 8
ccttctctca                                                           10

<210> SEQ ID NO 9
<211> LENGTH: 10
<212> TYPE: DNA
<213> ORGANISM: Artificial Sequence
<220> FEATURE:
<223> OTHER INFORMATION: Hypothetical sequence to demonstrate
      application.

<400> SEQUENCE: 9
ccttctccca                                                           10
```

```
<210> SEQ ID NO 10
<211> LENGTH: 20
<212> TYPE: DNA
<213> ORGANISM: Artificial Sequence
<220> FEATURE:
<223> OTHER INFORMATION: Hypothetical sequence to demonstrate
      application.

<400> SEQUENCE: 10
ctgagagaag gcccttcatt                                              20

<210> SEQ ID NO 11
<211> LENGTH: 20
<212> TYPE: DNA
<213> ORGANISM: Artificial Sequence
<220> FEATURE:
<223> OTHER INFORMATION: Hypothetical sequence to demonstrate
      application.

<400> SEQUENCE: 11
ctgggagaag gcccttcatt                                              20

<210> SEQ ID NO 12
<211> LENGTH: 87
<212> TYPE: DNA
<213> ORGANISM: Artificial Sequence
<220> FEATURE:
<223> OTHER INFORMATION: Hypothetical sequence to demonstrate
      application.

<400> SEQUENCE: 12
aactctaggt cggagtgctc cctgtatact taaaagtaag tcgtcgaact accacgacca    60
cttcagacac gacaggtcaa agacgct                                       87

<210> SEQ ID NO 13
<211> LENGTH: 87
<212> TYPE: DNA
<213> ORGANISM: Artificial Sequence
<220> FEATURE:
<223> OTHER INFORMATION: Hypothetical sequence to demonstrate
      pplication..

<400> SEQUENCE: 13
tcggagaaac tggacagcac agacttcacc ggcaccatca agctgctgaa tgaaaattca    60
tatgtccctc gtgaggctgg atctcaa                                       87

<210> SEQ ID NO 14
<211> LENGTH: 87
<212> TYPE: DNA
<213> ORGANISM: Artificial Sequence
<220> FEATURE:
<223> OTHER INFORMATION: Hypothetical sequence to demonstrate
      application.

<400> SEQUENCE: 14
tcggagaaac tggacagcac agacttcacc agcaccatca agctgctgaa tgaaaattca    60
tatgtccctc gtgaggctgg atctcaa                                       87

<210> SEQ ID NO 15
<211> LENGTH: 82
<212> TYPE: DNA
<213> ORGANISM: Artificial Sequence
<220> FEATURE:
<223> OTHER INFORMATION: Hypothetical sequence to demonstrate
      application.
```

-continued

```
<400> SEQUENCE: 15
gaaactggac agcacagact tcaccagcac catcaagctg ctgaatgaaa attcatatgt    60
ccctcgtgag gctggatctc aa                                            82

<210> SEQ ID NO 16
<211> LENGTH: 82
<212> TYPE: DNA
<213> ORGANISM: Artificial Sequence
<220> FEATURE:
<223> OTHER INFORMATION: Hypothetical sequence to demonstrate
      application.

<400> SEQUENCE: 16
ctttgacctg tcgtgtctga agtggtcgtg gtagttcgac gacttacttt taagtataca   60
gggagcactc cgacctagag tt                                            82

<210> SEQ ID NO 17
<211> LENGTH: 12
<212> TYPE: DNA
<213> ORGANISM: Artificial Sequence
<220> FEATURE:
<223> OTHER INFORMATION: Hypothetical sequence to demonstrate
      application.

<400> SEQUENCE: 17
tcaccggcac ca                                                       12
```